US008309687B2

(12) United States Patent
Wakamatsu et al.

(10) Patent No.: US 8,309,687 B2
(45) Date of Patent: Nov. 13, 2012

(54) BIOMARKER SPECIFIC FOR CANCER

(75) Inventors: Ai Wakamatsu, Tokyo (JP); Junichi Yamamoto, Sakura (JP); Takao Isogai, Inashiki-gun (JP)

(73) Assignee: Reverse Proteomics Research Institute Co., Ltd., Tokyo (JP)

( * ) Notice: Subject to any disclaimer, the term of this patent is extended or adjusted under 35 U.S.C. 154(b) by 291 days.

(21) Appl. No.: 12/531,358

(22) PCT Filed: Mar. 13, 2008

(86) PCT No.: PCT/JP2008/054573
§ 371 (c)(1),
(2), (4) Date: Sep. 15, 2009

(87) PCT Pub. No.: WO2008/114672
PCT Pub. Date: Sep. 25, 2008

(65) Prior Publication Data
US 2010/0100979 A1    Apr. 22, 2010

(30) Foreign Application Priority Data
Mar. 15, 2007   (JP) .................................. 2007-066425

(51) Int. Cl.
C07K 1/00       (2006.01)
C07K 14/00      (2006.01)
C07K 17/00      (2006.01)
C07K 4/00       (2006.01)
C07K 7/00       (2006.01)
A61K 38/00      (2006.01)

(52) U.S. Cl. ........................................ 530/350; 539/300
(58) Field of Classification Search .................. 530/350, 530/300
See application file for complete search history.

(56) References Cited

U.S. PATENT DOCUMENTS

| 6,762,052 B1 | 7/2004 | Cashman et al. |
| 2005/0196754 A1* | 9/2005 | Drmanac et al. ................... 435/6 |
| 2007/0105122 A1 | 5/2007 | Ota et al. |

FOREIGN PATENT DOCUMENTS

| EP | 0 712 932 A2 | 5/1996 |
| JP | 8-140674 A | 6/1996 |
| WO | WO 01/09317 A1 | 2/2001 |
| WO | WO 02/29103 A2 | 4/2002 |

OTHER PUBLICATIONS

Ring et al., Detection of circulating epithelial cells in the blood of patients with breast cancer: comparison of three techniques, Br J Cancer. 92(5):906-12, 2005.*
Amery et al., *Biochem. Journal*,357: 635-646 (2001).
Baes et al., *Molecular and Cellular Biology*, 14(3): 1544-1552 (1994).
Baumann et al., *Science*, 292, 1171-1175 (May 11, 2001).
Cashman et al., *Drug Metabolism and Disposition*, 29(12): 1629-1637 (2001).
Chen et al., *Journal of Pharmacology and Experimental Therapeutics*, 314(3): 1125-1133 (2005).
Dolphin et al., *European Journal of Biochemistry*, 235(3): 683-689 (1996).
Facchiano et al., *Journal of Biological Chemistry*, 278(10): 8751-8760 (2003).
Ferguson et al., *Molecular Pharmacology*, 68(3): 747-757 (2005).
Gecz et al., *Hum. Genet.*, 104(1): 56-63 (1999).
Hammond et al., *FEBS Letters*, 425(3): 391-395 (1998).
Hinderlich et al., *Journal of Biological Chemistry*, 272(39): 24313-24318 (1997).
Ishikawa et al., *Mol. Endocrinol.*, 4(6): 837-844 (1990).
Krust et al., *Proc. Natl. Acad. Sci. U.S.A.*, 86(14): 5310-5314 (1989).
Lehmann et al., *Nucleic Acids Res.*, 19(3): 573-578 (1991).
Lomri et al., *Proc. Natl. Acad. Sci. U.S.A.*, 89(5): 1685-1689 (1992).
Lomri et al., *Proc. Natl. Acad. Sci. U.S.A.*, 92(21): 9910 (1995).
Masuno et al., *Genomics*, 20(1): 141-142 (1994).
Mitrani-Rosenbaum et al., *Human Molecular Genetics*, 5(1): 159-163 (1996).
Pyo et al., *Journal of Biological Chemistry*, 280(21): 20722-20729 (2005).
Salama et al., *Biochem. Biophys. Res. Commun.*, 328(1): 221-226 (2005).
Shimizu et al., *Cytogenet. Cell Genet.*, 77: 261-263 (1997).
Smallwood et al., *Proc. Natl. Acad. Sci. U.S.A.*, 93(18): 9850-9857 (1996).
Sparks et al., *Glycobiology*, 15(11): 1102-1110 (2005).
Swales et al., *Journal of Biological Chemistry*, 280(5): 3458-3466 (2005).
Vollberg et al., *Molecular Endocrinology*, 6(5): 667-676 (1992).
Wang et al., *Journal of Biological Chemistry*, 279(44): 45855-45864 (2004).
Zhou et al., *Mutation Research*, 612(3): 165-171 (2006).

* cited by examiner

*Primary Examiner* — Wu-Cheng Winston Shen
(74) *Attorney, Agent, or Firm* — Leydig, Voit & Mayer, Ltd.

(57) ABSTRACT

It is an object of the present invention to provide diagnostic reagents, pharmaceuticals and the like for particular diseases, and providing means that are useful in developing such reagents, pharmaceuticals and the like. The present invention provides a novel polypeptide and a specific partial peptide thereof, as well as a novel polynucleotide and a specific partial nucleotide thereof, that can be used as cancer-specific biomarkers; an expression vector for such a polynucleotide and a specific partial peptide thereof; a transformant incorporating such an expression vector; an antisense molecule, RNAi-inducing nucleic acid (e.g., siRNA), aptamer, or antibody for a cancer-specific biomarker, and a composition comprising the same; a mammalian cell or non-human mammal wherein the expression or a function of a cancer-specific biomarker is regulated; a measuring means (e.g., primer set, nucleic acid probe, antibody, aptamer) for a cancer-specific biomarker, and a reagent comprising them and the like.

16 Claims, No Drawings

BIOMARKER SPECIFIC FOR CANCER

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 273,333 bytes ASCII (Text) file named "705453SequenceListing.txt," created Sep. 11, 2009.

TECHNICAL FIELD

The present invention provides a polypeptide and a partial peptide thereof, as well as a polynucleotide and a partial nucleotide thereof, that can be used as biomarkers specific for cancer; an expression vector; a transformant; an antisense molecule, an RNAi-inducing nucleic acid (e.g., siRNA), an aptamer, an antibody, and a composition comprising them; a mammalian cell or a non-human mammal; a measuring means for a biomarker specific for cancer (e.g., primer set, nucleic acid probe, antibody, aptamer), a measuring method and the like.

BACKGROUND ART

Although there have been remarkable advances in the analysis of human chromosome sequences thanks to the progress in human genome research, this does not mean that all the human genetic functions have been clarified. In humans, gene diversity is significantly associated with changes in gene functions. In fact, it is known that in humans, a plurality of mRNAs are transcribed from a particular region of a chromosome to produce different variants.

For the series of genes that have been discovered by the present inventors, and that can be used as biomarkers specific for cancer (abbreviated as "cancer-specific genes" or "cancer-specific genes 1 to 8" as required), known variants have been reported. Examples of such known variants include known variants of cancer-specific gene 1 (Genbank accession number: NM_006894.4; non-patent documents 1 and 2), cancer-specific gene 2 (Genbank accession number: NM_000966.3; non-patent documents 3 and 4), cancer-specific gene 3 (Genbank accession number: NM_016559.1; non-patent documents 5 and 6), cancer-specific gene 4 (Genbank accession number: NM_004114.2; non-patent documents 7 and 8), cancer-specific gene 5 (Genbank accession number: NM_005476.3; non-patent documents 9 and 10), cancer-specific gene 6 (Genbank accession number: NM_004849.1; non-patent documents 11 and 12), cancer-specific gene 7 (Genbank accession number: NM_022777.1), cancer-specific gene 8 (Genbank accession number: NM_005122.2; non-patent document 13 and 14).

However, it is not known that the cancer-specific genes 1 to 8 can be useful as biomarkers specific for cancer, and that the particular variants discovered by the present inventors exist in the cancer-specific genes 1 to 8.

Non-patent document 1: Lomri, N. et al., Proc. Natl. Acad. Sci. U.S.A. 89 (5), 1685-1689 (1992)
Non-patent document 2: Lomri, N. et al., Proc. Natl. Acad. Sci. U.S.A. 92 (21), 9910 (1995)
Non-patent document 3: Krust, A. et al., Proc. Natl. Acad. Sci. U.S.A. 86 (14), 5310-5314 (1989)
Non-patent document 4: Ishikawa, T. et al., Mol. Endocrinol. 4 (6), 837-844 (1990)
Non-patent document 5: Amery, L. et al., Biochem. J. 357 (PT 3), 635-646 (2001)
Non-patent document 6: Wang, X. et al., J. Biol. Chem. 279 (44), 45855-45864 (2004)
Non-patent document 7: Smallwood, P. M. et al., Proc. Natl. Acad. Sci. U.S.A. 93 (18), 9850-9857 (1996)
Non-patent document 8: Gecz, J. et al., Hum. Genet. 104 (1), 56-63 (1999)
Non-patent document 9: Mitrani-Rosenbaum, S. et al., Hum. Mol. Genet. 5 (1), 159-163 (1996)
Non-patent document 10: Salama, I. et al., Biochem. Biophys. Res. Commun. 328 (1), 221-226 (2005)
Non-patent document 11: Hammond, E. M. et al., FEBS Lett. 425 (3), 391-395 (1998)
Non-patent document 12: Baumann, P. et al. Science 292 (5519), 1171-1175 (2001)
Non-patent document 13: Baes, M. et al., Mol. Cell. Biol. 14 (3), 1544-1552 (1994)
Non-patent document 14: Masuno, M. et al., Genomics 20 (1), 141-142 (1994)

DISCLOSURE OF THE INVENTION

Problems to be Solved by the Invention

Analyzing a biomarker specific for a specified phenotype such as a particular disease leads to the development of a diagnostic reagent for a particular disease, and a pharmaceutical and the like for a particular disease, having a new mechanism of action. Based on the findings obtained by expression profile analysis of specified genes, the present invention is directed to providing diagnostic reagents, pharmaceuticals and the like for particular diseases, and providing means that are useful in developing such reagents, pharmaceuticals and the like.

Means of Solving the Problems

The present inventors conducted extensive investigations and discovered cancer-specific genes 1 to 8 as biomarkers specific for cancer. The present inventors also discovered novel variants of the cancer-specific genes 1 to 8 that can be used as biomarkers specific for cancer. Therefore, it is thought that by utilizing the cancer-specific genes 1 to 8 and/or novel variants thereof, it will become possible to diagnose cancer easily and rapidly. In particular, because the cancer-specific genes 1 to 8 and/or novel variants thereof are expressed specifically in specified cancer, the accuracy of the diagnosis of such cancer can be increased. It is also thought that by utilizing the cancer-specific genes 1 to 8 and/or novel variants thereof, it will become possible to develop a novel pharmaceutical, and the like.

Based on the findings shown above, the present inventors developed the present invention.

Accordingly, the present invention relates to the following aspects and the like:

[1] A polypeptide of any one of 1) to 8) below or a specific partial peptide thereof:
1) a polypeptide having an amino acid sequence shown by SEQ ID NO:10, SEQ ID NO:16 or SEQ ID NO:21, or substantially the same amino acid sequence thereas;
2) a polypeptide having an amino acid sequence shown by SEQ ID NO:39, SEQ ID NO:45 or SEQ ID NO:51, or substantially the same amino acid sequence thereas;
3) a polypeptide having an amino acid sequence shown by SEQ ID NO:75 or SEQ ID NO:83, or substantially the same amino acid sequence thereas;

4) a polypeptide having an amino acid sequence shown by SEQ ID NO:103, SEQ ID NO:109 or SEQ ID NO:115, or substantially the same amino acid sequence thereas;
5) a polypeptide having the amino acid sequence shown by SEQ ID NO:144, or substantially the same amino acid sequence thereas;
6) a polypeptide having the amino acid sequence shown by SEQ ID NO:163 or an amino acid sequence consisting of the 18th to 197th amino acid residues in the amino acid sequence shown by SEQ ID NO:163, or substantially the same amino acid sequence thereas;
7) a polypeptide having an amino acid sequence shown by SEQ ID NO:185 or SEQ ID NO:191 or an amino acid sequence consisting of the 25th to 146th amino acid residues in the amino acid sequence shown by SEQ ID NO:191, or substantially the same amino acid sequence thereas; or
8) a polypeptide having an amino acid sequence shown by SEQ ID NO:210, SEQ ID NO:221 or SEQ ID NO:227, or substantially the same amino acid sequence thereas.

[2] The polypeptide or specific partial peptide thereof according to [1] above, wherein the polypeptide is any one of the polypeptides 1) to 8) below:
1) a polypeptide consisting of an amino acid sequence shown by SEQ ID NO:10, SEQ ID NO:16 or SEQ ID NO:21;
2) a polypeptide consisting of an amino acid sequence shown by SEQ ID NO:39, SEQ ID NO:45 or SEQ ID NO:51;
3) a polypeptide consisting of an amino acid sequence shown by SEQ ID NO:75 or SEQ ID NO:83;
4) a polypeptide consisting of an amino acid sequence shown by SEQ ID NO:103, SEQ ID NO:109 or SEQ ID NO:115;
5) a polypeptide consisting of the amino acid sequence shown by SEQ ID NO:144;
6) a polypeptide consisting of the amino acid sequence shown by SEQ ID NO:163 or an amino acid sequence consisting of the 18th to 197th amino acid residues in the amino acid sequence shown by SEQ ID NO:163;
7) a polypeptide consisting of an amino acid sequence shown by SEQ ID NO:185 or SEQ ID NO:191 or an amino acid sequence consisting of the 25th to 146th amino acid residues in the amino acid sequence shown by SEQ ID NO:191; and
8) a polypeptide consisting of an amino acid sequence shown by SEQ ID NO:210, SEQ ID NO:221 or SEQ ID NO:227.

[3] The polypeptide or specific partial peptide thereof according to [1] or [2] above, which is fused with a polypeptide consisting of a heterologous amino acid sequence.

[4] A partial peptide specific for one of the polypeptides encoded by the cancer-specific genes 1 to 8, being any one of the partial peptides 1) to 8) below:
1) a partial peptide consisting of an amino acid sequence shown by SEQ ID NO:12 or SEQ ID NO:18, or a partial amino acid sequence thereof, or a partial peptide of a polypeptide consisting of the amino acid sequence shown by SEQ ID NO:21;
2) a partial peptide consisting of an amino acid sequence shown by SEQ ID NO:41, SEQ ID NO:47, SEQ ID NO:54, SEQ ID NO:56 or SEQ ID NO:57, or a partial amino acid sequence thereof;
3) a partial peptide consisting of the amino acid sequence shown by SEQ ID NO:80, or a partial amino acid sequence thereof;
4) a partial peptide consisting of an amino acid sequence shown by SEQ ID NO:105, SEQ ID NO:111 or SEQ ID NO:117, or a partial amino acid sequence thereof;
5) a partial peptide consisting of the amino acid sequence shown by SEQ ID NO:146, or a partial amino acid sequence thereof;
6) a partial peptide consisting of an amino acid sequence shown by SEQ ID NO:165, SEQ ID NO:167, or SEQ ID NO:169, or a partial amino acid sequence thereof;
7) a partial peptide consisting of an amino acid sequence shown by SEQ ID NO:187, SEQ ID NO:195 or SEQ ID NO:197, or a partial amino acid sequence thereof, or a partial peptide of a polypeptide consisting of the amino acid sequence shown by SEQ ID NO:191; and
8) a partial peptide consisting of an amino acid sequence shown by SEQ ID NO:212, SEQ ID NO:248, SEQ ID NO:215, SEQ ID NO:217, SEQ ID NO:223 or SEQ ID NO:229, or a partial amino acid sequence thereof.

[5] A polynucleotide that encodes the polypeptide of any one of [1] to [3] above, or the specific partial peptide of any one of [1] to [4] above.

[6] A polynucleotide of any one of 1) to 8) below or a specific partial nucleotide thereof:
1) a polynucleotide having a nucleic acid sequence shown by SEQ ID NO:8 or SEQ ID NO:14, or an ORF-corresponding nucleic acid sequence thereof, or substantially the same nucleic acid sequence thereas;
2) a polynucleotide having a nucleic acid sequence shown by SEQ ID NO:37, SEQ ID NO:43, SEQ ID NO:49 or SEQ ID NO:58, or an ORF-corresponding nucleic acid sequence thereof, or substantially the same nucleic acid sequence thereas;
3) a polynucleotide having a nucleic acid sequence shown by SEQ ID NO:73 or SEQ ID NO:81, or an ORF-corresponding nucleic acid sequence thereof, or substantially the same nucleic acid sequence thereas;
4) a polynucleotide having a nucleic acid sequence shown by SEQ ID NO:101, SEQ ID NO:107 or SEQ ID NO:113, or an ORF-corresponding nucleic acid sequence thereof, or substantially the same nucleic acid sequence thereas;
5) a polynucleotide having the nucleic acid sequence shown by SEQ ID NO:142, or an ORF-corresponding nucleic acid sequence thereof, or substantially the same nucleic acid sequence thereas;
6) a polynucleotide having the nucleic acid sequence shown by SEQ ID NO:161, or an ORF-corresponding nucleic acid sequence thereof or a nucleic acid sequence consisting of the 503rd to 1045th nucleotide residues in the nucleic acid sequence shown by SEQ ID NO:161, or substantially the same nucleic acid sequence thereas;
7) a polynucleotide having a nucleic acid sequence shown by SEQ ID NO:183 or SEQ ID NO:189, or an ORF-corresponding nucleic acid sequence thereof or a nucleic acid sequence consisting of the 379th to 747th nucleotide residues in the nucleic acid sequence shown by SEQ ID NO:189, or substantially the same nucleic acid sequence thereas; and
8) a polynucleotide having SEQ ID NO:208, SEQ ID NO:219 or SEQ ID NO:225, or an ORF-corresponding nucleic acid sequence thereof, or substantially the same nucleic acid sequence thereas.

[7] The polynucleotide or specific partial nucleotide thereof according to [6] above, wherein the any one of the polynucleotides 1) to 8) is any one of the polynucleotides 1) to 8) below:
1) a polynucleotide consisting of a nucleic acid sequence shown by SEQ ID NO:8 or SEQ ID NO:14, or an ORF-corresponding nucleic acid sequence thereof;
2) a polynucleotide consisting of a nucleic acid sequence shown by SEQ ID NO:37, SEQ ID NO:43, SEQ ID NO:49 or SEQ ID NO:58, or an ORF-corresponding nucleic acid sequence thereof;
3) a polynucleotide consisting of a nucleic acid sequence shown by SEQ ID NO:73 or SEQ ID NO:81, or an ORF-corresponding nucleic acid sequence thereof;

4) a polynucleotide consisting of a nucleic acid sequence shown by SEQ ID NO:101, SEQ ID NO:107 or SEQ ID NO:113, or an ORF-corresponding nucleic acid sequence thereof;
5) a polynucleotide consisting of the nucleic acid sequence shown by SEQ ID NO:142, or an ORF-corresponding nucleic acid sequence thereof;
6) a polynucleotide consisting of the nucleic acid sequence shown by SEQ ID NO:161, or an ORF-corresponding nucleic acid sequence thereof or a nucleic acid sequence consisting of the 503rd to 1045th nucleotide residues in the nucleic acid sequence shown by SEQ ID NO:161;
7) a polynucleotide consisting of a nucleic acid sequence shown by SEQ ID NO:183 or SEQ ID NO:189, or an ORF-corresponding nucleic acid sequence thereof or a nucleic acid sequence consisting of the 379th to 747th nucleotide residues in the nucleic acid sequence shown by SEQ ID NO:189; and
8) a polynucleotide consisting of SEQ ID NO:208, SEQ ID NO:219 or SEQ ID NO:225, or an ORF-corresponding nucleic acid sequence thereof.

[8] A partial nucleotide specific for a polynucleotide encoded by one of the cancer-specific genes 1 to 8, being any one of the partial nucleotides 1) to 8) below:
1) a partial nucleotide consisting of a nucleic acid sequence shown by SEQ ID NO:11, SEQ ID NO:13, SEQ ID NO:17, SEQ ID NO:19, SEQ ID NO:22, SEQ ID NO:25, SEQ ID NO:28, SEQ ID NO:31, SEQ ID NO:35 or SEQ ID NO:36, or a partial nucleic acid sequence thereof;
2) a partial nucleotide consisting of a nucleic acid sequence shown by SEQ ID NO:40, SEQ ID NO:42, SEQ ID NO:46, SEQ ID NO:48, SEQ ID NO:52, SEQ ID NO:53, SEQ ID NO:55, SEQ ID NO:63, SEQ ID NO:66, SEQ ID NO:70, SEQ ID NO:71 or SEQ ID NO:72, or a partial nucleic acid sequence thereof;
3) a partial nucleotide consisting of a nucleic acid sequence shown by SEQ ID NO:76, SEQ ID NO:77, SEQ ID NO:78, SEQ ID NO:79, SEQ ID NO:84, SEQ ID NO:85, SEQ ID NO:88, SEQ ID NO:89, SEQ ID NO:93, SEQ ID NO:99 or SEQ ID NO:100, or a partial nucleic acid sequence thereof;
4) a partial nucleotide consisting of SEQ ID NO:104, SEQ ID NO:106, SEQ ID NO:110, SEQ ID NO:112, SEQ ID NO:116, SEQ ID NO:118, SEQ ID NO:121, SEQ ID NO:125, SEQ ID NO:129, SEQ ID NO:133, SEQ ID NO:139, SEQ ID NO:140 or SEQ ID NO:141, or a partial nucleic acid sequence thereof;
5) a partial nucleotide consisting of a nucleic acid sequence shown by SEQ ID NO:145, SEQ ID NO:147, SEQ ID NO:150, SEQ ID NO:154 or SEQ ID NO:160, or a partial nucleic acid sequence thereof;
6) a partial nucleotide consisting of a nucleic acid sequence shown by SEQ ID NO:164, SEQ ID NO:166, SEQ ID NO:168, SEQ ID NO:175, SEQ ID NO:178 or SEQ ID NO:182, or a partial nucleic acid sequence thereof;
7) a partial nucleotide consisting of a nucleic acid sequence shown by SEQ ID NO:186, SEQ ID NO:188, SEQ ID NO:192, SEQ ID NO:193, SEQ ID NO:194, SEQ ID NO:196, SEQ ID NO:200, SEQ ID NO:203 or SEQ ID NO:207, or a partial nucleic acid sequence thereof; and
8) a partial nucleotide consisting of a nucleic acid sequence shown by SEQ ID NO:211, SEQ ID NO:213, SEQ ID NO:214, SEQ ID NO:216, SEQ ID NO:218, SEQ ID NO:222, SEQ ID NO:224, SEQ ID NO:228, SEQ ID NO:230, SEQ ID NO:233, SEQ ID NO:236, SEQ ID NO:239, SEQ ID NO:242, SEQ ID NO:246 or SEQ ID NO:247, or a partial nucleic acid sequence thereof.

[9] An expression vector for the polypeptide according to any one of [1] to [3] above or the specific partial peptide according to any one of [1] to [4] above, comprising the polynucleotide according to any one of [5] to [7] above or the specific partial nucleotide according to any one of [6] to [8] above, and a promoter operatively linked thereto.

[10] A transformant incorporating the expression vector according to [9] above.

[11] An antisense molecule comprising a nucleic acid sequence complementary to the nucleic acid sequence of the specific partial nucleotide according to [7] or [8] above, and capable of suppressing the expression of any one of the polypeptides encoded by the cancer-specific genes 1 to 8.

[12] An RNAi-inducing nucleic acid capable of suppressing the expression of any one of the polypeptides encoded by the cancer-specific genes 1 to 8, that is configured by a sense strand consisting of the nucleic acid sequence of the specific partial nucleotide according to [7] or [8] above, and an antisense strand consisting of a nucleic acid sequence complementary thereto, and that may have an overhang at the 5' terminus and/or 3' terminus of one or both of the sense strand and the antisense strand.

[13] The RNAi-inducing nucleic acid according to [12] above, wherein the RNAi-inducing nucleic acid is an siRNA.

[14] An aptamer capable of binding to any one of the polypeptides encoded by the cancer-specific genes 1 to 8 via a region corresponding to the specific partial peptide according to any one of [2] to [4] above.

[15] An antibody capable of binding to any one of the polypeptides encoded by the cancer-specific genes 1 to 8 via a region corresponding to the specific partial peptide according to any one of [2] to [4] above.

[16] The antibody according to [15] above, wherein the antibody is any one of the i) to iii) below:
i) a polyclonal antibody;
ii) a monoclonal antibody or a portion thereof;
iii) a chimeric antibody, a humanized antibody or a human antibody.

[17] A cell that produces the antibody according to [15] or [16] above.

[18] The cell according to [17] above, wherein the cell is a hybridoma.

[19] A composition comprising the polypeptide according to any one of [1] to [3] above, the antisense molecule according to [11] above, the RNAi-inducing nucleic acid according to [12] or [13] above, the aptamer according to [14] above, the antibody according to [15] or [16] above, or an expression vector therefor, and a pharmaceutically acceptable carrier.

[20] A mammalian cell or non-human mammal wherein the expression or a function of the polypeptide according to any one of [1] to [3] above is regulated.

[21] A primer set specific for any one of the polynucleotides encoded by the cancer-specific genes 1 to 8 or a specific partial nucleotide thereof, comprising the following (a) or (b):
(a) a sense primer corresponding to a first nucleic acid sequence of the polynucleotide according to [7] above or the specific partial nucleotide according to [7] or [8] above;
(b) an antisense primer corresponding to a nucleic acid sequence complementary to a second nucleic acid sequence of the polynucleotide according to [7] above or the specific partial nucleotide according to [7] or [8] above.

[22] A nucleic acid probe specific for any one of the polynucleotides encoded by the cancer-specific genes 1 to 8 or a specific partial nucleotide thereof, being any one of the following (a) or (b):
(a) a single-stranded polynucleotide comprising a nucleic acid sequence complementary to the nucleic acid sequence of the specific partial nucleotide according to [7] or [8] above; or (b) a double-stranded polynucleotide configured by a sense strand comprising the nucleic acid sequence of the specific partial nucleotide according to [7] or [8] above, and an antisense strand comprising a nucleic acid sequence complementary thereto.

[23] A reagent or kit for detection or quantification of any one of the polypeptides or polynucleotides encoded by the cancer-specific genes 1 to 8, comprising one or more substances or sets selected from among the aptamer according to [14] above, the antibody according to [15] or [16] above, the primer set according to [21] above and the nucleic acid probe according to [22] above.

[24] The reagent or kit according to [23] above, being a reagent or kit for diagnosis of cancer.

[25] A method of detecting or quantifying any one of the polypeptides or polynucleotides encoded by the cancer-specific genes 1 to 8, comprising measuring the expression of the polypeptide or polynucleotide in a biological sample or cell or tissue culture obtained from a mammal, wherein the biological sample or the culture contains a cancer cell or a cancer tissue.

[26] A method of detecting or quantifying the polypeptide according to [2] or [3] above or the polynucleotide according to [7] above, comprising measuring the expression of the polypeptide or the polynucleotide in a biological sample or cell or tissue culture obtained from a mammal.

[27] The method of detection or quantification according to [26] above, wherein the biological sample or the culture contains a cancer cell or a cancer tissue.

Effect of the Invention

A polypeptide of the present invention and a partial peptide of the present invention can be useful, for example, as a biomarker specific for cancer, and in developing a substance capable of specifically recognizing a polypeptide of the present invention or a known polypeptide, or a substance capable of comprehensively recognizing both a polypeptide of the present invention and a known polypeptide, and a substance capable of specifically regulating a function of a polypeptide of the present invention or a known polypeptide, or a substance capable of comprehensively regulating functions of both a polypeptide of the present invention and a known polypeptide.

A polynucleotide of the present invention and a partial nucleotide of the present invention can be useful, for example, as a biomarker specific for cancer, and in developing a substance capable of specifically recognizing a polynucleotide of the present invention or a known polynucleotide, or a substance capable of comprehensively recognizing both a polynucleotide of the present invention and a known polynucleotide, and a substance capable of specifically regulating the expression of a polypeptide of the present invention or a known polypeptide, or a substance capable of comprehensively regulating the expression of both a polypeptide of the present invention and a known polypeptide.

Related substances of the present invention (e.g., antisense molecules, RNAi-inducing nucleic acids such as siRNAs, aptamers and antibodies, and expression vectors therefor) can be useful as, for example, pharmaceuticals or reagents.

A cell of the present invention can be useful in, for example, producing a polypeptide of the present invention and a partial peptide of the present invention, and an antibody of the present invention. A cell of the present invention can also be useful in developing a pharmaceutical (e.g., a prophylactic or therapeutic drug for cancer), identifying a further marker gene specific for cancer, and analyzing a mechanism associated with cancer or cell proliferation.

An animal of the present invention can be useful in, for example, developing a pharmaceutical, identifying a further marker gene specific for cancer, and analyzing a mechanism associated with cancer or cell proliferation.

Measuring means (e.g., primer set, nucleic acid probe, antibody, aptamer) and measuring methods of the present invention can be useful in, for example, specific detection and quantitation of a polynucleotide of the present invention or a known polynucleotide, or a polypeptide of the present invention or a known polypeptide, or comprehensive detection and quantitation of both a polynucleotide of the present invention and a known polynucleotide, or both a polypeptide of the present invention and a known polypeptide. These means and methods can also be utilized for diagnosis of cancer and screening for pharmaceuticals, reagents or foods.

BEST MODE FOR CARRYING OUT THE INVENTION

1. Cancer-Specific Genes

A gene of the present invention can be a gene derived from an optionally chosen mammal. As examples of the mammal, primates and rodents, as well as laboratory animals, domestic animals, working animals, companion animals and the like can be mentioned. In detail, as examples of the mammal, humans, monkeys, rats, mice, rabbits, horses, cattle, goat, sheep, dogs, cats and the like can be mentioned. Preferably, the mammal is a human.

A gene of the present invention is capable of being expressed specifically in either a normal tissue or a cancer tissue and incapable of being expressed specifically in the other, or is capable of being expressed at a high level in either a normal tissue or a cancer tissue and expressed at a low level in the other. A gene of the present invention is also capable of being expressed at a higher or lower level in either a normal tissue or a cancer tissue, and/or capable of being expressed at a lower or higher level in the other, compared with a known polynucleotide and/or a known polypeptide. As examples of such normal tissues and/or cancer tissues, the brain (e.g., cerebrum, cerebral cortex, cerebellum, caudate nucleus, corpus callosum, hippocampus, substantia nigra, thalamus, hypothalamus, subthalamic nucleus, hypophysis), spinal cord, tongue, tonsil, stomach, pancreas, kidney, liver, gonads, thyroid, gall bladder, bone marrow, adrenal, skin, muscles (e.g., skeletal muscles, smooth muscles), lung, digestive tract (e.g., large intestine, colon, ileum, jejunum, duodenum, small intestine), blood vessels (e.g., arteries, veins), heart (e.g., pericardium), thymus, spleen, submandibular gland, blood (e.g., peripheral blood, cord blood), prostate, urinary bladder, testis, ovary, placenta, uterus (e.g., endometrium, cervix), trachea or bronchus, esophagus, bone or cartilage, joints, synovium, lymph nodes, breast, adipose tissue, glandular tissue (e.g., mammary glands, salivary glands), mesenchymal tissue and the like can be mentioned.

A gene of the present invention is capable of being expressed specifically in either a normal cell or a cancer cell and incapable of being expressed specifically in the other, or is capable of being expressed at a high level in either a normal cell or a cancer cell and expressed at a low level in the other. A gene of the present invention is also capable of being expressed at a higher or lower level in either a normal cell or a cancer cell, and/or capable of being expressed at a lower or higher level in the other, compared with a known polynucleotide and/or a known polypeptide. As examples of such normal cells and/or cancer cells, cells in the aforementioned tissues, and/or hepatocytes, splenocytes, nerve cells, glial cells, astrocytes, pancreatic β cells, bone marrow cells, mesangium cells, epidermal cells, epithelial cells, goblet cells, endothelial cells, fibroblasts, fibrocytes, fat cells, mast cells, hair papilla cells, synovial cells, chondrocytes, bone cells, osteoblasts, osteoclasts, mammary gland cells, interstitial cells or blood cells, or progenitor cells, stem cells or cancer cells thereof (e.g., epithelial cancers, non-epithelial cancers, leukemia cells) and the like can be mentioned. As blood cells, erythroblasts, granulocytes, monocytes, macrophages, myeloblasts, megakaryocytes, lymphocytes (e.g., T cells, B cells, NK cells) and the like can be mentioned.

As cancers, cancers in the aforementioned tissues and cells can be mentioned. As cancers, epithelial cancers, non-epithelial cancers, and cancers in hematopoietic tissue can be mentioned. In detail, as epithelial or non-epithelial cancers, gastrointestinal cancers (e.g., gastric cancer, colic cancer, large intestine cancer, rectal cancer), lung cancer (e.g., small-cell cancer, non-small-cell cancer), pancreatic cancer, renal cancer, hepatic cancer, thymus cancer, spleen cancer, thyroid cancer, adrenal cancer, prostatic cancer, urinary bladder cancer, ovary cancer, uterus cancer (e.g., endometrial cancer, cervical cancer), bone cancer, skin cancer, sarcomas (e.g., Kaposi's sarcoma), melanoma, blastomas (e.g., neuroblastoma), glandular cancer, squamous cell cancer, non-squamous cell cancer, and brain tumor can be mentioned. As cancers in hematopoietic tissue, leukemias (e.g., acute myelocytic leukemia (AML), chronic myelocytic leukemia (CML), acute lymphocytic leukemia (ALL), chronic lymphocytic leukemia (CLL), adult T cell leukemia (ATL), myelodysplastic syndrome (MDS)), lymphomas (e.g., T lymphoma, B lymphoma, Hodgkin lymphoma), and myeloma (multiple myeloma) can be mentioned. As used herein, the terms cancer and tumor can have the same definition.

Hereinafter, the polypeptides and partial peptides thereof, and polynucleotides and partial nucleotides thereof, provided by the present invention, are described.

1.1. Polypeptides and Partial Peptides Thereof

The present invention provides a polypeptide having an amino acid sequence shown by SEQ ID NO:X or substantially the same amino acid sequence thereas (abbreviated as "amino acid sequence shown by SEQ ID NO:X and the like" as required).

"SEQ ID NO:X" denotes the SEQ ID NO of an optionally chosen amino acid sequence disclosed herein. A polypeptide "having" an amino acid sequence shown by SEQ ID NO:X and the like means a polypeptide "consisting of" an amino acid sequence shown by SEQ ID NO:X and the like, and a polypeptide "comprising" the amino acid sequence and the like.

In one embodiment, substantially the same amino acid sequence as an amino acid sequence shown by SEQ ID NO:X can be an amino acid sequence having a specified amino acid sequence identity to the amino acid sequence shown by SEQ ID NO:X. The degree of amino acid sequence identity can be about 90% or more, preferably about 92% or more, more preferably about 95% or more, still more preferably about 96% or more, and most preferably about 97% or more, about 98% or more or about 99% or more. Amino acid sequence identity can be determined by a method known per se. Unless otherwise specified, amino acid sequence identity (%) is calculated by, for example, executing the commands for the maximum matching method, using the DNASIS sequence analytical software (Hitachi Software Engineering). The parameters for the calculation should be used in default settings. Amino acid sequence identity (%) can also be determined, without following the above procedures, using a program in common use in the art (for example, BLAST, FASTA and the like) in the default settings thereof. In another aspect, the identity (%) can be determined using an optionally chosen algorithm publicly known in the art, for example, the algorithms of Needleman et al. (1970) (J. Mol. Biol. 48: 444-453) and Myers and Miller (CABIOS, 1988, 4: 11-17) and the like. The algorithm of Needleman et al. is incorporated in the GAP program in the GCG software package, and the identity (%) can be determined by, for example, using BLOSUM 62 matrix or PAM250 matrix, with a gap weight of 16, 14, 12, 10, 8, 6 or 4, and a length weight of 1, 2, 3, 4, 5 or 6. The algorithm of Myers and Miller is incorporated in the ALIGN program, which is a portion of the GCG sequence alignment software package. When the ALIGN program is utilized to compare amino acid sequences, for example, PAM120 weight residue table, gap length penalty 12, gap penalty 4, can be used. For calculating amino acid sequence identity, the method that produces the least value among the above-mentioned methods may be employed.

In another embodiment, substantially the same amino acid sequence as an amino acid sequence shown by SEQ ID NO:X can be an amino acid sequence shown by SEQ ID NO:X wherein one or more amino acids have one or more modifications selected from among substitutions, additions, deletions and insertions. The number of amino acids modified is not particularly limited, as far as it is one or more; the number can be, for example, 1 to about 50, preferably 1 to about 30, more preferably 1 to about 20, still more preferably 1 to about 10, and most preferably 1 to about 5 (e.g., 1 or 2).

Substantially the same amino acid sequence as an amino acid sequence shown by SEQ ID NO:X may completely retain a characteristic portion thereof (e.g., a portion corresponding to a specific partial polypeptide described below), and may have another portion (e.g., a portion present in a known polypeptide) being substantially the same as the corresponding portion of the amino acid sequence shown by SEQ ID NO:X. Alternatively, substantially the same amino acid sequence as an amino acid sequence shown by SEQ ID NO:X may have a non-characteristic portion thereof being identical to the corresponding portion of the amino acid sequence shown by SEQ ID NO:X, and a characteristic portion thereof being substantially identical to the corresponding portion of the amino acid sequence shown by SEQ ID NO:X.

A polypeptide of the present invention can have a function that is homogenous or heterogeneous to that of a known polypeptide (e.g., known variant). A polypeptide of the present invention can also have an enhanced or reduced function compared with a known polypeptide (e.g., known variant).

In detail, the novel polypeptides of the cancer-specific genes 1 to 8 are as follows.

1) Cancer-Specific Gene 1

D-LIVER2001680.1 (SEQ ID NO:10)
D-LIVER2008912.1 (SEQ ID NO:16, SEQ ID NO:21)

As a known variant of the cancer-specific gene 1, for example, a variant disclosed in an Example (human flavin-containing monooxygenase 3 (FMO3), transcription variant 1; total number of nucleotides in the ORF nucleic acid sequence: 1599; total number of amino acids in the protein: 532; see GenBank accession number: NM_006894.4) has been reported. It has been reported that known variants of the cancer-specific gene 1 have a specified function (e.g., NADPH-dependent monooxygenase activity of one or more atoms selected from among nucleophilic nitrogen, sulfur and phosphorus atoms, or potential for metabolism of drugs, insecticides, foreign matter to living organisms and the like)

(see, e.g., Zhou, J. & Shephard, E. A. Mutat. Res. 612 (3), 165-171 (2006)). Generally, it is known that a plurality of variants resulting from a single locus (splicing variants) have similar functions, although the degree can vary. Therefore, novel variants of the cancer-specific gene 1 can also have these functions.

2) Cancer-Specific Gene 2
   D-HCHON2007878.1 (SEQ ID NO:39)
   D-NTONG2006230.1 (SEQ ID NO:45)
   D-SPLEN2005548.1 (SEQ ID NO:51)
   As a known variant of the cancer-specific gene 2, for example, a variant disclosed in an Example (human retinoic acid receptor γ (RARγ); total number of nucleotides in the ORF nucleic acid sequence: 1365; total number of amino acids in the protein: 454; see GenBank accession number: NM_000966.3) has been reported. It has been reported that known variants of the cancer-specific gene 2 have a specified function (e.g., potential for transcriptional regulation via a hetero-dimer with RXR (ligand dependency of retinoic acid and the like), potential for regulating the differentiation of cells such as keratinocytes) (see, e.g., Lehmann, J. M. et al., Nucleic Acids Res. 19 (3), 573-578 (1991); Vollberg, T. M. et al., Mol. Endocrinol. 6 (5), 667-676 (1992)). Generally, it is known that a plurality of variants resulting from a single locus (splicing variants) have similar functions, although the degree can vary. Therefore, novel variants of the cancer-specific gene 2 can also have these functions.

3) Cancer-Specific Gene 3
   D-BRCOC2007920.1 (SEQ ID NO:75)
   D-TKIDN2010471.1 (SEQ ID NO:83)
   As a known variant of the cancer-specific gene 3, for example, a variant disclosed in an Example (human peroxisome biosynthesis factor 5-like (PEX5L); total number of nucleotides in the ORF nucleic acid sequence: 1881; total number of amino acids in the protein: 626; see GenBank accession number: NM_016559.1) has been reported. It has been reported that known variants of the cancer-specific gene 3 have a specified function (e.g., TNFα-induced apoptosis inhibitory potential, capability of binding to phosphatidylethanolamine or peroxisome targeting signal 1 (PTS1), or peroxisome biosynthesis regulatory potential) (see, e.g., Wang, X. et al., J. Biol. Chem. 279 (44), 45855-45864 (2004); Amery, L., et al., Biochem. J. 357 (PT 3), 635-646 (2001)). Generally, it is known that a plurality of variants resulting from a single locus (splicing variants) have similar functions, although the degree can vary. Therefore, novel variants of the cancer-specific gene 3 can also have these functions.

4) Cancer-Specific Gene 4
   D-FEBRA2010013.1 (SEQ ID NO:103)
   D-FEBRA2001626.1 (SEQ ID NO:109)
   D-TKIDN2003621.1 (SEQ ID NO:115)
   As a known variant of the cancer-specific gene 4, for example, a variant disclosed in an Example (human fibroblast growth factor 13 (FGF13), transcription variant 1A; total number of nucleotides in the ORF nucleic acid sequence: 738; total number of amino acids in the protein: 245; see GenBank accession number: NM_004114.2) has been reported. Known variants of the cancer-specific gene 4 can have a specified function (e.g., cell proliferation or survival regulatory potential, potential for regulation of angiogenesis) (see, e.g., Facchiano, A. et al., J. Biol. Chem. 278 (10), 8751-8760 (2003); Smallwood, P. M. et al., Proc. Natl. Acad. Sci. U.S.A. 93 (18), 9850-9857 (1996)). Generally, it is known that a plurality of variants resulting from a single locus (splicing variants) have similar functions, although the degree can vary. Therefore, novel variants of the cancer-specific gene 4 can also have these functions.

5) Cancer-Specific Gene 5
   D-CTONG2001283.1 (SEQ ID NO:144)
   As a known variant of the cancer-specific gene 5, for example, a variant disclosed in an Example (human glucosamine (UDP-N-acetyl)-2-epimerase/N-acetylmannosamine kinase (GNE); total number of nucleotides in the ORF nucleic acid sequence: 2169; total number of amino acids in the protein: 722; see GenBank accession number: NM_005476.3) has been reported. It has been reported that known variants of the cancer-specific gene 5 have a specified function (e.g., UDP-N-acetylglucosamine 2-epimerase and/or N-acetylglucosamine kinase activity, or potential for biosynthesis of N-acetylneuraminic acid (NeuAc)) (see, e.g., Sparks, S. E. et al., Glycobiology 15 (11), 1102-1110 (2005); Hinderlich, S. et al., J. Biol. Chem. 272 (39), 24313-24318 (1997)). Generally, it is known that a plurality of variants resulting from a single locus (splicing variants) have similar functions, although the degree can vary. Therefore, novel variants of the cancer-specific gene 5 can also have these functions.

6) Cancer-Specific Gene 6
   D-OCBBF2013203.1 (SEQ ID NO:163)
   As a known variant of the cancer-specific gene 6, for example, a variant disclosed in an Example (human ATG5 autophagy-related 5 homologue (S. cerevisiae) (ATG5); total number of nucleotides in the ORF nucleic acid sequence: 828; total number of amino acids in the protein: 275; see GenBank accession number: NM_004849.1) has been reported. It has been reported that known variants of the cancer-specific gene 6 have a specified function (e.g., potential for interaction with FADD (Fas-associated protein with death domain), or potential for cell death induction) (see, e.g., Pyo, J. O. et al., J. Biol. Chem. 280 (21), 20722-20729 (2005)). Generally, it is known that a plurality of variants resulting from a single locus (splicing variants) have similar functions, although the degree can vary. Therefore, novel variants of the cancer-specific gene 6 can also have these functions.

The region consisting of the 1st to 17th amino acid residues in the amino acid sequence shown by SEQ ID NO:163 is estimated to be a signal region with the signal sequence estimation tool SignalP (http://www.cbs.dtu.dk/services/SignalP/). Therefore, the present invention also provides a polypeptide deprived of such a putative signal region (i.e., a polypeptide having an amino acid sequence consisting of the 18th to 197th amino acid residues in the amino acid sequence shown by SEQ ID NO:163, or substantially the same amino acid sequence thereas).

7) Cancer-Specific Gene 7
   D-BRAWH2011787.1 (SEQ ID NO:185)
   Z-BRALZ2001614-01 (SEQ ID NO:191)
   As a known variant of the cancer-specific gene 7, for example, a variant disclosed in an Example (human RAB, member RAS oncogene family-like 5 (RABL5); total number of nucleotides in the ORF nucleic acid sequence: 558; total number of amino acids in the protein: 185; see GenBank accession number: NM_022777.1) has been reported. Known variants of the cancer-specific gene 7 can have a specified function (e.g., capability of binding to GTP, or exocytosis or endocytosis regulatory potential) (see, e.g., Shimizu, F. et al., Cytogenet. Cell Genet. 77, 261-263 (1997)). Generally, it is known that a plurality of variants resulting from a single locus (splicing variants) have similar functions, although the degree can vary. Therefore, novel variants of the cancer-specific gene 7 can also have these functions.

The region consisting of the 1st to 24th amino acid residues in the amino acid sequence shown by SEQ ID NO:191 is estimated to be a signal region with the signal sequence estimation tools SignalP (see above) and PSORT II (http://psort.nibb.ac.jp/). Therefore, the present invention also provides a polypeptide deprived of such a putative signal region (i.e., a polypeptide having an amino acid sequence consisting of the 25th to 146th amino acid residues in the amino acid sequence shown by SEQ ID NO:191, or substantially the same amino acid sequence thereas).

8) Cancer-Specific Gene 8
D-TLIVE2001566.1 (SEQ ID NO:210)
D-TLIVE2006761.1 (SEQ ID NO:221)
D-LIVER2001320.1 (SEQ ID NO:227)

As a known variant of the cancer-specific gene 8, for example, a variant disclosed in an Example (human nuclear receptor subfamily 1, group I, member 3 (NR1I3); total number of nucleotides in the ORF nucleic acid sequence: 1047; total number of amino acids in the protein: 348; see GenBank accession number: NM_005122.2) has been reported. Known variants of the cancer-specific gene 8 can have a specified function (e.g., potential for regulation of transcription of types of cytochrome P450 such as CYP2B6, CYP2C8, and CYP2C9) (see, e.g., Ferguson, S. S. et al., Mol. Pharmacol. 68 (3), 747-757 (2005); Chen, Y. et al., J. Pharmacol. Exp. Ther. 314 (3), 1125-1133 (2005); Swales, K. et al., Biol. Chem. 280 (5), 3458-3466 (2005)). Generally, it is known that a plurality of variants resulting from a single locus (splicing variants) have similar functions, although the degree can vary. Therefore, novel variants of the cancer-specific gene 8 can also have these functions.

A polypeptide of the present invention can be useful in, for example, developing a substance capable of specifically recognizing a polypeptide of the present invention, a substance incapable of specifically recognizing a polypeptide of the present invention, or a substance capable of comprehensively recognizing both a polypeptide of the present invention and a known polypeptide, and in developing a substance capable of specifically regulating a function of a polypeptide of the present invention, a substance incapable of specifically regulating a function of a polypeptide of the present invention, or a substance capable of comprehensively recognizing functions of both a polypeptide of the present invention and a known polypeptide.

The present invention also provides a partial peptide.

"A partial peptide" consists of at least 6, preferably at least 8, more preferably at least 10, still more preferably at least 12, and most preferably at least 15, consecutive amino acid residues selected from among subject polypeptides, that can have a specified utility (e.g., use as an immunogenic or antigenic peptide, a functional peptide having a particular domain and the like).

"An insert amino acid sequence of a polypeptide of the present invention" refers to an amino acid sequence that is incorporated in a polypeptide of the present invention (e.g., novel variant), but lacked in a known polypeptide (e.g., known variant). Meanwhile, "an insert amino acid sequence of a known polypeptide" refers to an amino acid sequence that is incorporated in a known polypeptide (e.g., known variant), but lacked in a polypeptide of the present invention (e.g., novel variant). These insert amino acid sequences are obvious from the disclosure herein.

"A deleted amino acid sequence of a polypeptide of the present invention" refers to an amino acid sequence that is lacked in a polypeptide of the present invention (e.g., novel variant), but incorporated in a known polypeptide (e.g., known variant). Meanwhile, "a deleted amino acid sequence of a known polypeptide" refers to an amino acid sequence that is lacked in a known polypeptide (e.g., known variant), but incorporated in a polypeptide of the present invention (e.g., novel variant). These deleted amino acid sequences are obvious from the disclosure herein. "A deleted amino acid sequence of a polypeptide of the present invention" can have the same definition as that for "an insert amino acid sequence of a known polypeptide"; "a deleted amino acid sequence of a known polypeptide" can have the same definition as that for "an insert amino acid sequence of a polypeptide of the present invention".

A partial peptide of the present invention can be a) a specific partial peptide of a polypeptide of the present invention, capable of distinguishing a polypeptide of the present invention from a known polypeptide (abbreviated as "specific partial peptide A" as required), b) a specific partial peptide of a known polypeptide, capable of distinguishing a known polypeptide from a polypeptide of the present invention (abbreviated as "specific partial peptide B" as required), or c) a partial peptide common to both a polypeptide of the present invention and a known polypeptide (abbreviated as "shared partial peptide" as required). For these particular partial peptides, there appears a motivation for preparing them or utilizing them as markers on the basis of the present inventors' findings; however, without these findings, there is no motivation for preparing them or utilizing them as markers. Being partial peptides specific for the polypeptides encoded by the cancer-specific genes 1 to 8, the specific partial peptides A and B are abbreviated as "specific partial peptides of the present invention" or "specific partial peptides" as required.

The specific partial peptide A of the present invention is a partial peptide that is present only in a polypeptide having an amino acid sequence shown by SEQ ID NO:X and the like, and that is not present in any known polypeptide. As examples of the specific partial peptide A, i) a partial peptide consisting of an insert amino acid sequence of a polypeptide of the present invention or a partial amino acid sequence thereof, ii) a partial peptide consisting of an insert amino acid sequence of a polypeptide of the present invention or a terminal partial amino acid sequence thereof and an adjacent amino acid sequence thereof, iii) a partial peptide consisting of an amino acid sequence wherein both amino acid sequences present on the N-terminal side and C-terminal side relative to an insert amino acid sequence of a known polypeptide are linked together, formed as a result of exon deletion, and iv) an optionally chosen partial peptide in a polypeptide having an amino acid sequence shown by SEQ ID NO:X and the like (e.g., cases where a frame shift occurs because of exon insertion or deletion and the like) can be mentioned.

The specific partial peptide A of i) above consists of an insert amino acid sequence of a polypeptide of the present invention or a partial amino acid sequence thereof. Such partial amino acid sequences are obvious from the disclosure herein.

The specific partial peptide A of ii) above consists of an insert amino acid sequence of a polypeptide of the present invention or a terminal partial amino acid sequence thereof and an adjacent amino acid sequence thereof. As such terminal partial amino acid sequences, an amino acid sequence corresponding to an N-terminal portion of an insert amino acid sequence of a polypeptide of the present invention (abbreviated as "N-terminal partial amino acid sequence A" as required), and an amino acid sequence corresponding to a C-terminal portion of an insert amino acid sequence of a polypeptide of the present invention (abbreviated as "C-terminal partial amino acid sequence A" as required) can be mentioned. As such adjacent amino acid sequences, an amino acid sequence present on the N-terminal side relative to an insert amino acid sequence of a polypeptide of the present invention (abbreviated as "N-terminal adjacent amino acid sequence A" as required), and an amino acid sequence present on the C-terminal side relative to an insert amino acid sequence of a polypeptide of the present invention (abbreviated as "C-terminal adjacent amino acid sequence A" as required) can be mentioned. Therefore, the specific partial peptide A of ii) above can be a partial peptide consisting of an amino acid sequence spanning from a specified position of the N-terminal adjacent amino acid sequence A to a specified position of an insert amino acid sequence of a polypeptide of the present invention, a partial peptide consisting of an amino acid sequence spanning from a specified position of an insert amino acid sequence of a polypeptide of the present invention to a specified position of the C-terminal adjacent amino acid sequence A, or a partial peptide consisting of an amino acid sequence comprising the whole insert amino acid sequence of a polypeptide of the present invention, spanning from a specified position of the N-terminal adjacent amino acid sequence A to a specified position of the C-terminal adjacent amino acid sequence A. The number of amino acid residues in the insert amino acid sequence (or N-terminal or C-terminal partial amino acid sequence A) or adjacent amino acid sequence (or N-terminal or C-terminal adjacent amino acid sequence A), contained in the specific partial peptide A of ii) above, is not particularly limited, as far as it is a number that ensures the specificity of the specific partial peptide A of ii) above; the number can be, for example, at least 3, preferably at least 4, more preferably at least 5, still more preferably at least 6, and most preferably at least 7, 8, 9 or 10. Such terminal partial amino acid sequences and such adjacent amino acid sequences are obvious from the disclosure herein.

The specific partial peptide A of iii) above is a partial peptide not present in a known polypeptide, consisting of an amino acid sequence wherein both amino acid sequences present on the N-terminal side and C-terminal side relative to an insert amino acid sequence of a known polypeptide are linked together (in a polypeptide of the present invention, these amino acid sequences are linked together as a result of exon deletion). The number of amino acid residues in each amino acid sequence present on the N-terminal side and C-terminal side relative to an insert amino acid sequence of a known polypeptide, contained in the specific partial peptide A of iii) above, is not particularly limited, as far as it is a number that ensures the specificity of the specific partial peptide A of iii) above; the number can be, for example, at least 3, preferably at least 4, more preferably at least 5, still more preferably at least 6, and most preferably at least 7, 8, 9 or 10.

The specific partial peptide A of iv) above is an optionally chosen partial peptide in a polypeptide having an amino acid sequence shown by SEQ ID NO:X and the like (e.g., cases where a frame shift occurs because of exon insertion or deletion and the like). Regarding the specific partial peptide A of iv) above, as examples of such SEQ ID NO:X, SEQ ID NO:21 (cancer-specific gene 1: D-LIVER2008912.1), and SEQ ID NO:191 (cancer-specific gene 7: Z-BRALZ2001614-01) can be mentioned.

The specific partial peptide A of the present invention can be useful as, for example, a target for specifically detecting a polypeptide of the present invention, and as a marker specific for cancer. The specific partial peptide A of the present invention can also be useful in developing a substance capable of specifically recognizing a polypeptide of the present invention, or a substance incapable of specifically recognizing a polypeptide of the present invention, or developing a substance capable of specifically regulating a function of a polypeptide of the present invention, or a substance incapable of specifically regulating a function of a polypeptide of the present invention.

The specific partial peptide B of the present invention is a partial peptide that is present only in a known polypeptide, and that is not present in a polypeptide having an amino acid sequence shown by SEQ ID NO:X and the like. As examples of the specific partial peptide B, i) a partial peptide consisting of an insert amino acid sequence of a known polypeptide or a partial amino acid sequence thereof, ii) a partial peptide consisting of an insert amino acid sequence of a known polypeptide or a terminal partial amino acid sequence thereof and an adjacent amino acid sequence thereof, and iii) a partial peptide consisting of an amino acid sequence wherein both amino acid sequences present on the N-terminal side and C-terminal side relative to an insert amino acid sequence of a polypeptide of the present invention are linked together, formed as a result of exon deletion, can be mentioned.

The specific partial peptide B of i) above consists of an insert amino acid sequence of a known polypeptide or a partial amino acid sequence thereof. Such partial amino acid sequences are obvious from the disclosure herein.

The specific partial peptide B of ii) above consists of an insert amino acid sequence of a known polypeptide or a terminal partial amino acid sequence thereof and an adjacent amino acid sequence thereof. As such terminal partial amino acid sequences, an amino acid sequence corresponding to an N-terminal portion of an insert amino acid sequence of a known polypeptide (abbreviated as "N-terminal partial amino acid sequence B" as required), and an amino acid sequence corresponding to a C-terminal portion of an insert amino acid sequence of a known polypeptide (abbreviated as "C-terminal partial amino acid sequence B" as required) can be mentioned. As such adjacent amino acid sequences, an amino acid sequence present on the N-terminal side relative to an insert amino acid sequence of a known polypeptide (abbreviated as "N-terminal adjacent amino acid sequence B" as required), and an amino acid sequence present on the C-terminal side relative to an insert amino acid sequence of a known polypeptide (abbreviated as "C-terminal adjacent amino acid sequence B" as required) can be mentioned. Therefore, the specific partial peptide B of ii) above can be a partial peptide consisting of an amino acid sequence spanning from a specified position of the N-terminal adjacent amino acid sequence B to a specified position of an insert amino acid sequence of a known polypeptide, a partial peptide consisting of an amino acid sequence spanning from a specified position of an insert amino acid sequence of a known polypeptide to a specified position of the C-terminal adjacent amino acid sequence B, or a partial peptide consisting of an amino acid sequence comprising the whole insert amino acid sequence of a known polypeptide, spanning from a specified position of the N-terminal adjacent amino acid sequence B to a specified position of the C-terminal adjacent amino acid sequence B. The number of amino acid residues in the insert amino acid sequence (or N-terminal or C-terminal partial amino acid sequence B) or adjacent amino acid sequence (or N-terminal or C-terminal adjacent amino acid sequence B), contained in the specific partial peptide B of ii) above, is not particularly limited, as far as it is a number that ensures the specificity of the specific partial peptide B of ii) above; the number can be, for example, at least 3, preferably at least 4, more preferably at least 5, still more preferably at least 6, and most preferably at least 7, 8, 9 or 10. Such terminal partial amino acid sequences and such adjacent amino acid sequences are obvious from the disclosure herein.

The specific partial peptide B of iii) above is a partial peptide that is not present in a polypeptide of the present invention, consisting of an amino acid sequence wherein both amino acid sequences present on the N-terminal side and C-terminal side relative to an insert amino acid sequence of a polypeptide of the present invention are linked together (in a known polypeptide, these amino acid sequences are linked together as a result of exon deletion). The number of amino acid residues in each amino acid sequence present on the N-terminal side and C-terminal side relative to the insert amino acid sequence of a polypeptide of the present invention, contained in the specific partial peptide B of iii) above, is not particularly limited, as far as it is a number that ensures the specificity of the specific partial peptide B of iii) above; the number can be, for example, at least 3, preferably at least 4, more preferably at least 5, still more preferably at least 6, and most preferably at least 7, 8, 9 or 10, respectively.

The specific partial peptide B of the present invention can be useful as, for example a target for specifically detecting a known polypeptide, and as a marker specific for a cancer or non-cancer state (e.g., normal state). The specific partial peptide B of the present invention can also be useful in developing a substance capable of specifically recognizing a known polypeptide, or a substance incapable of specifically recognizing a known polypeptide, or developing a substance capable of specifically regulating a function of a known polypeptide, or a substance incapable of specifically regulating a function of a known polypeptide.

A shared partial peptide of the present invention can be a non-specific partial peptide that is present in both a polypeptide of the present invention and a known polypeptide. Such partial peptides are obvious from the disclosure herein. A shared partial peptide of the present invention can be useful as, for example, a target for comprehensively detecting both a polypeptide of the present invention and a known polypeptide, and as a marker specific for a cancer or non-cancer state (e.g., normal state). A shared partial peptide of the present invention can also be useful in developing a substance capable of comprehensively recognizing both a polypeptide of the present invention and a known polypeptide, or a substance capable of comprehensively regulating functions of both a polypeptide of the present invention and a known polypeptide.

A polypeptide of the present invention or a specific partial peptide thereof may be fused with a polypeptide consisting of a heterogeneous amino acid sequence. As such a polypeptide, a polypeptide that facilitates purification or solubilization can be mentioned. In detail, as such polypeptides, histidine tag, maltose-binding protein (MBP), glutathione-S-transferase (GST), calmodulin-binding peptide (CBP), FLAG, and the Fc region of IgG molecule can be mentioned.

A polypeptide of the present invention and a partial peptide thereof may be provided in the form of a salt. As examples of the salt, salts with inorganic bases (e.g., alkali metals such as sodium and potassium; alkaline earth metals such as calcium and magnesium; aluminum, ammonium), salts with organic bases (e.g., trimethylamine, triethylamine, pyridine, picoline, ethanolamine, diethanolamine, triethanolamine, dicyclohexylamine, N,N-dibenzylethylenediamine), salts with inorganic acids (e.g., hydrochloric acid, hydrobromic acid, nitric acid, sulfuric acid, phosphoric acid), salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), salts with basic amino acids (e.g., arginine, lysine, ornithine) or salts with acidic amino acids (e.g., aspartic acid, glutamic acid) and the like can be mentioned.

A polypeptide of the present invention and a partial peptide thereof can be prepared by a method known per se. For example, a polypeptide of the present invention and a partial peptide thereof 1) may be recovered from an expression site, 2) may be recovered from a transformant described below, which expresses a polypeptide of the present invention and a partial peptide thereof, or a culture supernatant thereof, 3) may be synthesized using a cell-free system based on a rabbit reticulocyte lysate, wheat germ lysate, *Escherichia coli* lysate and the like, or 4) may be synthesized organochemically (e.g., solid phase synthesis). A polypeptide of the present invention and a partial peptide thereof are purified as appropriate by methods based on differences in solubility, such as salting-out and solvent precipitation; methods based mainly on differences in molecular weight, such as dialysis, ultrafiltration, gel filtration, and SDS-polyacrylamide gel electrophoresis; methods based on differences in electric charge, such as ion exchange chromatography; methods based on specific affinity, such as affinity chromatography and use of antibody; methods based on differences in hydrophobicity, such as reverse phase high performance liquid chromatography; methods based on differences in isoelectric point, such as isoelectric focusing; and combinations thereof the like.

1.2. Polynucleotides and Partial Nucleotides Thereof

The present invention provides a polynucleotide having a nucleic acid sequence shown by SEQ ID NO:Y, or the nucleic acid sequence Y1 or the nucleic acid sequence Y2, or substantially the same nucleic acid sequence thereas (abbreviated as "nucleic acid sequence shown by SEQ ID NO:Y and the like" as required).

"SEQ ID NO:Y" denotes the SEQ ID NO of an optionally chosen nucleic acid sequence disclosed herein. A polynucleotide "having" SEQ ID NO:Y and the like means a polynucleotide "consisting of" SEQ ID NO:Y and the like, or a polynucleotide "comprising" the nucleic acid sequence and the like.

"The nucleic acid sequence Y1" denotes a nucleic acid sequence corresponding to the coding portion (that is, the entire open reading frame (ORF) or a portion thereof) in a nucleic acid sequence shown by SEQ ID NO:Y. In other words, "the nucleic acid sequence Y1" denotes a nucleic acid sequence shown by SEQ ID NO:Y when the nucleic acid sequence shown by SEQ ID NO:Y consists of a nucleic acid sequence corresponding to the coding portion only, and it denotes a nucleic acid sequence corresponding to the coding portion only when the nucleic acid sequence shown by SEQ ID NO:Y comprises nucleic acid sequences corresponding to both the coding portion and the non-coding portion.

"The nucleic acid sequence Y2" denotes a nucleic acid sequence corresponding to a non-coding portion (e.g., 5' or 3' noncoding region) in a nucleic acid sequence shown by SEQ ID NO:Y. In other words, "the nucleic acid sequence Y2" denotes a nucleic acid sequence shown by SEQ ID NO:Y when the nucleic acid sequence shown by SEQ ID NO:Y consists of a nucleic acid sequence corresponding to the non-coding portion only, and it denotes a nucleic acid sequence corresponding to the non-coding portion only when the nucleic acid sequence shown by SEQ ID NO:Y comprises nucleic acid sequences corresponding to both the non-coding portion and the coding portion.

Therefore, a nucleic acid sequence denoted by "SEQ ID NO:Y" can be denoted by any one of i) the nucleic acid sequence Y1 (when the nucleic acid sequence shown by SEQ ID NO:Y as a whole is a nucleic acid sequence corresponding to the coding portion), ii) the nucleic acid sequence Y2 (when the nucleic acid sequence shown by SEQ ID NO:Y as a whole is a nucleic acid sequence corresponding to the non-coding portion), or iii) a nucleic acid sequence comprising the nucleic acid sequence Y1 and the nucleic acid sequence Y2 (when the nucleic acid sequence shown by SEQ ID NO:Y comprises nucleic acid sequences corresponding to the coding portion and the non-coding portion).

In one embodiment, substantially the same nucleic acid sequence as a nucleic acid sequence shown by SEQ ID NO:Y, or the nucleic acid sequence Y1 or the nucleic acid sequence Y2 can be a nucleic acid sequence having a specified sequence identity to the nucleic acid sequence shown by SEQ ID NO:Y, or the nucleic acid sequence Y1 or the nucleic acid sequence Y2. The degree of nucleic acid sequence identity can be about 90% or more, preferably about 92% or more, more preferably about 95% or more, still more preferably about 96% or more, and most preferably about 97% or more, about 98% or more or about 99% or more. Nucleic acid sequence identity can be determined by a method known per se. For example, nucleic acid sequence identity (%) can be determined by the same method as that described above for amino acid sequence identity (%).

In another embodiment, substantially the same nucleic acid sequence as a nucleic acid sequence shown by SEQ ID NO:Y or the nucleic acid sequence Y1 or the nucleic acid sequence Y2 can be the nucleic acid sequence shown by SEQ ID NO:Y or the nucleic acid sequence Y1 or the nucleic acid sequence Y2, wherein one or more nucleotides have one or more modifications selected from among substitutions, additions, deletions and insertions. The number of nucleotides modified is not particularly limited, as far as it is one or more, and the number can be, for example, 1 to about 100, preferably 1 to about 70, more preferably 1 to about 50, still more preferably 1 to about 30, and most preferably 1 to about 20, 1 to about 10 or 1 to about 5 (e.g., 1 or 2).

In still another embodiment, substantially the same nucleic acid sequence as a nucleic acid sequence shown by SEQ ID NO:Y, or the nucleic acid sequence Y1 or the nucleic acid sequence Y2 can be a polynucleotide that can be hybridized to a nucleic acid sequence complementary to the nucleic acid sequence shown by SEQ ID NO:Y, or the nucleic acid sequence Y1 or the nucleic acid sequence Y2 under high stringent conditions. Hybridization conditions under high stringent conditions can be set with reference to reported conditions (see, e.g., Current Protocols in Molecular Biology, John Wiley & Sons, 6.3.1-6.3.6 (1999)). For example, as hybridization conditions under high stringent conditions, hybridization with 6×SSC (sodium chloride/sodium citrate)/45° C., followed by washing with 0.2×SSC/0.1% SDS/50 to 65° C. once or twice or more, can be mentioned.

Substantially the same nucleic acid sequence as a nucleic acid sequence shown by SEQ ID NO:Y, or the nucleic acid sequence Y1 or the nucleic acid sequence Y2 may completely retain a characteristic portion thereof (e.g., a portion corresponding to a specific partial nucleotide described below), and may have another portion (e.g., a portion present in a known polynucleotide) being substantially the same as the corresponding portion of the nucleic acid sequence shown by SEQ ID NO:Y, or the nucleic acid sequence Y1 or the nucleic acid sequence Y2. Alternatively, substantially the same nucleic acid sequence as a nucleic acid sequence shown by SEQ ID NO:Y, or the nucleic acid sequence Y1 or the nucleic acid sequence Y2 may have a non-characteristic portion thereof being the same as the corresponding portion of the nucleic acid sequence shown by SEQ ID NO:Y, or the nucleic acid sequence Y1 or the nucleic acid sequence Y2, and a characteristic portion thereof being substantially the same as the corresponding portion of the nucleic acid sequence shown by SEQ ID NO:Y, or the nucleic acid sequence Y1 or the nucleic acid sequence Y2.

A polynucleotide of the present invention is capable of encoding a polypeptide of the present invention. Therefore, a polynucleotide of the present invention can be a polynucleotide such that the polypeptide encoded thereby is capable of being functionally equivalent to a polypeptide of the present invention.

In detail, for the cancer-specific genes 1 to 8, the nucleic acid sequence Y of the polynucleotide, and the SEQ ID NO:Y and Ya-th to Yb-th of the ORF-corresponding portion thereof (Ya-th to Yb-th nucleotide residues in the nucleic acid sequence Y) are as follows.

1) Cancer-Specific Gene 1
 D-LIVER2001680.1 (SEQ ID NO:8 or SEQ ID NO:9, and 267th to 1805th)
 D-LIVER2008912.1 (SEQ ID NO:14 or SEQ ID NO:15, and 88th to 330th and 191st to 439th)

2) Cancer-Specific Gene 2
 D-HCHON2007878.1 (SEQ ID NO:37 or SEQ ID NO:38, and 160th to 1491st)
 D-NTONG2006230.1 (SEQ ID NO:43 or SEQ ID NO:44, and 38th to 1369th)
 D-SPLEN2005548.1 (SEQ ID NO:49 or SEQ ID NO:50, and 165th to 1293rd)

3) Cancer-Specific Gene 3
 D-BRCOC2007920.1 (SEQ ID NO:73 or SEQ ID NO:74, and 656th to 1960th)
 D-TKIDN2010471.1 (SEQ ID NO:81 or SEQ ID NO:82, and 305th to 2056th)

4) Cancer-Specific Gene 4
 D-FEBRA2010013.1 (SEQ ID NO:101 or SEQ ID NO:102, and 299th to 1066th)
 D-FEBRA2001626.1 (SEQ ID NO:107 or SEQ ID NO:108, and 177th to 944th)
 D-TKIDN2003621.1 (SEQ ID NO:113 or SEQ ID NO:114, and 268th to 867th)

5) Cancer-Specific Gene 5
 D-CTONG2001283.1 (SEQ ID NO:142 or SEQ ID NO:143, and 40th to 2085th)

6) Cancer-Specific Gene 6
 D-OCBBF2013203.1 (SEQ ID NO:161 or SEQ ID NO:162, and 452nd to 1045th)

A region consisting of the 452nd to 502nd nucleotide residues in a nucleic acid sequence shown by SEQ ID NO:161 or SEQ ID NO:162 is estimated to encode a signal region with the signal sequence estimation tool SignalP (see above). Therefore, the present invention also provides a polynucleotide deprived of a polynucleotide that encodes such a putative signal region, out of the ORF-corresponding portions (i.e., a polynucleotide having a nucleic acid sequence consisting of the 503rd to 1045th nucleotide residues in the nucleic acid sequence shown by the SEQ ID NO:161, or substantially the same nucleic acid sequence thereas).

7) Cancer-Specific Gene 7
 D-BRAWH2011787.1 (SEQ ID NO:183 or SEQ ID NO:184, and 100th to 546th)
 Z-BRALZ2001614-01 (SEQ ID NO:189 or SEQ ID NO:190, and 307th to 747th)

A region consisting of the 307th to 378th nucleotide residues in a nucleic acid sequence shown by SEQ ID NO:189 or SEQ ID NO:190 is estimated to encode a signal region with the signal sequence estimation tools SignalP and PSORT II (see above). Therefore, the present invention also provides a polynucleotide deprived of a polynucleotide that encodes such a putative signal region, out of the ORF-corresponding portions (i.e., a polynucleotide having a nucleic acid sequence consisting of the 379th to 747th nucleotide residues in the nucleic acid sequence shown by SEQ ID NO:189, or substantially the same nucleic acid sequence thereas).

8) Cancer-Specific Gene 8

D-TLIVE2001566.1 (SEQ ID NO:208 or SEQ ID NO:209, and 144th to 1037th)

D-TLIVE2006761.1 (SEQ ID NO:219 or SEQ ID NO:220, and 238th to 954th)

D-LIVER2001320.1 (SEQ ID NO:225 or SEQ ID NO:226, and 196th to 912nd)

A polynucleotide of the present invention can be useful in, for example, developing a substance capable of specifically recognizing a polynucleotide of the present invention, a substance incapable of specifically recognizing a polynucleotide of the present invention, or a substance capable of comprehensively recognizing both a polynucleotide of the present invention and a known polynucleotide, and developing a substance capable of specifically regulating the expression of a polypeptide of the present invention, a substance incapable of specifically regulating the expression of a polypeptide of the present invention, or a substance capable of comprehensively regulating the expression of both a polypeptide of the present invention and a known polypeptide.

The present invention also provides a partial nucleotide.

"A partial nucleotide" consists of at least 15, preferably at least 16, more preferably at least 18, still more preferably at least 20, and most preferably at least 22, 23, 24 or 25, consecutive nucleotide residues selected from among subject polynucleotides, that can have a specified utility (e.g., use as a probe, a primer, a polynucleotide that encodes an immunogenic or antigenic peptide, a polynucleotide that encodes a functional peptide having a particular domain and the like).

"An insert nucleic acid sequence of a polynucleotide of the present invention" refers to a nucleic acid sequence that is incorporated in a polynucleotide of the present invention (e.g., novel variant), but lacked in a known polynucleotide (e.g., known variant). Meanwhile, "an insert nucleic acid sequence of a known polynucleotide" refers to a nucleic acid sequence that is incorporated in a known polynucleotide (e.g., known variant), but lacked in a polynucleotide of the present invention (e.g., novel variant). These insert nucleic acid sequences are obvious from the disclosure herein.

"A deletion nucleic acid sequence of a polynucleotide of the present invention" refers to a nucleic acid sequence that is lacked in a polynucleotide of the present invention (e.g., novel variant), but inserted in a known polynucleotide (e.g., known variant). Meanwhile, "a deletion nucleic acid sequence of a known polynucleotide" refers to a nucleic acid sequence that is lacked in a known polynucleotide (e.g., known variant), but inserted in a polynucleotide of the present invention (e.g., novel variant). These deletion nucleic acid sequences are obvious from the disclosure herein. "A deletion nucleic acid sequence of a polynucleotide of the present invention" can have the same definition as that for "an insert nucleic acid sequence of a known polynucleotide"; "a deletion nucleic acid sequence of a known polynucleotide" can have the same definition as that for "an insert nucleic acid sequence of a polynucleotide of the present invention".

A partial nucleotide of the present invention can be a) a specific partial nucleotide of a polynucleotide of the present invention, capable of distinguishing a polynucleotide of the present invention from a known polynucleotide (abbreviated as "specific partial nucleotide A" as required), b) a specific partial nucleotide of a known polynucleotide, capable of distinguishing a known polynucleotide from a polynucleotide of the present invention (abbreviated as "specific partial nucleotide B" as required, or c) a partial nucleotide common to both a polynucleotide of the present invention and a known polynucleotide (abbreviated as "shared partial nucleotide" as required). For these particular partial nucleotides, there appears a motivation for preparing them or utilizing them as markers on the basis of the present inventors' findings, but without these findings, there is no motivation for preparing them or utilizing them as markers. Being partial nucleotides specific for polynucleotides encoded by cancer-specific genes 1 to 8, the specific partial nucleotides A and B are abbreviated as "specific partial nucleotides of the present invention" or "specific partial nucleotides" as required.

The specific partial nucleotide A of the present invention is a partial nucleotide that is present only in a polynucleotide having a nucleic acid sequence shown by SEQ ID NO:Y and the like, and that is not present in any known polynucleotide. As examples of the specific partial nucleotide A, i) a partial nucleotide consisting of an insert nucleic acid sequence of a polynucleotide of the present invention or a partial nucleic acid sequence thereof, ii) a partial nucleotide consisting of an insert nucleic acid sequence of a polynucleotide of the present invention or a terminal partial nucleic acid sequence thereof and an adjacent nucleic acid sequence thereof, and iii) a partial nucleotide consisting of a nucleic acid sequence wherein both nucleic acid sequences present on the 5' and 3' sides relative to an insert nucleic acid sequence of a known polynucleotide are linked together, formed as a result of exon deletion, can be mentioned.

The specific partial nucleotide A of i) above consists of an insert nucleic acid sequence of a polynucleotide of the present invention or a partial nucleic acid sequence thereof. Such partial nucleic acid sequences are obvious from the disclosure herein.

The specific partial nucleotide A of ii) above consists of an insert nucleic acid sequence of a polynucleotide of the present invention or a terminal partial nucleic acid sequence thereof and an adjacent nucleic acid sequence thereof. As such terminal partial nucleic acid sequences, a nucleic acid sequence corresponding to a 5'-terminal portion in an insert nucleic acid sequence of a polynucleotide of the present invention (abbreviated as "5'-terminal partial nucleic acid sequence A" as required), and a nucleic acid sequence corresponding to a 3'-terminal portion in an insert nucleic acid sequence of a polypeptide of the present invention (abbreviated as "3'-terminal partial nucleic acid sequence A" as required) can be mentioned. As such adjacent nucleic acid sequences, a nucleic acid sequence present on the 5' side relative to an insert nucleic acid sequence of a polynucleotide of the present invention (abbreviated as "5' adjacent nucleic acid sequence A" as required), and a nucleic acid sequence present on the 3' side relative to an insert nucleic acid sequence of a polynucleotide of the present invention (abbreviated as "3' adjacent nucleic acid sequence A" as required) can be mentioned. Therefore, the specific partial nucleotide A of ii) above can be a partial nucleotide consisting of a nucleic acid sequence spanning from a specified position of the 5' adjacent nucleic acid sequence A to a specified position of an insert nucleic acid sequence of a polynucleotide of the present invention, a partial nucleotide consisting of a nucleic acid sequence spanning from a specified position of an insert nucleic acid sequence of a polynucleotide of the present invention to a specified position of the 3' adjacent nucleic acid sequence A, or a partial nucleotide consisting of a nucleic acid sequence comprising the whole insert nucleic acid sequence of a polynucleotide of the present invention, spanning from a specified position of the 5' adjacent nucleic acid sequence A to a specified position of the 3' adjacent nucleic acid sequence A. The number of nucleotide residues in the insert nucleic acid sequence (or 5'-terminal or 3'-terminal partial nucleic acid sequence A) or adjacent nucleic acid sequence (or 5'-terminal or 3'-terminal adjacent nucleic acid sequence A), contained in the specific partial nucleotide A of ii) above, is not particularly limited, as far as it is a number that ensures the specificity of the specific partial nucleotide A of ii) above; the number can be, for example, at least 3, preferably at least 4, more preferably at least 5, still more preferably at least 6, and most preferably at least 7, 8, 9 or 10. Such terminal partial nucleic acid sequences and such adjacent nucleic acid sequences are obvious from the disclosure herein.

The specific partial nucleotide A of iii) above is a partial nucleotide not present in a known polynucleotide, which nucleotide consisting of a nucleic acid sequence wherein both nucleic acid sequences present on the 5' and 3' sides relative to an insert nucleic acid sequence of a known polynucleotide are linked together (in a polynucleotide of the present invention, these nucleic acid sequences are linked together as a result of exon deletion). The number of nucleotide residues in each nucleic acid sequence present on the 5' and 3' sides relative to an insert nucleic acid sequence of a known polynucleotide, contained in the specific partial nucleotide A of iii) above, is not particularly limited, as far as it is a number that ensures the specificity of the specific partial nucleotide A of iii) above; the number can be, for example, at least 3, preferably at least 4, more preferably at least 5, still more preferably at least 6, and most preferably at least 7, 8, 9 or 10, respectively.

The specific partial nucleotide A of the present invention can be useful as, for example, a target for specifically detecting a polynucleotide of the present invention, and as a biomarker specific for cancer. The specific partial nucleotide A of the present invention can also be useful in developing a substance capable of specifically recognizing a polynucleotide of the present invention, or a substance incapable of specifically recognizing a polynucleotide of the present invention, or developing a substance capable of specifically regulating the expression of a polypeptide of the present invention, or a substance incapable of specifically regulating the expression of a polypeptide of the present invention.

The specific partial nucleotide B of the present invention is a partial nucleotide that is present only in a known polynucleotide, and not present in a polynucleotide having a nucleic acid sequence shown by SEQ ID NO:X and the like. As examples of the specific partial nucleotide B, i) a partial nucleotide consisting of an insert nucleic acid sequence of a known polynucleotide or a partial nucleic acid sequence thereof, ii) a partial nucleotide consisting of an insert nucleic acid sequence of a known polynucleotide or a terminal partial nucleic acid sequence thereof and an adjacent nucleic acid sequence thereof, and iii) a partial nucleotide consisting of a nucleic acid sequence wherein both nucleic acid sequences present on the 5' and 3' sides relative to an insert nucleic acid sequence of a polynucleotide of the present invention are linked together, formed as a result of exon deletion, can be mentioned.

The specific partial nucleotide B of i) above consists of an insert nucleic acid sequence of a known polynucleotide or a partial nucleic acid sequence thereof. Such partial nucleic acid sequences are obvious from the disclosure herein.

The specific partial nucleotide B of ii) above consists of an insert nucleic acid sequence of a known polynucleotide or a terminal partial nucleic acid sequence thereof and an adjacent nucleic acid sequence thereof. As such terminal partial nucleic acid sequences, a nucleic acid sequence corresponding to a 5'-terminal portion in an insert nucleic acid sequence of a known polynucleotide (abbreviated as "5'-terminal partial nucleic acid sequence B" as required), and a nucleic acid sequence corresponding to a 3'-terminal portion in an insert nucleic acid sequence of a known polynucleotide (abbreviated as "3'-terminal partial nucleic acid sequence B" as required) can be mentioned. As such adjacent nucleic acid sequences, a nucleic acid sequence present on the 5' side relative to an insert nucleic acid sequence of a known polynucleotide (abbreviated as "5' adjacent nucleic acid sequence B" as required), and a nucleic acid sequence present on the 3' side relative to an insert nucleic acid sequence of a known polynucleotide (abbreviated as "3' adjacent nucleic acid sequence B" as required) can be mentioned. Therefore, the specific partial nucleotide B of ii) above can be a partial nucleotide consisting of a nucleic acid sequence spanning from a specified position of the 5' adjacent nucleic acid sequence B to a specified position of an insert nucleic acid sequence of a known polynucleotide, a partial nucleotide consisting of a nucleic acid sequence spanning from a specified position of an insert nucleic acid sequence of a known polynucleotide to a specified position of the 3' adjacent nucleic acid sequence B, or a partial nucleotide consisting of a nucleic acid sequence comprising the whole insert nucleic acid sequence of a known polynucleotide, spanning from a specified position of the 5' adjacent nucleic acid sequence B to a specified position of the 3' adjacent nucleic acid sequence B. The number of nucleotide residues in the insert nucleic acid sequence (or 5'-terminal or 3'-terminal partial nucleic acid sequence B) or adjacent nucleic acid sequence (or 5'-terminal or 3'-terminal adjacent nucleic acid sequence B), contained in the specific partial nucleotide B of ii) above, is not particularly limited, as far as it is a number that ensures the specificity of the specific partial nucleotide B of ii) above; the number can be, for example, at least 3, preferably at least 4, more preferably at least 5, still more preferably at least 6, and most preferably at least 7, 8, 9 or 10. Such terminal partial nucleic acid sequences and such adjacent nucleic acid sequences are obvious from the disclosure herein.

The specific partial nucleotide B of iii) above is a partial nucleotide not present in a polynucleotide of the present invention, consisting of a nucleic acid sequence wherein both nucleic acid sequences present on the 5' and 3' sides relative to an insert nucleic acid sequence of a polynucleotide of the present invention are linked together (in a known polynucleotide, these nucleic acid sequences are linked together as a result of exon deletion). The number of nucleotide residues in each nucleic acid sequence present on the 5' and 3' sides relative to an insert nucleic acid sequence of a polynucleotide of the present invention, contained in the specific partial nucleotide B of iii) above, is not particularly limited, as far as it is a number that ensures the specificity of the specific partial nucleotide B of iii) above, and the number can be, for example, at least 3, preferably at least 4, more preferably at least 5, still more preferably at least 6, and most preferably at least 7, 8, 9 or 10, respectively.

The specific partial nucleotide B of the present invention can be useful as, for example, as a target for specifically detecting a known polynucleotide, and as a biomarker specific for cancer or non-cancerous state (e.g., normal state). The specific partial nucleotide B of the present invention can also be useful in developing a substance capable of specifically recognizing a known polynucleotide, or a substance incapable of specifically recognizing a known polynucleotide, or developing a substance capable of specifically regulating the expression of a known polypeptide, or a substance incapable of specifically regulating the expression of a known polypeptide.

A shared partial nucleotide of the present invention can be a nonspecific partial nucleotide that is present in both a polynucleotide of the present invention and a known polynucleotide. Such partial nucleotides are obvious from the disclosure herein. A shared partial nucleotide of the present invention can be useful as, for example, a target for comprehensively detecting both a polynucleotide of the present invention and a known polynucleotide, and as a biomarker specific for cancer or non-cancerous state (e.g., normal state). A shared partial nucleotide of the present invention can also be useful in developing a substance capable of comprehensively recognizing both a polynucleotide of the present invention and a known polynucleotide, or a substance capable of comprehensively regulating the expression of both a polypeptide of the present invention and a known polypeptide.

A polynucleotide of the present invention and a partial nucleotide thereof are capable of encoding a polypeptide of the present invention or a partial peptide of the present invention. A polynucleotide of the present invention or a partial nucleotide of the present invention may be fused with a polynucleotide consisting of a heterogeneous nucleic acid sequence. As such heterogeneous nucleic acid sequences, those that encode the above-described heterogeneous amino acid sequences can be mentioned.

A polynucleotide of the present invention and a partial nucleotide thereof may be provided in the form of a salt. As the salt, those described above can be mentioned.

A polynucleotide of the present invention and a partial nucleotide thereof can be prepared by a method known per se. For example, the same nucleic acid sequence as a nucleic acid sequence shown by SEQ ID NO:Y, or the nucleic acid sequence Y1 or the nucleic acid sequence Y2 can be cloned using a specified tissue or cell. Moreover, substantially the same nucleic acid sequence as a nucleic acid sequence shown by SEQ ID NO:Y or the nucleic acid sequence Y1 or the nucleic acid sequence Y2 can be prepared by introducing a mutation into a polynucleotide cloned as described above. As examples of the method of mutagenesis, methods such as the synthetic oligonucleotide site-directed mutagenesis method, the gapped duplex method, a method of randomly introducing point mutations (for example, treatment with nitrous acid or sulfurous acid), the cassette mutation method, the linker scanning method, and the mismatch primer method can be mentioned.

2. Related Substances

The present invention provides a series of related substances that can be developed on the basis of a polypeptide of the present invention and a partial peptide of the present invention, and a polynucleotide of the present invention and a partial nucleotide of the present invention. The related substances of the present invention described below can be useful as, for example, pharmaceuticals (e.g., prophylactic or therapeutic drugs for cancer as mentioned above).

2.1. Antisense Molecules

The present invention provides antisense molecules.

The type of the antisense molecule may be a DNA or an RNA, or may be a DNA/RNA chimera. The antisense molecule may be one having a phosphodiester bond of the natural type, or a modified nucleotide of the thiophosphate type (P=O in phosphate bond replaced with P=S), 2'-O-methyl type or the like, which are stable to degrading enzymes. Other important factors for the designing of the antisense molecule include increases in water-solubility and cell membrane permeability and the like; these can also be cleared by choosing appropriate dosage forms such as those using liposome or microspheres. The length of the antisense molecule is not particularly limited, as far as the molecule is capable of specifically hybridizing to the transcription product; the antisense molecule may be of a sequence of about 15 nucleotides for the shortest, or of a sequence complementary to the entire sequence of the transcription product for the longest. Considering the ease of synthesis, antigenicity issue and the like, for example, oligonucleotides consisting of about 15 nucleotides or more, preferably about 15 to about 100 nucleotides, and more preferably about 18 to about 50 nucleotides, can be mentioned. Furthermore, the antisense molecule may be one capable of not only inhibiting the translation of the transcription product by hybridizing thereto, but also binding to a double-stranded DNA to form a triple strand (triplex) to inhibit the transcription into mRNA.

An antisense molecule of the present invention can comprise a nucleic acid sequence complementary to a nucleic acid sequence corresponding to a partial nucleotide of the present invention (e.g., specific partial nucleotides A and B of the present invention, a shared partial nucleotide of the present invention). Therefore, an antisense molecule of the present invention can be an antisense molecule specific for a polynucleotide of the present invention, an antisense molecule specific for a known polynucleotide, or an antisense molecule common to both a polynucleotide of the present invention and a known polynucleotide. An antisense molecule of the present invention can be useful in specifically suppressing the expression of a polypeptide of the present invention or a known polypeptide, or comprehensively suppressing the expression of both a polypeptide of the present invention and a known polypeptide.

2.2. RNAi-Inducing Nucleic Acids

The present invention provides RNAi-inducing nucleic acids.

An RNAi-inducible nucleic acid refers to a polynucleotide, preferably an RNA, capable of inducing the RNA interference (RNAi) effect when transferred into cells. The RNAi effect refers to the phenomenon in which a double-stranded RNA comprising the same nucleic acid sequence as that of mRNA, or a partial sequence thereof, suppresses the expression of the mRNA. To obtain the RNAi effect, it is preferable to use, for example, a double-stranded RNA having the same nucleic acid sequence as that of a target mRNA comprising at least 20 or more continuous bases (or a partial sequence thereof). The double-stranded structure may be configured by different strands, or may be a double strand conferred by stem loop structure of a single RNA. As examples of the RNAi-inducing nucleic acid, siRNA, miRNA and the like can be mentioned, and siRNA is preferable. The siRNA is not particularly limited, as far as it can induce RNAi, and the siRNA can be, for example, 21 to 27 bases long, preferably 21 to 25 bases long.

An RNAi-inducing nucleic acid of the present invention can be a double-stranded polynucleotide configured by a sense strand consisting of a nucleic acid sequence corresponding to a partial nucleotide of the present invention (e.g., specific partial nucleotides A and B of the present invention, a shared partial nucleotide of the present invention), and an antisense strand consisting of a nucleic acid sequence complementary thereto. An RNAi-inducing nucleic acid of the present invention may also have an overhang at the 5' terminus and/or 3' terminus of one or both of the sense strand and the antisense strand. The overhang can be one formed as a result of the addition of one to several (e.g., 1, 2 or 3) bases at the 5' terminus and/or 3' terminus of the sense strand and/or antisense strand. An RNAi-inducing nucleic acid of the present invention can be an RNAi-inducing nucleic acid specific for a polynucleotide of the present invention, an RNAi-inducing nucleic acid specific for a known polynucleotide, or an RNAi-inducing nucleic acid common to both a polynucleotide of the present invention and a known polynucleotide. An RNAi-inducing nucleic acid of the present invention can be useful in specifically suppressing the expression of a polypeptide of the present invention or a known polypeptide, or comprehensively suppressing the expression of both a polypeptide of the present invention and a known polypeptide.

2.3. Aptamers

The present invention provides aptamers.

An aptamer refers to a polynucleotide having a binding activity (or inhibitory activity) on a specified target molecule. An aptamer of the present invention can be an RNA, a DNA, a modified nucleotide or a mixture thereof. An aptamer of the present invention can also be in a linear or circular form. The length of the aptamer is not particularly limited, and can normally be about 16 to about 200 nucleotides, and can be, for example, about 100 nucleotides or less, preferably about 50 nucleotides or less, and more preferably about 40 nucleotides or less. The length of an aptamer of the present invention may be, for example, about 18, about 20, about 25 or about 30 nucleotides or more. The aptamer, for increasing the bindability, stability, drug delivering quality and the like, may be one wherein a sugar residue (e.g., ribose) of each nucleotide is modified. As examples of a portion of the sugar residue modified, ones wherein the oxygen atom at the 2'-position, 3'-position and/or 4'-position of the sugar residue is replaced with another atom and the like can be mentioned. As examples of types of modifications, fluorination, O-alkylation, O-allylation, S-alkylation, S-allylation and amination can be mentioned (see, e.g., Sproat et al., (1991) Nucle. Acid. Res. 19, 733-738; Cotton et al., (1991) Nucl. Acid. Res. 19, 2629-2635). The aptamer may be one wherein a purine or pyrimidine is altered. As examples of such alterations, alteration of the 5-position pyrimidine, alteration of the 8-position purine, alteration by an exocyclic amine, substitution by 4-thiouridine, and substitution by 5-bromo or 5-iodo-uracil can be mentioned. The phosphate group contained in an aptamer of the present invention may be altered to make it resistant to nuclease and hydrolysis. For example, the phosphate group may be substituted by a thioate, a dithioate or an amidate. An aptamer can be prepared according to available reports (for example, Ellington et al., (1990) Nature, 346, 818-822; Tuerk et al., (1990) Science, 249, 505-510).

An aptamer of the present invention is capable of binding specifically to a polypeptide of the present invention or a known polypeptide, or both a polypeptide of the present invention and a known polypeptide, via a region corresponding to a partial peptide of the present invention. Therefore, an aptamer of the present invention can be an aptamer specific for a polypeptide of the present invention, an aptamer specific for a known polypeptide, or an aptamer common to both a polypeptide of the present invention and a known polypeptide. Such a specific aptamer can be prepared by, for example, selecting (a) a polynucleotide that binds to a polypeptide of the present invention or a specific partial peptide thereof, and that does not bind to a known polypeptide, (b) a polynucleotide that binds to a known polypeptide or a specific partial peptide thereof, and that does not bind to a polypeptide of the present invention, or (c) a polynucleotide that binds to both a polypeptide of the present invention and a known polypeptide or to a shared partial peptide of the present invention, by the SELEX method.

2.4. Antibodies

The present invention provides antibodies.

An antibody of the present invention may be a polyclonal antibody (antiserum) or a monoclonal antibody, and can be prepared by a commonly known immunological technique. Although the monoclonal antibody may be of any isotype, IgG, IgM, IgA, IgD, IgE, or the like, IgG or IgM is preferable.

For example, the polyclonal antibody can be acquired by administering the above-described antigen (as required, may be prepared as a complex crosslinked to a carrier protein such as bovine serum albumin or KLH ((Keyhole Limpet Hemocyanin)), along with a commercially available adjuvant (for example, Freund's complete or incomplete adjuvant), to an animal subcutaneously or intraperitoneally about 2 to 4 times at intervals of 2 to 3 weeks (the antibody titer of partially drawn serum has been determined by a known antigen-antibody reaction and its elevation has been confirmed in advance), collecting whole blood about 3 to about 10 days after final immunization, and purifying the antiserum. As the animal to receive the antigen, mammals such as rats, mice, rabbits, goat, guinea pigs, and hamsters can be mentioned.

The monoclonal antibody can also be prepared by a cell fusion method. For example, the above-described antigen, along with a commercially available adjuvant, is subcutaneously or intraperitoneally administered to a mouse 2 to 4 times, and 3 days after final administration, the spleen or lymph nodes are collected, and leukocytes are collected. These leukocytes and myeloma cells (for example, NS-1, P3X63Ag8 and the like) are cell-fused to obtain a hybridoma that produces a monoclonal antibody against the factor. This cell fusion may be performed by the PEG method or the voltage pulse method. A hybridoma that produces the desired monoclonal antibody can be selected by detecting an antibody that binds specifically to the antigen, in the culture supernatant, using a widely known EIA or RIA method and the like. Cultivation of the hybridoma that produces the monoclonal antibody can be performed in vitro, or in vivo such as in ascitic fluid of a mouse or rat, preferably a mouse, and the antibody can be acquired from the culture supernatant of the hybridoma and the ascitic fluid of the animal.

An antibody of the present invention may also be a chimeric antibody, a humanized antibody or a human antibody.

A chimeric antibody means a monoclonal antibody derived from immunoglobulins of animal species having mutually different variable regions and constant regions. For example, a chimeric antibody can be a mouse/human chimeric monoclonal antibody whose variable region is a variable region derived from a mouse immunoglobulin, and whose constant region is a constant region derived from a human immunoglobulin. The constant region derived from a human immunoglobulin has an amino acid sequence unique depending on the isotype, such as IgG, IgM, IgA, IgD, and IgE, and the constant region of a recombinant chimeric monoclonal antibody in the present invention may be the constant region of a human immunoglobulin belonging to any isotype. The constant region of human IgG is preferable.

A chimeric antibody can be prepared by a method known per se. For example, a mouse/human chimeric monoclonal antibody can be prepared according to available reports (e.g., Jikken Igaku (extra issue), Vol. 6, No. 10, 1988 and JP-B-HEI-3-73280). In detail, a chimeric antibody can be prepared by inserting the $C_H$ gene acquired from the DNA that encodes a human immunoglobulin (C gene that encodes H chain constant region) downstream of the active $V_H$ gene acquired from the DNA that encodes a mouse monoclonal antibody isolated from a hybridoma that produces the mouse monoclonal antibody (rearranged VDJ gene that encodes H chain variable region), and inserting the $C_L$ gene acquired from the DNA that encodes a human immunoglobulin (C gene that encodes L chain constant region) downstream of the active $V_L$ gene acquired from the DNA that encodes a mouse monoclonal antibody isolated from the hybridoma (rearranged VJ gene that encodes L chain variable region), in a way that allows the expression of each gene, into one or separate expression vectors, transforming a host cell with the expression vector, and culturing the transformant cell.

A humanized antibody means a monoclonal antibody prepared by a gene engineering technique, for example, a human type monoclonal antibody wherein a portion or all of the complementarity-determining region of the ultra-variable region thereof is derived from a mouse monoclonal antibody, and the framework region of the variable region thereof and the constant region thereof are derived from a human immunoglobulin. The complementarity-determining regions of the ultra-variable region are three regions that are present in the ultra-variable region in the variable region of the antibody, and that complementarily directly bind to the antigen (Complementarity-determining regions; CDR1, CDR2, CDR3), and the framework regions of the variable region are four relatively highly conserved regions locating in the front and back of the three complementarity-determining regions (Framework; FR1, FR2, FR3, FR4). In other words, a humanized antibody means, for example, a monoclonal antibody wherein all regions other than a portion or all of the complementarity-determining region of the ultra-variable region of a mouse monoclonal antibody is replaced with a corresponding region of a human immunoglobulin.

A humanized antibody can be prepared by a method known per se. For example, a recombinant humanized antibody derived from a mouse monoclonal antibody can be prepared according to available reports (e.g., Japanese Patent Application Kohyo Publication No. HEI-4-506458 and JP-A-SHO-62-296890). In detail, from a hybridoma that produces a mouse monoclonal antibody, at least one mouse H chain CDR gene and at least one mouse L chain CDR gene corresponding to the mouse H chain CDR gene are isolated, and from a human immunoglobulin gene, the human H chain gene that encodes all regions other than the human H chain CDR corresponding to the mouse H chain gene and the human L chain gene that encodes all regions other than the human L chain CDR corresponding to the mouse L chain CDR are isolated. The mouse H chain CDR gene and human H chain gene isolated are introduced into an appropriate expression vector expressibly; likewise, the mouse L chain CDR gene and the human L chain gene are introduced into another appropriate expression vector expressively. Alternatively, the mouse H chain CDR gene/human H chain gene and the mouse L chain CDR gene/human L chain gene can be introduced into the same expression vector expressively. By transforming a host cell with the expression vector thus prepared to obtain a cell that produces a humanized antibody, and culturing the cell, a desired humanized antibody can be obtained from the culture supernatant.

A human antibody means an antibody wherein all regions comprising the variable regions and constant regions of the H chain and L chain constituting an immunoglobulin are derived from the gene that encodes a human immunoglobulin.

A human antibody can be prepared by a method known per se. For example, a human antibody can be produced by immunologically sensitizing with an antigen a transgenic animal prepared by incorporating at least a human immunoglobulin gene into a gene locus of a non-human mammal such as a mouse, in the same way as the above-described method of preparing a polyclonal antibody or a monoclonal antibody. For example, a transgenic mouse that produces a human antibody can be prepared according to available reports (Nature Genetics, Vol. 15, p. 146-156, 1997; Nature Genetics, Vol. 7, p. 13-21, 1994; Japanese Patent Application Kohyo Publication No. HEI-4-504365; International Patent Application Publication WO94/25585; Nature, Vol. 368, p. 856-859, 1994; and Japanese Patent Application Kohyo Publication No. HEI-6-500233).

An antibody of the present invention can also be a portion of an antibody of the present invention described above (e.g., monoclonal antibody). As examples of such antibodies, $F(ab')_2$, Fab', Fab, and Fv fragments, and single-chain antibodies can be mentioned.

An antibody of the present invention is capable of binding specifically to a polypeptide of the present invention or a known polypeptide, or both a polypeptide of the present invention and a known polypeptide, via a region corresponding to a partial peptide of the present invention. Therefore, an antibody of the present invention can be an antibody specific for a polypeptide of the present invention, an antibody specific for a known polypeptide, or an antibody common to both a polypeptide of the present invention and a known polypeptide. Such a specific antibody can be prepared by, for example, using a specific partial peptide of a polypeptide of the present invention, a specific partial peptide of a known polypeptide, or a shared partial peptide of the present invention as an antigen.

2.5. Expression Vectors

The present invention provides expression vectors for the above-described substances.

An expression vector of the present invention can comprise a polynucleotide that encodes a desired polypeptide to be expressed or a desired polynucleotide to be expressed, and a promoter operatively linked to the polynucleotide. "A promoter is operatively linked to a polynucleotide" means that the promoter is bound to a polynucleotide that encodes the gene in a way such that allows the expression of the polynucleotide under the control thereof, or the expression of the polypeptide encoded by the polynucleotide.

The backbone for an expression vector of the present invention is not particularly limited, as far as it allows production of a desired substance in a specified cell; for example, plasmid vectors and viral vectors can be mentioned. When an expression vector is used as a pharmaceutical, as vectors suitable for administration to mammals, viral vectors such as adenovirus, retrovirus, adeno-associated virus, herpesvirus, vaccinia virus, poxvirus, poliovirus, Sindbis virus, and Sendai virus can be mentioned.

When a prokaryotic cell is used as the host cell, an expression vector allowing the prokaryotic cell to be utilized as the host cell can be used. Such an expression vector can comprise, for example, elements such as a promoter-operator region, an initiation codon, a polynucleotide that encodes a polypeptide of the present invention or a partial peptide thereof, a stop codon, a terminator region and a replication origin. A promoter-operator region for expressing a polypeptide of the present invention in a bacterium comprises a promoter, an operator and a Shine-Dalgarno (SD) sequence. These elements may be ones known per se.

When a eukaryotic cell is used as the host cell, an expression vector allowing the eukaryotic cell to be utilized as the host cell can be used. In this case, the promoter used is not particularly limited, as far as it is capable of functioning in eukaryotic organisms such as mammals. When the expression of a polypeptide is desired, as examples of such promoters, viral promoters such as SV40-derived initial promoter, cytomegalovirus LTR, Rous sarcoma virus LTR, MoMuLVderived LTR, and adenovirus-derived initial promoter, and mammalian constituent protein gene promoters such as β-actin gene promoter, PGK gene promoter, and transferrin gene promoter, and the like can be mentioned. When the expression of a polynucleotide is desired, the promoter can be a polIII promoter (e.g., tRNA promoter, U6 promoter, H1 promoter).

An expression vector of the present invention can further comprise sites for transcription initiation and transcription termination, and a ribosome-binding site required for translation in the transcription region, a replication origin and a selection marker gene (e.g., ampicillin, tetracycline, kanamycin, spectinomycin, erythromycin, chloramphenicol) and the like. An expression vector of the present invention can be prepared by a method known per se (see, e.g., Molecular Cloning, $2^{nd}$ edition, Sambrook et al., Cold Spring Harbor Lab. Press (1989)).

3. Compositions

The present invention provides compositions comprising the above-described substances.

A composition of the present invention can comprise, in addition to the above-described substances, an optionally chosen carrier, for example, a pharmaceutically acceptable carrier. As examples of the pharmaceutically acceptable carrier, excipients such as sucrose, starch, mannitol, sorbitol, lactose, glucose, cellulose, talc, calcium phosphate, and calcium carbonate, binders such as cellulose, methylcellulose, hydroxypropylcellulose, polypropylpyrrolidone, gelatin, gum arabic, polyethylene glycol, sucrose, and starch, disintegrants such as starch, carboxymethylcellulose, hydroxypropylstarch, sodium-glycol-starch, sodium hydrogen carbonate, calcium phosphate, and calcium citrate, lubricants such as magnesium stearate, Aerosil, talc, and sodium lauryl sulfate, flavoring agents such as citric acid, menthol, glycyrrhizin ammonium salt, glycine, and orange flour, preservatives such as sodium benzoate, sodium hydrogen sulfite, methylparaben, and propylparaben, stabilizing agents such as citric acid, sodium citrate, and acetic acid, suspending agents such as methyl cellulose, polyvinylpyrrolidone, and aluminum stearate, dispersing agents such as surfactants, diluents such as water, physiological saline, and orange juice, and base waxes such as cacao butter, polyethylene glycol, and kerosene, and the like can be mentioned, which, however, are not to be construed as limiting.

Preparations suitable for oral administration are liquids prepared by dissolving an effective amount of a substance in a diluent such as water, physiological saline or orange juice, capsules, saches or tablets containing an effective amount of a substance in the form of solids or granules, suspensions prepared by suspending an effective amount of a substance in an appropriate dispersant, emulsions prepared by dispersing and emulsifying a solution, an effective amount of a substance is dissolved therein, in an appropriate dispersant, and the like.

Preparations suitable for parenteral administration (for example, intravenous injection, subcutaneous injection, intramuscular injection, topical injection, intraperitoneal administration and the like) are aqueous and non-aqueous isotonic sterile injectable liquids, which may contain an antioxidant, a buffer solution, a bacteriostatic agent, an isotonizing agent and the like. Aqueous and non-aqueous sterile suspensions can also be mentioned, which may contain a suspending agent, a solubilizer, a thickening agent, a stabilizer, an antiseptic and the like. These preparations can be enclosed in containers such as ampoules and vials for unit dosage or a plurality of dosages. It is also possible to freeze-dry the active ingredient and a pharmaceutically acceptable carrier, and store the preparation in a state that may be dissolved or suspended in an appropriate sterile vehicle just before use.

Although the dosage of a composition of the present invention varies depending on the activity and kind of active ingredient, seriousness of illness, recipient animal species, the recipient's drug tolerance, body weight, age, and the like, it is normally about 0.001 to about 500 mg/kg as the amount of active ingredient per day for an adult.

A composition of the present invention enables a regulation (e.g., promotion or suppression) of the expression or a function of a polypeptide of the present invention. A composition of the present invention can be useful as, for example, a pharmaceutical (e.g., a prophylactic or therapeutic drug for cancer as described above), reagent or food.

4. Cells

The present invention provides transformants that produce a polypeptide of the present invention or a partial peptide of the present invention, cells that produce an antibody of the present invention, and cells wherein the expression or a function of a polynucleotide or polypeptide of the present invention is regulated.

4.1. Transformants

A transformant of the present invention can be a cell transformed with an expression vector of the present invention, that expresses a polypeptide of the present invention or a partial peptide of the present invention. The host cell used to prepare the transformant is not particularly limited, as far as it is compatible with the expression vector, and capable of expressing the desired polynucleotide or polypeptide and the like; for example, primary culture cells or cell lines can be mentioned. In detail, as examples of such host cells, cells of prokaryotic organisms such as *Escherichia coli*, bacteria of the genus *Bacillus* (e.g., *Bacillus subtilis*), and *actinomyces*, and cells of eukaryotic organisms, such as yeast, insect cells, bird cells, and mammalian cells (e.g., cells derived from the above-described mammals: e.g., CHO cells) can be mentioned. A transformant of the present invention can be prepared by a method known per se (see, e.g., Molecular Cloning, $2^{nd}$ edition, Sambrook et al., Cold Spring Harbor Lab. Press (1989)).

Cultivation of the transformant can be performed in a nutrient medium such as a liquid medium by a method known per se. The medium preferably contains a carbon source, a nitrogen source, an inorganic substance and the like necessary for the growth of the transformant. Here, as examples of the carbon source, glucose, dextrin, soluble starch, sucrose and the like can be mentioned; as examples of the nitrogen source, inorganic or organic substances such as an ammonium salt, a nitrate salt, corn steep liquor, peptone, casein, meat extract, soybean cake, potato extract and the like can be mentioned; as examples of the inorganic substance, calcium chloride, sodium dihydrogen phosphate, magnesium chloride and the like can be mentioned. In addition, the medium may be supplemented with yeast extract, vitamins and the like. Culturing conditions, for example, temperature, medium pH and culturing time, are chosen as appropriate to allow a polypeptide of the present invention to be produced in a large amount. Culturing temperature is, for example, 30 to 37° C.

4.2. Antibody Producing Cells

An antibody-producing cell of the present invention can be an optionally chosen cell that produces an antibody of the present invention. As antibody-producing cells of the present invention, the above-described hybridomas, and a transformant cell incorporating an expression vector for one of the above-described antibodies can be mentioned. When an antibody-producing cell of the present invention is a transformant cell, details of the expression vector, host cell, cell culture and the like used to prepare the transformant cell can be the same as those described above.

4.3. Cells Wherein the Expression or a Function of a Polypeptide of the Present Invention is Regulated The present invention provides cells wherein the expression or a function of a polypeptide of the present invention is regulated.

A cell of the present invention can be an isolated and/or purified one. A cell of the present invention can be a cell derived from one of the above-described tissues, or a cell of one of the above-described kinds. A cell of the present invention can be derived from one of the above-described mammals. A cell of the present invention can be a primary culture cell or cell line, or a normal cell, or a cancer cell. A cell of the present invention can be a cell wherein the expression or a function of a polypeptide of the present invention is regulated specifically. A cell of the present invention can have a cancer cell-related action or cancer cell-related phenotype thereof being variable as a result of a regulation (e.g., promotion, suppression) of the expression or a function of a polypeptide of the present invention. A cell of the present invention can be a cell wherein the expression of a polypeptide of the present invention is regulated transiently, or a cell wherein the expression is regulated permanently (e.g., homozygosity- or heterozygousity-deficient cells). A cell of the present invention can also be a transformant or a non-transformant.

A cell of the present invention can be prepared by, for example, treating a cell with one of the above-described substances capable of regulating the expression or a function of a polynucleotide of the present invention or a polypeptide of the present invention (e.g., polypeptides of the present invention, antisense molecules, RNAi-inducing nucleic acids, antibodies, or expression vectors therefor). A cell of the present invention can also be prepared by isolating and/or purifying a cell from a transgenic animal or gene-deficient (so-called knockout) animal described below.

A cell wherein the expression or a function of a polypeptide of the present invention is regulated can be useful in, for example, developing a pharmaceutical (e.g., a prophylactic or therapeutic drug as described above), reagent or food, identifying a further marker gene specific for cancer, and analyzing mechanisms associated with cancer. These can be performed by, for example, an expression profile analysis comprising measuring the expression profile in a cell of the present invention using a microarray, protein chip (e.g., antibody chip, or non-antibody chip such as chip manufactured by Ciphergen) and the like, and comparing the profile with the expression profile of a control cell. A cell of the present invention can also be useful as a cell model of a cancer.

5. Animals

The present invention provides animals wherein the expression or a function of a polypeptide of the present invention is regulated.

An animal of the present invention can be an animal with or without a genome alteration. The species of an animal of the present invention can be, for example, the same as one of the above-described non-human mammals.

In one embodiment, an animal of the present invention can be a transgenic animal with a genome alteration. A transgenic animal of the present invention is capable of expressing a polypeptide of the present invention. A transgenic animal of the present invention is also capable of expressing a polypeptide of the present invention specifically in one of the above-described cells or tissues.

A transgenic animal of the present invention can be prepared by a method known per se. In more detail, a transgenic animal of the present invention can be prepared by, for example, introducing a polynucleotide of the present invention linked operatively to a specified promoter (e.g., a promoter that is non-specific or specific for one of the above-described cells or tissues) (e.g., may be in the form of an expression vector of the present invention) into a fertilized egg of an animal or another cell (e.g., unfertilized egg, spermatozoon or a progenitor cell thereof) in the initial stage of development. As examples of the method of gene introduction, the electroporation method, lipofection method, aggregation method, calcium phosphate coprecipitation method, and microinjection method can be mentioned. A transgenic animal of the present invention may be an animal prepared by mating a thus-prepared animal and another animal of the same species (e.g., animal model of cancer).

In another embodiment, an animal of the present invention can be a gene-deficient animal with a genome alteration. A gene-deficient animal of the present invention is incapable of expressing a polypeptide of the present invention. A gene-deficient animal of the present invention is also incapable of expressing a polypeptide of the present invention specifically in one of the above-described cells or tissues.

A gene-deficient animal of the present invention can be prepared by a method known per se. In more detail, a gene-deficient animal of the present invention can be prepared using an embryonic stem cell (ES cell) specifically lacking a cancer-specific gene. Such an ES cell can be prepared by, for example, introducing a specified targeting vector into ES cells, and selecting an ES cell showing homologous recombination from among the ES cells incorporating the targeting vector.

As a targeting vector, a targeting vector capable of inducing homologous recombination that causes specific expressional failure of a polynucleotide or polypeptide of the present invention can be used. Such a targeting vector comprises a first polynucleotide and second polynucleotide that are homologous or specifically homologous to a cancer-specific gene (of the polynucleotides, at least one comprises a splicing donor signal for the cancer-specific gene, and comprises a mutation that nullifies the splicing that produces at least one isoform in the signal), and, as required, a selection marker. A splicing donor signal for the cancer-specific gene, and a mutation that nullifies the splicing that produces at least one isoform in the signal can be easily determined by a person skilled in the art. The first and second polynucleotides are polynucleotides having a sequence identity and length that are sufficient to produce homologous recombination in the genomic DNA associated with the cancer-specific gene. The first and second polynucleotides are chosen in a way such that specific deficiency of a particular isoform is produced. As selection markers, positive selection markers (e.g., neomycin resistance gene, hygromycin B phosphotransferase (BPH) gene, blasticidin S deaminase gene, puromycin resistance gene), negative selection markers (e.g., herpes simplex virus (HSV) thymidine kinase (tk) gene, diphtheria toxin A fragment (DTA) gene) and the like can be mentioned. The targeting vector can comprise either a positive selection marker or a negative selection marker or both. The targeting vector may comprise two or more recombinase target sequences (e.g., loxP sequence, which is used in the Cre/loxP system derived from bacteriophage P1, FRT sequence, which is used in yeast-derived FLP/FRT system). The present invention also provides such a targeting vector.

As the method for introducing a targeting vector into an ES cell, a method known per se can be used. As examples of such methods, the calcium phosphate method, lipofection method/liposome method, electroporation method and the like can be mentioned. When a targeting vector is introduced into a cell, homologous recombination of the genomic DNA associated with the cancer-specific gene occurs in the cell. Although an ES cell may be established by culturing an inner cell mass separated from a blastocyst of an optionally chosen animal on feeder cells, an existing ES cell may be utilized.

To select an ES cell showing homologous recombination, cells after introduction of a targeting vector are screened for. For example, after selection is performed by positive selection, negative selection and the like, screening based on genotype (for example, PCR method, Southern blot hybridization method) is performed. It is also preferable to further perform karyotype analysis on the ES cell obtained. In the karyotype analysis, the absence of chromosome aberrations in the selected ES cell is checked. Karyotype analysis can be performed by a method known per se. It is preferable that the karyotype of the ES cell be confirmed in advance before introducing the targeting vector.

A gene-deficient animal of the present invention can be prepared by transplanting to an animal a chimeric embryo obtained by introducing an ES cell obtained as described above into an embryo, and then mating the chimeric animal obtained. As examples of the embryo, blastocysts, 8-cell stage embryos and the like can be mentioned. The embryo can be obtained by mating a female animal undergoing an overovulation treatment with a hormone preparation (for example, PMSG, which has FSH-like action, and hCG, which has LH action, are used) and the like with a male animal, and the like. As methods of introducing an ES cell into an embryo, the micromanipulation method, aggregation method and the like can be mentioned.

The animal receiving a chimeric embryo transplanted is preferably a pseudo-pregnant animal. A pseudo-pregnant animal can be obtained by mating a female animal in the normal sexual cycle with a male animal emasculated by vasoligation and the like. The animal incorporating the chimeric embryo becomes pregnant and delivers a chimeric animal. Next, it is determined whether or not the animal born is a chimeric animal. Whether or not the animal born is a chimeric animal can be determined by a method known per se, for example, by the body color or coat color. For the determination, a DNA may be extracted from a portion of the body and subjected to Southern blot analysis or PCR assay. The mating can be performed preferably between a wild-type animal and a chimeric animal, or between chimeric animals. Whether or not the deficiency of the cancer-specific gene has been introduced into the germ cell line of the chimeric animal and heterozygous offspring lacking the cancer-specific gene has been obtained can be determined by a method known per se with various characters as indexes; for example, this can be determined by the body color or coat color of the offspring animal. For the determination, a DNA may be extracted from a portion of the body and subjected to Southern blot analysis or PCR assay. Furthermore, by mating thus-obtained heterozygotes, a homozygote can be prepared. A gene-deficient animal of the present invention may also be an animal prepared by mating an animal thus prepared and another animal of the same species (e.g., animal model of cancer, transgenic animal).

In a still another embodiment, an animal of the present invention can be an animal without a genome alteration. Such an animal can be prepared by treating an animal with one of the above-described substances capable of regulating the expression or a function of a polynucleotide of the present invention or a polypeptide of the present invention (e.g., polypeptides of the present invention, antisense molecules, RNAi-inducing nucleic acids, antibodies, or expression vectors therefor). Such an animal can also be an animal capable or incapable of expressing a polypeptide of the present invention specifically in one of the above-described tissues by topical treatment. The animal treatment can be performed using a method mentioned with respect to a composition of the present invention.

An animal of the present invention can be useful in, for example, developing a pharmaceutical (e.g., a prophylactic or therapeutic drug as described above), reagent or food, identifying a further marker gene specific for cancer, and analyzing mechanisms associated with cancer. These can be performed by, for example, an expression profile analysis comprising measuring an expression profile (particularly expression profile of a cancer cell or tissue) using a microarray, protein chip (e.g., antibody chip, or non-antibody chip such as a chip manufactured by Ciphergen) and the like in an animal of the present invention, and comparing the profile with the expression profile of a control animal. An animal of the present invention can also be useful as an animal model of cancer.

6. Measuring Means and Measuring Method

The present invention provides measuring means (e.g., primer set, nucleic acid probe, antibody, aptamer) and measuring methods for target polynucleotides and polypeptides.

6.1. Primer Set and Method of Use Thereof

A primer set of the present invention can be used for specific detection and quantitation of a polynucleotide of the present invention or a known polynucleotide, or comprehensive detection and quantitation of both a polynucleotide of the present invention and a known polynucleotide. For example, such detection and quantitation can be achieved, after preparing total RNA from a biological sample, by utilizing a method of gene amplification such as a PCR (e.g., RT-PCR, real-time PCR, quantitative PCR), LAMP (Loop-mediated isothermal amplification) (see, e.g., WO00/28082), or ICAN (Isothermal and Chimeric primer-initiated Amplification of Nucleic acids) (see, e.g., WO00/56877). Because the number of primers required differs depending on the kind of the method of gene amplification, the number of primers is not particularly limited; for example, a primer set of the present invention can comprise two or more primers constituted by a sense and antisense primer. The two or more primers may be mixed in advance or not. Each of the sense and antisense primers is not particularly limited, as far as it is of a size enabling specific amplification of the target region; each primer consists of 12 (for example, at least about 15, preferably at least about 18, more preferably at least about 20 and the like) consecutive nucleotide residues. The sense and antisense primer, when the size of the polynucleotide amplified thereby is to be visually detected, can be designed to allow it to be visually detectable. The visually detectable size is not particularly limited, and can be, for example, at least about 50, preferably at least 70, more preferably at least about 100, still more preferably at least about 150, and most preferably at least about 200, about 300, about 400, about 500 or more nucleotide residues long.

The sense and antisense primer do not require that the polynucleotide amplified thereby be visually detected, and may be detected by a fluorescence signal and the like, as is commonly used in real-time PCR.

A primer set of the present invention can be a) a primer set specific for a polynucleotide of the present invention, capable of distinguishing a polynucleotide of the present invention from a known polynucleotide (abbreviated as "specific primer set A" as required), b) a primer set specific for a known polynucleotide, capable of distinguishing a known polynucleotide from a polynucleotide of the present invention (abbreviated as "specific primer set B" as required), or c) a primer set common to both a polynucleotide of the present invention and a known polynucleotide (abbreviated as "shared primer set" as required) wherein a polynucleotide of the present invention and a known polynucleotide do not distinguish each other.

The specific primer set A of the present invention can comprise i) a sense and antisense primer designed to make it possible to distinguish the size of the polynucleotide of the present invention or partial nucleotide thereof to be amplified from the size of the known polynucleotide or partial nucleotide thereof to be amplified, or ii) a sense and antisense primer designed to allow a polynucleotide of the present invention or a partial nucleotide thereof alone to be amplified, and not to allow a known polynucleotide to be amplified.

The sense and antisense primers of i) above are preferably, for example, a) a sense primer corresponding to a nucleic acid sequence present on the 5' side relative to the nucleic acid sequence of the above-described specific partial nucleotide A (particularly an insert nucleic acid sequence of a polynucleotide of the present invention), and an antisense primer corresponding to a nucleic acid sequence complementary to a nucleic acid sequence present on the 3' side relative to the nucleic acid sequence, or b) a sense primer corresponding to a nucleic acid sequence present on the 5' side relative to the nucleic acid sequence of the above-described specific partial nucleotide B (particularly an insert nucleic acid sequence of a known polynucleotide), and an antisense primer corresponding to a nucleic acid sequence complementary to a nucleic acid sequence present on the 3' side relative to the nucleic acid sequence.

The sense and antisense primers of ii) above are preferably, for example, a) a sense primer corresponding to the nucleic acid sequence of the above-described specific partial nucleotide A (particularly an insert nucleic acid sequence of a polynucleotide of the present invention), and a specified antisense primer, b) a specified sense primer, and a sense primer corresponding to the nucleic acid sequence of the above-described specific partial nucleotide A (particularly an insert nucleic acid sequence of a polynucleotide of the present invention).

The specific primer set B of the present invention can comprise i) a sense and antisense primer designed to make it possible to distinguish the size of the known polynucleotide or partial nucleotide thereof to be amplified from the size of the polynucleotide of the present invention or partial nucleotide thereof to be amplified, or ii) a sense and antisense primer designed to allow a known polynucleotide or a partial nucleotide thereof alone to be amplified, and not to allow a polynucleotide of the present invention to be amplified.

The sense and antisense primers of i) above are preferably, for example, a) a sense primer corresponding to a nucleic acid sequence present on the 5' side relative to the nucleic acid sequence of the above-described specific partial nucleotide B (particularly an insert nucleic acid sequence of a known polynucleotide), and an antisense primer corresponding to a nucleic acid sequence complementary to a nucleic acid sequence present on the 3' side relative to the nucleic acid sequence, or b) a sense primer corresponding to a nucleic acid sequence present on the 5' side relative to the nucleic acid sequence of the above-described specific partial nucleotide A (particularly an insert nucleic acid sequence of a polynucleotide of the present invention), and an antisense primer corresponding to a nucleic acid sequence complementary to a nucleic acid sequence present on the 3' side relative to the nucleic acid sequence.

The sense and antisense primers of ii) above are preferably, for example, a) a sense primer corresponding to the nucleic acid sequence of the above-described specific partial nucleotide B (particularly an insert nucleic acid sequence of a known polynucleotide), and a specified antisense primer, b) a specified sense primer, and a sense primer corresponding to the nucleic acid sequence of the above-described specific partial nucleotide B (particularly an insert nucleic acid sequence of a known polynucleotide), or c) a sense and antisense primer corresponding to the nucleic acid sequence of the above-described specific partial nucleotide B (particularly an insert nucleic acid sequence of a known polynucleotide).

A shared primer set of the present invention can comprise a sense and antisense primer designed to equalize the size of the known polynucleotide or partial nucleotide thereof to be amplified to the size of the polynucleotide of the present invention or partial nucleotide thereof to be amplified. Such a sense and antisense primer are preferably, for example, a sense and antisense primer designed not to allow the polynucleotide of the present invention or partial nucleotide thereof to be amplified, and the known polynucleotide or partial nucleotide thereof to be amplified, to comprise the nucleic acid sequences of the above-described specific partial nucleotides A and B.

6.2. Nucleic Acid Probe and Method of Use Thereof

A nucleic acid probe of the present invention can be used for specific detection and quantitation of a polynucleotide of the present invention or a known polynucleotide, or comprehensive detection and quantitation of both a polynucleotide of the present invention and a known polynucleotide. For example, such a detection and quantitation can be achieved, after preparing total RNA from a biological sample, by utilizing Northern blotting, a nucleic acid array wherein a nucleic acid probe of the present invention is immobilized, and the like. Although the nucleic acid probe can be a DNA, an RNA, a modified nucleic acid or a chimeric molecule thereof and the like, a DNA is preferable in consideration of safety, convenience and the like. The nucleic acid probe may also be any one of a single-stranded or a double-stranded polynucleotide. The size of the nucleic acid probe is not particularly limited, as far as it is capable of specifically hybridizing to the transcription product of the target gene; the size is, for example, at least about 15 or 16, preferably about 15 to about 1000, more preferably about 20 to about 500, and still more preferably about 25 to about 300. When a nucleic acid probe of the present invention is a single-stranded polynucleotide, the nucleic acid probe of the present invention can be the same as an antisense molecule of the present invention. When a nucleic acid probe of the present invention is a double-stranded polynucleotide, the nucleic acid probe of the present invention can be configured by an antisense molecule of the present invention and a polynucleotide molecule complementary thereto.

A nucleic acid probe of the present invention can be a) a nucleic acid probe specific for a polynucleotide of the present invention, capable of distinguishing a polynucleotide of the present invention from a known polynucleotide (abbreviated as "specific nucleic acid probe A" as required), b) a nucleic acid probe specific for a known polynucleotide, capable of distinguishing a known polynucleotide from a polynucleotide of the present invention (abbreviated as "specific nucleic acid probe B" as required), or c) a nucleic acid probe common to both a polynucleotide of the present invention and a known polynucleotide, wherein a polynucleotide of the present invention and a known polynucleotide do not distinguish each other (abbreviated as "shared nucleic acid probe" as required).

The specific nucleic acid probe A of the present invention can be a polynucleotide having a nucleic acid sequence complementary to the nucleic acid sequence of the above-described specific partial nucleotide A (particularly an insert nucleic acid sequence of a polynucleotide of the present invention) (a single-stranded polynucleotide), or a polynucleotide having the nucleic acid sequence of the above-described specific partial nucleotide A (particularly an insert nucleic acid sequence of a polynucleotide of the present invention) and a nucleic acid sequence complementary to the nucleic acid sequence (a double-stranded polynucleotide).

The specific nucleic acid probe B of the present invention can be a polynucleotide having a nucleic acid sequence complementary to the nucleic acid sequence of the above-described specific partial nucleotide B (particularly an insert nucleic acid sequence of a known polynucleotide) (a single-stranded polynucleotide), or a polynucleotide having the nucleic acid sequence of the above-described specific partial nucleotide B (particularly an insert nucleic acid sequence of a known polynucleotide) and a nucleic acid sequence complementary to the nucleic acid sequence (a double-stranded polynucleotide).

A shared nucleic acid probe of the present invention can be a polynucleotide having a nucleic acid sequence complementary to the nucleic acid sequence of the above-described shared partial nucleotide (a single-stranded polynucleotide), or a polynucleotide having a nucleic acid sequence complementary to the nucleic acid sequence of the above-described shared partial nucleotide and the nucleic acid sequence (a double-stranded polynucleotide).

A nucleic acid probe of the present invention may be provided in a state immobilized on a support (i.e., as an array). The support for such a nucleic acid array is not particularly limited, as far as it is a support in common use in the art; for example, membranes (e.g., nylon membranes), glass, plastics, metals, plates and the like can be mentioned. A nucleic acid array in the present invention can assume a form known per se; for example, an array wherein a nucleic acid is directly synthesized on a support (so-called affimetrix type), an array wherein a nucleic acid is immobilized on a support (so-called Stanford type), fiber-type array, and electrochemical array (ECA) can be mentioned.

6.3. Antibodies and Aptamers and Method of Use Thereof

An antibody and aptamer of the present invention can be used for specific detection and quantitation of a polypeptide of the present invention, a known polypeptide, or both a polypeptide of the present invention and a known polypeptide. For example, such a detection and quantitation can be achieved, after preparing an extract from a biological sample, or using a biological sample, by an immunological technique or an affinity-based method. As examples of such immunological techniques, enzyme immunoassay (EIA) (e.g., direct competitive ELISA, indirect competitive ELISA, sandwich ELISA), radioimmunoassay (RIA), fluorescent immunoassay (FIA), immunochromatography, luminescence immunoassay, spin immunoassay, Western blotting, and immunohistochemical staining can be mentioned. An affinity-based method can be performed in accordance with one of the above-described immunological techniques. The antibody and aptamer used for a measurement of a polypeptide of the present invention, a known polypeptide, or both a polypeptide of the present invention and a known polypeptide can be the same as the above-described antibody and aptamer of the present invention.

An antibody and aptamer of the present invention can be a) an antibody and aptamer specific for a polypeptide of the present invention, that make it possible to distinguish a polypeptide of the present invention from a known polypeptide (abbreviated as "specific antibody and aptamer A" as required), b) an antibody and aptamer specific for a known polypeptide, that make it possible to distinguish a known polypeptide from a polypeptide of the present invention (abbreviated as "specific antibody and aptamer B" as required), or c) an antibody and an aptamer common to both a polypeptide of the present invention and a known polypeptide, that do not distinguish between a polypeptide of the present invention and a known polypeptide (abbreviated as "shared antibody and aptamer" as required). The specific antibody and aptamer A of the present invention are capable of binding to the above-described specific partial peptide A (particularly a partial peptide consisting of an insert amino acid sequence of a polypeptide of the present invention). The specific antibody and aptamer B of the present invention are capable of binding to the above-described specific partial peptide B (particularly a partial peptide consisting of an insert amino acid sequence of a known polypeptide). A shared antibody and aptamer of the present invention are capable of binding to the above-described shared partial peptide.

An antibody and aptamer of the present invention may be provided in a form immobilized on a support (i.e., as an array). The support for such a nucleic acid array is not particularly limited, as far as it is a support in common use in the art; for example, membranes (e.g., nitrocellulose membranes), glass, plastics, metals, and plates (e.g., multiwell plates) can be mentioned.

6.4. Supplementary Matters Concerning Measuring Means of the Present Invention

A measuring means of the present invention can be provided in a form labeled with a labeling substance as required. As examples of the labeling substance, fluorescent substances such as FITC and FAM, luminescent substances such as luminol, luciferin and lucigenin, radioisotopes such as $^3$H, $^{14}$C, $^{32}$P, $^{35}$S, and $^{123}$I, affinity substances such as biotin and streptavidin, and the like can be mentioned.

A measuring means of the present invention may be provided in the form of a kit comprising an additional constituent, in addition to the measuring means. In this case, the various constituents contained in the kit can be provided in mutually isolated forms, for example, in forms housed in different containers. For example, when the measuring means is not labeled with a labeling substance, the kit can further comprise a labeling substance. A kit of the present invention can comprise two or more measuring means for two or more target genes (e.g., a combination of a cancer-specific gene and a known gene, a combination of two or more cancer-specific genes). When the measuring means of the present invention is provided in the form of an array, the array of the present invention can be one wherein two or more measuring means for two or more target genes are immobilized. A kit and array of the present invention can also comprise a measuring means as described above with respect to a housekeeping gene (e.g., GAPDH, β-actin).

6.5. Measuring Methods of the Present Invention

The present invention also provides a method of detecting or quantifying a target polypeptide or polynucleotide using a measuring means of the present invention.

A measurement of a target polynucleotide and polypeptide can be properly performed according to the kind of the measuring means by the above-described method.

In a method of the present invention, the expression level of a target polynucleotide or polypeptide in a biological sample obtained from one of the above-described mammals (e.g., human) or a culture (e.g., cell or tissue culture) can be measured. The biological sample is not particularly limited, as far as it is, for example, a sample containing a cell or tissue expressing the target polynucleotide or polynucleotide, or, if the target polynucleotide or polypeptide is secreted or oozed or the like, an animal-derived sample (e.g., blood, plasma, serum, saliva, cerebrospinal fluid, tear, urine) containing the polynucleotide or polypeptide secreted or oozed or the like. The biological sample can be one containing one of the above-described cells or tissues (e.g., a cancer cell or a cancer tissue containing the cancer cell). The biological sample used in the present invention, unless otherwise specified, can be a biological sample collected from a mammal in advance; in a particular aspect, a method of the present invention can comprise collecting a biological sample from a mammal.

In one embodiment, a method of the present invention can be utilized to diagnose of cancer (e.g., determination of onset or likelihood of onset). This method can comprise measuring the expression level of a target polynucleotide or polypeptide in a biological sample collected from an animal, and evaluating the onset or likelihood of onset of a target disease on the basis of the measured expression level or relative expression rate. For example, the measured expression level or relative expression rate is compared with the expression level in a mammal not suffering the target disease (e.g., normal animal). The expression level or expression rate in a mammal not suffering the target disease can be determined by a method known per se. By such a comparison, it is determined whether or not the animal possibly has the target disease, or whether or not the animal is likely to suffer the disease. It is known that in a mammal having a particular disease manifested, an expressional change in the gene associated with the disease is often observed. It is also known that before the onset of a particular disease, an expressional change in a particular gene is often observed. Therefore, by such an analysis, it is possible to determine the onset or likelihood of onset of a target disease. Such a method can be useful in, for example, conveniently determining and early detecting a target disease. Of course, a measuring means of the present invention and a reagent or kit of the present invention can also be utilized for such a determination.

In detail, the changes in the expression profiles of the cancer-specific genes 1 to 8 in cancer are as described in the following. Therefore, using a measuring means of the present invention that enables a specific measurement of a polynucleotide of the present invention and a partial nucleotide of the present invention (e.g., specific partial nucleotide A of the present invention, specific partial nucleotide B of the present invention, shared partial nucleotide of the present invention), and a polypeptide of the present invention and a partial peptide of the present invention (e.g., specific partial peptide A of the present invention, specific partial peptide B of the present invention, shared partial peptide of the present invention), by evaluating the degree of the expression of the cancer-specific genes 1 to 8 and/or relative expression ratios thereof, it is possible to diagnose of cancer.

1) Cancer-Specific Gene 1

Being a polynucleotide and polypeptide of the present invention related to the cancer-specific gene 1, D-LIVER2001680.1 can have the expression thereof in a specified tissue (e.g., Tongue, Liver) increased as a result of cancer transformation.

Being a polynucleotide and polypeptide of the present invention related to the cancer-specific gene 1, D-LIVER2008912.1 can have the expression thereof in a specified tissue (e.g., Liver) increased as a result of cancer transformation.

Known variants of the cancer-specific gene 1 can have the expression thereof in a particular tissue (e.g., Tongue, Liver) decreased as a result of cancer transformation.

Being a polynucleotide and polypeptide of the present invention related to the cancer-specific gene 1, D-LIVER2001680.1, compared with known variants of the cancer-specific gene 1, is capable of being expressed at a relatively lower level in a normal tissue (e.g., Liver), and expressed at a relatively higher level in a cancer tissue (e.g., Liver).

2) Cancer-Specific Gene 2

Being polynucleotides and polypeptides of the present invention related to the cancer-specific gene 2, D-HCHON2007878.1, D-NTONG2006230.1, and D-SPLEN2005548.1, compared with known variants of the cancer-specific gene 2, are capable of being expressed at a relatively higher level in normal tissues (e.g., Liver, Ovary, Uterus), and expressed at a relatively lower level in cancer tissues (e.g., Liver, Ovary, Uterus).

Being polynucleotides and polypeptides of the present invention related to the cancer-specific gene 2, D-HCHON2007878.1, D-NTONG2006230.1, and D-SPLEN2005548.1, compared with known variants of the cancer-specific gene 2, are capable of being expressed at a relatively higher level in a specified tissue (e.g., Lung), whether it is a normal tissue or a cancer tissue, and expressed at a relatively lower level in a specified tissue (e.g., Tongue), whether it is a normal tissue or a cancer tissue.

3) Cancer-Specific Gene 3

Being polynucleotides and polypeptides of the present invention related to the cancer-specific gene 3, D-BRCOC2007920.1 and D-TKIDN2010471.1 can have the expression thereof in a specified tissue (e.g., Kidney, Lung, Uterus, Tongue) decreased as a result of cancer transformation.

Known variants of the cancer-specific gene 3 can have the expression thereof in a specified tissue (e.g., Kidney, Lung, Uterus, Tongue) disappearing as a result of cancer transformation.

Being polynucleotides and polypeptides of the present invention related to the cancer-specific gene 3, D-BRCOC2007920.1 and D-TKIDN2010471.1 are expressed in a specified tissue (e.g., Kidney, Lung, Uterus, Tongue), whether it is a normal tissue or a cancer tissue, whereas known variants of the cancer-specific gene 3 are expressed only in normal tissues, and have the expression thereof disappearing in cancer tissues.

4) Cancer-Specific Gene 4

Being polynucleotides and polypeptides of the present invention related to the cancer-specific gene 4, D-FEBRA2010013.1 and D-FEBRA2001623.1 can have the expression thereof in a particular tissue (e.g., Kidney, Ovary) increased as a result of cancer transformation.

Being a polynucleotide and polypeptide of the present invention related to the cancer-specific gene 4, D-TKIDN2003621.1 can have the expression thereof in a particular tissue (e.g., Kidney, Ovary, Tongue) increased as a result of cancer transformation.

Known variants of the cancer-specific gene 4 can have the expression thereof in a particular tissue (e.g., Kidney, Ovary, Tongue) decreased as a result of cancer transformation.

5) Cancer-Specific Gene 5

Being a polynucleotide and polypeptide of the present invention related to the cancer-specific gene 5, D-CTONG2001283.1 can have the expression thereof in a specified tissue (e.g., Ovary, Uterus, Stomach, Tongue) increased as a result of cancer transformation.

Known variants of the cancer-specific gene 5 can have the expression thereof in a specified tissue (e.g., Ovary, Uterus, Stomach, Tongue) decreased as a result of cancer transformation.

6) Cancer-Specific Gene 6

Being a polynucleotide and polypeptide of the present invention related to the cancer-specific gene 6, D-OCBBF2013203.1 can have the expression thereof in a specified tissue (e.g., Lung, Tongue) increased, and the expression thereof in a specified tissue (e.g., Kidney) decreased, as a result of cancer transformation.

Known variants of the cancer-specific gene 6 have the expression thereof in a specified tissue (e.g., Lung, Tongue) decreased as a result of cancer transformation, with no major change in the expression thereof in a specified tissue (e.g., Kidney).

7) Cancer-Specific Gene 7

Being a polynucleotide and polypeptide of the present invention related to the cancer-specific gene 7, D-BRAWH2011787.1 can have the expression thereof in a specified tissue (e.g., Ovary, Uterus, Tongue) decreased as a result of cancer transformation.

Known variants of the cancer-specific gene 7 can have the expression thereof in a specified tissue (e.g., Ovary, Uterus, Tongue) increased as a result of cancer transformation.

8) Cancer-Specific Gene 8

The expression pattern near the N-terminus of the ORF of D-TLIVE2001566.1, being a polynucleotide and polypeptide of the present invention related to the cancer-specific gene 8, can have the expression thereof in a specified tissue (e.g., Lung) decreased as a result of cancer transformation.

The expression pattern near the N-terminus of the ORF of a known variant of the cancer-specific gene 8 can have the expression thereof in a specified tissue (e.g., Lung) increased as a result of cancer transformation.

The pattern near the C-terminus of the ORF of D-TLIVE2001566.1, being a polynucleotide and polypeptide of the present invention related to the cancer-specific gene 8, can have the expression thereof in a specified tissue (e.g., Ovary, Tongue) decreased as a result of cancer transformation.

The pattern near the C-terminus of the ORF of a known variant of the cancer-specific gene 8 can have the expression thereof in a specified tissue (e.g., Ovary, Tongue) increased as a result of cancer transformation.

In another embodiment, a method of the present invention can be utilized for screening for a pharmaceutical, reagent or food and the like. For example, in one methodology, the screening method can comprise determining whether or not a test substance is capable of regulating (e.g., increasing or decreasing) the number of cancer cells. Because the number of cancer cells and the expression level of a cancer-specific gene can correlate with each other, such a screening can be performed by measuring the expression level of the cancer-specific gene. In another methodology, the screening method can comprise determining whether or not a test substance is capable of regulating the expression or a function of a target polynucleotide or polypeptide. Such a screening method can be utilized as, for example, a screening method for a pharmaceutical effective for a specified disease (e.g., cell proliferative diseases such as cancer, etc.) and the like, comprising selecting a test substance capable of regulating the expression or a function of a target, and a screening method for a pharmaceutical with a decreased specified action (e.g., adverse reactions such as cell proliferation regulatory action) and the like, comprising selecting a test substance incapable of regulating the expression or a function of a target. The test material subjected to the screening method can be a commonly known or a novel compound or a composition; as examples, nucleic acids, glucides, lipids, proteins, peptides, organic low molecular compounds, compound libraries prepared using combinatorial chemistry technology, random peptide libraries prepared by solid phase synthesis or the phage display method, or naturally occurring ingredients derived from microorganisms, animals, plants, marine organisms and the like, existing pharmaceuticals, reagents or foods and the like can be mentioned. In the screening method, mammals, cells and tissues (e.g., cancer cell and a cancer tissue), or reconstitution systems (non-cell systems) as described above can be used. Pharmaceuticals and the like obtained by the screening method are also provided by the present invention.

The disclosures in all publications mentioned herein, including patents and patent application specifications, are incorporated herein by reference to the extent that all of them have been given expressly.

EXAMPLES

The present invention is hereinafter described in further detail with reference to Examples; however, the present invention is not limited to the Examples and the like by any means.

Example 1

Preparation and Sequence Analysis of Human cDNA Libraries (1) Preparation and Sequence Analysis of cDNA Libraries by the Improved Oligocap Method
1) Extraction and Purchase of mRNAs From human tissues (shown below), by a method described in a literature document (J. Sambrook, E. F. Fritsch & T. Maniatis, Molecular Cloning Second edition, Cold Spring harbor Laboratory Press, 1989), mRNAs were extracted as total RNAs. After cultivation of cultured human cells or primary culture human cells (shown below) by the methods described in the catalogues thereof, mRNAs were extracted as total RNAs by a method described in a literature document (J. Sambrook, E. F. Fritsch & T. Maniatis, Molecular Cloning Second edition, Cold Spring harbor Laboratory Press, 1989).

Hereinafter, the relationships between the names of libraries and the derivations thereof are shown in the order of "name of library: derivation". If a library was generated by subtraction, how to generate the subtraction library is also shown.

<Extraction of mRNAs from Human Tissues>
NTONG: Tongue; CTONG: Tongue, Tumor; FCBBF: Brain, Fetal; OCBBF: Brain, Fetal; PLACE: Placenta; SYNOV: Synovial membrane tissue from rheumatoid arthritis; CORDB: Cord blood.

<Extraction of mRNAs from Cultured Cells>
BNGH4: H4 cell (ATCC #HTB-148); IMR32: IMR32 cell (ATCC #CCL-127); SKNMC: SK-N-MC cell (ATCC #HTB-10); 3NB69: NB69 cell (RCB #RCB0480); BGGI1: GI1 cell (RCB #RCB0763); NB9N4: NB9 cell (RCB #RCB0477); SKNSH: SK-N-SH cell (RCB #RCB0426); AHMSC: HMSC cell (Human mesenchymal cell); CHONS: Chondrocyte; ERLTF: TF-1 cell (erythroleukemia); HELAC: HeLa cell; JCMLC: leukemia cell (Leukemia, myelogenous); MESTC: Mesenchyme stem cell; N1ESE: Mesenchymal stem cell; NCRRM: Embryonal carcinoma; NCRRP: Embryonal carcinoma treated with retinoic acid (RA) to induce differentiation; T1ESE: Mesenchymal stem cell treated with trichostatin and 5-azacytidine to induce differentiation; NT2RM: NT2 cell (STRATAGENE #204101); NT2RP: NT2 cell treated with retinoic acid (RA) to induce differentiation for 5 weeks; NT2RI: NT2 cell treated with RA to induce differentiation for 5 weeks, and thereafter treated with a growth inhibitor for 2 weeks; NT2NE: NT2 cell treated with RA and treated with a growth inhibitor to induce nerve differentiation, followed by nerve concentration and recovery (NT2 Neuron); NTISM: a library generated by subtracting cDNAs that overlap with the mRNA of undifferentiated NT2 cells from a cDNA library prepared from an mRNA of NT2 cell (STRATAGENE #204101) treated with RA to induce differentiation for 5 weeks, and thereafter treated with a growth inhibitor for 2 weeks, using Subtract Kit (Invitrogen #K4320-01) (NT2RI-NT2RM). RCB indicates that the cell line was supplied by the RIKEN Gene Bank—Cell Development Bank, and ATCC indicates that the cell line was supplied by the American Type Culture Collection.

<Extraction of mRNAs from Primary Culture Cells>
ASTRO: Normal Human Astrocyte NHA5732, Takara Shuzo #CC2565; DFNES: Normal Human Dermal Fibroblasts (Neonatal Skin); NHDF-Neo) NHDF2564, Takara Shuzo #CC2509; MESAN: Normal human mesangial cells NHMC56046-2, Takara Shuzo #CC2559; NHNPC: Normal human neural progenitor cells NHNP5958, Takara Shuzo #CC2599; PEBLM: Human peripheral blood mononuclear cells HPBMC5939, Takara Shuzo #CC2702; HSYRA: HS-RA (Human synoviocytes from rheumatoid arthritis), Toyobo #T404K-05; PUAEN: Human pulmonary artery endothelial cells, Toyobo #T302K-05; UMVEN: Human umbilical vein endothelial cells HUVEC, Toyobo #T200K-05; HCASM: HCASMC (Human coronary artery smooth muscle cells), Toyobo #T305K-05; HCHON: HC (Human Chondrocytes), Toyobo #T402K-05; HHDPC: HDPC (Human dermal papilla cells), Toyobo #THPCK-001; CD34C: CD34+ cell (AllCells, LLC #CB14435M); D3OST: CD34+ cells treated with osteoclast differentiation factor (ODF) to induce differentiation for 3 days; D6OST: CD34+ cells treated with an ODF to induce differentiation for 6 days; D9OST: CD34+ cells treated with ODF to induce differentiation for 9 days; ACTVT: activated T-cell; LYMPB: Lymphoblast, EB virus transferred B cell; NETRP: Neutrophil.

Next, mRNAs extracted as total RNAs from the human tissues shown below were purchased. Hereinafter, the relationships between the names of libraries and the derivations thereof are shown in the order of "name of library: derivation". If a library was generated by subtraction, how to generate the subtraction library is also shown.

<mRNAs from Human Tissues Purchased as Total RNAs>
ADRGL: Adrenal gland, CLONTECH #64016-1; BRACE: Brain, cerebellum, CLONTECH #64035-1; BRAWH: Brain, whole, CLONTECH #64020-1; FEBRA: Brain, Fetal, CLONTECH #64019-1; FELIV: Liver, Fetal, CLONTECH #64018-1; HEART: Heart, CLONTECH #64025-1; HLUNG: Lung, CLONTECH #64023-1; KIDNE: Kidney, CLONTECH #64030-1; LIVER: Liver, CLONTECH #64022-1; MAMGL: Mammary Gland, CLONTECH #64037-1; PANCR: Pancreas, CLONTECH #64031-1; PROST: Prostate, CLONTECH #64038-1; SALGL: Salivary Gland, CLONTECH #64026-1; SKMUS: Skeletal Muscle, CLONTECH #64033-1; SMINT: Small Intestine, CLONTECH #64039-1; SPLEN: Spleen, CLONTECH #64034-1; STOMA: Stomach, CLONTECH #64090-1; TBAES: Breast, Tumor, CLONTECH #64015-1; TCERX: Cervix, Tumor, CLONTECH #64010-1; TCOLN: Colon, Tumor, CLONTECH #64014-1; TESTI: Testis, CLONTECH #64027-1; THYMU: Thymus, CLONTECH #64028-1; TLUNG: Lung, Tumor, CLONTECH #64013-1; TOVAR: Ovary, Tumor, CLONTECH #64011-1; TRACH: Trachea, CLONTECH #64091-1; TUTER: Uterus, Tumor, CLONTECH #64008-1; UTERU: Uterus, CLONTECH #64029-1; ADIPS: Adipose, Invitrogen #D6005-01; BLADE: Bladder, Invitrogen #D6020-01; BRALZ: Brain, cortex, Alzheimer, Invitrogen #D6830-01; CERVX: Cervix, Invitrogen #D6047-01; COLON: Colon, Invitrogen #D6050-0; NESOP: Esophagus, Invitrogen #D6060-01; PERIC: Pericardium, Invitrogen #D6105-01; RECTM: Rectum, Invitrogen #D6110-01; TESOP: Esophageal, Tumor, Invitrogen #D6860-01; TKIDN: Kidney, Tumor, Invitrogen #D6870-01; TLIVE: Liver, Tumor, Invitrogen #D6880-01; TSTOM: Stomach, Tumor, Invitrogen #D6920-01; BEAST: Adult Breast, STRATAGENE #735044; FEHRT: Heart, Fetal, STRATAGENE #738012; FEKID: Kidney, Fetal, STRATAGENE #738014; FELNG: Lung, Fetal, STRATAGENE #738020; NOVAR: Adult Ovary, STRATAGENE #735260; BRASW: a library generated by subtracting cDNAs that overlap with the mRNA of BRAWH (Brain, whole, CLONTECH #64020-1) from a cDNA library prepared from the mRNA of BRALZ (Brain, cortex, Alzheimer, Invitrogen #D6830-01), using Subtract Kit (Invitrogen #K4320-01) (BRALZ-BRAWH).

Furthermore, mRNAs extracted and purified as polyA(+) RNAs from the human tissues shown below were purchased. From an RNA prepared by mixing polyA(+) RNA derived from each tissue with polyA(−) RNA, a cDNA library was prepared. The polyA(−) RNA was prepared by removing the polyA(+) RNA from the total RNA of Brain, whole, CLONTECH #64020-1 by means of oligo dT cellulose. Hereinafter, the relationships between the names of libraries and the derivations thereof are shown in the order of "name of library: derivation".

<mRNAs from Human Tissues Purchased as PolyA(+) RNAs>
BRAMY: Brain, amygdala, CLONTECH #6574-1; BRCAN: Brain, caudate nucleus, CLONTECH #6575-1; BRCOC: Brain, corpus callosum, CLONTECH #6577-1; BRHIP: Brain, hippocampus, CLONTECH #6578-1; BRSSN: Brain, substantia nigra, CLONTECH #6580-1; BRSTN: Brain, subthalamic nucleus, CLONTECH #6581-1; BRTHA: Brain, thalamus, CLONTECH #6582-1.

2) Preparation of cDNA Libraries by the Improved Oligocap Method

From each RNA, by a method (WO 01/04286) developed by improving the oligocap method [M. Maruyama and S. Sugano, Gene, 138: 171-174 (1994)], a cDNA library was prepared. Using an Oligo-cap linker (SEQ ID NO:1) and an Oligo dT primer (SEQ ID NO:2), as described in WO 01/04286, BAP (Bacterial Alkaline Phosphatase) treatment, TAP (Tobacco Acid Pyrophosphatase) treatment, RNA ligation, synthesis of first strand cDNA and removal of RNA were performed. Next, using 5' (SEQ ID NO:3) and 3' (SEQ ID NO:4) PCR primers, by PCR (polymerase chain reaction), the first strand cDNA was converted to a double-stranded cDNA, and cleaved with SfiI. Next, the cDNA fragment, usually fractionated into 2 kb or more (3 kb or more as the case may be), was cloned into the vector pME18SFL3 (GenBank AB009864, Expression vector), previously cleaved with DraIII, in a determined orientation of the cDNA, whereby a cDNA library was prepared.

The relationships between the names of the cDNA libraries used for 5'-terminal sequence analysis of the cDNAs and the derivations thereof are shown in Tables 1-1 to 1-6. The number of the 5'-terminal sequences of the cDNAs in each cDNA library after mapping onto the human genome are also shown in Tables 1-1 to 1-6.

3) 5'-Terminal Sequence Analysis of cDNAs from cDNA Libraries Prepared by the Improved Oligocap Method The 5'-terminal nucleic acid sequences of cDNAs acquired from each cDNA library, after a sequencing reaction using a DNA sequencing reagent (BigDye Terminator Cycle Sequencing FS Ready Reaction Kit, manufactured by PE Biosystems) according to the manual, were analyzed using a DNA sequencer (ABI PRISM 3700, manufactured by PE Biosystems). For the data obtained, a database was constructed. The 5'-terminus full-length rate of each cDNA library prepared by the improved oligocap method was 90% on average, being a high full-length rate (calculated with the protein coding region of a known mRNA as an index).

4) Full-Length cDNA Nucleic Acid Analysis

For cDNAs selected for full-length cDNA nucleic acid analysis, the nucleic acid sequence of each full-length cDNA was determined. The nucleic acid sequences were determined mainly by a primer walking method based on the dideoxy terminator method using a custom-synthesized DNA primer. Specifically, a sequencing reaction was performed using a custom-synthesized DNA primer with a DNA sequencing reagent manufactured by PE Biosystem as directed in the manual, after which the DNA nucleic acid sequence was analyzed using a sequencer manufactured by the same company. The full-length nucleic acid sequence was finally established by completely overlapping the partial nucleic acid sequences determined by the above-described method. Next, the region of translation into protein was estimated from the determined full-length cDNA nucleic acid sequence, and the amino acid sequence was determined.

(2) Preparation of cDNA Libraries by the Oligocap Method and Sequence Analysis

1) Preparation of cDNA Libraries by the Oligocap Method

Being human fetal testis derived teratocarcinoma cells, NT-2 neuronal precursor cells (purchased from Stratagene), which can be differentiated into nerve cells by retinoic acid treatment, were used after being treated per the attached manual as follows.

NT-2 cells cultured without differentiation induction with retinoic acid (NT2RM)

NT-2 cells cultured, followed by differentiation induction by the addition of retinoic acid, then cultured for 2 days and 2 weeks (NT2RP)

Cultured human cell SK-N-MC (ATCC HTB-10) (SKNMC), cultured human cell Y79 (ATCC HTB-18) (Y79AA), cultured human cell GI1 (RCB RCB0763) (BGGI1), cultured human cell H4 (ATCC HTB-148) (BNGH4), cultured human cell IMR32 (ATCC CCL-127) (IMR32), and cultured human cell NB9 (RCB #RCB0477) (NB9N4) were cultured by the methods described in the catalogues thereof. RCB indicates that the cell line was supplied by the RIKEN Gene Bank—Cell Development Bank, and ATCC indicates that the cell line was supplied by the American Type Culture Collection.

The cultured cells of each line were collected, and by a method described in a literature document (J. Sambrook, E. F. Fritsch & T. Maniatis, Molecular Cloning Second edition, Cold Spring harbor Laboratory Press 1989), mRNAs were extracted. Furthermore, poly(A)+ RNAs were purified by means of oligo dT cellulose.

Likewise, from human placenta tissue (PLACE), human ovarian cancer tissue (OVARC), tissue rich in head portion from 10-week-gestational fetal human (HEMBA), tissue rich in trunk portion from 10-week-gestational fetal human (HEMBB), human mammary gland tissue (MAMMA), human thyroid tissue (THYRO), and human vascular endothelial tissue primary culture cell (VESEN), by a method described in a literature document (J. Sambrook, E. F. Fritsch & T. Maniatis, Molecular Cloning Second edition, Cold Spring harbor Laboratory Press, 1989), mRNAs were extracted. Furthermore, poly(A)+ RNAs were purified by means of oligo dT cellulose.

From all these poly(A)+ RNAs, by the oligocap method [M. Maruyama and S. Sugano, Gene, 138: 171-174 (1994)], respective cDNA libraries were prepared. Using an Oligo-cap linker (SEQ ID NO:1) and an Oligo dT primer (SEQ ID NO:2), as directed in a literature document [Suzuki and Sugano, Protein, Nucleic Acid and Enzyme, 41: 197-201 (1996), Y. Suzuki et al., Gene, 200: 149-156 (1997)], BAP (Bacterial Alkaline Phosphatase) treatment, TAP (Tobacco Acid Phosphatase) treatment, RNA ligation, synthesis of first strand cDNA and removal of RNA were performed. Next, using 5' (SEQ ID NO:3) and 3' (SEQ ID NO:4) PCR primers, the first strand cDNA was converted to a double-stranded cDNA by PCR (polymerase chain reaction), and cleaved with SfiI. Next, the cDNA was cloned into the vector pUC19FL3 (for some cases of NT2RM and NT2RP) or pME18SFL3 (GenBank AB009864, Expression vector), previously cleaved with DraIII, in a determined orientation of the cDNA, whereby a cDNA library was prepared.

The relationships between the names of the cDNA libraries used for 5'-terminal sequence analysis of the cDNAs and the derivations thereof are shown in Tables 1-1 to 1-6. The number of 5'-terminal sequences of the cDNAs in each cDNA library after mapping onto the human genome are also shown in Tables 1-1 to 1-6.

TABLE 1-1

| | Improved oligocap method | | number of 5'-terminal sequences (only those which permitted mapping onto human genome) |
|---|---|---|---|
| CORDB | Cord blood | Extraction of mRNAs from human tissues | 708 |

TABLE 1-1-continued

| | Improved oligocap method | | number of 5'-terminal sequences (only those which permitted mapping onto human genome) |
|---|---|---|---|
| CTONG | Tongue, Cancer | Extraction of mRNAs from human tissues | 31,371 |
| FCBBF | Brain, Fetal | Extraction of mRNAs from human tissues | 31,986 |
| NTONG | Tongue | Extraction of mRNAs from human tissues | 7,125 |
| OCBBF | Brain, Fetal | Extraction of mRNAs from human tissues | 47,574 |
| PLACE | Placenta | Extraction of mRNAs from human tissues | 33,231 |
| SYNOV | Synovial membrane tissue from rheumatoid arthritis | Extraction of mRNAs from human tissues | 27,489 |
| BRAMY | Brain, amygdala, CLONTECH #6574-1 | mRNAs from human tissues purchased as polyA(+) RNAs | 58,640 |
| BRCAN | Brain, caudate nucleus, CLONTECH #6575-1 | mRNAs from human tissues purchased as polyA(+) RNAs | 25,786 |
| BRCOC | Brain, corpus callosum, CLONTECH #6577-1 | mRNAs from human tissues purchased as polyA(+) RNAs | 16,718 |
| BRHIP | Brain, hippocampus, CLONTECH #6578-1 | mRNAs from human tissues purchased as polyA(+) RNAs | 57,918 |
| BRSSN | Brain, substantia nigra, CLONTECH #6580-1 | mRNAs from human tissues purchased as polyA(+) RNAs | 15,897 |
| BRSTN | Brain, subthalamic nucleus, CLONTECH #6581-1 | mRNAs from human tissues purchased as polyA(+) RNAs | 16,308 |
| BRTHA | Brain, thalamus, CLONTECH #6582-1 | mRNAs from human tissues purchased as polyA(+) RNAs | 53,267 |
| ADIPS | Adipose, Invitrogen #D6005-01 | mRNAs from human tissues purchased as total RNAs | 608 |
| ADRGL | Adrenal gland, CLONTECH #64016-1 | mRNAs from human tissues purchased as total RNAs | 10,223 |
| BEAST | Adult Breast, STARATAGENE #735044 | mRNAs from human tissues purchased as total RNAs | 2,731 |
| BLADE | Bladder, Invitrogen #D6020-01 | mRNAs from human tissues purchased as total RNAs | 8,431 |
| BRACE | Brain, cerebellum, CLONTECH #64035-1 | mRNAs from human tissues purchased as total RNAs | 82,880 |
| BRALZ | Brain, cortex, Alzheimer, Invitrogen #D6830-01 | mRNAs from human tissues purchased as total RNAs | 16,360 |
| BRASW | A library generated by subtracting cDNAs that overlap with the mRNA of BRAWH (Brain, whole, CLONTECH #64020-1) from a cDNA library prepared from the mRNA of BRALZ (Brain, cortex, Alzheimer, Invitrogen #D6830-01), using Subtract Kit (Invitrogen #K4320-01) (BRALZ-BRAWH) | mRNAs from human tissues purchased as total RNAs | 157 |
| BRAWH | Brain, whole, CLONTECH #64020-1 | mRNAs from human tissues purchased as total RNAs | 59,069 |
| CERVX | Cervix, Invitrogen #D6047-01 | mRNAs from human tissues purchased as total RNAs | 2,836 |

TABLE 1-2

| | Improved oligocap method | | number of 5'-terminal sequences (only those which permitted mapping onto human genome) |
|---|---|---|---|
| COLON | Colon, Invitrogen #D6050-0 | mRNAs from human tissues purchased as total RNAs | 8,398 |
| FEBRA | Brain, Fetal, CLONTECH #64019-1 | mRNAs from human tissues purchased as total RNAs | 23,578 |
| FEHRT | Heart, Fetal, STARATAGENE #738012 | mRNAs from human tissues purchased as total RNAs | 2,859 |
| FEKID | Kidney, Fetal, STARATAGENE #738014 | mRNAs from human tissues purchased as total RNAs | 2,747 |
| FELIV | Liver, Fetal, CLONTECH #64018-1 | mRNAs from human tissues purchased as total RNAs | 186 |
| FELNG | Lung, Fetal, STARATAGENE #738020 | mRNAs from human tissues purchased as total RNAs | 2,764 |
| HEART | Heart, CLONTECH #64025-1 | mRNAs from human tissues purchased as total RNAs | 8,889 |
| HLUNG | Lung, CLONTECH #64023-1 | mRNAs from human tissues purchased as total RNAs | 16,146 |
| KIDNE | Kidney, CLONTECH #64030-1 | mRNAs from human tissues purchased as total RNAs | 17,008 |
| LIVER | Liver, CLONTECH #64022-1 | mRNAs from human tissues purchased as total RNAs | 6,843 |
| MAMGL | Mammary Gland, CLONTECH #64037-1 | mRNAs from human tissues purchased as total RNAs | 182 |
| NESOP | Esophagus, Invitrogen #D6060-01 | mRNAs from human tissues purchased as total RNAs | 2,690 |
| NOVAR | Adult Ovary, STARATAGENE #735260 | mRNAs from human tissues purchased as total RNAs | 2,486 |
| PANCR | Pancreas, CLONTECH #64031-1 | mRNAs from human tissues purchased as total RNAs | 179 |
| PERIC | Pericardium, Invitrogen #D6105-01 | mRNAs from human tissues purchased as total RNAs | 8,781 |
| PROST | Prostate, CLONTECH #64038-1 | mRNAs from human tissues purchased as total RNAs | 16,671 |
| RECTM | Rectum, Invitrogen #D6110-01 | mRNAs from human tissues purchased as total RNAs | 2,723 |
| SALGL | Salivary Gland, CLONTECH #64026-1 | mRNAs from human tissues purchased as total RNAs | 183 |
| SKMUS | Skeletal Muscle, CLONTECH #64033-1 | mRNAs from human tissues purchased as total RNAs | 8,424 |
| SMINT | Small Intestine, CLONTECH #64039-1 | mRNAs from human tissues purchased as total RNAs | 16,767 |
| SPLEN | Spleen, CLONTECH #64034-1 | mRNAs from human tissues purchased as total RNAs | 33,950 |
| STOMA | Stomach, CLONTECH #64090-1 | mRNAs from human tissues purchased as total RNAs | 8,685 |
| TBAES | Breast, Tumor, CLONTECH #64015-1 | mRNAs from human tissues purchased as total RNAs | 8,416 |

TABLE 1-2-continued

| | Improved oligocap method | | number of 5'-terminal sequences (only those which permitted mapping onto human genome) |
|---|---|---|---|
| TCERX | Cervix, Tumor, CLONTECH #64010-1 | mRNAs from human tissues purchased as total RNAs | 2,797 |

TABLE 1-3

| | Improved oligocap method | | number of 5'-terminal sequences (only those which permitted mapping onto human genome) |
|---|---|---|---|
| TCOLN | Colon, Tumor, CLONTECH #64014-1 | mRNAs from human tissues purchased as total RNAs | 2,798 |
| TESOP | Esophageal, Tumor, Invitrogen #D6860-01 | mRNAs from human tissues purchased as total RNAs | 8,500 |
| TESTI | Testis, CLONTECH #64027-1 | mRNAs from human tissues purchased as total RNAs | 90,188 |
| THYMU | Thymus, CLONTECH #64028-1 | mRNAs from human tissues purchased as total RNAs | 70,578 |
| TKIDN | Kidney, Tumor, Invitrogen #D6870-01 | mRNAs from human tissues purchased as total RNAs | 15,970 |
| TLIVE | Liver, Tumor, Invitrogen #D6880-01 | mRNAs from human tissues purchased as total RNAs | 8,627 |
| TLUNG | Lung, Tumor, CLONTECH #64013-1 | mRNAs from human tissues purchased as total RNAs | 2,844 |
| TOVAR | Ovary, Tumor, CLONTECH #64011-1 | mRNAs from human tissues purchased as total RNAs | 2,722 |
| TRACH | Trachea, CLONTECH #64091-1 | mRNAs from human tissues purchased as total RNAs | 52,352 |
| TSTOM | Stomach, Tumor, Invitrogen #D6920-01 | mRNAs from human tissues purchased as total RNAs | 2,757 |
| TUTER | Uterus, Tumor, CLONTECH #64008-1 | mRNAs from human tissues purchased as total RNAs | 2,668 |
| UTERU | Uterus, CLONTECH #64029-1 | mRNAs from human tissues purchased as total RNAs | 49,561 |
| ACTVT | Activated T-cell | Extraction of mRNAs from primary culture human cells | 679 |
| ASTRO | Normal Human Astrocyte NHA5732, Takara Shuzo #CC2565 | Extraction of mRNAs from primary culture human cells | 17,162 |
| CD34C | CD34+ cell (AllCells, LLC #CB14435M) | Extraction of mRNAs from primary culture human cells | 1,420 |
| D3OST | CD34+ cells treated with osteoclast differentiation factor (ODF) to induce differentiation for 3 days | Extraction of mRNAs from primary culture human cells | 5,092 |
| D6OST | CD34+ cells treated with osteoclast differentiation factor (ODF) to induce differentiation for 6 days | Extraction of mRNAs from primary culture human cells | 888 |
| D9OST | CD34+ cells treated with osteoclast differentiation factor (ODF) to induce differentiation for 9 days | Extraction of mRNAs from primary culture human cells | 4,407 |

TABLE 1-3-continued

| | Improved oligocap method | | number of 5'-terminal sequences (only those which permitted mapping onto human genome) |
|---|---|---|---|
| DFNES | Normal Human Dermal Fibroblasts (Neonatal Skin; NHDF-Neo) NHDF2564, Takara Shuzo #CC2509 | Extraction of mRNAs from primary culture human cells | 10,103 |
| HCASM | HCASMC (Human coronary artery smooth muscle cells), Toyobo #T305K-05 | Extraction of mRNAs from primary culture human cells | 8,949 |

TABLE 1-4

| | Improved oligocap method | | number of 5'-terminal sequences(only those which permitted mapping onto human genome) |
|---|---|---|---|
| HCHON | HC (Human Chondrocytes), Toyobo #T402K-05 | Extraction of mRNAs from primary culture human cells | 9,397 |
| HHDPC | HDPC (Human dermal papilla cells), Toyobo #THPCK-001 | Extraction of mRNAs from primary culture human cells | 8,453 |
| HSYRA | HS-RA (Human synoviocytes from rheumatioid arthritis), Toyobo #T404K-05 | Extraction of mRNAs from primary culture human cells | 7,955 |
| LYMPB | Lymphoblast, EB virus transferred B cell | Extraction of mRNAs from primary culture human cells | 2,617 |
| MESAN | Normal human mesangial cells NHMC56046-2, Takara Shuzo | Extraction of mRNAs from primary culture human cells | 16,053 |
| NETRP | Neutrophil | Extraction of mRNAs from primary culture human cells | 9,170 |
| NHNPC | Normal human neural progenitor cells NHNP5958, Takara Shuzo | Extraction of mRNAs from primary culture human cells | 2,377 |
| PEBLM | Human peripheral blood mononuclear cells HPBMC5939, Takara Shuzo #CC2702 | Extraction of mRNAs from primary culture human cells | 7,900 |
| PUAEN | Human pulmonary artery endothelial cells, Toyobo #T302K-05 | Extraction of mRNAs from primary culture human cells | 10,544 |
| UMVEN | Human umbilical vein endothelial cells HUVEC, Toyobo | Extraction of mRNAs from primary culture human cells | 631 |
| 3NB69 | NB69 cell (RCB #RCB0480) | Extraction of mRNAs from cultured human cells | 8,153 |
| AHMSC | HMSC cell (Human mesenchymal cell) | Extraction of mRNAs from cultured human cells | 668 |
| BGGI1 | GI1 cell (Gioma separated from gliosarcoma; RCB #RCB0763) | Extraction of mRNAs from cultured human cells | 1,899 |
| BNGH4 | H4 cell (Neuroglioma; ATCC #HTB-148) | Extraction of mRNAs from cultured human cells | 7,699 |
| CHONS | Chondrocyte; Cell Applications, Inc. #1205F | Extraction of mRNAs from cultured human cells | 2,687 |
| ERLTF | TF-1 cell (erythroleukemia) | Extraction of mRNAs from cultured human cells | 2,169 |
| HELAC | HeLa cell (from cervical cancer) | Extraction of mRNAs from cultured human cells | 676 |
| IMR32 | IMR32 cell (Neuroblastoma; ATCC #CCL-127) | Extraction of mRNAs from cultured human cells | 16,867 |
| JCMLC | Leukemia, myelogenous | Extraction of mRNAs from cultured human cells | 2,156 |
| MESTC | Mesenchyme stem cell | Extraction of mRNAs from cultured human cells | 687 |

TABLE 1-5

| | Improved oligocap method | | number of 5'-terminal sequences(only those which permitted mapping onto human genome) |
|---|---|---|---|
| N1ESE | Mesenchymal stem cell | Extraction of mRNAs from cultured human cells | 2,624 |
| NB9N4 | NB9 cell (Neuroblastoma; RCB #RCB0477) | Extraction of mRNAs from cultured human cells | 1,759 |
| NCRRM | Embryonal carcinoma | Extraction of mRNAs from cultured human cells | 698 |
| NCRRP | Embryonal carcinoma treated with retinoic acid (RA) to induce differentiation | Extraction of mRNAs from cultured human cells | 691 |
| NT2NE | NT2 cell treated with RA and treated with a growth inhibitor to induce nerve differentiation, followed by nerve concentration and recovery (NT2 Neuron) | Extraction of mRNAs from cultured human cells | 16,337 |
| NT2RI | NT2 cell treated with RA to induce differentiation for 5 weeks, and thereafter treated with a growth inhibitor for 2 weeks | Extraction of mRNAs from cultured human cells | 32,662 |
| NT2RM | NT2 cell (STARATAGENE #204101) | Extraction of mRNAs from cultured human cells | 2,026 |
| NT2RP | NT2 cell treated with retinoic acid (RA) to induce differentiation for 5 weeks | Extraction of mRNAs from cultured human cells | 24,634 |
| NTISM | a library generated by subtracting cDNAs that overlap with the mRNA of undifferentiated NT2 cells from a cDNA library prepared from an mRNA of NT2 cell (STARATAGENE #204101) treated with RA to induce differentiation for 5 weeks, and thereafter treated with a growth inhibitor for 2 weeks, using Subtract Kit (Invitrogen #K4320-01) (NT2RI-NT2RM) | Extraction of mRNAs from cultured human cells | 180 |
| SKNMC | SK-N-MC cell (Neuroepithelioma; ATCC #HTB-10) | Extraction of mRNAs from cultured human cells | 7,607 |
| SKNSH | SK-N-SH cell (Neuroblastoma; RCB #RCB0426) | Extraction of mRNAs from cultured human cells | 8,662 |
| T1ESE | Mesenchymal stem cell treated with trichostatin and 5-azacytidine to induce differentiation | Extraction of mRNAs from cultured human cells | 2,685 |

TABLE 1-6

| | Oligocap method | | number of 5'-terminal sequences(only those which permitted mapping onto human genome) |
|---|---|---|---|
| HEMBA | tissue rich in head portion from 10-week-gestational fetal human (whole embryo, mainly head) | mRNAs from human tissues | 7,033 |
| HEMBB | tissue rich in trunk portion from 10-week-gestational fetal human (whole embryo, mainly body) | mRNAs from human tissues | 2,581 |
| MAMMA | Mammary Gland | mRNAs from human tissues | 2,987 |
| OVARC | Ovary, Tumor | mRNAs from human tissues | 2,058 |
| PLACE | Placenta | mRNAs from human tissues | 12,859 |
| THYRO | Thyroid gland | mRNAs from human tissues | 1,863 |

TABLE 1-6-continued

| | | | |
|---|---|---|---|
| VESEN | Human umbilical vein endothelial cells | Extraction of mRNAs from primary culture human cells | 1,309 |
| NB9N3 | NB9 cell (Neuroblastoma; RCB #RCB0477) | Extraction of mRNAs from cultured human cells | 96 |
| NT2RM | NT2 cell (STARATAGENE #204101) | Extraction of mRNAs from cultured human cells | 5,375 |
| NT2RP | NT2 cell treated with retinoic acid (RA) to induce differentiation for 2 days and 2 weeks | Extraction of mRNAs from cultured human cells | 14,608 |
| Y79AA | Y79 cell (Retinoblastoma; ATCC HTB-18) | Extraction of mRNAs from cultured human cells | 2,377 |
| BGGI1 | GI1 cell (Gioma separated from gliosarcoma; RCB #RCB0763) | Extraction of mRNAs from cultured human cells | 62 |
| BNGH4 | H4 cell (Neuroglioma; ATCC #HTB-148) | Extraction of mRNAs from cultured human cells | 89 |
| IMR32 | IMR32 cell (Neuroblastoma; ATCC #CCL-127) | Extraction of mRNAs from cultured human cells | 94 |
| SKNMC | SK-N-MC cell (Neuroepithelioma; ATCC #HTB-10) | Extraction of mRNAs from cultured human cells | 92 |

| | either oligocap method or improved oligocap method, not distinguished | | The number of the 5'-terminal sequences (only those which permitted mapping onto human genome) |
|---|---|---|---|
| BGGI1 | GI1 cell (Gioma separated from gliosarcoma; RCB #RCB0763) | Extraction of mRNAs from cultured human cells | 1 |
| BNGH4 | H4 cell (Neuroglioma; ATCC #HTB-148) | Extraction of mRNAs from cultured human cells | 3 |
| IMR32 | IMR32 cell (Neuroblastoma; ATCC #CCL-127) | Extraction of mRNAs from cultured human cells | 1 |
| SKNMC | SK-N-MC cell (Neuroepithelioma; ATCC #HTB-10) | Extraction of mRNAs from cultured human cells | 1 |
| NT2RM | NT2 cell (STARATAGENE #204101) | Extraction of mRNAs from cultured human cells | 48 |
| | Total | | 1,440,790 |

2) 5'-Terminal Sequence Analysis of cDNAs from cDNA Libraries Prepared by the Oligocap Method The 5'-terminal or 3'-terminal nucleic acid sequences of cDNAs acquired from each cDNA library, after a sequencing reaction using a DNA sequencing reagent (Dye Terminator Cycle Sequencing FS Ready Reaction Kit, dRhodamine Terminator Cycle Sequencing FS Ready Reaction Kit or BigDye Terminator Cycle Sequencing FS Ready Reaction Kit, manufactured by PE Biosystems) according to the manual, were analyzed for DNA nucleic acid sequences using a DNA sequencer (ABI PRISM 377, manufactured by PE Biosystems). For the data obtained, a database was constructed. The 5'-terminus full-length rate of each cDNA library prepared by the oligocap method was 60% on average (calculated with the protein coding region of a known mRNA as an index).

3) Full-Length cDNA Nucleic Acid Analysis

For cDNAs selected for full-length cDNA nucleic acid analysis, the nucleic acid sequence of each full-length cDNA was determined. The nucleic acid sequences were determined mainly by a primer walking method based on the dideoxy terminator method using a custom-synthesized DNA primer. Specifically, a sequencing reaction was performed using a custom-synthesized DNA primer with a DNA sequencing reagent manufactured by PE Biosystem as directed in the manual, after which the DNA nucleic acid sequence was analyzed using a sequencer manufactured by the same company. For some clones, a DNA sequencer manufactured by Licor was also utilized. For some cDNAs, no custom primer was used, but the shotgun method, in which cDNA-containing plasmids are randomly cleaved, was used with a DNA sequencer to determine the DNA nucleic acid sequence. The full-length nucleic acid sequence was finally established by completely overlapping the partial nucleic acid sequences determined by the above-described method. Next, the region of translation into protein was estimated from the determined full-length nucleic acid sequence, and the amino acid sequence was determined.

Example 2

Genome Mapping and Clustering (1) Sequence Data Set

The following sequences were used as a data set.

Human genome sequence: UCSC hg 17 (NCBI Build 35) (http://www.genome.ucsc.edu/)

Human full-length cDNAs, 19,265 sequences, newly acquired and subjected to full-length cDNA sequence analysis by us Out of human full-length cDNA sequences acquired and subjected to full-length cDNA sequence analysis by us, and registered with an existing public database (DDBJ/GenBank/EMBL) (accession numbers: AB038269, AB045981, AB056476, AB056477, AK000001 to AK002212, AK021413 to AK027260, AK027263 to AK027902, AK054561 to AK058202, AK074029 to AK074481, AK074483 to AK075325, AK075326 to AK075566, AK090395 to AK098842, AK122580 to AK129030, AK129488 to AK131107, AK131190 to AK131575, AK160364 to AK160386, AK172724 to AK172740, AK172741 to AK172866), 30,754 sequences that can be used for genome mapping 2039 sequences that had been registered with the database HUGE of Kazusa DNA Research Institute by Feb. 3, 2005 (http://www.kazusa.or.jp/huge/)

Human full-length cDNAs, 20,878 sequences, that had been listed on the Full Length Clone List on the website of Mammalian Gene Collection (http://mgc.nci.nih.gov/) and included in GenBank gbpri (ftp://ftp.ncbi.nih.gov/genbank/) by Jan. 30, 2005

Human full-length cDNAs, 9,280 sequences, that had been registered as Deutsches Krebsforschungszentrum (DKFZ) in GenBank gbpri before Jan. 30, 2005

Human full-length cDNAs, 13,984 sequences, being constituent sequences of the human RefSeq sequences of the Jan. 31, 2005 version (http://www.ncbi.nlm.nih.gov/RefSeq/), registered as mRNAs, and included in GenBank gbpri Human RefSeq sequences of the Jan. 31, 2005 version (http://www.ncbi.nlm.nih.gov/RefSeq/), 28,931 sequences Out of the human genome assemble sequences in Feb. 10, 2005 Ensembl (http://www.ensembl.org/) (NCBI35.nov_26.35), 33,666 sequences of NCBI35.nov_26.35 that had been mapped to the hg 17 human genome in UCSC (University of California, Santa Cruz, http://www.genome.ucsc.edu/)

Human cDNA 5'-terminal sequence, 1,456,213 sequences, and 3'-terminal sequence, 109,283 sequences, subjected to sequence analysis in our project (including published sequences with accession numbers: AU116788 to AU160826, AU279383 to AU280837, DA000001 to DA999999, DB000001 to DB384947)

(2) Genome Mapping

The above-described data set was subjected to genome mapping using BLASTN (ftp://ftp.ncbi.nih.gov/blast/), under the conditions of Identity of 95% or more and consensus length of 50 base pairs (bp) or more. About 99% of the sequences in the data set used for the mapping permitted genome mapping.

(3) Clustering

After the genome mapping, a sequence group contained in a genome region, as a single assembly, was allowed to form a cluster. Hence, each cluster was chosen in a way such that the outer sides of both ends of each genome region in the sequence group would not overlap the sequences mapped on each genome region. As a result, a total of 87,173 clusters existed. Therefrom, 17,535 clusters configured solely with human cDNA 3'-terminal sequences that were acquired and subjected to sequence analysis in our project were excluded, leaving 69,638 clusters. Of these clusters, 36,782 clusters were excluded since they were configured solely with human cDNA 5'-terminal sequences that were acquired and subjected to sequence analysis in our project (those having none of full-length cDNA, RefSeq, and Ensembl sequences were excluded). As a result, 32,856 clusters were found to comprise at least one of full-length cDNAs, RefSeq, and Ensembl sequences. By selecting clusters comprising one or more of full-length cDNAs, RefSeq, and Ensembl sequences, which are expected to have an ORF (open reading frame, coding region) with a reliability above a given level, 21,703 clusters were acquired. For these 21,703 clusters, expression specificity was determined.

Example 3

Experimental Procedures for Real-Time PCR (1) Synthesis of Template cDNAs
1) Human mRNA (Human Total RNA) Used as Template A reaction was carried out with 50 µg of Human Total RNA per 150 µl of the system.

To 50 µg of Total RNA dissolved in 87 µl of $H_2O$, 10 µl of a random primer (concentration 65 ng/µl) and 7.5 µl of dNTP Mix (concentration 10 mM each dNTP Mix) were added. This was followed by incubation at 65° C. for 5 minutes and on ice for 1 minute. 30 µl of 5× reaction buffer solution (attached to the Invitrogen SuperScript III RT kit) and 7.5 µl of 0.1M DTT and 3 µl of RNase Inhibitor (STRATAGENE) and 5 µl of SuperScript III RT (Invitrogen) were added. This was followed by incubation at 25° C. for 5 minutes, incubation at 50° C. for 60 minutes, and incubation at 70° C. for 15 minutes. After the reaction, phenol-chloroform extraction was performed to deactivate the enzyme. By adding 3 µl of EDTA (0.5M) and 22.5 µl of 0.1N NaOH, alkali treatment was performed to degradate the RNA. After 30 µl of Tris (1M pH 7.8) was added to neutralize the reaction liquid, ethanol precipitation was performed, and the precipitate was dissolved in 100 µl of TE buffer solution.

Human mRNAs from the mRNA sources (Human Total RNAs) were acquired by the method described in Example 1.

A list of the human mRNAs used in the experiments is shown in Table 2.

TABLE 2

| | Human total RNA purchased | Product name | Manufacturer | Catalog number |
|---|---|---|---|---|
| 1 | Bone Marrow | Human Bone Marrow Total RNA | Clontech | 636548 |
| 2 | Brain, whole | Human Brain Total RNA | Clontech | 636530 |
| 3 | Heart | Human Heart Total RNA | Clontech | 636532 |
| 4 | Kidney | Human Kidney Total RNA | Clontech | 636529/636514 |
| 5 | Liver | Human Liver Total RNA | Clontech | 636531 |
| 6 | Lung | Human Lung Total RNA | Clontech | 636524 |
| 7 | Thymus | Human Thymus Total RNA | Clontech | 636549 |
| 8 | Uterus | Human Uterus Total RNA | Clontech | 636551/636513 |
| 9 | Spinal Cord | Human Spinal Cord Total RNA | Clontech | 636554 |
| 10 | Colon | Human Colon Total RNA | Clontech | 636521 |
| 12 | Colon Tumor | Human Colon Tumor Total RNA | Clontech | 636634 |
| 13 | Kidney Tumor | Human Kidney Tumor Total RNA | Clontech | 636632 |
| 14 | Liver Tumor | Human Liver Total RNA | CHEMICOM | RNA569 |
| 15 | Lung Tumor | Human Lung Tumor Total RNA | Clontech | 636633 |
| 16 | Ovary | Human Ovary Total RNA | Clontech | 636555 |
| 17 | Ovary Tumor | Human Ovary Tumor Total RNA | Clontech | 636631 |

TABLE 2-continued

| | | | |
|---|---|---|---|
| 18 Spleen | Human Spleen Total RNA | Clontech | 636525 |
| 19 Stomach | Human Stomach Total RNA | Clontech | 636522 |
| 20 Stomach Tumor | Human Stomach Tumor Total RNA | Clontech | 636629 |
| 21 Uterus Tumor | Human Uterus Tumor Total RNA | Clontech | 636628 |

| | Extraction of human total RNA from an RNA source | Explanation of the derivation of mRNA |
|---|---|---|
| 1 | Tongue (normal) | Normal tongue tissue |
| 2 | Tongue Tumor | Tongue tumor tissue |

(2) Design of Primers and Probes

Using Primer Express software 3.0, the primer design software attached to the Applied Biosystems real-time PCR 7500 Fast, with the sequences of portions that serve as the borders of the changing region, primers and probes were designed to allow the individual detection of cDNAs having other splice patterns transcribed from the same chromosome region as the cDNA to be comparatively examined under the conditions recommended by the software. Using the designed primers, real-time PCR was performed, and they were confirmed to produce a single band and to be capable of specifically detecting only one kind of cDNA.

(3) Expressional Analysis Using Real-Time PCR
1) mRNAs Used

The experiments on the five clusters chr12-1158, chr7-927, chr6-836, chr1+2890, and chr1-1273, out of the 8 experimental systems, were performed using SYBR GREEN as a real-time PCR reaction system and, as template cDNAs, Colon, Colon Tumor, Kidney, Kidney Tumor, Liver, Liver Tumor, Lung, Lung Tumor, Ovary, Ovary Tumor, Stomach, Stomach Tumor, Uterus, Uterus Tumor, Tongue (normal), Tongue Tumor, Brain (whole), blood cell type mixture (Mix, blood cells and related tissues) [Bone Marrow, Thymus, Spinal Cord, Spleen], and internal organ tissue mixture (Mix, viscous tissues) [Heart, Kidney, Liver, Lung, Colon, Stomach].

The experiments on the three clusters chr3-353, chrX-148, and chr9-1456 were performed using TaqMan manufactured by Applied Biosystems as a real-time PCR reaction system and using Colon, Colon Tumor, Kidney, Kidney Tumor, Liver, Liver Tumor, Lung (whole), Lung Tumor, Ovary, Ovary Tumor, Stomach, Stomach Tumor, Uterus, Uterus Tumor, Tongue (normal), Tongue Tumor, Brain (whole), blood cell type mixture (Mix, blood cells and related tissues) [Bone Marrow, Thymus, Spinal Cord, Spleen].

2) Reaction System Using SYBR GREEN

The SYBR GREEN I Dye assay chemistry is an experimental system based on the characteristic of SYBR GREEN to emit strong fluorescence by binding to a double-stranded DNA. When the DNA denatures to single-stranded during the PCR reaction, SYBR GREEN leaves from the DNA and the fluorescence decreases rapidly; however, with the subsequent annealing/extension reaction, it binds to the double-stranded DNA to emit fluorescence again. In the SYBR GREEN I Dye assay chemistry, fluorescence intensity, which increases with every PCR cycle, is detected.

To a cDNA derived from each tissue, 0.2 µl (equivalent to 100 ng of Total RNA), as the template, Forward Primer (final concentration 250 nM), Reverse Primer (final concentration 250 nM), and SYBR Green PCR Master Mix (ABI 4309155) were added, to make a total volume of 20 µl. For endogenous control, GAPDH (Accession No; NM_002046.2) always served as a reaction control for all templates.

A PCR was performed under the conditions shown below, which represent the standard protocol for Applied Biosystems real-time PCR 7500 Fast. After an initial step at 50° C. for 2 minutes and at 95° C. for 10 minutes, denaturation at 95° C. for 15 seconds and annealing elongation at 60° C. for 1 minute were repeated in 40 cycles.
GAPDH-F (SEQ ID NO:5): Forward Primer for endogenous control GAPDH
GAPDH-R (SEQ ID NO:6): Reverse Primer for endogenous control GAPDH
3) Reaction System Using Taqman The TaqMan assay chemistry is an experimental system employing the TaqMan probe, a probe phosphorylated at the 3' terminus and labeled with a Fluorescenin-series fluorescent dye (reporter) at the 5' terminus, and a Rhodamine-series fluorescent dye (quencher) at the 3' terminus. When the TaqMan probe occurs alone, the fluorescence energy of the reporter is consumed as excitation energy for the quencher, and the fluorescence of the reporter is suppressed, because the fluorescence wavelength is close to that of the quencher even if reporter excitation light is irradiated. However, when the TaqMan probe is degradated by the 5'-3' exonuclease activity of DNA polymerase during the elongation from the primer in the PCR reaction, the fluorescent dye of the reporter leaves from the 5' terminus of the TaqMan probe, and the distance from the fluorescent dye of the quencher increases, resulting in the emission of fluorescence. In the TaqMan assay chemistry, the fluorescence intensity from the reporter, which increases with every PCR cycle, is detected.

To 0.2 µl (equivalent to 100 ng as converted to Total RNA) of a cDNA derived from each tissue as a template, Forward Primer (final concentration 900 nM), Reverse Primer (final concentration 900 nM), TaqMan Probe (final concentration 250 nM), and TaqMan Fast Universal PCR Master Mix (ABI 466073) were added, to make a total volume of 20 µl. For endogenous control, GAPDH always served as a reaction control for all templates.

A PCR was performed under the conditions shown below, which represent the Fast protocol for Applied Biosystems real-time PCR 7500 Fast. After enzyme activation 95° C. for 20 seconds, denaturation at 95° C. for 3 seconds and annealing elongation at 60° C. for 30 seconds were repeated in 40 cycles. GAPDH-Probe (SEQ ID NO:7): TaqMan Probe for endogenous control GAPDH (4) Method of Statistical Analysis of Data The results were analyzed using a relative quantitation method.

Using the RQ study software for Applied Biosystems real-time PCR 7500 Fast, a threshold was set in an exponential functional amplification region of the amplification curve. The number of cycles at that time was used as the Ct (threshold cycle). To make a correction for initial RNA content, the Ct of the endogenous control GAPDH was subtracted from the Ct obtained, and this value was used as the dCt [dCt=Target Ct−ENDOGENOUS Ct (GAPDH)]. The dCt of the sample serving as the reference standard (control) was further subtracted from the dCt obtained, and this value was used as the ddCt [ddCt=Target dCt−Control dCt]. On the basis of this value, relative value was calculated, and this was used as the RQ[RQ=$2^{-ddCt}$]. On the basis of this result, a logarithmic graph was generated, and the amounts amplified and hence expression levels with each primer and probe were compared.

In each Example, analytical results for RQ and $Log_{10}$ RQ are shown. RQ values are shown to the first decimal point. For samples not allowing detection by real-time PCR, "Undet." was written in the fields for RQ value and the value of $Log_{10}$ RQ. $Log_{10}$ RQ values are shown to the second decimal point. However, for the blood cell type mixture (Mix, blood cells and related tissues) (RQ value "1.0") as a control, "0.0" was written in the field for $Log_{10}$ RQ values.

Example 4

Cluster chr1+2890 (Data Set: 127)

(1) Cluster Analysis
1) Cluster Characteristics

An analysis was performed on 9 sequences of full-length cDNAs subjected to genome mapping onto the cluster chr1+2890 (Human genome UCSC hg18 (NCBI Build34) chromosome 1, 167,790,000 bp to 167,820,000 bp) [D-LIVER2001680.1, D-LIVER2008912.1, Z-TLIVE2004966-01, ENST00000008553, M83772.1, NM_001002294.1, NM_006894.4, Z47552.1, BC032016.1]. They were classifiable according to expression pattern difference into the following 3 kinds.
[1] D-LIVER2001680.1
[2] D-LIVER2008912.1
[3] ENST00000008553, M83772.1, NM_001002294.1, NM_006894.4, Z47552.1, BC032016.1

[1] and [2] are cDNAs that were newly acquired and subjected to full-length cDNA sequence analysis by us, having a different ORF from that of [3], which is registered with a public DB (DDBJ/Genbank/EMBL).

[1], compared with the known [3], had a different ORF region because of the insertion of an exon different from other patterns in the ORF region.

[2], compared with the known [3], had a different ORF region because of the insertion of an exon different from other patterns in the ORF region.

It was found that the ORF regions present in the 3 kinds of cDNA patterns [1] to [3] have different splice patterns due to exon insertion, from the same chromosome region, resulting in alterations of the amino acid sequences to produce diverse proteins and mRNAs.
2) Characteristics of D-LIVER2001680.1 ([1]), which was Newly Subjected to Full-Length cDNA Sequence Analysis by Us
127_[1]_1-N0 (SEQ ID NO:8): The entire nucleic acid sequence region of D-LIVER2001680.1
127_[1]_1-NA0 (SEQ ID NO:9): Both the entire nucleic acid sequence region and amino acid sequence of D-LIVER2001680.1
127_[1]_1-A0 (SEQ ID NO:10): The entire amino acid sequence region of D-LIVER2001680.1

This is a variant in which a 138-base exon (SEQ ID NO:11) is inserted into the region at the 208th to 209th bases of NM_006894.4, which is registered with an existing public DB and serves for control, and the translation initiation point shifts toward the 3' side relative to NM_006894.4, and the translation initiation point is present on the inserted exon region. The N-terminal amino acids differed by 24 residues (SEQ ID NO:12), compared with NM_006894.4.
127_[1]_1-N1 (SEQ ID NO:11): A 138-base insert nucleic acid sequence region of D-LIVER2001680.1
127_[1]_1-A1 (SEQ ID NO:12): A 24-residue insert amino acid sequence region of D-LIVER2001680.1
127_[1]_1-N2 (SEQ ID NO:13): An ORF nucleic acid sequence region in the 138-base insert region of D-LIVER2001680.1
127_[1]_1-A2 (identical to SEQ ID NO:12): An ORF amino acid sequence region in the 138-base insert region of D-LIVER2001680.1

A calculation for estimating transmembrane domains with the use of SOSUI (http://bp.nuap.nagoya-u.ac.jp/sosui/) showed that transmembrane domains were present at two positions, i.e., the 5th to 27th amino acids and the 510th to 532nd amino acids of NM_006894.4; however, in D-LIVER2001680.1, because the translation initiation point differed from that in NM_006894.4, and existed in the exon region inserted, the transmembrane region at the 5th to 27th amino acids had disappeared.
3) Characteristics of D-LIVER2008912.1 ([2]), which was Newly Subjected to Full-Length cDNA Sequence Analysis by Us
3)-1
127_[2]_1-N0 (SEQ ID NO:14): The entire nucleic acid sequence region of D-LIVER2008912.1
127_[2]_1-NA0 (SEQ ID NO:15): Both the entire nucleic acid sequence region of D-LIVER2008912.1 and amino acid sequence with the 88th base as the translation initiation point
127_[2]_1-A0 (SEQ ID NO:16): The entire amino acid sequence region of D-LIVER2008912.1 with the 88th base as the translation initiation point This is a variant in which a 609-base exon (SEQ ID NO:17) is inserted into the region at the 208th to 209th by of NM_006894.4, which is registered with an existing public DB and serves for control; because of the emergence of a stop codon on the insert sequence to cause the ORF to be terminated on the insert sequence, although the translation initiation point did not change, the C-terminal amino acids differed by 36 residues (SEQ ID NO:18) from NM_006894.4.
127_[2]_1-N1 (SEQ ID NO:17): A 609-base insert nucleic acid sequence region of D-LIVER2008912.1
127_[2]_1-A1 (SEQ ID NO:18): A 36-residue insert amino acid sequence region of D-LIVER2008912.1
127_[2]_1-N 2 (SEQ ID NO:19): An ORF nucleic acid sequence region in the 609-base insert region of D-LIVER2008912.1
127_[2]_1-A2 (identical to SEQ ID NO:18): An ORF amino acid sequence region in the 609-base insert region of D-LIVER2008912.1

With this change, "Flavin-binding monooxygenase like", the Pfam motif present at the 2nd to 532nd amino acids of NM_006894.4, disappeared (http://pfam.janelia.org/).

The transmembrane domains present at the two positions of the 5th to 27th amino acids and the 510th to 532nd amino acids of NM_006894.4, observed in the calculation for estimating transmembrane domains with the use of SOSUI, had disappeared.
3)-2
127_[2]_2-N0 (identical to SEQ ID NO:14): The entire nucleic acid sequence region of D-LIVER2008912.1

127_[2]_2-NA0 (SEQ ID NO:20): Both the entire nucleic acid sequence region of D-LIVER2008912.1 and amino acid sequence with the 191st base as the translation initiation point
127_[2]_2-A0 (SEQ ID NO:21): The entire amino acid sequence region of D-LIVER2008912.1 with the 191st base as the translation initiation point A variant in which a 609-base exon (SEQ ID NO:17) is inserted into the region at the 208th to 209th by of NM_006894.4, which is registered with an existing public DB and serves for control; because of the translation initiated from the translation initiation point of a different frame to cause the ORF to be terminated on the insert exon, the entire amino acid sequence region changed, resulting in an amino acid sequence lacking homology to NM_006894.4.

127_[2]_2-N1 (SEQ ID NO:22): An ORF nucleic acid sequence region in the 609-base insert region of D-LIVER2008912.1
127_[2]_2-A1 (identical to SEQ ID NO:20 and SEQ ID NO:21): An ORF amino acid sequence region altered by the 609-base insert region of D-LIVER2008912.1

With this change, "Flavin-binding monooxygenase like", the Pfam motif present at the 2nd to 532nd amino acids of NM_006894.4, disappeared.

The transmembrane domains present at the two positions of the 5th to 27th amino acids and the 510th to 532nd amino acids of NM_006894.4, observed in the calculation for estimating transmembrane domains with the use of SOSUI, had disappeared.

4) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

127_01: A region specifically extracted by means of the sequence information on regions with an exon insertion of the cDNA pattern [1]: an ORF-altering exon insert region in the cDNA pattern [1], which was newly acquired and subjected to full-length cDNA sequence analysis by us
→Fragment 127_01 (SEQ ID NO:25) amplified by Primer127_01F (SEQ ID NO:23) and Primer127_01R (SEQ ID NO:24) 127_02: A region specifically extracted by means of the sequence information on regions with an exon insertion of the cDNA pattern [2]: an ORF-altering exon insert region in the cDNA pattern [2], which was newly acquired and subjected to full-length cDNA sequence analysis by us
→Fragment 127_02 (SEQ ID NO:28) amplified by Primer127_02F (SEQ ID NO:26) and Primer127_02R (SEQ ID NO:27) 127_03: A specific region that is distinguishable from both the insert regions [1] and [2] of the cDNA pattern [3], which is registered with an existing public DB, serving as a control for comparing [1] and [2]
→Fragment 127_03 (SEQ ID NO:31) amplified by Primer127_03F (SEQ ID NO:29) and Primer127_03R (SEQ ID NO:30) 127_04: A common region shared by all of [1] to [3]: a region common to all patterns, serving for control to compare the overall expression levels of the cDNA patterns [1] and [2], which were newly acquired and subjected to full-length cDNA sequence analysis by us, and the cDNA pattern [3], which is registered with an existing public DB
→Fragment 127_04 (SEQ ID NO:34) amplified by Primer127_04F (SEQ ID NO:32) and Primer127_04R (SEQ ID NO:33)

By mapping the 5'-terminal sequences of about 1.44 million sequences acquired using the oligocap method onto the human genome sequence, and comparatively analyzing them, the exon regions specific for the cDNA patterns [1] to [3] shown above, respectively, were found to be expressed at the following frequencies.

In the cDNA pattern [1], which was newly analyzed by us, two 5'-terminal sequences were present, the derivations thereof being Liver for 1 sequence (analytical parameter 6,843), and Liver Tumor for 1 sequence (analytical parameter 8,627).

In the cDNA pattern [2], which was newly analyzed by us, two 5'-terminal sequences were present, the derivations thereof being Liver for 1 sequence (analytical parameter 6,843), and Liver Tumor for 1 sequence (analytical parameter 8,627).

In the pattern [3], which is registered with an existing public DB and serves for control, twenty-eight 5'-terminal sequences were present, the derivations thereof being Thalamus for 8 sequences (analytical parameter 53,267), Liver Tumor for 7 sequences (analytical parameter 8,627), Liver for 6 sequences (analytical parameter 6,843), Amygdala for 2 sequences (analytical parameter 58,640), Breast for 2 sequences (analytical parameter 2,731), Corpus Callosum for 1 sequence (analytical parameter 16,718), Pericardium for 1 sequence (analytical parameter 8,781), and Trachea for 1 sequence (analytical parameter 52,352).

From these results, it was found that the exon insertion pattern [1] was abundantly expressed in Liver and Liver Tumor. It was also found that the exon insertion pattern [2] was also abundantly expressed in Liver and Liver Tumor. In the known pattern [3], expression was observed in Liver, Liver Tumor, Thalamus, Amygdala, Breast and the like. Hence, it was thought that in this chromosome region, a selection mechanism for mRNA pattern changes resulting in an amino acid sequence alteration due to exon selectivity and the expression of different proteins might arise, as in the patterns [1] and [2], in a particular tissue.

(2) Expression Specificity Analysis by Real-Time PCR

Hence, to detect protein expression or mRNA expression diversity changes due to exon selectivity among different tissues, details of expression levels were analyzed by real-time PCR. The results are shown in Table 3.

TABLE 3

|  | RQ Score | | | | $Log_{10}$RQ Score | | | |
| --- | --- | --- | --- | --- | --- | --- | --- | --- |
|  | 127_01 | 127_02 | 127_03 | 127_04 | 127_01 | 127_02 | 127_03 | 127_04 |
| 01 Colon | 0.0 | 0.3 | 0.1 | 0.2 | −1.39 | −0.56 | −1.00 | −0.74 |
| 02 Colon Tumor | Undet. | Undet. | Undet. | 0.0 | Undet. | Undet. | Undet. | −1.40 |
| 03 Kidney | 1.1 | 1.1 | 2.4 | 2.0 | 0.05 | 0.04 | 0.38 | 0.30 |
| 04 Kidney Tumor | 0.3 | 0.2 | 1.1 | 0.7 | −0.58 | −0.75 | 0.06 | −0.16 |
| 05 Liver | 268.2 | 200.4 | 395.6 | 237.5 | 2.43 | 2.30 | 2.60 | 2.38 |
| 06 Liver Tumor | 446.3 | 254.2 | 280.5 | 174.4 | 2.65 | 2.40 | 2.45 | 2.24 |

TABLE 3-continued

| | RQ Score | | | | Log₁₀RQ Score | | | |
|---|---|---|---|---|---|---|---|---|
| | 127_01 | 127_02 | 127_03 | 127_04 | 127_01 | 127_02 | 127_03 | 127_04 |
| 07 Lung | 1.7 | 2.4 | 5.4 | 14.3 | 0.23 | 0.38 | 0.73 | 1.16 |
| 08 Lung Tumor | 0.0 | 0.2 | 0.1 | 0.1 | −1.74 | −0.71 | −1.19 | −0.88 |
| 09 Ovary | 0.0 | 1.7 | 0.1 | 0.5 | −1.31 | 0.23 | −1.04 | −0.32 |
| 10 Ovary Tumor | 0.1 | 1.5 | 0.1 | 0.6 | −1.05 | 0.18 | −1.07 | −0.21 |
| 11 Stomach | 3.8 | 9.9 | 7.3 | 6.3 | 0.58 | 1.00 | 0.87 | 0.80 |
| 12 Stomach Tumor | 0.0 | 0.0 | 0.2 | 0.6 | −1.60 | −1.38 | −0.64 | −0.26 |
| 13 Uterus | 0.6 | 0.8 | 1.1 | 1.2 | −0.20 | −0.12 | 0.02 | 0.08 |
| 14 Uterus Tumor | 0.4 | 0.4 | 0.6 | 1.0 | −0.42 | −0.35 | −0.25 | 0.00 |
| 15 Tongue | 0.1 | 4.9 | 1.7 | 2.6 | −0.88 | 0.69 | 0.23 | 0.41 |
| 16 Tongue Tumor | 0.2 | 2.0 | 0.5 | 1.1 | −0.72 | 0.31 | −0.33 | 0.03 |
| 17 Brain, whole | 0.3 | 0.8 | 0.3 | 0.5 | −0.59 | −0.08 | −0.46 | −0.34 |
| 18 Mix, blood cells and related tissues | 1.0 | 1.0 | 1.0 | 1.0 | 0.0 | 0.0 | 0.0 | 0.0 |

Expression levels were compared between tumor tissues and normal tissues using the 8 kinds of organs shown in Example 3. The expression was also compared with the blood cell mixture (Mix, blood cells and related tissues) and brain sample shown in Example 3 as experimental controls.

A wide difference was observed in two kinds of organs: Tongue and Liver. For the other organs, like the increase or decrease in the amplification of the fragment 127_04 (SEQ ID NO:34), which is common to all patterns, the amplification of the fragments of the other patterns increased or decreased (Table 3).

In Tongue, comparing normal tissues and tumor tissues, only the newly analyzed expression pattern 127_01 (SEQ ID NO:25) was more abundantly expressed in tumor tissues than in normal tissues, whereas the expression pattern shown by 127_02 (SEQ ID NO:28), and the pattern 127_03 (SEQ ID NO:31), which was registered with an existing public DB, were more abundantly expressed in normal tissues than in tumor tissues (Table 3).

In Liver, comparing normal tissues and tumor tissues, the newly analyzed expression patterns shown by 127_01 (SEQ ID NO:25) and 127_02 (SEQ ID NO:28) were more abundantly expressed in tumor tissues than in normal tissues, whereas the pattern 127_03 (SEQ ID NO:31), which was registered with an existing public DB, was abundantly expressed in normal tissues than in tumor tissues (Table 3).

These results demonstrated that by using the newly acquired cDNA regions 127_[1]_1-N1 (SEQ ID NO:11) and 127_[2]_1-N1 (SEQ ID NO:17) shown by the detection regions 127_01 (SEQ ID NO:25) and 127_02 (SEQ ID NO:28) as tumor markers, it is possible to use the cDNA regions as diagnostic/therapeutic markers for the two kinds of tumors of Liver and Tongue. It also seems possible to develop a new drug by means of a compound, antibody, siRNA or the like that targets a region that exhibits specificity.

The following regions also seem to be useful as diagnostic/therapeutic markers.
Upstream sequence 127_[1]_1_N3 (SEQ ID NO:35), which comprises the 370th to 394th bases primed by Primer127_01R (SEQ ID NO:24) in D-LIVER2001680.1 of the cDNA pattern [1]
Upstream sequence 127_[2]_1-N3 (SEQ ID NO:36), which comprises the 295th to 315th bases primed by Primer127_02R (SEQ ID NO:27) in D-LIVER2008912.1 of the cDNA pattern [2]
Region 127_01 (SEQ ID NO:25) amplified by Primer127_01F (SEQ ID NO:23) and Primer127_01R (SEQ ID NO:24) in the cDNA pattern [1]
Region 127_02 (SEQ ID NO:28) amplified by Primer127_02F (SEQ ID NO:26) and Primer127_02R (SEQ ID NO:27) in the cDNA pattern [2]

Example 5

Cluster chr12-1158 (Data Set: 087)

(1) Cluster Analysis
1) Cluster Characteristics
An analysis was performed on 10 sequences of full-length cDNAs subjected to genome mapping onto the chr12-1158 (Human genome UCSC hg18 (NCBI Build34) chromosome 12, 51,890,000 bp to 51,915,000 bp) [D-HCHON2007878.1, D-NTONG2006230.1, D-SPLEN2005548.1, D-FCBBF3007219.1, D-HCHON2002384.1, BC019098.2, ENST00000327550, ENST00000338561, M24857.1, NM_000966.3]. They were classifiable according to expression pattern difference into 5 kinds, which mainly included the following 2 kinds with a focus on their transcription initiation points.
[1] D-HCHON2007878.1, D-NTONG2006230.1, D-SPLEN2005548.1, ENST00000338561
[2] D-HCHON2002384.1, BC019098.2, ENST00000327550, M24857.1, NM_000966.3

Of the sequences belonging to [1], D-HCHON2007878.1, D-NTONG2006230.1, and D-SPLEN2005548.1 are cDNAs that were newly acquired and subjected to full-length cDNA sequence analysis by us, having a transcription initiation point different from that of [2], which was registered with an existing public DB (DDBJ/Genbank/EMBL), and having a different ORF.

[1] had a different amino acid sequence region, because of the expression thereof from a chromosome region located downstream of the known [2].

It was found that the ORF regions present in the 2 kinds of cDNA patterns [1] to [2] cause expression starting at different transcription initiation points, from the same chromosome region, resulting in alterations of the amino acid sequences on the N-terminal side to produce diverse proteins and mRNAs.
2) Characteristics of D-HCHON2007878.1 ([1]), which was Newly Acquired and Subjected to Full-Length cDNA Sequence Analysis by Us
087_[1]_1-N0 (SEQ ID NO:37): The entire nucleic acid sequence region of D-HCHON2007878.1
087_[1]_1-NA0 (SEQ ID NO:38): Both the entire nucleic acid sequence region and amino acid sequence of D-HCHON2007878.1

087_[1]_1-A0 (SEQ ID NO:39): The entire amino acid sequence region of D-HCHON2007878.1

The sequence at the 1st to 309th bases of D-HCHON2007878.1 (SEQ ID NO:40) is an exon that is not present in NM_000966.3, which is registered with an existing public DB and serves for control, lacking homology to NM_000966.3. Because the translation initiation point is present on this exon, the amino acids on the N-terminal side changed by 50 residues (SEQ ID NO:41).

087_[1]_1-N1 (SEQ ID NO:40): A 309-base insert nucleic acid sequence region of D-HCHON2007878.1

087_[1]_1-A1 (SEQ ID NO:41): A 50-residue insert amino acid sequence region of D-HCHON2007878.1

087_[1]_1-N2 (SEQ ID NO:42): An ORF nucleic acid sequence region in the 309-base insert region of D-HCHON2007878.1

087_[1]_1-A2 (identical to SEQ ID NO:41): An ORF amino acid sequence region in the 309-base insert region of D-HCHON2007878.1

3) Characteristics of D-NTONG2006230.1 ([1]), which was Newly Acquired and Subjected to Full-Length cDNA Sequence Analysis by Us 087_[1]_2-N0 (SEQ ID NO:43): The entire nucleic acid sequence region of D-NTONG2006230.1

087_[1]_2-NA0 (SEQ ID NO:44): Both the entire nucleic acid sequence region and amino acid sequence of D-NTONG2006230.1

087_[1]_2-A0 (SEQ ID NO:45): The entire amino acid sequence region of D-NTONG2006230.1

The sequence at the 1st to 187th bases of D-NTONG2006230.1 (SEQ ID NO:46) is an exon that is not present in NM_000966.3, which is registered with an existing public DB and serves for control, lacking homology to NM_000966.3. Because the translation initiation point is present on this exon, the amino acids on the N-terminal side changed by 50 residues (SEQ ID NO:47).

087_[1]_2-N1 (SEQ ID NO:46): A 187-base insert nucleic acid sequence region of D-NTONG2006230.1

087_[1]_2-A1 (SEQ ID NO:47): A 50-residue insert amino acid sequence region of D-NTONG2006230.1

087_[1]_2-N2 (SEQ ID NO:48): An ORF nucleic acid sequence region in the 187-base insert region of D-NTONG2006230.1

087_[1]_2-A2 (identical to SEQ ID NO:47): An ORF amino acid sequence region in the 187-base insert region of D-NTONG2006230.1

4) Characteristics of D-SPLEN2005548.1 ([1]), which was Newly Acquired and Subjected to Full-Length cDNA Sequence Analysis by Us 087_[1]_3-N0 (SEQ ID NO:49): The entire nucleic acid sequence region of D-SPLEN2005548.1

087_[1]_3-NA0 (SEQ ID NO:50): Both the entire nucleic acid sequence region and amino acid sequence of D-SPLEN2005548.1

087_[1]_3-A0 (SEQ ID NO:51): The entire amino acid sequence region of D-SPLEN2005548.1

The sequence at the 1st to 430th bases of D-SPLEN2005548.1 (SEQ ID NO:52) is an exon that is not present in NM_000966.3, which is registered with an existing public DB and serves for control, lacking homology to NM_000966.3. Also, a 28-base exon is inserted into the region at the 762nd to 763rd bases of NM_000966.3 (SEQ ID NO:53). With these changes, the amino acids on the N-terminal side differed by 148 residues (SEQ ID NO:54), compared with the ORF of NM_000966.3.

087_[1]_3-N1 (SEQ ID NO:52): A 430-base insert nucleic acid sequence region of D-SPLEN2005548.1

087_[1]_3-N2 (SEQ ID NO:53): A 28-base insert nucleic acid sequence region of D-SPLEN2005548.1

087_[1]_3-A1 (SEQ ID NO:54): An altered 148-residue amino acid sequence region of D-SPLEN2005548.1

087_[1]_3-N3 (SEQ ID NO:55): An ORF nucleic acid sequence to region in the 430-base insert region of D-SPLEN2005548.1

087_[1]_3-A2 (SEQ ID NO:56): An ORF amino acid sequence region related to the 430-base insert region of D-SPLEN2005548.1

087_[1]_3-N4 (identical to SEQ ID NO:53): An ORF nucleic acid sequence region in the 28-base insert region of D-SPLEN2005548.1

087_[1]_3-A3 (SEQ ID NO:57): An ORF amino acid sequence region related to the 28-base insert region of D-SPLEN2005548.1

5) Characteristics of D-HCHON2002384.1 ([2]), which was Newly Acquired and Subjected to Full-Length cDNA Sequence Analysis by Us 087_[2]_1-N0 (SEQ ID NO:58): The entire nucleic acid sequence region of D-HCHON2002384.1

087_[2]_1-NA0 (SEQ ID NO:59): Both the entire nucleic acid sequence region and amino acid sequence of D-HCHON2002384.1

087_[2]_1-A0 (SEQ ID NO:60): The entire amino acid sequence region of D-HCHON2002384.1

Compared with NM_000966.3, which is registered with an existing public DB and serves for control, D-HCHON2002384.1 had a 5'UTR longer by 56 bases, but there were no changes in the other regions, the ORF region being identical to NM_000966.3.

6) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

087_01—A specific region present on the N-terminal side of the cDNA pattern [1]: a transcription initiation region of the cDNA pattern [1], which was newly subjected to full-length cDNA sequence analysis by us, being a novel region not registered with an existing public DB →Fragment 087_01 (SEQ ID NO:63) amplified by Primer087_01F (SEQ ID NO:61) and Primer087_01R (SEQ ID NO:62) 087_03—A specific region present on the N-terminal side of the cDNA pattern [2], which is registered with an existing public DB, serving as a control for comparing [1]: a transcription initiation point region specific for [2], which serves as a control for a comparison with the transcription initiation regions of the cDNA patterns [1] and [2], which were newly subjected to full-length cDNA sequence analysis by us →Fragment 087_03 (SEQ ID NO:66) amplified by Primer087_03F (SEQ ID NO:64) and Primer087_03R (SEQ ID NO:65) 087_04—A common region shared by all of [1] to [2]: a region common to all patterns, serving for control to compare the overall expression levels of the cDNA pattern [1], which was newly subjected to full-length cDNA sequence analysis by us, and the cDNA pattern [2], which is registered with an existing public DB →Fragment 087_04 (SEQ ID NO:69) amplified by Primer087_04F (SEQ ID NO:67) and Primer087_04R (SEQ ID NO:68)

By mapping the 5'-terminal sequences of about 1.44 million sequences acquired using the oligocap method onto the human genome sequence, and comparatively analyzing them, the regions specific for the two kinds of cDNA patterns [1] and [2] shown above, respectively, were found to be expressed at the following frequencies.

With a transcription initiation points of the pattern [1], sixty-nine 5'-terminal sequences were present, the derivations thereof all being normal tissues. With a transcription initiation point of the pattern [2], one hundred nine 5'-terminal sequences were present, the derivations thereof being tumor tissues for 52 sequences and normal tissues for 57 sequences.

From this result, it was found that the expression from a transcription initiation point of [2], which is registered with an existing public DB, was abundant in tumor tissues, whereas the expression of [1] was abundant in normal tissues. Thereby, it was found that a mechanism worked in which a pathologic change, known as a tumor, in a tissue causes a change in the transcription factor or a loss of the control of transcription, which in turn alters the ratio of a plurality of proteins expressed from the same chromosome.

(2) Expression Specificity Analysis by Real-Time PCR

An extensive analysis was performed by real-time PCR to show what changes were produced in protein expression in terms of pathologic changes. The results are shown in Table 4 and Table 5.

TABLE 4

|  | RQ Score | | | $Log_{10}$RQ Score | | |
|---|---|---|---|---|---|---|
|  | 087_01 | 087_03 | 087_04 | 087_01 | 087_03 | 087_04 |
| 01 Colon | 1.5 | 1.3 | 1.2 | 0.17 | 0.11 | 0.06 |
| 02 Colon Tumor | 0.0 | Undet. | 0.1 | −1.53 | Undet. | −1.21 |
| 03 Kidney | 1.0 | 1.4 | 1.1 | 0.02 | 0.14 | 0.03 |
| 04 Kidney Tumor | 0.5 | 0.3 | 0.4 | −0.33 | −0.48 | −0.44 |
| 05 Liver | 0.5 | 0.3 | 0.4 | −0.33 | −0.56 | −0.45 |
| 06 Liver Tumor | 0.8 | 2.0 | 0.8 | −0.10 | 0.30 | −0.12 |
| 07 Lung | 1.5 | 1.5 | 2.1 | 0.19 | 0.17 | 0.33 |
| 08 Lung Tumor | 1.1 | 0.5 | 0.7 | 0.03 | −0.28 | −0.14 |
| 09 Ovary | 5.9 | 3.9 | 2.0 | 0.77 | 0.59 | 0.31 |
| 10 Ovary Tumor | 0.3 | 2.1 | 0.8 | −0.48 | 0.32 | −0.11 |
| 11 Stomach | 1.2 | 4.3 | 2.1 | 0.08 | 0.63 | 0.32 |
| 12 Stomach Tumor | 0.1 | 1.8 | 1.3 | −1.21 | 0.25 | 0.12 |
| 13 Uterus | 9.3 | 7.6 | 8.8 | 0.97 | 0.88 | 0.95 |
| 14 Uterus Tumor | 0.2 | 2.0 | 1.1 | −0.63 | 0.29 | 0.04 |
| 15 Tongue | 5.0 | 11.4 | 1.3 | 0.70 | 1.06 | 0.13 |
| 16 Tongue Tumor | 0.3 | 8.8 | 3.6 | −0.58 | 0.94 | 0.55 |
| 17 Brain, whole | 0.5 | 1.1 | 0.9 | −0.29 | 0.06 | −0.06 |
| 18 Mix, blood cells and related tissues | 1.0 | 1.0 | 1.0 | 0.0 | 0.0 | 0.0 |

TABLE 5

|  | RQ | | | $Log_{10}$RQ | | |
|---|---|---|---|---|---|---|
|  | 087_01 | 087_03 | 087_04 | 087_01 | 087_03 | 087_04 |
| 01 Colon | 1.1 | 0.8 | 1.0 | 0.03 | −0.12 | −0.01 |
| 02 Colon Tumor | 0.4 | 0.2 | 0.3 | −0.45 | −0.75 | −0.55 |
| 03 Kidney | 0.9 | 1.0 | 1.1 | −0.05 | −0.01 | 0.02 |
| 04 Kidney Tumor | 0.4 | 0.2 | 0.3 | −0.42 | −0.61 | −0.51 |
| 05 Liver | 0.4 | 0.2 | 0.3 | −0.43 | −0.61 | −0.46 |
| 06 Liver Tumor | 0.6 | 1.3 | 0.6 | −0.21 | 0.13 | −0.23 |
| 07 Lung | 4.4 | 1.1 | 0.0 | 0.64 | 0.05 | −1.33 |
| 08 Lung Tumor | 0.9 | 0.5 | 0.7 | −0.07 | −0.34 | −0.17 |
| 09 Ovary | 5.9 | 3.3 | 2.0 | 0.77 | 0.51 | 0.30 |
| 10 Ovary Tumor | 0.4 | 1.4 | 0.7 | −0.37 | 0.15 | −0.16 |
| 11 Stomach | 1.2 | 2.9 | 2.0 | 0.07 | 0.46 | 0.30 |
| 12 Stomach Tumor | 0.1 | 0.9 | 0.8 | −1.06 | −0.04 | −0.10 |
| 13 Uterus | 8.1 | 5.4 | 8.9 | 0.91 | 0.73 | 0.95 |
| 14 Uterus Tumor | 0.2 | 1.3 | 1.5 | −0.81 | 0.13 | 0.18 |
| 15 Tongue | 3.8 | 7.0 | 1.2 | 0.58 | 0.85 | 0.06 |
| 16 Tongue Tumor | 0.3 | 6.2 | 3.4 | −0.53 | 0.79 | 0.53 |
| 17 Brain, whole | 0.5 | 1.1 | 0.9 | −0.32 | 0.02 | −0.04 |
| 18 Mix, blood cells and related tissues | 1.0 | 1.0 | 1.0 | 0.0 | 0.0 | 0.0 |
| 19 Mix, viscus tissue | 0.6 | 1.4 | 1.0 | −0.25 | 0.16 | 0.01 |

Expression levels were compared between tumor tissues and normal tissues using the 8 kinds of organs shown in Example 3. The expression was also compared with the blood cell mixture (Mix, blood cells and related tissues) and brain sample shown in Example 3 as experimental controls.

A wide difference was observed in five kinds of organs: Liver, Ovary, Lung, Uterus, and Tongue. For the other organs, like the increase or decrease in the amplification of the fragment 087_04 (SEQ ID NO:69), which is common to all patterns, the amplification of the fragments of the other patterns increased or decreased.

In Tongue and Lung, comparing normal tissues and tumor tissues, 087_03 (SEQ ID NO:66), which was registered with an existing public DB, and the newly analyzed pattern 087_01 (SEQ ID NO:63), showed no change in the balance thereof, compared with normal cases, even after tumorization. In Tongue, whether it was a normal tissue or a tumor tissue, 087_03 (SEQ ID NO:66) was more abundantly expressed; in Lung, whether it was a normal tissue or a tumor tissue, 087_01 (SEQ ID NO:63) was expressed more frequently (Table 4 and Table 5).

However, it was found that in Liver, Ovary, and Uterus, comparing normal tissues and tumor tissues, the newly analyzed pattern 087_01 (SEQ ID NO:63) was more abundantly expressed than 087_03 (SEQ ID NO:66), which was registered with an existing public DB, in normal tissues, but in tumor tissues, the balance changed, and the pattern 087_01 (SEQ ID NO:63) was less abundantly expressed than 087_03 (SEQ ID NO:66) (Table 4 and Table 5).

These results demonstrated that by using the newly acquired cDNA regions 087_[1]_1-N1 (SEQ ID NO:40), 087_[1]_2-N1 (SEQ ID NO:46) and 087_[1]_3-N1 (SEQ ID NO:52) shown by the detection regions 087_01 (SEQ ID NO:63) and 087_03 (SEQ ID NO:66) as tumor markers, it is possible to use the cDNA regions as diagnostic/therapeutic markers for the three kinds of tumors of Liver, Ovary, and Uterus. It also seems possible to develop a new drug by means of a compound, antibody, siRNA or the like that targets a region that exhibits specificity.

The following regions also seem to be useful as diagnostic/therapeutic markers.
Upstream sequence 087_[1]_1-N3 (SEQ ID NO:70), which comprises the 321st to 342nd bases primed by Primer087_01R (SEQ ID NO:62) in D-HCHON2007878.1 of the cDNA pattern [1]
Upstream sequence 087_[1]_2-N3 (SEQ ID NO:71), which comprises the 199th to 220th bases primed by Primer087_01R (SEQ ID NO:62) in D-NTONG2006230.1 of the cDNA pattern [1]
Upstream sequence 087_[1]_3-N5 (SEQ ID NO:72), which comprises the 442nd to 463rd bases primed by Primer087_01R (SEQ ID NO:62) in D-SPLEN2005548.1 of the cDNA pattern [1]
Region 087_01 (SEQ ID NO:63) amplified by Primer087_01F (SEQ ID NO:61) and Primer087_01R (SEQ ID NO:62) in the cDNA pattern [1]

Example 6

Cluster chr3-353 (Data Set: 077)

(1) Cluster Analysis
1) Cluster Characteristics
An analysis was performed on 11 sequences of full-length cDNAs subjected to genome mapping onto the cluster chr3-353 (Human genome UCSC hg18 (NCBI Build34) chromosome 3, 181,000,000 bp to 181,250,000 bp) [D-BRCOC2007920.1, D-TKIDN2010471.1, D-BRCOC2001299.1, D-BRAMY3013614.1, D-OCBBF2019249.1, D-BRAMY2012419.1, AB032593.1, BC036183.1, ENST00000263962, ENST00000263963, NM_016559.1]. They were classifiable according to expression pattern difference into 9 kinds, which mainly included the following 2 kinds with a focus on their transcription initiation points.
[1] D-BRCOC2007920.1, D-TKIDN2010471.1
[2] AB032593.1, ENST00000263963, NM_016559.1

[1] is a cDNA that was newly acquired and subjected to full-length cDNA sequence analysis by us, having a transcription initiation point different from that of [2], which was been registered with an existing public DB, and having a different ORF.

[1] had a different amino acid sequence portion because of the expression thereof from a chromosome region upstream of the known [2].

It was found that the ORF regions present in the 2 kinds of cDNA patterns [1] and [2] cause expression starting at different transcription initiation points, from the same chromosome region, resulting in alterations of the amino acid sequences on the N-terminal side to produce diverse proteins and mRNAs.

2) Characteristics of D-BRCOC2007920.1 ([1]), which was Newly Acquired and Subjected to Full-Length cDNA Sequence Analysis by Us
077_[1]_1-N0 (SEQ ID NO:73): The entire nucleic acid sequence region of D-BRCOC2007920.1
077_[1]_1-NA0 (SEQ ID NO:74): Both the entire nucleic acid sequence region and amino acid sequence of D-BRCOC2007920.1
077_[1]_1-A0 (SEQ ID NO:75): The entire amino acid sequence region of D-BRCOC2007920.1

The sequence at the 1st to 205th bases of D-BRCOC2007920.1 (SEQ ID NO:76) is an exon that is not present in NM_016559.1, which is registered with an existing public DB and serves for control, lacking homology to NM_016559.1. Also, the 105-base exon present at the 224th to 328th bases of NM_016559.1 (SEQ ID NO:79) is lacked and not present in the region at the 277th to 278th bases of D-BRCOC2007920.1 (SEQ ID NO:77). With these changes, the translation initiation point of D-BRCOC2007920.1 shifts toward the 3' side, relative to NM_016559.1, and the 656th base of D-BRCOC2007920.1 becomes the translation initiation point. For this reason, the amino acid sequence shortened by 192 residues, compared with NM_016559.1.
077_[1]_1-N1 (SEQ ID NO:76): A 205-base insert nucleic acid sequence region of D-BRCOC2007920.1
077_[1]_1-N2 (SEQ ID NO:77): A deletion nucleic acid sequence region of D-BRCOC2007920.1
077_[1]_1-N3 (SEQ ID NO:78): A 655-base 5'UTR region of an ORF with the 656th base of D-BRCOC2007920.1 as the translation initiation point
077_[1]_C-N1 (SEQ ID NO:79): A 105-base exon nucleic acid sequence present at the 224th to 328th bases of NM_016559.1 inserted into the region at the 277th to 278th bases of D-BRCOC2007920.1
077_[1]_C-A1 (SEQ ID NO:80): A 35-residue amino acid sequence of the 105-base exon present at the 224th to 328th bases of NM_016559.1 inserted into the region at the 277th to 278th bases of D-BRCOC2007920.1
3) Characteristics of D-TKIDN2010471.1 ([1]), which was Newly Acquired and Subjected to Full-Length cDNA Sequence Analysis by Us
077_[1]_2-N0 (SEQ ID NO:81): The entire nucleic acid sequence region of D-TKIDN2010471.1

077_[1]_2-NA0 (SEQ ID NO:82): Both the entire nucleic acid sequence region and amino acid sequence of D-TKIDN2010471.1

077_[1]_2-A0 (SEQ ID NO:83): The entire amino acid sequence region of D-TKIDN2010471.1

The sequence at the 1st to 196th bases of D-TKIDN2010471.1 (SEQ ID NO:84) is an exon that is not present in NM_016559.1, which is registered with an existing public DB, and serves for control, lacking homology to NM_016559.1. With this change, the translation initiation point of D-TKIDN2010471.1 shifts toward the 3' side relative to NM_016559.1, and the 305th base of D-TKIDN2010471.1 becomes the translation initiation point (SEQ ID NO:85). For this reason, the amino acid sequence shortened by 43 residues, compared with NM_016559.1.

077_[1]_2-N1 (SEQ ID NO:84): A 196-base insert nucleic acid sequence region of D-TKIDN2010471.1

077_[1]_2-N2 (SEQ ID NO:85): A 304-base 5'UTR region of an ORF with the 305th base of D-TKIDN2010471.1 as the translation initiation point 4) Expression Specificity Analysis and Design of Primers for Real-Time PCR and Taqman Probes To clearly distinguish between the characteristic regions shown above, and examine the respective expression levels thereof, the following regions were used as detection regions. It seemed possible to compare the expression levels of the individual characteristic regions by comparing the expression levels of the detection regions.

077_01—A specific region present on the N-terminal side of the cDNA pattern [1]: a transcription initiation region of the cDNA pattern [1], which was newly acquired and subjected to full-length cDNA sequence analysis by us →Fragment 077_01-1 (SEQ ID NO:88) of D-BRCOC2007920.1 amplified by Primer077_01F (SEQ ID NO:86) and Primer077_01R (SEQ ID NO:87)

TaqMan probe used 077_01TP: (SEQ ID NO:90)

→Fragment 077_01-2 (SEQ ID NO:89) of D-TKIDN2010471.1 amplified by Primer077_01F (SEQ ID NO:86) and Primer077_01R (SEQ ID NO:87)

TaqMan probe used 077_01TP: (SEQ ID NO:90)

077_04—A specific region present on the N-terminal side of the cDNA pattern [2], which is registered with an existing public DB, serving as a control for comparing [1]: a transcription initiation point region specific for [2], which serves as a control for a comparison with the transcription initiation region of the cDNA pattern [1], which was newly acquired and subjected to full-length cDNA sequence analysis by us →Fragment 077_04 (SEQ ID NO:93) amplified by Primer077_04F (SEQ ID NO:91) and Primer077_04R (SEQ ID NO:92)

TaqMan probe used 077_04TP: (SEQ ID NO:94)

077_07—A common region shared by all of [1] to [2]: a region common to all patterns, serving for control to compare the overall expression levels of the cDNA pattern [1], which was newly acquired and subjected to full-length cDNA sequence analysis by us, and the cDNA pattern [2], which is registered with an existing public DB →Fragment 077_07 (SEQ ID NO:97) amplified by Primer077_07F (SEQ ID NO:95) and Primer077_07R (SEQ ID NO:96)

TaqMan probe used 077_07TP: (SEQ ID NO:98)

By mapping the 5'-terminal sequences of about 1.44 million sequences acquired using the oligocap method onto the human genome sequence, and comparatively analyzing them, the exon regions specific for the two kinds of cDNA patterns [1] and [2] shown above, respectively, were found to be expressed at the following frequencies.

In the cDNA pattern [1], which was newly acquired and subjected to analysis by us, nine 5'-terminal sequences were present, the derivations thereof being brain tissues for 8 sequences and tumor tissues for 1 sequence.

In the cDNA pattern [2], which is registered with an existing public DB, six 5'-terminal sequences were present, the derivations thereof being brain tissues for 5 sequences and tumor tissues for 1 sequence.

From this result, it was found that the pattern [1] was abundantly expressed in brain tissues and also expressed in tumor tissues.

(2) Expression Specificity Analysis by Real-Time PCR

An extensive analysis was performed by real-time PCR to show what changes were produced in protein expression in terms of pathologic changes. The results are shown in Table 6.

TABLE 6

|  | RQ | | | $Log_{10}RQ$ | | |
| --- | --- | --- | --- | --- | --- | --- |
|  | 077_01 | 077_04 | 077_07 | 077_01 | 077_04 | 077_07 |
| 01 Colon | 0.0 | Undet. | 0.0 | −3.20 | Undet. | −2.78 |
| 02 Colon Tumor | 556.0 | Undet. | 0.0 | 2.75 | Undet. | −3.18 |
| 03 Kidney | 0.0 | 0.0 | 0.0 | −2.44 | −3.16 | −2.36 |
| 04 Kidney Tumor | 0.0 | Undet. | 0.0 | −2.80 | Undet. | −2.95 |
| 05 Liver | Undet. | 115617.5 | Undet. | Undet. | 5.06 | Undet. |
| 06 Liver Tumor | 0.0 | Undet. | Undet. | −2.60 | Undet. | Undet. |
| 07 Lung | 0.0 | 0.0 | 0.0 | −2.28 | −2.04 | −1.73 |
| 08 Lung Tumor | 0.0 | Undet. | 0.0 | −3.66 | Undet. | −2.49 |
| 09 Ovary | 0.1 | 0.1 | 0.1 | −0.93 | −1.14 | −1.16 |
| 10 Ovary Tumor | 0.0 | Undet. | 0.0 | −3.07 | Undet. | −3.21 |
| 11 Stomach | 0.0 | 0.0 | 0.0 | −1.68 | −2.60 | −2.17 |
| 12 Stomach Tumor | 0.0 | Undet. | Undet. | −3.53 | Undet. | Undet. |
| 13 Uterus | 0.0 | 0.0 | 0.0 | −2.74 | −2.05 | −2.44 |
| 14 Uterus Tumor | 0.0 | Undet. | 0.0 | −3.61 | Undet. | −3.65 |
| 15 Tongue | 0.3 | 0.0 | 0.0 | −0.57 | −2.69 | −2.56 |
| 16 Tongue Tumor | 0.1 | Undet. | 0.0 | −0.99 | Undet. | −3.09 |
| 17 Brain, whole | 0.9 | 1.7 | 2.9 | −0.02 | 0.24 | 0.46 |
| 18 Mix, blood cells and related tissues | 1.0 | 1.0 | 1.0 | 0.0 | 0.0 | 0.0 |

Expression levels were compared between tumor tissues and normal tissues using the 8 kinds of organs shown in Example 3. The expression was also compared with the blood cell mixture (Mix, blood cells and related tissues) and brain sample shown in Example 3 as experimental controls.

A wide difference was observed in four kinds of organs: Kidney, Lung, Uterus, and Tongue. For the other organs, like the increase or decrease in the amplification of the fragment 077_07 (SEQ ID NO:97), which is common to all patterns, the amplification of the fragments of the other patterns increased or decreased.

In Kidney, Lung, Uterus, and Tongue, comparing normal tissues and tumor tissues, the newly analyzed transcription initiation points shown by 077_01-1 (SEQ ID NO:88) and 077_01-2 (SEQ ID NO:89) were expressed equivalently in normal tissues and tumor tissues, whereas the transcription initiation point of the pattern 077_04 (SEQ ID NO:93), which was registered with an existing public DB, was observable in normal tissues but undetectable in tumor tissues (Table 6).

These results demonstrated that by using the newly acquired cDNA regions 077_[1]_1-N1 (SEQ ID NO:76) and 077_[1]_2-N1 (SEQ ID NO:84) shown by the detection regions 077_01-1 (SEQ ID NO:88) and 077_01-2 (SEQ ID NO:89) as tumor markers, it is possible to use the cDNA regions as diagnostic/therapeutic markers for the four kinds of tumors of Kidney, Lung, Uterus, and Tongue. It also seems possible to develop a new drug by means of a compound, antibody, siRNA or the like that targets a region that exhibits specificity.

The following regions also seem to be useful as diagnostic/therapeutic markers.
Upstream sequence 077_[1]_1-N4 (SEQ ID NO:99), which comprises the 184th to 211th bases primed by Primer077_01R (SEQ ID NO:87) in D-BRCOC2007920.1 of the cDNA pattern [1]
Upstream sequence 077_[1]_2-N3 (SEQ ID NO:100), which comprises the 175th to 202nd bases primed by Primer077_01R (SEQ ID NO:87) in D-TKIDN2010471.1 of the cDNA pattern [1]
Region 077_01-1 (SEQ ID NO:88) amplified by Primer077_01F (SEQ ID NO:86) and Primer077_01R (SEQ ID NO:87) in D-BRCOC2007920.1 of the cDNA pattern [1]
Region 077_01-2 (SEQ ID NO:89) amplified by Primer077_01F (SEQ ID NO:86) and Primer077_01R (SEQ ID NO:87) in D-TKIDN2010471.1 of the cDNA pattern [1]

Example 7

Cluster chrX-148 (Data Set: 003)

(1) Cluster Analysis
1) Cluster Characteristics
An analysis was performed on 11 sequences of full-length cDNAs subjected to genome mapping onto the cluster chrX-148 (Human genome UCSC hg18 (NCBI Build34) chromosome X, 137,400,000 bp to 138,100,000 bp) [D-TKIDN2003621.1, D-FEBRA2001626.1, D-FEBRA2010013.1, AF100143.1, AF100144.1, BC012347.1, BC034340.1, ENST00000305414, ENST00000315930, NM_004114.2, NM_033642.1]. They were classifiable according to expression pattern difference into the following 4 kinds.
[1] D-FEBRA2010013.1, D-FEBRA2001626.1
[2] D-TKIDN2003621.1
[3] AF100144.1, ENST00000305414, NM_033642.1
[4] AF100143.1, BC012347.1, BC034340.1, ENST00000315930, NM_004114.2

[1] and [2] are cDNAs that were newly acquired and subjected to full-length cDNA sequence analysis by us, having a transcription initiation point different from that of [3] and [4], which were registered with an existing public DB, and having a different ORF.

[1] was expressed from a chromosome region located upstream of the known [3] and [4], and did not share an exon with [3] and [4] to the 3rd exon of D-FEBRA2010013.1 or the 2nd exon of D-FEBRA2001626.1, but shared an exon in the region at the 4th exon and beyond. Because of the presence of the translation initiation point on the 2nd exon of D-FEBRA2010013.1 or the 1st exon of D-FEBRA2001626.1, the amino acid sequence on the N-terminal side differed.

Although [2] has the same transcription initiation point and translation initiation point as those of [1], the different ORF region thereof was different because of the deletion of a portion corresponding to the 3rd exon of [2].

[3] and [4], which are registered with an existing public DB, also had different amino acid sequences on the N-terminal side because they had mutually different transcription initiation points and translation initiation points.

The ORF regions present in the 4 kinds of cDNA patterns [1] to [4] have the same region in common on the C-terminal sides thereof, with variation existing in the exons located upstream thereof. Hence, it was found that the region causes expression starting at different transcription initiation points, from the same chromosome region, and has exon deletions, resulting in alterations of the amino acid sequences on the N-terminal side to produce diverse proteins and mRNAs.

2) Characteristics of D-FEBRA2010013.1 ([1]), which was Newly Acquired and Subjected to Full-Length cDNA Sequence Analysis by Us
003_[1]_1-N0 (SEQ ID NO:101): The entire nucleic acid sequence region of D-FEBRA2010013.1
003_[1]_1-NA0 (SEQ ID NO:102): Both the entire nucleic acid sequence region and amino acid sequence of D-FEBRA2010013.1
003_[1]_1-A0 (SEQ ID NO:103): The entire amino acid sequence region of D-FEBRA2010013.1
The sequence at the 1st to 513th bases of D-FEBRA2010013.1 (SEQ ID NO:104) is a variant incorporating an exon that is not present in NM_004114.2, which is registered with an existing public DB and serves for control; because of the presence thereof along with the translation initiation point on the exon inserted, the N-terminal amino acids differed by 72 residues (SEQ ID NO:105), compared with NM_004114.2.
003_[1]_1-N1 (SEQ ID NO:104): A 513-base insert nucleic acid sequence region of D-FEBRA2010013.1
003_[1]_1-A1 (SEQ ID NO:105): A 72-residue insert amino acid sequence region of D-FEBRA2010013.1
003_[1]_1-N2 (SEQ ID NO:106): An ORF nucleic acid sequence region in the 513-base insert region of D-FEBRA2010013.1
003_[1]_1-A2 (identical to SEQ ID NO:105): An ORF amino acid region related to the 513-base insert region of D-FEBRA2010013.1

3) Characteristics of D-FEBRA2001626.1 ([1]), which was Newly Acquired and Subjected to Full-Length cDNA Sequence Analysis by Us
003_[1]_2-N0 (SEQ ID NO:107): The entire nucleic acid sequence region of D-FEBRA2001626.1
003_[1]_2-NA0 (SEQ ID NO:108): Both the entire nucleic acid sequence region and amino acid sequence of D-FEBRA2001626.1
003_[1]_2-A0 (SEQ ID NO:109): The entire amino acid sequence region of D-FEBRA2001626.1

The sequence at the 1st to 391st bases of D-FEBRA2001626.1 (SEQ ID NO:110) is a variant incorporating an exon that is not present in NM_004114.2, which is registered with an existing public DB and serves for control; because of the presence thereof along with the translation initiation point on the exon inserted, the N-terminal amino acids differed by 72 residues (SEQ ID NO:111), compared with NM_004114.2.

003_[1]_2-N1 (SEQ ID NO:110): A 391-base insert nucleic acid sequence region of D-FEBRA2001626.1

003_[1]_2-A1 (SEQ ID NO:111): A 72-residue insert amino acid sequence region of D-FEBRA2001626.1

003_[1]_2-N2 (SEQ ID NO:112): An ORF nucleic acid sequence region in the 391-base insert region of D-FEBRA2001626.1

003_[1]_2-A2 (identical to SEQ ID NO:111): An ORF amino acid region related to the 391-base insert region of D-FEBRA2001626.1

4) Characteristics of D-TKIDN2003621.1 ([2]), which was Newly Acquired and Subjected to Full-Length cDNA Sequence Analysis by Us 003_[2]_1-N0 (SEQ ID NO:113): The entire nucleic acid sequence region of D-TKIDN2003621.1

003_[2]_1-NA0 (SEQ ID NO:114): Both the entire nucleic acid sequence region and amino acid sequence of D-TKIDN2003621.1

003_[2]_1-A0 (SEQ ID NO:115): The entire amino acid sequence region of D-TKIDN2003621.1

The sequence at the 1st to 315th bases of D-TKIDN2003621.1 (SEQ ID NO:116) is a variant incorporating an exon that is not present in NM_004114.2, which is registered with an existing public DB and serves for control; because of the presence thereof along with the translation initiation point on the exon inserted, the N-terminal amino acids differed by 16 residues (SEQ ID NO:117), compared with NM_004114.2.

003_[2]_1-N1 (SEQ ID NO:116): A 315-base insert nucleic acid sequence region of D-TKIDN2003621.1

003_[2]_1-A1 (SEQ ID NO:117): A 16-residue insert amino acid sequence region of D-TKIDN2003621.1

003_[2]_1-N2 (SEQ ID NO:118): An ORF nucleic acid sequence region in the 315-base insert region of D-TKIDN2003621.1

003_[2]_1-A2 (identical to SEQ ID NO:117): An ORF amino acid region related to the 315-base insert region of D-TKIDN2003621.1

5) Expression Specificity Analysis and Design of Primers for Real-Time PCR and Taqman Probes To clearly distinguish between the characteristic regions shown above, and examine the respective expression levels thereof, the following regions were used as detection regions. It seemed possible to compare the expression levels of the individual characteristic regions by comparing the expression levels of the detection regions.

003_01—A specific region present on the N-terminal side of the cDNA pattern [1]: a transcription initiation region of the cDNA pattern [1], which was newly subjected to full-length cDNA sequence analysis by us, being a novel region not registered with an existing public DB →Fragment 003_01 (SEQ ID NO:121) amplified by Primer003_01F (SEQ ID NO:119) and Primer003_01R (SEQ ID NO:120)

TaqMan probe used 003_01TP: (SEQ ID NO:122)

003_02—A region specifically extracted by means of the sequence information at the border of an exon deletion region in the cDNA pattern [2]: an ORF-altering exon deletion region in the cDNA pattern [2], which was newly subjected to full-length cDNA sequence analysis by us →Fragment 003_02 (SEQ ID NO:125) amplified by Primer003_02F (SEQ ID NO:123) and Primer003_02R (SEQ ID NO:124)

TaqMan probe used 003_02TP: (SEQ ID NO:126)

003_03—A specific region present on the N-terminal side of the cDNA pattern [3], which is registered with an existing public DB, serving as a control for comparing [1] and [2]: a transcription initiation point region specific for [3], which serves as a control for a comparison with the transcription initiation regions of the cDNA patterns [1] and [2], which were newly subjected to full-length cDNA sequence analysis by us →Fragment 003_03 (SEQ ID NO:129) amplified by Primer003_03F (SEQ ID NO:127) and Primer003_03R (SEQ ID NO:128)

TaqMan probe used 003_03TP: (SEQ ID NO:130)

003_04—A specific region present on the N-terminal side of the cDNA pattern [4], which is registered with an existing public DB, serving as a control for comparing [1] and [2]: a transcription initiation point region specific for [4], which serves as a control for a comparison with the transcription initiation regions of the cDNA patterns [1] and [2], which were newly subjected to full-length cDNA sequence analysis by us →Fragment 003_04 (SEQ ID NO:133) amplified by Primer003_04F (SEQ ID NO:131) and Primer003_04R (SEQ ID NO:132)

TaqMan probe used 003_04TP: (SEQ ID NO:134)

003_05—A common region shared by all of [1] to [4]: a region common to all patterns, serving for control to compare the overall expression levels of the cDNA patterns [1] and [2], which were newly subjected to full-length cDNA sequence analysis by us, and the cDNA patterns [3] and [4], which are registered with an existing public DB →Fragment 003_05 (SEQ ID NO:137) amplified by Primer003_05F (SEQ ID NO:135) and Primer003_05R (SEQ ID NO:136)

TaqMan probe used 003_05TP: (SEQ ID NO:138)

By mapping the 5'-terminal sequences of about 1.44 million sequences acquired using the oligocap method onto the human genome sequence, and comparatively analyzing them, the exon regions specific for the four kinds of cDNA patterns [1] to [4] shown above, respectively, were found to be expressed at the following frequencies.

In the cDNA pattern [1], which was newly acquired and analyzed by us, seventeen 5'-terminal sequences were present, the derivations thereof being brain tissues for 12 sequences, tumor tissues for 4 sequences, and other tissues for 1 sequence.

In the cDNA pattern [2], which was newly acquired and analyzed by us, seven 5'-terminal sequences were present, the derivations thereof being brain tissues for 4 sequences, tumor tissues for 1 sequence, and other tissues for 2 sequences.

In the cDNA pattern [3], which is registered with an existing public DB, no 5'-terminal sequences were present.

In the cDNA pattern [4], which is registered with an existing public DB, thirty-two 5'-terminal sequences were present, the derivations thereof being brain tissues for 27 sequences, tumor tissues for 1 sequence, and other tissues for 4 sequences.

From this result, it was found that the expression in brain tissues was abundant, and the expression in tumor tissues increased relatively in the patterns [1] and [2]. Thereby, it was found that a mechanism of exon selectivity worked in which a pathologic change, known as a tumor, in a tissue, or a change in the transcription factor or a loss of the control of transcription alters the ratio of a plurality of proteins expressed from the same chromosome.

(2) Expression Specificity Analysis by Real-Time PCR

An extensive analysis was performed by real-time PCR to show what changes were produced in protein expression in terms of pathologic changes. The results are shown in Table 7.

TABLE 7

| | RQ | | | | | $Log_{10}RQ$ | | | | |
|---|---|---|---|---|---|---|---|---|---|---|
| | 003_01 | 003_02 | 003_03 | 003_04 | 003_05 | 003_01 | 003_02 | 003_03 | 003_04 | 003_05 |
| 01 Colon | 1.6 | 1.9 | 0.5 | 0.6 | 0.8 | 0.20 | 0.28 | −0.31 | −0.20 | −0.09 |
| 02 Colon Tumor | 0.6 | 0.3 | 0.2 | 0.1 | 0.3 | −0.25 | −0.53 | −0.62 | −0.99 | −0.54 |
| 03 Kidney | 1.3 | 3.2 | 0.5 | 0.4 | 0.7 | 0.12 | 0.50 | −0.27 | −0.38 | −0.13 |
| 04 Kidney Tumor | 1.4 | 4.0 | 0.2 | 0.1 | 0.6 | 0.16 | 0.61 | −0.63 | −1.11 | −0.23 |
| 05 Liver | 0.6 | 0.7 | 0.2 | 0.1 | 0.2 | −0.23 | −0.17 | −0.80 | −1.00 | −0.70 |
| 06 Liver Tumor | 1.0 | 1.2 | 0.6 | 0.3 | 0.6 | 0.01 | 0.06 | −0.24 | −0.49 | −0.24 |
| 07 Lung | 1.4 | 3.3 | 2.4 | 2.5 | 2.7 | 0.13 | 0.51 | 0.37 | 0.40 | 0.44 |
| 08 Lung Tumor | 0.7 | 1.3 | 0.7 | 0.0 | 0.5 | −0.14 | 0.12 | −0.14 | −1.87 | −0.31 |
| 09 Ovary | 1.2 | 2.2 | 1.1 | 1.2 | 1.1 | 0.07 | 0.34 | 0.06 | 0.08 | 0.06 |
| 10 Ovary Tumor | 2.4 | 5.2 | 0.5 | 0.1 | 0.8 | 0.38 | 0.72 | −0.30 | −1.01 | −0.09 |
| 11 Stomach | 3.7 | 5.3 | 2.0 | 1.0 | 2.0 | 0.57 | 0.72 | 0.31 | 0.00 | 0.31 |
| 12 Stomach Tumor | 3.6 | 4.6 | 0.7 | 0.1 | 1.0 | 0.55 | 0.66 | −0.15 | −1.20 | 0.00 |
| 13 Uterus | 3.9 | 3.1 | 2.4 | 2.3 | 3.2 | 0.59 | 0.49 | 0.38 | 0.35 | 0.51 |
| 14 Uterus Tumor | 0.1 | 0.1 | 0.1 | 0.1 | 0.1 | −0.90 | −0.92 | −1.05 | −0.94 | −0.83 |
| 15 Tongue | 2.5 | 1.6 | 0.6 | 0.1 | 0.5 | 0.39 | 0.19 | −0.24 | −0.85 | −0.29 |
| 16 Tongue Tumor | 1.3 | 1.8 | 0.3 | 0.0 | 0.3 | 0.11 | 0.25 | −0.50 | −1.74 | −0.51 |
| 17 Brain, whole | 3.9 | 3.1 | 11.1 | 10.4 | 11.3 | 0.59 | 0.50 | 1.05 | 1.02 | 1.05 |
| 18 Mix, blood cells and related tissues | 1.0 | 1.0 | 1.0 | 1.0 | 1.0 | 0.0 | 0.0 | 0.0 | 0.0 | 0.0 |

Expression levels were compared between tumor tissues and normal tissues using the 8 kinds of organs shown in Example 3. The expression was also compared with the blood cell mixture (Mix, blood cells and related tissues) and brain sample shown in Example 3 as experimental controls.

A wide difference was observed in three kinds of organs: Kidney, Ovary, and Tongue. For the other organs, like the increase or decrease in the amplification of the fragment 003_05 (SEQ ID NO:137), which is common to all patterns, the amplification of the fragments of other patterns increased or decreased.

In Kidney and Ovary, comparing normal tissues and tumor tissues, in the patterns 003_03 (SEQ ID NO:129) and 003_04 (SEQ ID NO:133), which were registered with an existing public DB, and the fragment 003_05 (SEQ ID NO:137), which is common to all patterns, the expression level decreased, compared with normal cases, as a result of tumorization (Table 7).

However, in the patterns 003_01 (SEQ ID NO:121) and 003_02 (SEQ ID NO:125), which were newly analyzed by us, the expression level increased, compared with normal cases, as a result of tumorization.

In Tongue, comparing normal tissues and tumor tissues, only in the pattern 003_02 (SEQ ID NO:125), the expression level increased, compared with normal cases, as a result of tumorization. In the patterns 003_03 (SEQ ID NO:129) and 003_04 (SEQ ID NO:133), which were registered with an existing public DB, the pattern 003_01 (SEQ ID NO:121), which was newly analyzed by us, and the fragment 003_05 (SEQ ID NO:137), which is common to all patterns, the expression level decreased, compared with normal cases, as a result of tumorization (Table 7).

In the five other kinds of tissues, no change was observed between normal tissues and tumor tissues.

These results demonstrated that by using the newly acquired cDNA regions 003_[1]_1-N1 (SEQ ID NO:104), 003_[1]_2-N1 (SEQ ID NO:110) and 003_[2]_1-N1 (SEQ ID NO:116) shown by the detection regions 003_01 (SEQ ID NO:121) and 003_02 (SEQ ID NO:125) as tumor markers, it is possible to use the cDNA regions as diagnostic/therapeutic markers for the three kinds of tumors of Kidney, Ovary, and Tongue. It also seems possible to develop a new drug by means of a compound, antibody, siRNA or the like that targets a region that exhibits specificity.

The following regions also seem to be useful as diagnostic/therapeutic markers.

Upstream sequence 003_[1]_1-N3 (SEQ ID NO:139), which comprises the 536th to 559th bases primed by Primer003_01R (SEQ ID NO:120) in D-FEBRA2010013.1 of the cDNA pattern [1].

Upstream sequence 003_[1]_2-N3 (SEQ ID NO:140), which comprises the 414th to 437th bases primed by Primer003_01R (SEQ ID NO:120) in D-FEBRA2001626.1 of the cDNA pattern [1].

Upstream sequence 003_[2]_1-N3 (SEQ ID NO:141), which comprises the 380th to 398th bases primed by Primer003_02R (SEQ ID NO:124) in D-TKIDN2003621.1 of the cDNA pattern [2].

Region 003_01 (SEQ ID NO:121) amplified by Primer003_01F (SEQ ID NO:119) and Primer003_01R (SEQ ID NO:120) in the cDNA pattern [1]

Region 003_02 (SEQ ID NO:125) amplified by Primer003_02F (SEQ ID NO:123) and Primer003_02R (SEQ ID NO:124) in the cDNA pattern [2]

Example 8

Cluster chr9-1456 (Data Set: 062)

(1) Cluster Analysis
1) Cluster Characteristics

An analysis was performed on 6 sequences of full-length cDNAs subjected to genome mapping onto the chr9-1456 (Human genome UCSC hg18 (NCBI Build34) chromosome 9, 36,200,000 bp to 36,270,000 bp) [D-CTONG2001283.1, D-BRHIP2021365.1, AF155663.1, AJ238764.1, ENST00000339267, NM_005476.3]. They are classified mainly into the following 2 kinds with a focus on expression pattern differences in their transcription initiation points.
[1] D-CTONG2001283.1
[2] ENST00000339267, NM_005476.3

[1] is a cDNA that was newly acquired and subjected to full-length cDNA sequence analysis by us, having a transcription initiation point different from that of [2], which was registered with an existing public DB, and having a different ORF.

[1] had a different amino acid sequence portion because of the expression thereof from a chromosome region upstream of the known [2].

It was found that the ORF regions present in the 2 kinds of cDNA patterns [1] to [2] cause expression starting at different transcription initiation points, from the same chromosome region, resulting in alterations of the amino acid sequences on the N-terminal side to produce diverse proteins and mRNAs.

2) Characteristics of D-CTONG2001283.1 ([1]), which was Newly Acquired and Subjected to Full-Length cDNA Sequence Analysis by Us 062_[1]_1-N0 (SEQ ID NO:142): The entire nucleic acid sequence region of D-CTONG2001283.1

062_[1]_1-NA0 (SEQ ID NO:143): Both the entire nucleic acid sequence region and amino acid sequence of D-CTONG2001283.1

062_[1]_1-A0 (SEQ ID NO:144): The entire amino acid sequence region of D-CTONG2001283.1

The sequence at the 1st to 80th bases of D-CTONG2001283.1 (SEQ ID NO:145) is a variant incorporating an exon that is not present in NM_005476.3, which is registered with an existing public DB and serves for control; because of the presence thereof along with the translation initiation point on the exon inserted, the N-terminal amino acids differed by 14 residues (SEQ ID NO:146), compared with NM_005476.3.

062_[1]_1-N1 (SEQ ID NO:145): An 80-base insert nucleic acid sequence region of D-CTONG2001283.1

062_[1]_1-A1 (SEQ ID NO:146): A 14-residue insert amino acid sequence region of D-CTONG2001283.1

062_[1]_1-N2 (SEQ ID NO:147): An ORF nucleic acid sequence region in the 80-base insert region of D-CTONG2001283.1

062_[1]_1-A2 (identical to SEQ ID NO:146): An ORF amino acid region related to the 80-base insert region of D-CTONG2001283.1

3) Expression Specificity Analysis and Design of Primers for Real-Time PCR and Taqman Probes To clearly distinguish between the characteristic regions shown above, and examine the respective expression levels thereof, the following regions were used as detection regions. It seemed possible to compare the expression levels of the individual characteristic regions by comparing the expression levels of the detection regions.

062_01—A specific region present on the N-terminal side of the cDNA pattern [1]: a transcription initiation region of the cDNA pattern [1], which was newly subjected to full-length cDNA sequence analysis by us, being a novel region not registered with an existing public DB →Fragment 062_01 (SEQ ID NO:150) amplified by Primer062_01F (SEQ ID NO:148) and Primer062_01R (SEQ ID NO: 149)

TaqMan probe used 062_01TP: (SEQ ID NO:151)

062_03—A specific region present on the N-terminal side of the cDNA pattern [2], which is registered with an existing public DB, serving as a control for comparing [1]: a transcription initiation point region specific for [2], which serves as a control for a comparison with the transcription initiation regions of the cDNA patterns [1] and [2], which were newly subjected to full-length cDNA sequence analysis by us →Fragment 062_03 (SEQ ID NO:154) amplified by Primer062_03F (SEQ ID NO:152) and Primer062_03R (SEQ ID NO:153)

TaqMan probe used 062_03TP: (SEQ ID NO:155)

062_05—A common region shared by all of [1] to [2]: a region common to all patterns, serving for control to compare the overall expression levels of the cDNA pattern [1], which was newly subjected to full-length cDNA sequence analysis by us, and the cDNA pattern [2], which is registered with an existing public DB →Fragment 062_05 (SEQ ID NO:158) amplified by Primer062_05F (SEQ ID NO:156) and Primer062_05R (SEQ ID NO:157)

TaqMan probe used 062_05TP: (SEQ ID NO:159)

By mapping the 5'-terminal sequences of about 1.44 million sequences acquired using the oligocap method onto the human genome sequence, and comparatively analyzing them, the exon regions specific for the two kinds of cDNA patterns [1] to [2] shown above, respectively, were found to be expressed at the following frequencies.

In the cDNA pattern [1], which was newly acquired and subjected to analysis by us, twenty-four 5'-terminal sequences were present, the derivations thereof being Trachea for 20 sequences, Tongue Tumor for 3 sequences, and Prostate for 1 sequence. In the cDNA pattern [2], which is registered with an existing public DB, fourteen 5'-terminal sequences were present, the derivations thereof being Tongue Tumor for 4 sequences, brain tissues for 7 sequences, and other tissues for 2 sequences.

In the cDNA pattern [1], which was newly acquired and analyzed by us, it was found that the expression was abundant in Trachea, and also observed in Tongue Tumor tissues and the like.

(2) Expression Specificity Analysis by Real-Time PCR

An extensive analysis was performed by real-time PCR to show what changes were produced in protein expression in terms of pathologic changes. The results are shown in Table 8.

TABLE 8

|  | RQ | | | $Log_{10}RQ$ | | |
| --- | --- | --- | --- | --- | --- | --- |
|  | 062_01 | 062_03 | 062_05 | 062_01 | 062_03 | 062_05 |
| 01 Colon | 18.3 | 0.7 | 3.9 | 1.26 | −0.18 | 0.59 |
| 02 Colon Tumor | 9.3 | 0.6 | 2.7 | 0.97 | −0.22 | 0.43 |
| 03 Kidney | 2.4 | 0.8 | 1.0 | 0.37 | −0.11 | 0.01 |
| 04 Kidney Tumor | 1.1 | 0.5 | 0.6 | 0.02 | −0.27 | −0.21 |
| 05 Liver | 8.7 | 4.9 | 12.1 | 0.94 | 0.69 | 1.08 |
| 06 Liver Tumor | 2.1 | 5.1 | 5.2 | 0.32 | 0.71 | 0.72 |
| 07 Lung | 6.2 | 2.3 | 5.4 | 0.80 | 0.36 | 0.73 |
| 08 Lung Tumor | 0.1 | 0.4 | 0.6 | −0.83 | −0.39 | −0.20 |
| 09 Ovary | 1.0 | 0.8 | 1.5 | 0.02 | −0.09 | 0.17 |
| 10 Ovary Tumor | 2.5 | 0.3 | 0.4 | 0.40 | −0.54 | −0.39 |
| 11 Stomach | 1.9 | 0.9 | 1.7 | 0.27 | −0.03 | 0.24 |

TABLE 8-continued

|  | RQ | | | Log$_{10}$RQ | | |
| --- | --- | --- | --- | --- | --- | --- |
|  | 062_01 | 062_03 | 062_05 | 062_01 | 062_03 | 062_05 |
| 12 Stomach Tumor | 29.2 | 0.4 | 8.3 | 1.47 | −0.39 | 0.92 |
| 13 Uterus | 1.6 | 2.3 | 2.2 | 0.22 | 0.37 | 0.35 |
| 14 Uterus Tumor | 5.1 | 0.3 | 1.0 | 0.71 | −0.49 | 0.02 |
| 15 Tongue | 1.5 | 1.9 | 0.1 | 0.17 | 0.27 | −0.83 |
| 16 Tongue Tumor | 3.8 | 1.5 | 1.5 | 0.58 | 0.17 | 0.18 |
| 17 Brain, whole | 0.8 | 1.6 | 1.4 | −0.07 | 0.22 | 0.15 |
| 18 Mix, blood cells and related tissues | 1.0 | 1.0 | 1.0 | 0.0 | 0.0 | 0.0 |

Expression levels were compared between tumor tissues and normal tissues using the 8 kinds of organs shown in Example 3. The expression was also compared with the blood cell mixture (Mix, blood cells and related tissues) and brain sample as experimental controls.

A wide difference was observed in four kinds of organs: Ovary, Uterus, Stomach, and Tongue. For the other organs, like the increase or decrease in the amplification of the fragment 062_05 (SEQ ID NO:158), which is common to all patterns, the amplification of the fragments of the other patterns increased or decreased.

In Ovary, Uterus, Stomach, and Tongue, comparing normal tissues and tumor tissues, the transcription initiation point shown by 062_01 (SEQ ID NO:150), which was newly acquired and subjected to analysis by us, was more abundantly expressed in tumor tissues than in normal tissues, whereas the transcription initiation point of the pattern 062_03 (SEQ ID NO:154), which was registered with an existing public DB, was more abundantly expressed in normal tissues than in tumor tissues (Table 8).

The expression of the shared region shown by 062_05 (SEQ ID NO:158) was less abundant in tumor tissues in Ovary and Uterus, and in Stomach and Tongue, the expression was less abundant in normal tissues (Table 8).

These results demonstrated that by using the newly acquired cDNA region 062_[1]_1-N1 (SEQ ID NO:145) shown by the detection region 062_01 (SEQ ID NO:150) as a tumor marker, it is possible to use the cDNA region as a diagnostic/therapeutic marker for the four kinds of tumors of Ovary, Uterus, Stomach, and Tongue. It also seems possible to develop a new drug by means of a compound, antibody, siRNA or the like that targets a region that exhibits specificity.

The following regions also seem to be useful as diagnostic/therapeutic markers.

Upstream sequence 062_[1]_1-N3 (SEQ ID NO:160), which comprises the 59th to 80th bases primed by Primer062_01R (SEQ ID NO:149) in D-CTONG2001283.1 of the cDNA pattern [1].

Region 062_91 (SEQ ID NO:150) amplified by Primer062_01F (SEQ ID NO:148) and Primer062_01R (SEQ ID NO:149) in the cDNA pattern [1].

Example 9

Cluster chr6-836 (Data Set: 125)

(1) Cluster Analysis
1) Cluster Characteristics

An analysis was performed on 9 sequences of full-length cDNAs subjected to genome mapping onto the cluster chr6-836 (Human genome UCSC hg18 (NCBI Build34) chromosome 6, 106,720,000 bp to 106,900,000 bp) [D-OCBBF2013203.1, BC002699.2, BX537904.1, C-PLACE1004316, ENST00000263322, ENST00000343245, ENST00000360666, NM_004849.1, Y11588.1]. They were classifiable according to expression pattern difference into the following 3 kinds.

[1] D-OCBBF2013203.1
[2] BC002699.2, C-PLACE1004316 (AK001899.1), ENST00000263322, ENST00000343245, NM_004849.1, Y11588.1
[3] BX537904.1, ENST00000360666

[1] is a cDNA that was newly acquired and subjected to full-length cDNA sequence analysis by us, having a different ORF from that of [2] and [3], which had been registered with a public DB.

[1], compared with the known [2] and [3], had a different ORF because of the deletion of a portion corresponding to the 3rd exon in the ORF region.

It was found that the ORF regions present in the 3 kinds of cDNA patterns [1] to [3] have different splicing patterns such as exon deletions and insertions, from the same chromosome region, resulting in alterations of the amino acid sequences to produce diverse proteins and mRNAs.

2) Characteristics of D-OCBBF2013203.1 ([1]), which was Newly Acquired and Subjected to Full-Length cDNA Sequence Analysis by Us 125_[1]_1-N0 (SEQ ID NO:161): The entire nucleic acid sequence region of D-OCBBF2013203.1

125_[1]_1-NA0 (SEQ ID NO:162): Both the entire nucleic acid sequence region and amino acid sequence of D-OCBBF2013203.1

125_[1]_1-A0 (SEQ ID NO:163): The entire amino acid sequence region of D-OCBBF2013203.1

The 128-base exon (SEQ ID NO:168) present at the 435th to 562nd bases of NM_004849.1, which is registered with an existing public DB and serves for control, is lacked and not present in the region at the 453rd to 454 bases of D-OCBBF2013203.1 (SEQ ID NO:164). With this change, although the translation initiation point of D-OCBBF2013203.1 was present on the same exon as that on which the translation initiation point of NM_004849.1 was present, because of the alteration of the frame due to deletion of the 128 bases, and the ATG of a different frame served as the translation initiation point, the N-terminus differed by 1 residue.

125_[1]_1-N1 (SEQ ID NO:164): A deletion nucleic acid sequence region of D-OCBBF2013203.1

125_[1]_1-A1 (SEQ ID NO:165): An amino acid region altered as a result of deletion of D-OCBBF2013203.1

125_[1]_1-N2 (SEQ ID NO:166): An ORF nucleic acid region in the deletion nucleic acid region of D-OCBBF2013203.1

125_[1]_1-A2 (SEQ ID NO:167): An ORF amino acid region related to the deletion nucleic acid region of D-OCBBF2013203.1

125_[1]_C-N1 (SEQ ID NO:168): The 128-base insert nucleic acid sequence present at the 435th to 562nd bases of NM_004849.1 inserted into the region at the 277th to 278th bases of D-OCBBF2013203.1

125_[1]_C-A1 (SEQ ID NO:169): An amino acid region related to the 128-base insert nucleic acid sequence present at the 435th to 562nd bases of NM_004849.1 inserted into the region at the 277th to 278th bases of D-OCBBF2013203.1

In D-OCBBF2013203.1, by secretion signal sequence estimation with SignalP, a signal sequence was estimated in the N-terminal region at the 1st to 16th residues (http://www.cbs.dtu.dk/services/SignalP/). In the known cDNA patterns [2] and [3], no signal sequence was estimated; the sequence was produced as a result of the deletion of the 128 bases.

3) Characteristics of C-PLACE1004316 (AK001899.1) ([2]), which was Acquired and Subjected to Full-Length cDNA Sequence Analysis by Us, and is Registered with a Public DB 125_[2]_1-N0 (SEQ ID NO:170): The entire nucleic acid sequence region of C-PLACE1004316

125_[2]_1-NA0 (SEQ ID NO:171): Both the entire nucleic acid sequence region and amino acid sequence of C-PLACE1004316

125_[2]_1-A0 (SEQ ID NO:172): The entire amino acid sequence region of C-PLACE1004316

4) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

125_01—A region specifically extracted by means of the sequence information at the border of an exon deletion region in the cDNA pattern [1]: an ORF-altering exon deletion region in the cDNA pattern [1], which was newly subjected to full-length cDNA sequence analysis by us →Fragment 125_01 (SEQ ID NO:175) amplified by Primer125_01F (SEQ ID NO:173) and Primer125_01R (SEQ ID NO:174)

125_02—A specific region that is distinguishable from the deletion region [1] of the cDNA pattern [2], which is registered with an existing public DB, serving as a control for comparing [1]

→Fragment 125_02 (SEQ ID NO:178) amplified by Primer 125_02F (SEQ ID NO:176) and Primer 125_02R (SEQ ID NO:177)

125_03—A common region shared by [1] and [2]: a region common to all patterns, serving for control to compare the overall expression levels of the cDNA pattern [1], which was newly subjected to full-length cDNA sequence analysis by us, and the cDNA pattern [2], which is registered with an existing public DB →Fragment 125_03 (SEQ ID NO:181) amplified by Primer125_03F (SEQ ID NO:179) and Primer125_03R (SEQ ID NO:180)

By mapping the 5'-terminal sequences of about 1.44 million sequences acquired using the oligocap method onto the human genome sequence, and comparatively analyzing them, the exon regions specific for the three kinds of cDNA patterns [1] to and [3] shown above, respectively, were found to be expressed at the following frequencies.

In the cDNA pattern [1], which was newly acquired and subjected to full-length cDNA sequence analysis by us, five 5'-terminal sequences were present, the derivations thereof being Kidney, Tumor for 1 sequence (analytical parameter 15,970), Placenta for 1 sequence (analytical parameter 46,090), Brain, Fetal for 1 sequence (analytical parameter 47,574), Brain, thalamus for 1 sequence (analytical parameter 53,267), and SK-N-SH cells (Neuroblastoma) for 1 sequence (analytical parameter 8,662).

In the cDNA pattern [2], which is registered with an existing public DB, twenty-nine 5'-terminal sequences were present, the derivations thereof all being normal tissues; they were expressed in various tissues, such as Testis, Heart, Synovial membrane tissue from rheumatoid arthritis, and Thymus.

In the cDNA pattern [3], which is registered with an existing public DB, no 5'-terminal sequences were present.

From this result, it was found that the exon deletion pattern [1] was expressed in Brain, Fetal, tumor tissues and the like. The expression of the known sequence [2] was observed in various organs. Hence, it was thought that in this chromosome region, a selection mechanism for mRNA pattern changes resulting in an amino acid alteration due to exon selectivity and the expression of different proteins might arise in a particular tissue, as in the pattern [1].

(2) Expression Specificity Analysis by Real-Time PCR

To detect protein expression diversity changes due to exon selectivity among different tissues, details of expression levels were analyzed by real-time PCR. The results are shown in Table 9.

TABLE 9

| | RQ | | | $\log_{10}$RQ | | |
|---|---|---|---|---|---|---|
| | 125_01 | 125_02 | 125_03 | 125_01 | 125_02 | 125_03 |
| 01 Colon | 0.7 | 0.6 | 0.5 | −0.16 | −0.19 | −0.33 |
| 02 Colon Tumor | Undet. | 0.0 | Undet. | Undet. | −2.28 | Undet. |
| 03 Kidney | 1.2 | 0.9 | 1.0 | 0.07 | −0.06 | −0.02 |
| 04 Kidney Tumor | 0.5 | 0.8 | 0.6 | −0.31 | −0.08 | −0.19 |
| 05 Liver | 0.4 | 0.5 | 0.4 | −0.41 | −0.30 | −0.36 |
| 06 Liver Tumor | 1.8 | 2.3 | 2.5 | 0.24 | 0.37 | 0.39 |
| 07 Lung | 0.0 | 1.0 | 0.0 | −2.68 | −0.01 | −1.95 |
| 08 Lung Tumor | 0.1 | 0.1 | 0.1 | −0.94 | −0.92 | −0.94 |
| 09 Ovary | 2.7 | 2.0 | 2.5 | 0.43 | 0.29 | 0.39 |
| 10 Ovary Tumor | 1.1 | 0.8 | 0.9 | 0.06 | −0.11 | −0.05 |
| 11 Stomach | 2.1 | 3.0 | 2.9 | 0.31 | 0.47 | 0.47 |
| 12 Stomach Tumor | 0.0 | 0.2 | 0.0 | −2.63 | −0.67 | −1.93 |
| 13 Uterus | 1.4 | 1.4 | 1.4 | 0.16 | 0.15 | 0.14 |
| 14 Uterus Tumor | 0.1 | 0.7 | 0.1 | −1.26 | −0.18 | −0.92 |
| 15 Tongue | 0.7 | 1.0 | 0.8 | −0.14 | 0.00 | −0.09 |
| 16 Tongue Tumor | 0.9 | 0.9 | 0.9 | −0.06 | −0.05 | −0.05 |
| 17 Brain, whole | 2.6 | 1.0 | 1.4 | 0.42 | 0.01 | 0.16 |
| 18 Mix, blood cells and related tissues | 1.0 | 1.0 | 1.0 | 0.0 | 0.0 | 0.0 |

Expression levels were compared between tumor tissues and normal tissues using the 8 kinds of organs shown in Example 3. The expression was also compared with the blood cell mixture (Mix, blood cells and related tissues) and brain sample shown in Example 3 as experimental controls.

A wide difference was observed in three kinds of organs: Kidney, Lung, and Tongue. For the other organs, like the increase or decrease in the amplification of the fragment 125_03 (SEQ ID NO:181), which is common to all patterns, the amplification of the fragments of the other patterns increased or decreased.

In Lung and Tongue, comparing normal tissues and tumor tissues, the newly analyzed expression pattern shown by 125_01 (SEQ ID NO:175) was more abundantly expressed in tumor tissues than in normal tissues, whereas the pattern 125_02 (SEQ ID NO:178), which was registered with an existing public DB, was more abundantly expressed in normal tissues than in tumor tissues (Table 9).

In Kidney, comparing normal tissues and tumor tissues, the newly analyzed expression pattern shown by 125_01 (SEQ ID NO:175) was more abundantly expressed in normal tissues than in tumor tissues, whereas the pattern 125_02 (SEQ ID NO:178), which was registered with an existing public DB, exhibited no difference in expression level between normal tissues and tumor tissues (Table 9).

These results demonstrated that by using the newly acquired cDNA region 125_[1]_1-N1 (SEQ ID NO:164) shown by the detection region 125_01 (SEQ ID NO:175) as a tumor marker, it is possible to use the cDNA region as a diagnostic/therapeutic marker for the three kinds of tumors of Kidney, Lung, and Tongue. It also seems possible to develop a new drug by means of a compound, antibody, siRNA or the like that targets a region that exhibits specificity.

The following regions also seem to be useful as diagnostic/therapeutic markers.

Upstream sequence 125_[1]_1-N3 (SEQ ID NO:182), which comprises the 546th to 567th bases primed by Primer125_01R (SEQ ID NO:174) in D-OCBBF2013203.1 of the cDNA pattern [1]. Region 125_01 (SEQ ID NO:175) amplified by Primer125_01F (SEQ ID NO:173) and Primer125_01R (SEQ ID NO:174) in the cDNA pattern [1]

Example 10

Cluster chr7-927 (Data Set: 141)

(1) Cluster Analysis
1) Cluster Characteristics

An analysis was performed on 10 sequences of full-length cDNAs subjected to genome mapping onto the cluster chr7-927 (Human genome UCSC hg18 (NCBI Build34) chromosome 7, 100,548,000 to 100,560,000 bp) [D-BRAWH2011787.1, Z-BRALZ2001614-01, AL157469.1, BC004522.2, BC009823.2, C-MAMMA1001785, C-OVARC1000058, ENST00000275737, ENST00000315322, NM_022777.1]. They were classified according to expression pattern difference into several kinds, which mainly included the following 3 kinds.

[1] D-BRAWH2011787.1
[2] Z-BRALZ2001614-01
[3] BC009823.2, C-MAMMA1001785 (AK024179.1), ENST00000315322, NM_022777.1

[1] and [2] are cDNAs that were newly acquired and subjected to full-length cDNA sequence analysis by us, having an ORF different from that of [3], which was registered with an existing public DB.

[1], compared with the known [3], had a different ORF region because of the insertion of an exon different from other patterns in the ORF region.

[2], compared with the known [3], had a different ORF because of an exon deletion and exon insertion different from other patterns in the ORF region.

It was found that the ORF regions present in the 3 kinds of cDNA patterns [1] to [3] have different splice patterns such as exon insertions and deletions, from the same chromosome region, resulting in alterations of the amino acid sequences to produce diverse proteins and mRNAs.

2) Characteristics of D-BRAWH2011787.1 ([1]), which was Newly Acquired and Subjected to Full-Length cDNA Sequence Analysis by Us 141_[1]_1-N0 (SEQ ID NO:183): The entire nucleic acid sequence region of D-BRAWH2011787.1

141_[1]_1-NA0 (SEQ ID NO:184): Both the entire nucleic acid sequence region and amino acid sequence of D-BRAWH2011787.1

141_[1]_1-A0 (SEQ ID NO:185): The entire amino acid sequence region of D-BRAWH2011787.1

A variant in which a 713-base exon (SEQ ID NO:186) is inserted into the region at the 449th to 450th by of NM_022777.1, which is registered with an existing public DB and serves for control; because of the emergence of a stop codon on the insert sequence to cause the ORF to be terminated on the insert sequence, although the translation initiation point did not change, the C-terminal amino acids differed by 12 residues (SEQ ID NO:187), compared with NM_022777.1.

141_[1]_1-N1 (SEQ ID NO:186): A 713-base insert nucleic acid sequence region of D-BRAWH2011787.1

141_[1]_1-A1 (SEQ ID NO:187): A 12-residue insert amino acid sequence region of D-BRAWH2011787.1

141_[1]_1-N2 (SEQ ID NO:188): An ORF nucleic acid sequence region in the 713-base insert region of D-BRAWH2011787.1

141_[1]_1-A2 (identical to SEQ ID NO:187): An ORF amino acid sequence region in the 713-base insert region of D-BRAWH2011787.1

3) Characteristics of Z-BRALZ2001614-01 ([2]), which was Newly Acquired and Subjected to Full-Length cDNA Sequence Analysis by Us 141_[2]_1-N0 (SEQ ID NO:189): The entire nucleic acid sequence region of Z-BRALZ2001614-01

141_[2]_1-NA0 (SEQ ID NO:190): Both the entire nucleic acid sequence region and amino acid sequence of Z-BRALZ2001614-01

141_[2]_1-A0 (SEQ ID NO:191): The entire amino acid sequence region of Z-BRALZ2001614-01

A variant in which the 167-base exon present at the 80th to 246th bases of NM_022777.1 (SEQ ID NO:196), which is registered with an existing public DB and serves for control, is lacked and not present in the region at the 127th to 128th bases of Z-BRALZ2001614-01 (SEQ ID NO:192), and in which an 847-base exon (SEQ ID NO:193) is inserted into the region of the 449th to 450th by of NM_022777.1.

With these changes, because of the translation of the ORF of Z-BRALZ2001614-01 initiated from the translation initiation point of a different exon and different frame from NM_022777.1 to cause the ORF to be terminated on the insert exon, the entire amino acid sequence region was altered, resulting in an amino acid sequence lacking homology to NM_022777.1.

141_[2]_1-N1 (SEQ ID NO:192): A deletion nucleic acid sequence region of Z-BRALZ2001614-01

141_[2]_1-N2 (SEQ ID NO:193): An 847-base insert nucleic acid sequence region of Z-BRALZ2001614-01
141_[2]_1-A1 (identical to SEQ ID NO:190 and SEQ ID NO:191):
An ORF amino acid sequence region altered as a result of deletion of Z-BRALZ2001614-01 and insertion of 847 bases
141_[2]_1-N3 (SEQ ID NO:194): An ORF nucleic acid sequence region in the 847-base insert region of Z-BRALZ2001614-01
141_[2]_1-A2 (SEQ ID NO:195): An ORF amino acid sequence region altered by the 847-base insert region of Z-BRALZ2001614-01
141_[2]_C-N1 (SEQ ID NO:196): A 167-base insert nucleic acid sequence present at the 80th to 246th bases of NM_022777.1 inserted into the region at the 127th to 128th bases of Z-BRALZ2001614-01
141_[2]_C-A1 (SEQ ID NO:197): An amino acid region related to the 167-base insert nucleic acid sequence present at the 80th to 246th bases of NM_022777.1 inserted into the region at the 127th to 128th bases of Z-BRALZ2001614-01

4) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

141_01—A region specifically extracted by means of the sequence information on regions with an exon insertion of the cDNA pattern [1]: an ORF-altering exon insert region in the cDNA pattern [1], which was newly subjected to full-length cDNA sequence analysis by us
→Fragment 141_01 (SEQ ID NO:200) amplified by Primer141_01F (SEQ ID NO:198) and Primer141_01R (SEQ ID NO:199)

141_02—A specific region that is distinguishable from the insert region [1] of the cDNA pattern [3], which is registered with an existing public DB, serving as a control for comparing [1]
→Fragment 141_02 (SEQ ID NO:203) amplified by Primer141_02F (SEQ ID NO:201) and Primer141_02R (SEQ ID NO:202)

141_04—A common region shared by [1], [2], and [3]: a region common to all patterns, serving for control to compare the overall expression levels of the cDNA patterns [1] and [2], which were newly subjected to full-length cDNA sequence analysis by us, and the cDNA pattern [3], which is registered with an existing public DB
→Fragment 141_04 (SEQ ID NO:206) amplified by Primer141_04F (SEQ ID NO:204) and Primer141_04R (SEQ ID NO:205)

By mapping the 5'-terminal sequences of about 1.44 million sequences acquired using the oligocap method onto the human genome sequence, and comparatively analyzing them, the exon regions specific for the three kinds of cDNA patterns [1], [2], and [3] shown above, respectively, were found to be expressed at the following frequencies.

In the cDNA pattern [1], which was newly acquired and subjected to full-length cDNA sequence analysis by us, one 5'-terminal sequence was present, the derivation thereof being Brain, whole for 1 sequence (analytical parameter 59,069).

In the cDNA pattern [2], which was newly acquired and subjected to full-length cDNA sequence analysis by us, one 5'-terminal sequence was present, the derivation thereof being Brain, cortex, Alzheimer for 1 sequence (analytical parameter 16,360).

In the cDNA pattern [3], which is registered with an existing public DB, four 5'-terminal sequences were present, the derivations thereof being Brain, Fetal for 1 sequence (analytical parameter 31,986), Mammary Gland for 1 sequence (analytical parameter 2,987), Esophageal, Tumor for 1 sequence (analytical parameter 8,500), and Testis for 1 sequence (analytical parameter 90,188).

From this result, it was found that the patterns [1] and [2] were expressed in the brain. The expression of the known sequence [3] was observed in various organs. Hence, it was thought that in this chromosome region, a selection mechanism for mRNA pattern changes resulting in an amino acid alteration due to exon selectivity and the expression of different proteins might arise in a particular tissue, as in the patterns [1] and [2].

(2) Expression Specificity Analysis by Real-Time PCR

To detect protein expression diversity changes due to exon selectivity among different tissues, details of expression levels were analyzed by real-time PCR. The results are shown in Table 10.

TABLE 10

|  | RQ | | | Log₁₀RQ | | |
| --- | --- | --- | --- | --- | --- | --- |
|  | 141_01 | 141_02 | 141_04 | 141_01 | 141_02 | 141_04 |
| 01 Colon | 0.5 | 0.6 | 0.6 | −0.33 | −0.22 | −0.19 |
| 02 Colon Tumor | Undet. | 0.1 | 0.5 | Undet. | −0.91 | −0.32 |
| 03 Kidney | 1.6 | 2.8 | 2.7 | 0.19 | 0.44 | 0.43 |
| 04 Kidney Tumor | 0.6 | 1.2 | 1.2 | −0.22 | 0.09 | 0.09 |
| 05 Liver | 0.1 | 0.6 | 0.6 | −0.85 | −0.23 | −0.23 |
| 06 Liver Tumor | 3.6 | 1.6 | 1.5 | 0.55 | 0.22 | 0.19 |
| 07 Lung | Undet. | 3.9 | 6.9 | Undet. | 0.59 | 0.84 |
| 08 Lung Tumor | 0.7 | 0.8 | 0.9 | −0.16 | −0.08 | −0.04 |
| 09 Ovary | 2.2 | 1.4 | 1.9 | 0.33 | 0.14 | 0.27 |
| 10 Ovary Tumor | 1.8 | 1.9 | 2.8 | 0.24 | 0.27 | 0.45 |
| 11 Stomach | 0.9 | 1.2 | 1.3 | −0.05 | 0.08 | 0.11 |
| 12 Stomach Tumor | 0.0 | 0.7 | 1.4 | −1.71 | −0.17 | 0.15 |
| 13 Uterus | 0.7 | 2.3 | 2.3 | −0.15 | 0.35 | 0.37 |
| 14 Uterus Tumor | 0.1 | 3.2 | 3.5 | −0.96 | 0.51 | 0.54 |
| 15 Tongue | 5.8 | 0.7 | 0.7 | 0.77 | −0.18 | −0.15 |
| 16 Tongue Tumor | 1.9 | 0.7 | 0.7 | 0.27 | −0.15 | −0.14 |
| 17 Brain, whole | 4.3 | 1.6 | 1.7 | 0.63 | 0.20 | 0.22 |
| 18 Mix, blood cells and related tissues | 1.0 | 1.0 | 1.0 | 0.0 | 0.0 | 0.0 |

Expression levels were compared between tumor tissues and normal tissues using the 8 kinds of organs shown in Example 3. The expression was also compared with the blood cell mixture (Mix, blood cells and related tissues) and brain sample shown in Example 3 as experimental controls.

A wide difference was observed in three kinds of organs: Ovary, Uterus, and Tongue. For the other organs, like the increase or decrease in the amplification of the fragment 141_04 (SEQ ID NO:206), which is common to all patterns, the amplification of the fragments of the other patterns increased or decreased.

In the three kinds of organs of Ovary, Uterus, and Tongue, comparing normal tissues and tumor tissues, the newly analyzed expression pattern shown by 141_01 (SEQ ID NO:200) was more abundantly expressed in normal tissues than in tumor tissues, whereas the pattern 141_02 (SEQ ID NO:203), which was registered with an existing public DB, was more abundantly expressed in tumor tissues than in normal tissues (Table 10).

These results demonstrated that by using the newly acquired cDNA region 141_[1]_1-N1 (SEQ ID NO:186) shown by the detection region 141_01 (SEQ ID NO:200) as a tumor marker, it is possible to use the cDNA region as a diagnostic/therapeutic marker for the three kinds of tumors of Ovary, Uterus, and Tongue. It also seems possible to develop a new drug by means of a compound, antibody, siRNA or the like that targets a region that exhibits specificity.

The following regions also seem to be useful as diagnostic/therapeutic markers.

Upstream sequence 141_[1]_1-N3 (SEQ ID NO:207), which comprises the 628th to 650th bases primed by Primer141_01R (SEQ ID NO:199) in D-BRAWH2011787.1 of the cDNA pattern [1]. Region 141_01 (SEQ ID NO:200) amplified by Primer141_01F (SEQ ID NO:198) and Primer141_01R (SEQ ID NO:199) in the cDNA pattern [1]

Example 11

Cluster chr1-1273 (Data Set: 130)

(1) Cluster Analysis
1) Cluster Characteristics

An analysis was performed on 8 sequences of full-length cDNAs subjected to genome mapping onto the cluster chr1-1273 (Human genome UCSC hg18 (NCBI Build34) chromosome 1, 158,012,000 bp to 158,022,000 bp) [D-TLIVE2001566.1, D-TLIVE2006761.1, D-LIVER2001320.1, Z-TLIVE2000085-01, BC069626.1, BC069651.1, ENST00000289912, NM_005122.2]. They were classifiable according to expression pattern difference mainly into the following 3 kinds.
[1] D-TLIVE2001566.1
[2] D-TLIVE2006761.1, D-LIVER2001320.1
[3] BC069626.1, ENST00000289912, NM_005122.2

[1] and [2] are cDNAs that were newly acquired and subjected to full-length cDNA sequence analysis by us, having a different ORF from that of [3], which was registered with an existing public DB.

[1], compared with the known [3], had a different ORF region because of the presence of an exon deletion and insertion at a total of two sites different from the other patterns in the ORF region.

[2], compared with the known [3], had a different ORF is region because of the insertion of an exon different from the other patterns in the ORF region.

It was found that the ORF regions present in the 3 kinds of cDNA patterns [1] to [3] have different splice patterns such as exon insertions, from the same chromosome region, resulting in alterations of the amino acid sequences to produce diverse proteins and mRNAs.

2) Characteristics of D-TLIVE2001566.1 ([1]), which was Newly Acquired and Subjected to Full-Length cDNA Sequence Analysis by Us 130_[1]_1-N0 (SEQ ID NO:208): The entire nucleic acid sequence region of D-TLIVE2001566.1

130_[1]_1-NA0 (SEQ ID NO:209): Both the entire nucleic acid sequence region and amino acid sequence of D-TLIVE2001566.1

130_[1]_1-A0 (SEQ ID NO:210): The entire amino acid sequence region of D-TLIVE2001566.1

The 140-base exon present at the 126th to 265th bases of NM_005122.2 (SEQ ID NO:214), which is registered with an existing public DB and serves for control, is lacked and not present in the region at the 163rd to 164th bases of D-TLIVE2001566.1 (SEQ ID NO:211). Because the translation initiation point of NM_005122.2 was present on this inserted 140-base exon (2nd exon), whereas the translation initiation point of D-TLIVE2001566.1 was present on the 1st exon, which is shared by D-TLIVE2001566.1 and NM_005122.2, the N-terminus differed by 7 residues.

130_[1]_1-N1 (SEQ ID NO:211): A deletion nucleic acid sequence region of D-TLIVE2001566.1

130_[1]_1-A1 (SEQ ID NO:212): An amino acid region altered as a result of deletion of D-TLIVE2001566.1

130_[1]_1-N2 (SEQ ID NO:213): An ORF nucleic acid region in the deletion nucleic acid region of D-TLIVE2001566.1

130_[1]_1-A2 (SEQ ID NO:248): An ORF amino acid region related to the deletion nucleic acid region of D-TLIVE2001566.1

130_[1]_C-N1 (SEQ ID NO:214): A 140-base insert nucleic acid sequence present at the 126th to 265th bases of NM_005122.2 inserted into the region at the 163rd to 164th bases of D-TLIVE2001566.1

130_[1]_C-A1 (SEQ ID NO:215): An amino acid region related to the 140-base insert nucleic acid sequence present at the 126th to 265th bases of NM_005122.2 inserted into the region at the 163rd to 164th bases of D-TLIVE2001566.1

This is a variant in which a 466-base exon (SEQ ID NO:216) is inserted into the region at the 1,077th to 1,078th bases of NM_005122.2, serving for control; because of the emergence of a stop codon on the insert sequence to cause the ORF to be terminated on the insert sequence, although the translation initiation point did not change, the C-terminal amino acids differed by 20 residues (SEQ ID NO:217), compared with NM_005122.2.

130_[1]_1-N3 (SEQ ID NO:216): A 466-base insert nucleic acid sequence region of D-TLIVE2001566.1

130_[1]_1-A3 (SEQ ID NO:217): A 20-residue insert amino acid sequence region of D-TLIVE2001566.1

130_[1]_1-N4 (SEQ ID NO:218): An ORF nucleic acid sequence region in the 466-base insert region of D-TLIVE2001566.1

130_[1]_1-A4 (identical to SEQ ID NO:217): An ORF amino acid sequence region in the 466-base insert region of D-TLIVE2001566.1

3) Characteristics of D-TLIVE2006761.1 ([2]), which was Newly Acquired and Subjected to Full-Length cDNA Sequence Analysis by Us 130_[2]_1-N0 (SEQ ID NO:219): The entire nucleic acid sequence to region of D-TLIVE2006761.1

130_[2]_1-NA0 (SEQ ID NO:220): Both the entire nucleic acid sequence region and amino acid sequence of D-TLIVE2006761.1

130_[2]_1-A0 (SEQ ID NO:221): The entire amino acid sequence region of D-TLIVE2006761.1

This is a variant in which a 40-base exon (SEQ ID NO:222) is inserted into the region at the 852nd to 853rd bases of NM_005122.2, which is registered with an existing public DB and serves for control; because of the emergence of a stop codon on the insert sequence to cause the ORF to be terminated on the insert sequence, although the translation initiation point did not change, the C-terminal amino acids differed by 7 residues (SEQ ID NO:223), compared with NM_005122.2.

130_[2]_1-N1 (SEQ ID NO:222): A 40-base insert nucleic acid sequence region of D-TLIVE2006761.1

130_[2]_1-A1 (SEQ ID NO:223): A 7-residue insert amino acid sequence region of D-TLIVE2006761.1

130_[2]_1-N2 (SEQ ID NO:224): An ORF nucleic acid sequence region in the 40-base insert region of D-TLIVE2006761.1

130_[2]_1-A2 (identical to SEQ ID NO:223): An ORF amino acid sequence region in the 40-base insert region of D-TLIVE2006761.1

4) Characteristics of D-LIVER2001320.1 ([2]), which was Newly Acquired and Subjected to Full-Length cDNA Sequence Analysis by Us 130_[2]_2-N0 (SEQ ID NO:225): The entire nucleic acid sequence region of D-LIVER2001320.1

130_[2]_2-NA0 (SEQ ID NO:226): Both the entire nucleic acid sequence region and amino acid sequence of D-LIVER2001320.1

130_[2]_2-A0 (SEQ ID NO:227): The entire amino acid sequence region of D-LIVER2001320.1

A variant in which a 95-base exon (SEQ ID NO:228) is inserted into the region at the 852nd to 853rd bases of NM_005122.2, which is registered with an existing public DB and serves for control; because of the emergence of a stop codon on the insert sequence to cause the ORF to be terminated on the insert sequence, although the translation initiation point did not change, the C-terminal amino acids differed by 7 residues (SEQ ID NO:229), compared with NM_005122.2.

130_[2]_2-N1 (SEQ ID NO:228): A 95-base insert nucleic acid sequence region of D-LIVER2001320.1

130_[2]_2-A1 (SEQ ID NO:229): A 7-residue insert amino acid sequence region of D-LIVER2001320.1

130_[2]_2-N2 (SEQ ID NO:230): An ORF nucleic acid sequence region in the 95-base insert region of D-LIVER2001320.1

130_[2]_2-A2 (identical to SEQ ID NO:229): An ORF amino acid sequence region in the 95-base insert region of D-LIVER2001320.1

5) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

130_01—A region specifically extracted by means of the sequence information on regions with an exon deletion of the cDNA pattern [1]: an ORF-altering exon deletion region in the cDNA pattern [1], which was newly subjected to full-length cDNA sequence analysis by us
 →Fragment 130_01 (SEQ ID NO:233) amplified by Primer130_01F (SEQ ID NO:231) and Primer130_01R (SEQ ID NO:232)

130_02—A specific region that is distinguishable from the deletion region [1] of the cDNA pattern [3], which is registered with an existing public DB, serving as a control for comparing [1]
 →Fragment 130_02 (SEQ ID NO:236) amplified by Primer130_02F (SEQ ID NO:234) and Primer130_02R (SEQ ID NO:235)

130_05—A region specifically extracted by means of the sequence information on regions with an exon insertion of the cDNA pattern [1]: an ORF-altering exon insert region in the cDNA pattern [1], which was newly subjected to full-length cDNA sequence analysis by us
 →Fragment 130_05 (SEQ ID NO:239) amplified by Primer130_05F (SEQ ID NO:237) and Primer130_05R (SEQ ID NO:238)

130_06—A specific region that is distinguishable from both the insert region [1] of the cDNA pattern [3], which is registered with an existing public DB, serving as a control for comparing [1]
 →Fragment 130_06 (SEQ ID NO:242) amplified by Primer130_06F (SEQ ID NO:240) and Primer130_06R (SEQ ID NO:241)

130_07—A common region shared by all of [1] to [3]: a region common to all patterns, serving for control to compare the overall expression levels of the cDNA pattern [1], which was newly subjected to full-length cDNA sequence analysis by us, and the cDNA pattern [3], which is registered with an existing public DB
 →Fragment 130_07 (SEQ ID NO:245) amplified by Primer130_07F (SEQ ID NO:243) and Primer130_07R (SEQ ID NO:244)

By mapping the 5'-terminal sequences of about 1.44 million sequences acquired using the oligocap method onto the human genome sequence, and comparatively analyzing them, the exon regions specific for the three kinds of cDNA patterns [1], [2], and [3] shown above, respectively, were found to be expressed at the following frequencies.

In the cDNA pattern [1], which was newly acquired and subjected to full-length cDNA sequence analysis by us, one 5'-terminal sequence was present, the derivation thereof being Liver, Tumor for 1 sequence (analytical parameter 8,627).

In the cDNA pattern [2], which was newly acquired and subjected to full-length cDNA sequence analysis by us, two 5'-terminal sequences were present, the derivations thereof being Liver for 1 sequence (analytical parameter 6,843) and Liver, Tumor for 1 sequence (analytical parameter 8,627).

In the patterns that could not be identified as either the cDNA pattern [2], which was newly acquired and subjected to full-length cDNA sequence analysis by us, or the cDNA pattern [3], which is registered with an existing public DB, eight 5'-terminal sequences were present, the derivations thereof being Liver, Tumor for 4 sequences (analytical parameter 8,627), Kidney for 2 sequences (analytical parameter 17,008), Adult Breast for 1 sequence (analytical parameter 2,731), and Brain, thalamus for 1 sequence (analytical parameter 53,267).

From this result, it was found that the exon deletion/insertion pattern [1] was expressed only in Liver, Tumor. It was thought that in this chromosome region, a selection mechanism for mRNA pattern changes resulting in an amino acid alteration due to exon selectivity and the expression of different proteins might arise in a particular tissue, as in the pattern [1].

(2) Expression Specificity Analysis by Real-Time PCR

To detect protein expression diversity changes due to exon selectivity among different tissues, details of expression levels were analyzed by real-time PCR. The results are shown in Table 11.

TABLE 11

|  | RQ | | | | | Log$_{10}$RQ | | | | |
| --- | --- | --- | --- | --- | --- | --- | --- | --- | --- | --- |
|  | 130_01 | 130_02 | 130_05 | 130_06 | 130_07 | 130_01 | 130_02 | 130_05 | 130_06 | 130_07 |
| 01 Colon | 0.1 | 0.8 | 0.6 | 3.5 | 0.7 | −0.96 | −0.11 | −0.23 | 0.54 | −0.15 |
| 02 Colon Tumor | Undet. | Undet. | Undet. | Undet. | Undet. | Undet. | Undet. | Undet. | Undet. | Undet. |
| 03 Kidney | 208.4 | 149.5 | 3.1 | 852.8 | 18.2 | 2.32 | 2.17 | 0.50 | 2.93 | 1.26 |
| 04 Kidney Tumor | 0.0 | 0.1 | Undet. | 13.0 | 0.2 | −1.48 | −1.01 | Undet. | 1.11 | −0.80 |
| 05 Liver | 1450.2 | 1325.2 | 13.1 | 9390.6 | 139.0 | 3.16 | 3.12 | 1.12 | 3.97 | 2.14 |
| 06 Liver Tumor | 3130.1 | 2204.1 | 46.4 | 15055.5 | 302.1 | 3.50 | 3.34 | 1.67 | 4.18 | 2.48 |
| 07 Lung | 0.2 | 0.1 | Undet. | Undet. | 0.3 | −0.70 | −1.00 | Undet. | Undet. | −0.48 |
| 08 Lung Tumor | 0.0 | 0.2 | 0.1 | 0.5 | 0.2 | −1.39 | −0.62 | −1.16 | −0.33 | −0.68 |
| 09 Ovary | 1.2 | 2.2 | 0.7 | 1.1 | 1.2 | 0.09 | 0.34 | −0.17 | 0.05 | 0.06 |
| 10 Ovary Tumor | 0.2 | 0.8 | 0.5 | 2.4 | 0.8 | −0.72 | −0.11 | −0.31 | 0.39 | −0.07 |
| 11 Stomach | 0.2 | 0.9 | 0.9 | 5.8 | 0.6 | −0.63 | −0.04 | −0.07 | 0.76 | −0.25 |
| 12 Stomach Tumor | 0.0 | 0.1 | 0.0 | Undet. | 0.1 | −1.42 | −1.27 | −1.76 | Undet. | −0.89 |
| 13 Uterus | 0.5 | 1.6 | 0.8 | 3.4 | 1.9 | −0.31 | 0.20 | −0.11 | 0.53 | 0.27 |
| 14 Uterus Tumor | 0.0 | 0.0 | 0.0 | Undet. | 0.1 | −2.07 | −1.34 | −2.13 | Undet. | −1.06 |
| 15 Tongue | 3.3 | 7.9 | 3.1 | 4.9 | 5.4 | 0.52 | 0.90 | 0.49 | 0.69 | 0.73 |
| 16 Tongue Tumor | 1.2 | 2.5 | 0.8 | 6.3 | 2.0 | 0.07 | 0.39 | −0.12 | 0.80 | 0.30 |
| 17 Brain, whole | 1.9 | 6.0 | 2.4 | 3.3 | 3.5 | 0.27 | 0.78 | 0.39 | 0.52 | 0.55 |
| 18 Mix, blood cells and related tissues | 1.0 | 1.0 | 1.0 | 1.0 | 1.0 | 0.0 | 0.0 | 0.0 | 0.0 | 0.0 |

Expression levels were compared between tumor tissues and normal tissues using the 8 kinds of organs shown in Example 3. The expression was also compared with the blood cell mixture (Mix, blood cells and related tissues) and brain sample shown in Example 3 as experimental controls.

A wide difference was observed in three kinds of organs: Lung, Ovary, and Tongue. For the other organs, like the increase or decrease in the amplification of the fragment 130_07, which is common to all patterns, the amplification of the fragments of the other patterns increased or decreased.

Of the newly analyzed sequences, the expression pattern with the deletion shown by 130_01 (SEQ ID NO:233) on the N-terminal side, in Lung, comparing normal tissues and tumor tissues, was more abundantly expressed in normal tissues than in tumor tissues, whereas the pattern 130_02 (SEQ ID NO:236), which was registered with an existing public DB, serving as a control for the region, was more abundantly expressed in tumor tissues than in normal tissues (Table 11).

Of the newly analyzed sequences, the expression pattern with the insertion shown by 130_05 (SEQ ID NO:239) on the C-terminal side, in Ovary and Tongue, comparing normal tissues and tumor tissues, was more abundantly expressed in normal tissues than in tumor tissues, whereas the pattern 130_06 (SEQ ID NO:242), which was registered with an existing public DB, serving as a control for the region, was more abundantly expressed in tumor tissues than in normal tissues (Table 11).

These results demonstrated that by using the newly acquired cDNA regions 130_[1]_1-N1 (SEQ ID NO:211) and 130_[1]_1-N3 (SEQ ID NO:216) shown by the detection regions 130_01 (SEQ ID NO:233) and 130_05 (SEQ ID NO:239) as tumor markers, it is possible to use the cDNA regions as diagnostic/therapeutic markers for the three kinds of tumors of Lung, Ovary, and Tongue. It also seems possible to develop a new drug by means of a compound, antibody, siRNA or the like that targets a region that exhibits specificity.

The following regions also seem to be useful as diagnostic/therapeutic markers.

Upstream sequence 130_[1]_1-N5 (SEQ ID NO:246), which comprises the 152nd to 175th bases primed by Primer130_01R (SEQ ID NO:232) in D-TLIVE2001566.1 of the cDNA pattern [1]

Downstream sequence 130_[1]_1-N6 (SEQ ID NO:247), which comprises the 945th to 960th bases primed by Primer130_05F (SEQ ID NO:237) in D-TLIVE2001566.1 of the cDNA pattern [1]

Region 130_01 (SEQ ID NO:233) amplified by Primer130_01F (SEQ ID NO:231) and Primer130_01R (SEQ ID NO:232) in the cDNA pattern [1]

Region 130_05 (SEQ ID NO:239) amplified by Primer130_05F (SEQ ID NO:237) and Primer130_05R (SEQ ID NO:238) in the cDNA pattern [1]

Example 12

OFR Information on Full-Length cDNA Sequences and Results of Homology Analysis and Results of Analysis of Motif and the Like To determine the functions of 19 sequences of full-length cDNAs that were newly acquired and subjected to full-length cDNA sequence analysis by us, ORF estimation and annotation analysis were performed. Results of the annotation analysis can be updated when the database or analytical software for comparison is upgraded. Thereby, it is sometimes possible to newly add an annotation to sequences with no annotation given under the same conditions.

1) Estimation of ORFs of cDNAs Undergoing Full-Length cDNA Sequence Analysis

Using ORF estimation/evaluation systems such as ATGpr (A. Salamov et al. (1998) Bioinformatics 14: 384-390) and TRins (K. Kimura et al. (2003) Genome Informatics 14: 456-457), ORFs were estimated from full-length cDNA sequences. The ORF region information estimated from the full-length cDNA sequences is shown below.

The ORF regions were denoted in compliance with the rules of "DDBJ/EMBL/GenBank Feature Table Definition" (http://www.ncbi.nlm.nih.gov/collab/FT/index.html). The ORF start position is the first character of the methionine-encoding base "ATG", and the stop position represents the third character of the stop codon. These are indicated by a partition "..". However, for the ORFs that do not have a stop codon, the stop position is indicated with the use of ">" in compliance with the denotation rules.

| Name of cDNA sequence | ORF region |
|---|---|
| D-LIVER2001680.1 | 267 . . . 1805 |
| D-LIVER2008912.1 | 88 . . . 330 |
| D-LIVER2008912.1 | 191 . . . 439 |
| D-HCHON2007878.1 | 160 . . . 1491 |
| D-NTONG2006230.1 | 38 . . . 1369 |
| D-SPLEN2005548.1 | 165 . . . >1293 |
| D-HCHON2002384.1 | 489 . . . 1853 |
| D-BRCOC2007920.1 | 656 . . . 1960 |
| D-TKIDN2010471.1 | 305 . . . 2056 |
| D-FEBRA2010013.1 | 299 . . . 1066 |
| D-FEBRA2001626.1 | 177 . . . 944 |
| D-TKIDN2003621.1 | 268 . . . 867 |
| D-CTONG2001283.1 | 40 . . . 2085 |
| D-OCBBF2013203.1 | 452 . . . 1045 |
| D-BRAWH2011787.1 | 100 . . . 546 |
| Z-BRALZ2001614-01 | 307 . . . 747 |
| D-TLIVE2001566.1 | 144 . . . 1037 |
| D-TLIVE2006761.1 | 238 . . . 954 |
| D-LIVER2001320.1 | 196 . . . 912 |

2) Results of Homology Analysis Using BLASTP (SwissProt)

Homology analysis was performed on the 19 ORF sequences shown in Example 12-1), using BLASTP (blastall 2.2.6; ftp://ftp.ncbi.nih.gov/blast/), for SwissProt of the Aug. 22, 2006 version (ftp://us.expasy.org/databases/swiss-prot/). Based on the results of the homology analysis, the sequences showing the highest homology with an E-value of 1E-10 or less are shown below. In the following cases, however, the applicable candidate is not selected, but the next candidate is shown.
Having a definition beginning with "ALU SUBFAMILY"
Having a definition beginning with "Alu subfamily"
Having a definition beginning with "!!!! ALU SUBFAMILY"
Having a definition beginning with "B-CELL GROWTH FACTOR PRECURSOR"
Having a definition including "NRK2"
Having a definition beginning with "PROLINE-RICH"
Having a definition beginning with "GLYCINE-RICH"
Having a definition beginning with "EXTENSIN PRECURSOR"
Having a definition beginning with "COLLAGEN"
Having a definition beginning with "100 KD"
Having a definition beginning with "RETROVIRUS-RELATED POL POLYPROTEIN"
Having a definition beginning with "CUTICLE COLLAGEN"
Having a definition beginning with "HYPOTHETICAL"
Having a definition beginning with "Hypothetical"
Having a definition beginning with "SALIVARY PROLINE-RICH PROTEIN"
Having a definition beginning with "IMMEDIATE-EARLY PROTEIN"
Having the accession No "P49646"

Individual data are shown with the name of cDNA sequence, ORF region, hit data accession number, hit data definition, hit data keyword, E-value, consensus length (amino acid length), and identity, separated by "//" in this order.
D-LIVER2001680.1//267..1805//P31513//Dimethylaniline monooxygenase[N-oxide-forming] 3 (EC 1.14.13.8) (Hepaticflavin-containing monooxygenase 3) (FMO 3) (Dimethylaniline oxidase 3) (FMO form 2) (FMO II)//Disease mutation; Endoplasmic reticulum; FAD; Flavoprotein; Membrane; Microsome; Monooxygenase; NADP; Oxidoreductase; Polymorphism; Transmembrane.//0//487//99
D-LIVER2008912.1_88IN//88..330//Q7YS44//Dimethylaniline monooxygenase[N-oxide-forming] 3 (EC 1.14.13.8) (Hepaticflavin-containing monooxygenase 3) (FMO 3)(Dimethylaniline oxidase 3)//Endoplasmic reticulum; FAD; Flavoprotein; Membrane; Microsome; Monooxygenase; NADP; Oxidoreductase; Transmembrane.//7E-19//43//100
D-LIVER2008912.1//191..439//Q6B4Z3//Ubiquitously transcribed Y chromosometetratricopeptide repeat protein (Ubiquitouslytranscribed TPR protein on the Y chromosome)//Nuclear protein; Repeat; TPR repeat.//0.000000000000001//37//66
D-HCHON2007878.1//160..1491//P22932//Retinoic acid receptor gamma-2 (RAR-gamma-2)//3D-structure; Alternative splicing; DNA-binding; Metal-binding; Nuclear protein; Receptor; Transcription; Transcription regulation; Zinc; Zinc-finger.//0//442//99
D-NTONG2006230.1//38..1369//P22932//Retinoic acid receptor gamma-2 (RAR-gamma-2)//3D-structure; Alternative splicing; DNA-binding; Metal-binding; Nuclear protein; Receptor; Transcription; Transcription regulation; Zinc; Zinc-finger.//0//443//100
D-SPLEN2005548.1//165..>1293//P20787//Retinoic acid receptor gamma-B (RAR-gamma-B)//Alternative splicing; DNA-binding; Metal-binding; Nuclear protein; Receptor; Transcription; Transcription regulation; Zinc; Zinc-finger.//1E-131//228//99
D-HCHON2002384.1//489..1853//P13631//Retinoic acid receptor gamma-1 (RAR-gamma-1)//3D-structure; Alternative splicing; DNA-binding; Metal-binding; Nuclear protein; Receptor; Transcription; Transcription regulation; Zinc; Zinc-finger.//0//454//100
D-BRCOC2007920.1//656..1960//Q8IYB4//PEX5-related protein (Peroxin-5-related protein) (Pex5Rp) (PEX5-like protein) (PEX2-related protein)//Alternative splicing; Membrane; Phosphorylation; Repeat; TPR repeat.//0//433//99
D-TKIDN2010471.1//305..2056//Q8IYB4//PEX5-related protein (Peroxin-5-related protein) (Pex5Rp) (PEX5-like protein) (PEX2-related protein)//Alternative splicing; Membrane; Phosphorylation; Repeat; TPR repeat.//0//583//100
D-FEBRA2010013.1//299..1066//Q5RDS9//Fibroblast growth factor 13 (FGF-13)//Growth factor.//1E-103//184//96
D-FEBRA2001626.1//177..944//Q5RDS9//Fibroblast growth factor 13 (FGF-13)//Growth factor.//1E-103//184//96
D-TKIDN2003621.1//268..867//Q5RDS9//Fibroblast growth factor 13 (FGF-13)//Growth factor.//1E-104//185//94
D-CTONG2001283.1//40..2085//Q9Y223//Bifunctional UDP-N-acetylglucosamine-2-epimerase/N-acetylmannosamine kinase (UDP-GlcNAc-2-epimerase/ManAc kinase) [Includes: UDP-N-acetylglucosamine 2-epimerase (EC 5.1.3.14) (Uridinediphosphate-N-acetylglucosamine-2-epimerase)(UDP-GlcNAc-2-epimerase); N-acetylmannosamine kinase (EC 2.7.1.60) (ManAc kinase)]//Allosteric enzyme; ATP-binding; Disease mutation; Isomerase; Kinase; Multifunctional enzyme; Nucleotide-binding; Phosphorylation; Transferase.//0//670//98
D-OCBBF2013203.1//452..1045//Q5R792//Autophagy protein 5 (APG5-like)//Autophagy; Ubl conjugation.//1E-114//195//99
D-TLIVE2001566.1//144..1037//Q14994//Orphan nuclear receptor NR1I3 (Constitutive androstane receptor) (Constitutive activator of retinoid response) (Constitutive active response) (CAR) (Orphan nuclear receptor MB67)//3D-structure; Activator; Alternative splicing; DNA-binding;

Metal-binding; Nuclear protein; Polymorphism; Receptor; Transcription; Transcription regulation; Zinc; Zinc-finger.//1E-153//270//97
D-TLIVE2006761.1//238..954//Q14994//Orphan nuclear receptor NR1I3 (Constitutive androstane receptor) (Constitutive activator of retinoid response) (Constitutive active response) (CAR) (Orphan nuclear receptor MB67)//3D-structure; Activator; Alternative splicing; DNA-binding; Metal-binding; Nuclear protein; Polymorphism; Receptor; Transcription; Transcription regulation; Zinc; Zinc-finger.//1E-134//231//100
D-LIVER2001320.1//196..912//Q14994//Orphan nuclear receptor NR1I3 (Constitutive androstane receptor) (Constitutive activator of retinoid response) (Constitutive active response) (CAR) (Orphan nuclear receptor MB67)//3D-structure; Activator; Alternative splicing; DNA-binding; Metal-binding; Nuclear protein; Polymorphism; Receptor; Transcription; Transcription regulation; Zinc; Zinc-finger.//1E-134//231//100

3) Results of Homology Analysis Using BLASTP (RefSeq)

Homology analysis was performed on the 19 ORF sequences shown in Example 12-1), using BLASTP (blastall 2.2.6; ftp://ftp.ncbi.nih.gov/blast/), for RefSeq of the Jul. 15, 2006 version (human, mouse, rat; ftp://ftp.ncbi.nih.gov/refseq/). Based on the results of the homology analysis, the sequences showing the highest homology with an E-value of 1E-10 or less are shown below. In the following cases, however, the applicable candidate is not selected, but the next candidate is shown.

Having a definition beginning with "hypothetical protein FLJ"
Having a definition beginning with "KIAA"
Having a definition beginning with "hypothetical protein DKFZ"
Having a definition beginning with "DKFZ"
Having a definition beginning with "RIKEN cDNA"
Having a definition beginning with "hypothetical protein MGC"
Having a definition of "hypothetical protein"
Having a definition beginning with "hypothetical protein PP"
Having the definition as "neuronal thread protein"
Having a definition beginning with "clone FLB"
Having a definition beginning with "hypothetical protein PRO"
Having the definition as "PRO0483 protein"
Having a definition including "MNC"
Having a definition including "MOST-1"
Having a definition beginning with "similar to"
Having a definition including "TPR gene on Y"
Having a definition beginning with "HSPC"
Having a definition beginning with "CGI-"

Individual data are shown with the name of cDNA sequence, ORF region, hit data accession number, hit data definition, E-value, consensus length (amino acid length), and identity separated by "//" in this order.
D-LIVER2001680.1//267..1805//NP_008825.4//flavin containing monooxygenase 3 isoform 1 [*Homo sapiens*]//0//487//99
D-LIVER2008912.1_88IN//88..330//NP_008825.4//flavin containing monooxygenase 3 isoform 1 [*Homo sapiens*]//7E-20//44//100
D-LIVER2008912.1//191..439//NP_872601.1//tetratricopeptide repeat protein isoform 1 [*Homo sapiens*]//0.000000000000003//37//66
D-HCHON2007878.1//160..1491//NP_000957.1//retinoic acid receptor, gamma [*Homo sapiens*]//0//408//90
D-NTONG2006230.1//38..1369//NP_000957.1//retinoic acid receptor, gamma [*Homo sapiens*]//0//409//90
D-SPLEN2005548.1//165..>1293//NP_035374.2//retinoic acid receptor, gamma [*Mus musculus*]//1E-131//228//99
D-HCHON2002384.1//489..1853//NP_000957.1//retinoic acid receptor, gamma [*Homo sapiens*]//0//454//100
D-BRCOC2007920.1//656..1960//NP_057643.1//PXR2b protein [*Homo sapiens*]//0//433//99
D-TKIDN2010471.1//305..2056//NP_057643.1//PXR2b protein [*Homo sapiens*]//0//583//100
D-FEBRA2010013.1//299..1066//NP_004105.1//fibroblast growth factor 13 isoform 1A [*Homo sapiens*]//1E-103//184//96
D-FEBRA2001626.1//177..944//NP_004105.1//fibroblast growth factor 13 isoform 1A [*Homo sapiens*]//1E-103//184//96
D-TKIDN2003621.1//268..867//NP_004105.1//fibroblast growth factor 13 isoform 1A [*Homo sapiens*]//1E-104//185//94
D-CTONG2001283.1//40..2085//NP_005467.1//UDP-N-acetylglucosamine-2-epimerase/N-acetylmannosamine kinase [*Homo sapiens*]//0//670//98
D-OCBBF2013203.1//452..1045//NP_004840.1//APG5 autophagy 5-like [*Homo sapiens*]//1E-115//194//98
D-BRAWH2011787.1//100..546//NP_073614.1//RAB, member RAS oncogene family-like 5 [*Homo sapiens*]//4E-79//136//100
D-TLIVE2001566.1//144..1037//NP_005113.1//nuclear receptor subfamily 1, group I, member 3 [*Homo sapiens*]//1E-155//270//99
D-TLIVE2006761.1//238..954//NP_005113.1//nuclear receptor subfamily 1, group I, member 3 [*Homo sapiens*]//1E-134//231//100
D-LIVER2001320.1//196..912//NP_005113.1//nuclear receptor subfamily 1, group I, member 3 [*Homo sapiens*]//1E-134//231//100

4) Results of Motif Homology Analysis Using Pfam

Motif homology analysis was performed on the 19 ORF sequences shown in Example 12-1), using Pfam (ftp://ftp-.sanger.ac.uk/pub/databases/Pfam/). The analytical program used was hmmpfam v2.3.2, and the analysis was performed for the November 2005 version of Pfam19.0. Based on the results of the homology analysis, the sequences showing the highest homology with an E-value of 1E-10 or less are shown below.

Individual data are shown with the name of cDNA sequence and ORF region, followed by hit data accession number, hit data name, hit data description, E-value, and InterPro ID, separated by "¥" in this order, presented repeatedly using as many "//" partitions as the hit data.
D-LIVER2001680.1//267..1805//PF00743.9¥FMO-like¥Flavin-binding monooxygenase-like¥0¥IPR000960
D-HCHON2007878.1//160..1491//PF00105.9¥zf-C4¥Zinc finger, C4 type (two domains)¥1.4e-56¥IPR001628//PF00104.18¥Hormone_recep¥Ligand-binding domain of nuclear hormone receptor¥2.5e-20¥IPR000536
D-NTONG2006230.1//38..1369//PF00105.9¥zf-C4¥Zinc finger, C4 type (two domains)¥1.4e-56¥IPR001628//PF00104.18¥Hormone_recep¥Ligand-binding domain of nuclear hormone receptor¥2.5e-20¥IPR000536
D-SPLEN2005548.1//165..>1293//PF00105.9¥zf-C4¥Zinc finger, C4 type (two domains)¥2.1e-24¥IPR001628//PF00104.18¥Hormone_recep¥Ligand-binding domain of nuclear hormone receptor¥2.5e-20¥IPR000536
D-HCHON2002384.1//489..1853//PF00105.9¥zf-C4¥Zinc finger, C4 type (two domains)¥1.4e-56¥IPR001628//

PF00104.18¥Hormone_recep¥Ligand-binding domain of nuclear hormone receptor¥2.5e-20¥IPR000536
D-FEBRA2010013.1//299..1066//
PF00167.8¥FGF¥Fibroblast growth factor¥4.6e-51¥IPR002348
D-FEBRA2001626.1//177..944//
PF00167.8¥FGF¥Fibroblast growth factor¥4.6e-51¥IPR002348
D-TKIDN2003621.1//268..867//
PF00167.8¥FGF¥Fibroblast growth factor¥4.6e-51¥IPR002348
D-CTONG2001283.1//40..2085//PF02350.8¥Epimerase_2¥UDP-N-acetylglucosamine 2-epimerase¥3e-42¥IPR003331//PF00480.9¥ROK¥ROK family¥1.3e-39¥1IPR000600
D-OCBBF2013203.1//452..1045//
PF04106.2¥APG5¥Autophagy protein Apg5¥9.4e-135¥IPR007239
D-TLIVE2001566.1//144..1037//
PF00104.18¥Hormone_recep¥Ligand-binding domain of nuclear hormone receptor¥1.6e-12¥IPR000536//PF00105.9¥zf-C4¥Zinc finger, C4 type (two domains)¥1e-10¥IPR001628
D-TLIVE2006761.1//238..954//PF00105.9¥zf-C4¥Zinc finger, C4 type (two domains)¥9.3e-43¥IPR001628
D-LIVER2001320.1//196..912//PF00105.9¥zf-C4¥Zinc finger, C4 type (two domains)¥9.3e-43¥IPR001628

5) Transmembrane Domain Estimation Analysis Using SOSUI

Transmembrane domain estimation analysis was performed on the 19 ORF sequences shown in Example 12-1), using SOSUI (http://bp.nuap.nagoya-u.ac.jp/sosui/). For the analysis, SOSUI version 1.5 was used. The sequences that permitted an estimation of the transmembrane domain in the SOSUI analysis are shown below.

Individual data are shown with the name of cDNA sequence, ORF region, and number of passes through transmembrane domain separated by "//". D-LIVER2001680.1//267..1805//1

6) N-Terminal Secretion Signal Sequence Estimation Analysis Using PSORT

N-terminal secretion signal sequence estimation was performed on the 19 ORF sequences shown in Example 12-1), using PSORT (http://psort.nibb.ac.jp/). PSORT II was used for the analysis. The sequences that permitted an estimation of the N-terminal secretion signal sequence in the PSORT analysis are shown below. Individual data are shown with the name of cDNA sequence and ORF region separated by "//".
Z-BRALZ2001614-01//307..747

7) N-Terminal Secretion Signal Sequence Estimation Analysis Using SignalP ver. 3.0

N-terminal secretion signal sequence estimation was performed on the 19 ORF sequences shown in Example 12-1), using SignalP (http://www.cbs.dtu.dk/services/SignalP/). SignalP version 3.0 was used for the analysis. Sequences that permitted an estimation of the N-terminal secretion signal sequence in the SignalP analysis are shown below.

Individual data are shown with the name of cDNA sequence and ORF region separated by "//".
D-OCBBF2013203.1//452..1045
Z-BRALZ2001614-01//307..747

Summary of Examples 1 to 12

Although there have been remarkable advances in the analysis of human chromosome sequences thanks to the progress in human genome research, this does not mean that all the human genetic functions have been clarified. We analyzed human genes with a focus on the diversity thereof, and showed that the diversity is largely associated with gene functional changes.

By comparing human genome sequence information and data on human cDNAs, which are products of transcription therefrom, it was found that a plurality of mRNAs are transcribed from certain regions of chromosome. They occur in two cases: a case wherein there are different ORF regions estimated to encode and produce different proteins, and another case wherein there are different 5'UTR regions or 3'UTR regions, which are noncoding regions, and the same protein is produced. With an emphasis on cDNAs estimated to encode proteins different from those of known cDNAs that have already been analyzed, in particular, we performed search and sequence analysis of such cDNAs. Hence, it was found that the cause of the diversity resides mainly in transcription initiation point selectivity and exon selectivity. Regarding transcription initiation point selectivity, a change of the transcription factor used in a certain chromosome region produced a different position for transcription initiation, resulting in the cDNA diversity. As for exon selectivity, an increase or decrease in the exon used, despite transcription from the same chromosome region, at the time of transcription and splicing, resulted in the cDNA diversity.

How the genetic diversity is associated with gene functions was analyzed on the basis of our own information on the expression frequencies of mRNAs by the 5'-terminal sequences of about 1.50 million human cDNAs (5'-onepass sequences). Hence, a large number of cases were found wherein gene functions seemed to be significantly influenced by diversity features, including variation of transcription initiation region selective in a certain organ, and deletion of exon in a certain condition. We discovered genes whose diversity varies depending on tumorization of tissues, and conducted extensive analyses.

Regarding the analytical method, the expression levels were compared using real-time PCR (polymerase chain reaction). For example, assuming an exon estimated to be inserted selectively only when a tissue tumorizes, a primer that specifically detects the exon region (01) is designed, a primer that specifically detects the pattern in which the exon is not inserted (02) is designed, and a primer that detects a region having both patterns in common (03) is designed. With the use of these 3 kinds of primers, the amounts amplified in normal tissues and tumor tissues are compared. The specific region detection results for 01 and 02 are compared between the normal tissues and tumor tissues with the amount amplified for the shared region 03 as the control, whereby it is possible to know how the exon selectivity worked. Hence, the correlation between the exon selectivity and the tissue-specific expression can be assessed.

By this method, we discovered many genes whose diversity is associated with tissue-specific expression. Being specific for the tissue in which the gene is expressed suggests that the diversity may significantly influence the function of the gene. Hence, by using a specific region with some diversity as a gene marker, it seems possible to detect the fact of tumorization of the tissue at high sensitivity. Furthermore, for example, by proceeding to develop a pharmaceutical targeting a region specific for a tumor tissue, it seems possible to develop a pharmaceutical that has no influence on normal tissues with lower prevalence of adverse reactions.

This application is based on a patent application No. 2007-066425 filed in Japan (filing date: Mar. 15, 2007), the contents of which are incorporated in full herein by this reference.

SEQUENCE LISTING

<160> NUMBER OF SEQ ID NOS: 248

<210> SEQ ID NO 1
<211> LENGTH: 30
<212> TYPE: RNA
<213> ORGANISM: Artificial Sequence
<220> FEATURE:
<223> OTHER INFORMATION: synthesized oligo-cap linker used for oligo-cap
      method

<400> SEQUENCE: 1
agcaucgagu cggccuuguu ggccuacugg                                    30

<210> SEQ ID NO 2
<211> LENGTH: 42
<212> TYPE: DNA
<213> ORGANISM: Artificial Sequence
<220> FEATURE:
<223> OTHER INFORMATION: synthesized oligo(dT) primer used for oligo-cap
      method

<400> SEQUENCE: 2
gcggctgaag acggcctatg tggccttttt ttttttttt tt                       42

<210> SEQ ID NO 3
<211> LENGTH: 21
<212> TYPE: DNA
<213> ORGANISM: Artificial Sequence
<220> FEATURE:
<223> OTHER INFORMATION: forward primer used for preparing cDNA library

<400> SEQUENCE: 3
agcatcgagt cggccttgtt g                                             21

<210> SEQ ID NO 4
<211> LENGTH: 21
<212> TYPE: DNA
<213> ORGANISM: Artificial Sequence
<220> FEATURE:
<223> OTHER INFORMATION: reverse primer used for preparing cDNA library

<400> SEQUENCE: 4
gcggctgaag acggcctatg t                                             21

<210> SEQ ID NO 5
<211> LENGTH: 22
<212> TYPE: DNA
<213> ORGANISM: Artificial Sequence
<220> FEATURE:
<223> OTHER INFORMATION: forward primer used for detecting a
      polynucleotide encoding GAPDH

<400> SEQUENCE: 5
ccaggtggtc tcctctgact tc                                            22

<210> SEQ ID NO 6
<211> LENGTH: 19
<212> TYPE: DNA
<213> ORGANISM: Artificial Sequence
<220> FEATURE:
<223> OTHER INFORMATION: reverse primer used for detecting a
      polynucleotide encoding GAPDH

<400> SEQUENCE: 6
gtggtcgttg agggcaatg                                                19

<210> SEQ ID NO 7
<211> LENGTH: 25
<212> TYPE: DNA
<213> ORGANISM: Artificial Sequence
<220> FEATURE:
<223> OTHER INFORMATION: probe used for detecting a polynucleotide
      encoding GAPDH

<400> SEQUENCE: 7
acagcgacac ccactcctcc acctt                                          25

<210> SEQ ID NO 8
<211> LENGTH: 1830
<212> TYPE: DNA
<213> ORGANISM: Homo sapiens

<400> SEQUENCE: 8 attttctct ttcaaactgc ccagacggtt ggacaggacg tagacacaca gaagaaaaga      60
agacaaagaa cgggttacca tggggaagaa agtggccatc attggagctg gtgtgagtgg    120
cttggcctcc atcaggagct gtctggaaga ggggctggag cccacctgct ttgagaagag    180
caatgacatt gggggcctgt ggaaattttc aaggagccat gagtgaaggc gtacaagagg    240
ggtcttgcca ctgaaaaaaa taagaaatgc cagcatccac cagaagccag aagcggcaag    300
gaatggattc tctcctggag cctctgaaaa tgaacatgga ccatgcagag gagggcaggg    360
ctagcattta caaatcagtc ttttccaact cttccaaaga gatgatgtgt tcccagact    420 tcccatttcc cgatgacttc cccaacttta tgcacaacag caagatccag gaatatatca    480
ttgcatttgc caagaaaag aacctcctga gtacataca atttaagaca tttgtatcca     540
gtgtaaataa acatcctgat tttgcaacta ctggccagtg ggatgttacc actgaaaggg    600
atggtaaaaa agagtcggct gtctttgatg ctgtaatggt ttgttctgga catcatgtgt    660
atcccaacct accaaaagag tccttttccag gactaaacca cttttaaaggc aaatgcttcc    720 acagcaggga ctataaagaa ccagttgtat tcaatggaaa gcgtgtcctg gtggttggcc    780
tggggaattc gggctgtgat attgccacag aactcagccg cacagcagaa caggtcatga    840
tcagttccag aagtggctcc tgggtgatga gccgggtctg ggacaatggt tatccttggg    900
acatgctgct cgtcactcga tttgaacct tcctcaagaa caatttaccg acagccatct    960
ctgactggtt gtacgtgaag cagatgaatg caagattcaa gcatgaaaac tatggcttga   1020
tgcctttaaa tggagtcctg aggaaagagc ctgtatttaa tgatgagctc ccagcaagca   1080
ttctgtgtgg cattgtgtcc gtaaagccta acgtgaagga attcacagag acctcggcca   1140 ttttgagga tgggaccata tttgagggca ttgactgtgt aatctttgca acagggtata   1200
gttttgccta cccttccttt gatgagtcta tcatcaaaag cagaaacaat gagatcattt   1260
tatttaaagg agtatttcct cccctacttg agaagtcaac catagcagtg attggctttg   1320
tccagtccct tgggggctgcc attcccacag ttgacctcca gtcccgctgg gcagcacaag   1380
taataaaggg aacttgtact ttgccttcta tggaagacat gatgaatgat attaatgaga   1440
aaatggagaa aaagcgcaaa tggtttggca aaagcgagac catacagaca gattacattg   1500
tttatatgga tgaactctcc tccttcattg gggcaaagcc caacatccca tggctgtttc   1560
tcacagatcc caaattggcc atggaagttt attttggccc ttgtagtccc taccagttta   1620
ggctggtggg cccagggcag tggccaggag ccagaaatgc catactgacc cagtgggacc   1680
ggtcgttgaa acccatgcag acacgagtgg tcggagact tcagaagcct tgcttcttt    1740 tccattggct gaagctcttt gcaattccta ttctgttaat cgctgttttc cttgtgttga   1800

```
cctaatcatc attttctcta ggatttctga                                  1830

<210> SEQ ID NO 9
<211> LENGTH: 1830
<212> TYPE: DNA
<213> ORGANISM: Homo sapiens
<221> NAME/KEY: CDS
<222> LOCATION: (267)..(1805)

<400> SEQUENCE: 9
atttttctct ttcaaactgc ccagacggtt ggacaggacg tagacacaca gaagaaaaga    60
agacaaagaa cgggttacca tggggaagaa agtggccatc attggagctg gtgtgagtgg   120
cttggcctcc atcaggagct gtctggaaga ggggctggag cccacctgct ttgagaagag   180
caatgacatt gggggcctgt ggaaattttc aaggagccat gagtgaaggc gtacaagagg   240
ggtcttgcca ctgaaaaaaa taagaa atg cca gca tcc acc aga agc cag aag    293
                               Met Pro Ala Ser Thr Arg Ser Gln Lys
                               1               5 cgg caa gga atg gat tct ctc ctg gag cct ctg aaa atg aac atg gac    341
Arg Gln Gly Met Asp Ser Leu Leu Glu Pro Leu Lys Met Asn Met Asp
 10              15                  20                  25 cat gca gag gag ggc agg gct agc att tac aaa tca gtc ttt tcc aac    389
His Ala Glu Glu Gly Arg Ala Ser Ile Tyr Lys Ser Val Phe Ser Asn
                 30                  35                  40 tct tcc aaa gag atg atg tgt ttc cca gac ttc cca ttt ccc gat gac    437
Ser Ser Lys Glu Met Met Cys Phe Pro Asp Phe Pro Phe Pro Asp Asp
             45                  50                  55 ttc ccc aac ttt atg cac aac agc aag atc cag gaa tat atc att gca    485
Phe Pro Asn Phe Met His Asn Ser Lys Ile Gln Glu Tyr Ile Ile Ala
         60                  65                  70 ttt gcc aaa gaa aag aac ctc ctg aag tac ata caa ttt aag aca ttt    533
Phe Ala Lys Glu Lys Asn Leu Leu Lys Tyr Ile Gln Phe Lys Thr Phe
     75                  80                  85 gta tcc agt gta aat aaa cat cct gat ttt gca act act ggc cag tgg    581
Val Ser Ser Val Asn Lys His Pro Asp Phe Ala Thr Thr Gly Gln Trp
 90                  95                 100                 105 gat gtt acc act gaa agg gat ggt aaa aaa gag tcg gct gtc ttt gat    629
Asp Val Thr Thr Glu Arg Asp Gly Lys Lys Glu Ser Ala Val Phe Asp
                110                 115                 120 gct gta atg gtt tgt tct gga cat cat gtg tat ccc aac cta cca aaa    677
Ala Val Met Val Cys Ser Gly His His Val Tyr Pro Asn Leu Pro Lys
                125                 130                 135 gag tcc ttt cca gga cta aac cac ttt aaa ggc aaa tgc ttc cac agc    725
Glu Ser Phe Pro Gly Leu Asn His Phe Lys Gly Lys Cys Phe His Ser
                140                 145                 150 agg gac tat aaa gaa cca gtt gta ttc aat gga aag cgt gtc ctg gtg    773
Arg Asp Tyr Lys Glu Pro Val Val Phe Asn Gly Lys Arg Val Leu Val
155                 160                 165 gtt ggc ctg ggg aat tcg ggc tgt gat att gcc aca gaa ctc agc cgc    821
Val Gly Leu Gly Asn Ser Gly Cys Asp Ile Ala Thr Glu Leu Ser Arg
170                 175                 180                 185 aca gca gaa cag gtc atg atc agt tcc aga agt ggc tcc tgg gtg atg    869
Thr Ala Glu Gln Val Met Ile Ser Ser Arg Ser Gly Ser Trp Val Met
                190                 195                 200 agc cgg gtc tgg gac aat ggt tat cct tgg gac atg ctc gtc act        917
Ser Arg Val Trp Asp Asn Gly Tyr Pro Trp Asp Met Leu Val Thr
                205                 210                 215 cga ttt gga acc ttc ctc aag aac aat tta ccg aca gcc atc tct gac    965
Arg Phe Gly Thr Phe Leu Lys Asn Asn Leu Pro Thr Ala Ile Ser Asp
                220                 225                 230
```

```
tgg ttg tac gtg aag cag atg aat gca aga ttc aag cat gaa aac tat      1013
Trp Leu Tyr Val Lys Gln Met Asn Ala Arg Phe Lys His Glu Asn Tyr
235                 240                 245 ggc ttg atg cct tta aat gga gtc ctg agg aaa gag cct gta ttt aat      1061
Gly Leu Met Pro Leu Asn Gly Val Leu Arg Lys Glu Pro Val Phe Asn
250                 255                 260                 265 gat gag ctc cca gca agc att ctg tgt ggc att gtg tcc gta aag cct      1109
Asp Glu Leu Pro Ala Ser Ile Leu Cys Gly Ile Val Ser Val Lys Pro
                270                 275                 280 aac gtg aag gaa ttc aca gag acc tcg gcc att ttt gag gat ggg acc      1157
Asn Val Lys Glu Phe Thr Glu Thr Ser Ala Ile Phe Glu Asp Gly Thr
            285                 290                 295 ata ttt gag ggc att gac tgt gta atc ttt gca aca ggg tat agt ttt      1205
Ile Phe Glu Gly Ile Asp Cys Val Ile Phe Ala Thr Gly Tyr Ser Phe
        300                 305                 310 gcc tac ccc ttc ctt gat gag tct atc atc aaa agc aga aac aat gag      1253
Ala Tyr Pro Phe Leu Asp Glu Ser Ile Ile Lys Ser Arg Asn Asn Glu
    315                 320                 325 atc att tta ttt aaa gga gta ttt cct ccc cta ctt gag aag tca acc      1301
Ile Ile Leu Phe Lys Gly Val Phe Pro Pro Leu Leu Glu Lys Ser Thr
330                 335                 340                 345 ata gca gtg att ggc ttt gtc cag tcc ctt ggg gct gcc att ccc aca      1349
Ile Ala Val Ile Gly Phe Val Gln Ser Leu Gly Ala Ala Ile Pro Thr
                350                 355                 360 gtt gac ctc cag tcc cgc tgg gca gca caa gta ata aag gga act tgt      1397
Val Asp Leu Gln Ser Arg Trp Ala Ala Gln Val Ile Lys Gly Thr Cys
            365                 370                 375 act ttg cct tct atg gaa gac atg atg aat gat att aat gag aaa atg      1445
Thr Leu Pro Ser Met Glu Asp Met Met Asn Asp Ile Asn Glu Lys Met
        380                 385                 390 gag aaa aag cgc aaa tgg ttt ggc aaa agc gag acc ata cag aca gat      1493
Glu Lys Lys Arg Lys Trp Phe Gly Lys Ser Glu Thr Ile Gln Thr Asp
    395                 400                 405 tac att gtt tat atg gat gaa ctc tcc tcc ttc att ggg gca aag ccc      1541
Tyr Ile Val Tyr Met Asp Glu Leu Ser Ser Phe Ile Gly Ala Lys Pro
410                 415                 420                 425 aac atc cca tgg ctg ttt ctc aca gat ccc aaa ttg gcc atg gaa gtt      1589
Asn Ile Pro Trp Leu Phe Leu Thr Asp Pro Lys Leu Ala Met Glu Val
                430                 435                 440 tat ttt ggc cct tgt agt ccc tac cag ttt agg ctg gtg ggc cca ggg      1637
Tyr Phe Gly Pro Cys Ser Pro Tyr Gln Phe Arg Leu Val Gly Pro Gly
            445                 450                 455 cag tgg cca gga gcc aga aat gcc ata ctg acc cag tgg gac cgg tcg      1685
Gln Trp Pro Gly Ala Arg Asn Ala Ile Leu Thr Gln Trp Asp Arg Ser
        460                 465                 470 ttg aaa ccc atg cag aca cga gtg gtc ggg aga ctt cag aag cct tgc      1733
Leu Lys Pro Met Gln Thr Arg Val Val Gly Arg Leu Gln Lys Pro Cys
    475                 480                 485 ttc ttt ttc cat tgg ctg aag ctc ttt gca att cct att ctg tta atc      1781
Phe Phe Phe His Trp Leu Lys Leu Phe Ala Ile Pro Ile Leu Leu Ile
490                 495                 500                 505 gct gtt ttc ctt gtg ttg acc taa tcatcatttt ctctaggatt tctga          1830
Ala Val Phe Leu Val Leu Thr
                510
```

<210> SEQ ID NO 10
<211> LENGTH: 512
<212> TYPE: PRT
<213> ORGANISM: Homo sapiens

<400> SEQUENCE: 10

```
Met Pro Ala Ser Thr Arg Ser Gln Lys Arg Gln Gly Met Asp Ser Leu
1               5                   10                  15

Leu Glu Pro Leu Lys Met Asn Met Asp His Ala Glu Glu Gly Arg Ala
            20                  25                  30

Ser Ile Tyr Lys Ser Val Phe Ser Asn Ser Lys Glu Met Met Cys
        35                  40                  45

Phe Pro Asp Phe Pro Phe Pro Asp Asp Phe Pro Asn Phe Met His Asn
    50                  55                  60

Ser Lys Ile Gln Glu Tyr Ile Ile Ala Phe Ala Lys Glu Lys Asn Leu
65                  70                  75                  80

Leu Lys Tyr Ile Gln Phe Lys Thr Phe Val Ser Ser Val Asn Lys His
                85                  90                  95

Pro Asp Phe Ala Thr Thr Gly Gln Trp Asp Val Thr Thr Glu Arg Asp
                100                 105                 110

Gly Lys Lys Glu Ser Ala Val Phe Asp Ala Val Met Val Cys Ser Gly
            115                 120                 125

His His Val Tyr Pro Asn Leu Pro Lys Glu Ser Phe Pro Gly Leu Asn
        130                 135                 140

His Phe Lys Gly Lys Cys Phe His Ser Arg Asp Tyr Lys Glu Pro Val
145                 150                 155                 160

Val Phe Asn Gly Lys Arg Val Leu Val Val Gly Leu Gly Asn Ser Gly
                165                 170                 175

Cys Asp Ile Ala Thr Glu Leu Ser Arg Thr Ala Glu Gln Val Met Ile
            180                 185                 190

Ser Ser Arg Ser Gly Ser Trp Val Met Ser Arg Val Trp Asp Asn Gly
        195                 200                 205

Tyr Pro Trp Asp Met Leu Leu Val Thr Arg Phe Gly Thr Phe Leu Lys
    210                 215                 220

Asn Asn Leu Pro Thr Ala Ile Ser Asp Trp Leu Tyr Val Lys Gln Met
225                 230                 235                 240

Asn Ala Arg Phe Lys His Glu Asn Tyr Gly Leu Met Pro Leu Asn Gly
                245                 250                 255

Val Leu Arg Lys Glu Pro Val Phe Asn Asp Glu Leu Pro Ala Ser Ile
            260                 265                 270

Leu Cys Gly Ile Val Ser Val Lys Pro Asn Val Lys Glu Phe Thr Glu
        275                 280                 285

Thr Ser Ala Ile Phe Glu Asp Gly Thr Ile Phe Glu Gly Ile Asp Cys
    290                 295                 300

Val Ile Phe Ala Thr Gly Tyr Ser Phe Ala Tyr Pro Phe Leu Asp Glu
305                 310                 315                 320

Ser Ile Ile Lys Ser Arg Asn Asn Glu Ile Ile Leu Phe Lys Gly Val
                325                 330                 335

Phe Pro Pro Leu Leu Glu Lys Ser Thr Ile Ala Val Ile Gly Phe Val
            340                 345                 350

Gln Ser Leu Gly Ala Ala Ile Pro Thr Val Asp Leu Gln Ser Arg Trp
        355                 360                 365

Ala Ala Gln Val Ile Lys Gly Thr Cys Thr Leu Pro Ser Met Glu Asp
    370                 375                 380

Met Met Asn Asp Ile Asn Glu Lys Met Glu Lys Lys Arg Lys Trp Phe
385                 390                 395                 400

Gly Lys Ser Glu Thr Ile Gln Thr Asp Tyr Ile Val Tyr Met Asp Glu
                405                 410                 415

Leu Ser Ser Phe Ile Gly Ala Lys Pro Asn Ile Pro Trp Leu Phe Leu
```

|   |   |   | 420 |   |   |   | 425 |   |   |   | 430 |   |
|---|---|---|---|---|---|---|---|---|---|---|---|---|

Thr Asp Pro Lys Leu Ala Met Glu Val Tyr Phe Gly Pro Cys Ser Pro
            435                440                445

Tyr Gln Phe Arg Leu Val Gly Pro Gly Gln Trp Pro Gly Ala Arg Asn
    450                    455                460

Ala Ile Leu Thr Gln Trp Asp Arg Ser Leu Lys Pro Met Gln Thr Arg
465                    470                475                480

Val Val Gly Arg Leu Gln Lys Pro Cys Phe Phe His Trp Leu Lys
            485                490                495

Leu Phe Ala Ile Pro Ile Leu Leu Ile Ala Val Phe Leu Val Leu Thr
            500                505                510

<210> SEQ ID NO 11
<211> LENGTH: 127
<212> TYPE: DNA
<213> ORGANISM: Homo sapiens

<400> SEQUENCE: 11
aggagccatg agtgaaggcg tacaagaggg gtcttgccac tgaaaaaaat aagaaatgcc      60
agcatccacc agaagccaga agcggcaagg aatggattct ctcctggagc ctctgaaaat     120
gaacatg                                                              127

<210> SEQ ID NO 12
<211> LENGTH: 24
<212> TYPE: PRT
<213> ORGANISM: Homo sapiens

<400> SEQUENCE: 12

Met Pro Ala Ser Thr Arg Ser Gln Lys Arg Gln Gly Met Asp Ser Leu
1               5                   10                  15

Leu Glu Pro Leu Lys Met Asn Met
            20

<210> SEQ ID NO 13
<211> LENGTH: 72
<212> TYPE: DNA
<213> ORGANISM: Homo sapiens

<400> SEQUENCE: 13
atgccagcat ccaccagaag ccagaagcgg caaggaatgg attctctcct ggagcctctg      60
aaaatgaaca tg                                                         72

<210> SEQ ID NO 14
<211> LENGTH: 828
<212> TYPE: DNA
<213> ORGANISM: Homo sapiens

<400> SEQUENCE: 14
tttcaaactg cccagacggt tggacaggac gtagacacac agaagaaaag aagacaaaga      60
acgggtagga aaattaaaaa ggttaccatg gggaagaaag tggccatcat tggagctggt     120
gtgagtggct tggcctccat caggagctgt ctggaagagg ggctggagcc cacctgcttt     180
gagaagagca tgacattggg ggcctgtgg aaatttcaa cagagtttct ctcttgttgc       240
ccaggctgga gtgcaatggc acaatctgag ctcactacaa cctccacctc ctgggatcaa     300
ggaattctcc tgcctcagcc tcccgaatag ttgggattac aggtgtgtgc catcacgccc     360
cgctaatttt tgtatttta gtagagatgg ggtttcgcca tgttggccag ctggtctcg      420 aactcctgac ctcaggtgat acacccgcct cggcctccca aagtgctgga attataggca     480

```
tgagccacca ctcctggcca gccatatctt atacacagtg atcttaacca aagcctcata      540
ctcaaattta gtttgcaaga cgttgctgaa gatagaacgc actgctgata tggctattga      600
gaggaacaca gccaaagaca gctaatttgt cttttcttgc tgctcgagga agactttaaa      660
atttgaacct ggcagcatag gttgataaaa ctgaactgca acatgtgcta cccttcaaga      720
aaaagaaagg atagcccaga gggtagagcc tcaggccctg agggcagagg cctgagccaa      780
agccttcaag cctgaaggaa tttgtcctac tggatttcaa aattgctt                   828

<210> SEQ ID NO 15
<211> LENGTH: 828
<212> TYPE: DNA
<213> ORGANISM: Homo sapiens
<221> NAME/KEY: CDS
<222> LOCATION: (88)..(330)

<400> SEQUENCE: 15
tttcaaactg cccagacggt tggacaggac gtagacacac agaagaaaag aagacaaaga       60
acgggtagga aaattaaaaa ggttacc atg ggg aag aaa gtg gcc atc att gga      114
                                Met Gly Lys Lys Val Ala Ile Ile Gly
                                 1               5 gct ggt gtg agt ggc ttg gcc tcc atc agg agc tgt ctg gaa gag ggg        162
Ala Gly Val Ser Gly Leu Ala Ser Ile Arg Ser Cys Leu Glu Glu Gly
 10              15                  20                  25 ctg gag ccc acc tgc ttt gag aag agc aat gac att ggg ggc ctg tgg        210
Leu Glu Pro Thr Cys Phe Glu Lys Ser Asn Asp Ile Gly Gly Leu Trp
             30                  35                  40 aaa ttt tca aca gag ttt ctc tct tgt tgc cca ggc tgg agt gca atg        258
Lys Phe Ser Thr Glu Phe Leu Ser Cys Cys Pro Gly Trp Ser Ala Met
         45                  50                  55 gca caa tct gag ctc act aca acc tcc acc tcc tgg gat caa gga att        306
Ala Gln Ser Glu Leu Thr Thr Thr Ser Thr Ser Trp Asp Gln Gly Ile
     60                  65                  70 ctc ctg cct cag cct ccc gaa tag ttgggattac aggtgtgtgc catcacgccc       360
Leu Leu Pro Gln Pro Pro Glu
 75              80 cgctaatttt tgtattttta gtagagatgg ggtttcgcca tgttggccag gctggtctcg      420
aactcctgac ctcaggtgat acacccgcct cggcctccca aagtgctgga attataggca      480
tgagccacca ctcctggcca gccatatctt atacacagtg atcttaacca aagcctcata      540
ctcaaattta gtttgcaaga cgttgctgaa gatagaacgc actgctgata tggctattga      600
gaggaacaca gccaaagaca gctaatttgt cttttcttgc tgctcgagga agactttaaa      660
atttgaacct ggcagcatag gttgataaaa ctgaactgca acatgtgcta cccttcaaga      720
aaaagaaagg atagcccaga gggtagagcc tcaggccctg agggcagagg cctgagccaa      780
agccttcaag cctgaaggaa tttgtcctac tggatttcaa aattgctt                   828

<210> SEQ ID NO 16
<211> LENGTH: 80
<212> TYPE: PRT
<213> ORGANISM: Homo sapiens

<400> SEQUENCE: 16

Met Gly Lys Lys Val Ala Ile Ile Gly Ala Gly Val Ser Gly Leu Ala
 1               5                  10                  15

Ser Ile Arg Ser Cys Leu Glu Glu Gly Leu Glu Pro Thr Cys Phe Glu
                 20                  25                  30

Lys Ser Asn Asp Ile Gly Gly Leu Trp Lys Phe Ser Thr Glu Phe Leu
```

```
                35                  40                  45
Ser Cys Cys Pro Gly Trp Ser Ala Met Ala Gln Ser Glu Leu Thr Thr
        50                  55                  60

Thr Ser Thr Ser Trp Asp Gln Gly Ile Leu Leu Pro Gln Pro Pro Glu
65                  70                  75                  80

<210> SEQ ID NO 17
<211> LENGTH: 609
<212> TYPE: DNA
<213> ORGANISM: Homo sapiens

<400> SEQUENCE: 17
acagagtttc tctcttgttg cccaggctgg agtgcaatgg cacaatctga gctcactaca       60
acctccacct cctgggatca aggaattctc ctgcctcagc ctcccgaata gttgggatta      120
caggtgtgtg ccatcacgcc ccgctaattt ttgtattttt agtagagatg gggtttcgcc      180
atgttggcca ggctggtctc gaactcctga cctcaggtga tacacccgcc tcggcctccc      240
aaagtgctgg aattataggc atgagccacc actcctggcc agccatatct tatacacagt      300
gatcttaacc aaagcctcat actcaaattt agtttgcaag acgttgctga agatagaacg      360
cactgctgat atggctattg agaggaacac agccaaagac agctaatttg tcttttcttg      420
ctgctcgagg aagactttaa aatttgaacc tggcagcata ggttgataaa actgaactgc      480
aacatgtgct acccttcaag aaaaagaaag gatagcccag agggtagagc tcaggccct       540 gagggcagag gcctgagcca aagccttcaa gcctgaagga atttgtccta ctggatttca      600
aaattgctt                                                              609

<210> SEQ ID NO 18
<211> LENGTH: 36
<212> TYPE: PRT
<213> ORGANISM: Homo sapiens

<400> SEQUENCE: 18

Thr Glu Phe Leu Ser Cys Cys Pro Gly Trp Ser Ala Met Ala Gln Ser
1               5                   10                  15

Glu Leu Thr Thr Thr Ser Thr Ser Trp Asp Gln Gly Ile Leu Leu Pro
            20                  25                  30

Gln Pro Pro Glu
        35

<210> SEQ ID NO 19
<211> LENGTH: 111
<212> TYPE: DNA
<213> ORGANISM: Homo sapiens

<400> SEQUENCE: 19
acagagtttc tctcttgttg cccaggctgg agtgcaatgg cacaatctga gctcactaca       60
acctccacct cctgggatca aggaattctc ctgcctcagc ctcccgaata g               111

<210> SEQ ID NO 20
<211> LENGTH: 828
<212> TYPE: DNA
<213> ORGANISM: Homo sapiens
<221> NAME/KEY: CDS
<222> LOCATION: (191)..(439)

<400> SEQUENCE: 20
tttcaaactg cccagacggt tggacaggac gtagacacac agaagaaaag aagacaaaga       60
acgggtagga aaattaaaaa ggttaccatg gggaagaaag tggccatcat tggagctggt      120
```

```
gtgagtggct tggcctccat caggagctgt ctggaagagg ggctggagcc cacctgcttt    180
gagaagagca atg aca ttg ggg gcc tgt gga aat ttt caa cag agt ttc     229
            Met Thr Leu Gly Ala Cys Gly Asn Phe Gln Gln Ser Phe
              1               5                  10 tct ctt gtt gcc cag gct gga gtg caa tgg cac aat ctg agc tca cta    277
Ser Leu Val Ala Gln Ala Gly Val Gln Trp His Asn Leu Ser Ser Leu
    15                  20                  25 caa cct cca cct cct ggg atc aag gaa ttc tcc tgc ctc agc ctc ccg    325
Gln Pro Pro Pro Pro Gly Ile Lys Glu Phe Ser Cys Leu Ser Leu Pro
30                  35                  40                  45 aat agt tgg gat tac agg tgt gtg cca tca cgc ccc gct aat ttt tgt    373
Asn Ser Trp Asp Tyr Arg Cys Val Pro Ser Arg Pro Ala Asn Phe Cys
                50                  55                  60 att ttt agt aga gat ggg gtt tcg cca tgt tgg cca ggc tgg tct cga    421
Ile Phe Ser Arg Asp Gly Val Ser Pro Cys Trp Pro Gly Trp Ser Arg
65                  70                  75 act cct gac ctc agg tga tacacccgcc tcggcctccc aaagtgctgg            469
Thr Pro Asp Leu Arg
                80 aattataggc atgagccacc actcctggcc agccatatct tatacacagt gatcttaacc   529 aaagcctcat actcaaattt agtttgcaag acgttgctga agatagaacg cactgctgat   589 atggctattg agaggaacac agccaaagac agctaatttg tctttttcttg ctgctcgagg  649 aagactttaa aatttgaacc tggcagcata ggttgataaa actgaactgc aacatgtgct   709 acccttcaag aaaagaaag gatagcccag agggtagagc ctcaggccct gagggcagag    769 gcctgagcca aagccttcaa gcctgaagga atttgtccta ctggatttca aaattgctt    828

<210> SEQ ID NO 21
<211> LENGTH: 82
<212> TYPE: PRT
<213> ORGANISM: Homo sapiens

<400> SEQUENCE: 21

Met Thr Leu Gly Ala Cys Gly Asn Phe Gln Gln Ser Phe Ser Leu Val
  1               5                  10                  15

Ala Gln Ala Gly Val Gln Trp His Asn Leu Ser Ser Leu Gln Pro Pro
                 20                  25                  30

Pro Pro Gly Ile Lys Glu Phe Ser Cys Leu Ser Leu Pro Asn Ser Trp
             35                  40                  45

Asp Tyr Arg Cys Val Pro Ser Arg Pro Ala Asn Phe Cys Ile Phe Ser
 50                  55                  60

Arg Asp Gly Val Ser Pro Cys Trp Pro Gly Trp Ser Arg Thr Pro Asp
65                  70                  75                  80

Leu Arg

<210> SEQ ID NO 22
<211> LENGTH: 220
<212> TYPE: DNA
<213> ORGANISM: Homo sapiens

<400> SEQUENCE: 22
acagagtttc tctcttgttg cccaggctgg agtgcaatgg cacaatctga gctcactaca    60
acctccacct cctgggatca aggaattctc ctgcctcagc ctcccgaata gttgggatta   120
caggtgtgtg ccatcacgcc ccgctaattt ttgtattttt agtagagatg gggtttcgcc   180
atgttggcca ggctggtctc gaactcctga cctcaggtga                         220
```

-continued

<210> SEQ ID NO 23
<211> LENGTH: 19
<212> TYPE: DNA
<213> ORGANISM: Artificial Sequence
<220> FEATURE:
<223> OTHER INFORMATION: forward primer used for specifically detecting
      the variant of the present invention (D-LIVER2001680.1)

<400> SEQUENCE: 23
cggcaaggaa tggattctc                                                    19

<210> SEQ ID NO 24
<211> LENGTH: 25
<212> TYPE: DNA
<213> ORGANISM: Artificial Sequence
<220> FEATURE:
<223> OTHER INFORMATION: reverse primer used for specifically detecting
      the variant of the present invention (D-LIVER2001680.1)

<400> SEQUENCE: 24
gaagagttgg aaaagactga tttgt                                             25

<210> SEQ ID NO 25
<211> LENGTH: 101
<212> TYPE: DNA
<213> ORGANISM: Artificial Sequence
<220> FEATURE:
<223> OTHER INFORMATION: partial polynucleotide specific to the variant
      of the present invention (D-LIVER2001680.1), which is obtained by
      PCR using forward primer (SEQ ID NO:23) and reverse primer
      (SEQ ID NO:24)

<400> SEQUENCE: 25
cggcaaggaa tggattctct cctggagcct ctgaaaatga acatggacca tgcagaggag       60
ggcagggcta gcatttacaa atcagtcttt tccaactctt c                          101

<210> SEQ ID NO 26
<211> LENGTH: 27
<212> TYPE: DNA
<213> ORGANISM: Artificial Sequence
<220> FEATURE:
<223> OTHER INFORMATION: forward primer used for specifically detecting
      the variant of the present invention (D-LIVER2008912.1)

<400> SEQUENCE: 26
aattttcaac agagtttctc tcttgtt                                           27

<210> SEQ ID NO 27
<211> LENGTH: 21
<212> TYPE: DNA
<213> ORGANISM: Artificial Sequence
<220> FEATURE:
<223> OTHER INFORMATION: reverse primer used for specifically detecting
      the variant of the present invention (D-LIVER2008912.1)

<400> SEQUENCE: 27
aggcaggaga attccttgat c                                                 21

<210> SEQ ID NO 28
<211> LENGTH: 104
<212> TYPE: DNA
<213> ORGANISM: Artificial Sequence
<220> FEATURE:
<223> OTHER INFORMATION: partial polynucleotide specific to the variant
      of the present invention (D-LIVER2008912.1), which is obtained by
      PCR using forward primer (SEQ ID NO:26) and reverse primer
      (SEQ ID NO:27)

```
<400> SEQUENCE: 28
aattttcaac agagtttctc tcttgttgcc caggctggag tgcaatggca caatctgagc      60
tcactacaac ctccacctcc tgggatcaag gaattctcct gcct                     104

<210> SEQ ID NO 29
<211> LENGTH: 21
<212> TYPE: DNA
<213> ORGANISM: Artificial Sequence
<220> FEATURE:
<223> OTHER INFORMATION: forward primer used for specifically detecting
      the known variant of the gene of the present invention
      (NM_006894.4)

<400> SEQUENCE: 29
tggaaatttt cagaccatgc a                                               21

<210> SEQ ID NO 30
<211> LENGTH: 24
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_006894.4)

<400> SEQUENCE: 30
atctctttgg aagagttgga aaag                                            24

<210> SEQ ID NO 31
<211> LENGTH: 77
<212> TYPE: DNA
<213> ORGANISM: Artificial Sequence
<220> FEATURE:
<223> OTHER INFORMATION: partial polynucleotide specific to the known
      variant of the gene of the present invention (NM_006894.4),
      which is obtained by PCR using forward primer (SEQ ID NO:29) and
      reverse primer (SEQ ID NO:30)

<400> SEQUENCE: 31
tggaaatttt cagaccatgc agaggagggc agggctagca tttacaaatc agtcttttcc      60
aactcttcca aagagat                                                    77

<210> SEQ ID NO 32
<211> LENGTH: 21
<212> TYPE: DNA
<213> ORGANISM: Artificial Sequence
<220> FEATURE:
<223> OTHER INFORMATION: forward primer used for detecting the variants
      of the gene of the present invention (D-LIVER2001680.1,
      D-LIVER2008912.1 and NM_006894.4)

<400> SEQUENCE: 32
catcaggagc tgtctggaag a                                               21

<210> SEQ ID NO 33
<211> LENGTH: 17
<212> TYPE: DNA
<213> ORGANISM: Artificial Sequence
<220> FEATURE:
<223> OTHER INFORMATION: reverse primer used for detecting the variants
      of the gene of the present invention (D-LIVER2001680.1,
      D-LIVER2008912.1 and NM_006894.4)

<400> SEQUENCE: 33
cacaggcccc caatgtc                                                    17
```

```
<210> SEQ ID NO 34
<211> LENGTH: 72
<212> TYPE: DNA
<213> ORGANISM: Artificial Sequence
<220> FEATURE:
<223> OTHER INFORMATION: partial polynucleotide common to the variants
      of the gene of the present invention (D-LIVER2001680.1,
      D-LIVER2008912.1 and NM_006894.4), which is obtained by PCR using
      forward primer (SEQ ID NO:32) and reverse primer (SEQ ID NO:33)

<400> SEQUENCE: 34
catcaggagc tgtctggaag aggggctgga gcccacctgc tttgagaaga gcaatgacat      60
tgggggcctg tg                                                         72

<210> SEQ ID NO 35
<211> LENGTH: 394
<212> TYPE: DNA
<213> ORGANISM: Homo sapiens

<400> SEQUENCE: 35
atttttctct ttcaaactgc ccagacggtt ggacaggacg tagacacaca gaagaaaaga     60
agacaaagaa cgggttacca tggggaagaa agtggccatc attggagctg gtgtgagtgg    120
cttggcctcc atcaggagct gtctggaaga ggggctggag cccacctgct ttgagaagag    180
caatgacatt gggggcctgt ggaaattttc aaggagccat gagtgaaggc gtacaagagg    240
ggtcttgcca ctgaaaaaaa taagaaatgc cagcatccac cagaagccag aagcggcaag    300
gaatggattc tctcctggag cctctgaaaa tgaacatgga ccatgcagag gagggcaggg    360
ctagcattta caaatcagtc ttttccaact cttc                                394

<210> SEQ ID NO 36
<211> LENGTH: 315
<212> TYPE: DNA
<213> ORGANISM: Homo sapiens

<400> SEQUENCE: 36
tttcaaactg cccagacggt tggacaggac gtagacacac agaagaaaag aagacaaaga     60
acgggtagga aaattaaaaa ggttaccatg gggaagaaag tggccatcat tggagctggt    120
gtgagtggct tggcctccat caggagctgt ctggaagagg gctggagcc cacctgcttt     180 gagaagagca atgacattgg gggcctgtgg aaattttcaa cagagtttct ctcttgttgc    240
ccaggctgga gtgcaatggc acaatctgag ctcactacaa cctccacctc tgggatcaa    300 ggaattctcc tgcct                                                     315

<210> SEQ ID NO 37
<211> LENGTH: 1836
<212> TYPE: DNA
<213> ORGANISM: Homo sapiens

<400> SEQUENCE: 37
ctcttccccg cccacccctt acccgcatgc agcccagcgc cctatgctag ccctccccct     60 cccccctgc tggagcgggg cgccgccggg ggaggagggg gaatcggctg cgggtccttg     120
gtgtttccag cacccagttt cccttcaagc cgggtcgcga tgtacgactg tatggaaacg    180
tttgccccgg gtccgcgacg gctgtacggg cggccgggc ccggggccgg cttgctgcgc     240
agagccaccg gcggctcctg tttcgccgga cttgaatctt ttgcctggcc gcaacccgcc    300
agcctgcaat cggtggagac acagagcacc agctcagagg agatggtgcc cagctcgccc    360
tcgccccctc cgcctcctcg ggtctacaag ccatgcttcg tgtgcaatga caagtcctct    420
```

```
ggctaccact atggggtcag ctcttgtgaa ggctgcaagg gcttctttcg ccgaagcatc      480
cagaagaaca tggtgtacac gtgtcaccgc gacaaaaact gtatcatcaa caaggtgacc      540
aggaatcgct gccagtactg ccggctacag aagtgcttcg aagtgggcat gtccaaggaa      600
gctgtgcgaa atgaccggaa caagaagaag aaagaggtgg aggaagaagg gtcacctgac      660
agctatgagc tgagccctca gttagaagag ctcatcacca aggtcagcaa agcccatcag      720
gagactttcc cctcgctctg ccagctgggc aagtatacca cgaactccag tgcagaccac      780
cgcgtgcagc tggatctggg gctgtgggac aagttcagtg agctggctac caagtgcatc      840
atcaagatcg tggagtttgc caagcggttg cctggcttta cagggctcag cattgctgac      900
cagatcactc tgctcaaagc tgcctgccta gatatcctga tgctgcgtat ctgcacaagg      960
tacaccccag agcaggacac catgaccttc tccgacgggc tgaccctgaa ccggacccag     1020
atgcacaatg ccggcttcgg gccctcaca gaccttgtct ttgcctttgc tgggcagctc     1080
ctgcccctgg agatggatga caccgagaca gggctgctca gcgccatctg cctcatctgc     1140
ggagaccgca tggacctgga ggagcccgaa aaagtggaca agctgcagga gccactgctg     1200
gaagccctga gctgtacgc ccggcgccgg cggcccagcc agcccctacat gttcccaagg     1260 atgctaatga aaatcaccga cctccggggc atcagcacta agggagctga agggccatt      1320 actctgaaga tggagattcc aggcccaatg cctcccttaa tccgagagat gctggagaac     1380
cctgaaatgt ttgaggatga ctcctcgcag cctggtcccc accccaatgc tctagcgag      1440 gatgaggttc ctggaggcca gggcaaaggg ggcctgaagt cccagcctg accagggccc     1500 ctgacctccc cgctgtgggg gttggggctt caggcagcag actgaccatc tcccagaccg     1560
ccagtgactg ggggaggacc tgctctgccc tctccccacc ccttccaatg agctccttgt     1620
ttttgccaaa gtttctaggg gtgcctctgt gttcatcccc ttcctgatct aaccggctcc     1680
ctcgccagtc ccggggggcct gccctgctcc caccaggaga gagggcaaag ggatgagcct     1740
gggtttggac tctaaaatct cagcactgcc ccatgggtcc tagacttccc agggcaagag     1800
gaagaccctg ccattccaca gcccttcct ctgcca                                1836
```

<210> SEQ ID NO 38
<211> LENGTH: 1836
<212> TYPE: DNA
<213> ORGANISM: Homo sapiens
<221> NAME/KEY: CDS
<222> LOCATION: (160)..(1491)

<400> SEQUENCE: 38

```
ctcttccccg cccacccctt acccgcatgc agcccagcgc cctatgctag ccctccccct       60 cccccctgc tggagcgggg cgccgccggg ggaggagggg gaatcggctg cgggtccttg      120
gtgtttccag cacccagttt cccttcaagc cgggtcgcg atg tac gac tgt atg        174
                                              Met Tyr Asp Cys Met
                                                1               5 gaa acg ttt gcc ccg ggt ccg cga cgg ctg tac ggg gcg gcc ggg ccc        222
Glu Thr Phe Ala Pro Gly Pro Arg Arg Leu Tyr Gly Ala Ala Gly Pro
         10                  15                  20 ggg gcc ggc ttg ctg cgc aga gcc acc ggc ggc tcc tgt ttc gcc gga        270
Gly Ala Gly Leu Leu Arg Arg Ala Thr Gly Gly Ser Cys Phe Ala Gly
     25                  30                  35 ctt gaa tct ttt gcc tgg ccg caa ccc gcc agc ctg caa tcg gtg gag        318
Leu Glu Ser Phe Ala Trp Pro Gln Pro Ala Ser Leu Gln Ser Val Glu
 40                  45                  50 aca cag agc acc agc tca gag gag atg gtg ccc agc tcg ccc tcg ccc        366
Thr Gln Ser Thr Ser Ser Glu Glu Met Val Pro Ser Ser Pro Ser Pro
 55                  60                  65
```

-continued

```
          55                  60                  65
cct ccg cct cct cgg gtc tac aag cca tgc ttc gtg tgc aat gac aag    414
Pro Pro Pro Pro Arg Val Tyr Lys Pro Cys Phe Val Cys Asn Asp Lys
70                  75                  80                  85 tcc tct ggc tac cac tat ggg gtc agc tct tgt gaa ggc tgc aag ggc    462
Ser Ser Gly Tyr His Tyr Gly Val Ser Ser Cys Glu Gly Cys Lys Gly
                90                  95                 100 ttc ttt cgc cga agc atc cag aag aac atg gtg tac acg tgt cac cgc    510
Phe Phe Arg Arg Ser Ile Gln Lys Asn Met Val Tyr Thr Cys His Arg
            105                 110                 115 gac aaa aac tgt atc atc aac aag gtg acc agg aat cgc tgc cag tac    558
Asp Lys Asn Cys Ile Ile Asn Lys Val Thr Arg Asn Arg Cys Gln Tyr
        120                 125                 130 tgc cgg cta cag aag tgc ttc gaa gtg ggc atg tcc aag gaa gct gtg    606
Cys Arg Leu Gln Lys Cys Phe Glu Val Gly Met Ser Lys Glu Ala Val
    135                 140                 145 cga aat gac cgg aac aag aag aag aaa gag gtg gag gaa gaa ggg tca    654
Arg Asn Asp Arg Asn Lys Lys Lys Lys Glu Val Glu Glu Glu Gly Ser
150                 155                 160                 165 cct gac agc tat gag ctg agc cct cag tta gaa gag ctc atc acc aag    702
Pro Asp Ser Tyr Glu Leu Ser Pro Gln Leu Glu Glu Leu Ile Thr Lys
                170                 175                 180 gtc agc aaa gcc cat cag gag act ttc ccc tcg ctc tgc cag ctg ggc    750
Val Ser Lys Ala His Gln Glu Thr Phe Pro Ser Leu Cys Gln Leu Gly
            185                 190                 195 aag tat acc acg aac tcc agt gca gac cac cgc gtg cag ctg gat ctg    798
Lys Tyr Thr Thr Asn Ser Ser Ala Asp His Arg Val Gln Leu Asp Leu
        200                 205                 210 ggg ctg tgg gac aag ttc agt gag ctg gct acc aag tgc atc atc aag    846
Gly Leu Trp Asp Lys Phe Ser Glu Leu Ala Thr Lys Cys Ile Ile Lys
    215                 220                 225 atc gtg gag ttt gcc aag cgg ttg cct ggc ttt aca ggg ctc agc att    894
Ile Val Glu Phe Ala Lys Arg Leu Pro Gly Phe Thr Gly Leu Ser Ile
230                 235                 240                 245 gct gac cag atc act ctg ctc aaa gct gcc tgc cta gat atc ctg atg    942
Ala Asp Gln Ile Thr Leu Leu Lys Ala Ala Cys Leu Asp Ile Leu Met
                250                 255                 260 ctg cgt atc tgc aca agg tac acc cca gag cag gac acc atg acc ttc    990
Leu Arg Ile Cys Thr Arg Tyr Thr Pro Glu Gln Asp Thr Met Thr Phe
            265                 270                 275 tcc gac ggg ctg acc ctg aac cgg acc cag atg cac aat gcc ggc ttc   1038
Ser Asp Gly Leu Thr Leu Asn Arg Thr Gln Met His Asn Ala Gly Phe
        280                 285                 290 ggg ccc ctc aca gac ctt gtc ttt gcc ttt gct ggg cag ctc ctg ccc   1086
Gly Pro Leu Thr Asp Leu Val Phe Ala Phe Ala Gly Gln Leu Leu Pro
    295                 300                 305 ctg gag atg gat gac acc gag aca ggg ctg ctc agc gcc atc tgc ctc   1134
Leu Glu Met Asp Asp Thr Glu Thr Gly Leu Leu Ser Ala Ile Cys Leu
310                 315                 320                 325 atc tgc gga gac cgc atg gac ctg gag gag ccc gaa aaa gtg gac aag   1182
Ile Cys Gly Asp Arg Met Asp Leu Glu Glu Pro Glu Lys Val Asp Lys
                330                 335                 340 ctg cag gag cca ctg ctg gaa gcc ctg agg ctg tac gcc cgg cgc cgg   1230
Leu Gln Glu Pro Leu Leu Glu Ala Leu Arg Leu Tyr Ala Arg Arg Arg
            345                 350                 355 cgg ccc agc cag ccc tac atg ttc cca agg atg cta atg aaa atc acc   1278
Arg Pro Ser Gln Pro Tyr Met Phe Pro Arg Met Leu Met Lys Ile Thr
        360                 365                 370 gac ctc cgg ggc atc agc act aag gga gct gaa agg gcc att act ctg   1326
Asp Leu Arg Gly Ile Ser Thr Lys Gly Ala Glu Arg Ala Ile Thr Leu
```

-continued

```
              375                 380                 385
aag atg gag att cca ggc cca atg cct ccc tta atc cga gag atg ctg     1374
Lys Met Glu Ile Pro Gly Pro Met Pro Pro Leu Ile Arg Glu Met Leu
390                 395                 400                 405 gag aac cct gaa atg ttt gag gat gac tcc tcg cag cct ggt ccc cac     1422
Glu Asn Pro Glu Met Phe Glu Asp Asp Ser Ser Gln Pro Gly Pro His
                410                 415                 420 ccc aat gcc tct agc gag gat gag gtt cct gga ggc cag ggc aaa ggg     1470
Pro Asn Ala Ser Ser Glu Asp Glu Val Pro Gly Gly Gln Gly Lys Gly
            425                 430                 435 ggc ctg aag tcc cca gcc tga ccagggcccc tgacctcccc gctgtggggg        1521
Gly Leu Lys Ser Pro Ala
            440 ttggggcttc aggcagcaga ctgaccatct cccagaccgc cagtgactgg gggaggacct   1581 gctctgccct ctccccaccc cttccaatga gctccttgtt tttgccaaag tttctagggg   1641 tgcctctgtg ttcatcccct tcctgatcta accggctccc tcgccagtcc cgggggcctg   1701 ccctgctccc accaggagag agggcaaagg gatgagcctg ggtttggact ctaaaatctc   1761 agcactgccc catgggtcct agacttccca gggcaagagg aagaccctgc cattccacag   1821 ccccttcctc tgcca                                                    1836

<210> SEQ ID NO 39
<211> LENGTH: 443
<212> TYPE: PRT
<213> ORGANISM: Homo sapiens

<400> SEQUENCE: 39

Met Tyr Asp Cys Met Glu Thr Phe Ala Pro Gly Pro Arg Arg Leu Tyr
1               5                   10                  15

Gly Ala Ala Gly Pro Gly Ala Gly Leu Leu Arg Arg Ala Thr Gly Gly
                20                  25                  30

Ser Cys Phe Ala Gly Leu Glu Ser Phe Ala Trp Pro Gln Pro Ala Ser
            35                  40                  45

Leu Gln Ser Val Glu Thr Gln Ser Thr Ser Ser Glu Glu Met Val Pro
        50                  55                  60

Ser Ser Pro Ser Pro Pro Pro Arg Val Tyr Lys Pro Cys Phe
65                  70                  75                  80

Val Cys Asn Asp Lys Ser Ser Gly Tyr His Tyr Gly Val Ser Ser Cys
                85                  90                  95

Glu Gly Cys Lys Gly Phe Phe Arg Arg Ser Ile Gln Lys Asn Met Val
            100                 105                 110

Tyr Thr Cys His Arg Asp Lys Asn Cys Ile Ile Asn Lys Val Thr Arg
        115                 120                 125

Asn Arg Cys Gln Tyr Cys Arg Leu Gln Lys Cys Phe Glu Val Gly Met
    130                 135                 140

Ser Lys Glu Ala Val Arg Asn Asp Arg Asn Lys Lys Lys Glu Val
145                 150                 155                 160

Glu Glu Glu Gly Ser Pro Asp Ser Tyr Glu Leu Ser Pro Gln Leu Glu
                165                 170                 175

Glu Leu Ile Thr Lys Val Ser Lys Ala His Gln Glu Thr Phe Pro Ser
            180                 185                 190

Leu Cys Gln Leu Gly Lys Tyr Thr Thr Asn Ser Ser Ala Asp His Arg
        195                 200                 205

Val Gln Leu Asp Leu Gly Leu Trp Asp Lys Phe Ser Glu Leu Ala Thr
    210                 215                 220
```

```
Lys Cys Ile Ile Lys Ile Val Glu Phe Ala Lys Arg Leu Pro Gly Phe
225                 230                 235                 240

Thr Gly Leu Ser Ile Ala Asp Gln Ile Thr Leu Leu Lys Ala Ala Cys
                245                 250                 255

Leu Asp Ile Leu Met Leu Arg Ile Cys Thr Arg Tyr Thr Pro Glu Gln
            260                 265                 270

Asp Thr Met Thr Phe Ser Asp Gly Leu Thr Leu Asn Arg Thr Gln Met
        275                 280                 285

His Asn Ala Gly Phe Gly Pro Leu Thr Asp Leu Val Phe Ala Phe Ala
    290                 295                 300

Gly Gln Leu Leu Pro Leu Glu Met Asp Asp Thr Glu Thr Gly Leu Leu
305                 310                 315                 320

Ser Ala Ile Cys Leu Ile Cys Gly Asp Arg Met Asp Leu Glu Glu Pro
                325                 330                 335

Glu Lys Val Asp Lys Leu Gln Glu Pro Leu Leu Glu Ala Leu Arg Leu
            340                 345                 350

Tyr Ala Arg Arg Arg Pro Ser Gln Pro Tyr Met Phe Pro Arg Met
        355                 360                 365

Leu Met Lys Ile Thr Asp Leu Arg Gly Ile Ser Thr Lys Gly Ala Glu
370                 375                 380

Arg Ala Ile Thr Leu Lys Met Glu Ile Pro Gly Pro Met Pro Pro Leu
385                 390                 395                 400

Ile Arg Glu Met Leu Glu Asn Pro Glu Met Phe Glu Asp Asp Ser Ser
            405                 410                 415

Gln Pro Gly Pro His Pro Asn Ala Ser Ser Glu Asp Glu Val Pro Gly
        420                 425                 430

Gly Gln Gly Lys Gly Gly Leu Lys Ser Pro Ala
    435                 440

<210> SEQ ID NO 40
<211> LENGTH: 309
<212> TYPE: DNA
<213> ORGANISM: Homo sapiens

<400> SEQUENCE: 40
ctcttccccg cccaccccctt acccgcatgc agcccagcgc cctatgctag ccctcccct      60 cccccctgc tggagcgggg cgccgccggg ggaggagggg gaatcggctg cgggtccttg    120
gtgtttccag cacccagttt cccttcaagc cgggtcgcga tgtacgactg tatggaaacg    180
tttgccccgg gtccgcgacg gctgtacggg cggccgggc ccggggccgg cttgctcgc     240 agagccaccg gcggctcctg tttcgccgga cttgaatctt ttgcctggcc gcaacccgcc    300
agcctgcaa                                                           309

<210> SEQ ID NO 41
<211> LENGTH: 50
<212> TYPE: PRT
<213> ORGANISM: Homo sapiens

<400> SEQUENCE: 41

Met Tyr Asp Cys Met Glu Thr Phe Ala Pro Gly Pro Arg Arg Leu Tyr
1               5                   10                  15

Gly Ala Ala Gly Pro Gly Ala Gly Leu Leu Arg Arg Ala Thr Gly Gly
                20                  25                  30

Ser Cys Phe Ala Gly Leu Glu Ser Phe Ala Trp Pro Gln Pro Ala Ser
        35                  40                  45

Leu Gln
```

<210> SEQ ID NO 42
<211> LENGTH: 150
<212> TYPE: DNA
<213> ORGANISM: Homo sapiens

<400> SEQUENCE: 42

| | |
|---|---|
| atgtacgact gtatggaaac gtttgccccg ggtccgcgac ggctgtacgg ggcggccggg | 60 |
| cccggggccg gcttgctgcg cagagccacc ggcggctcct gtttcgccgg acttgaatct | 120 |
| tttgcctggc cgcaacccgc cagcctgcaa | 150 |

<210> SEQ ID NO 43
<211> LENGTH: 1660
<212> TYPE: DNA
<213> ORGANISM: Homo sapiens

<400> SEQUENCE: 43

| | |
|---|---|
| gtttccagca cccagtttcc cttcaagccg gtcgcgatg tacgactgta tggaaacgtt | 60 |
| tgccccgggt ccgcgacggc tgtacggggc ggccgggccc ggggccggct tgctgcgcag | 120 |
| agccaccggc ggctcctgtt tcgccggact tgaatctttt gcctggccgc aacccgccag | 180 |
| cctgcaatcg gtggagacac agagcaccag ctcagaggag atggtgccca gctgccctc | 240 |
| gcccctccg cctcctcggg tctacaagcc atgcttcgtg tgcaatgaca gtcctctgg | 300 |
| ctaccactat ggggtcagct cttgtgaagg ctgcaagggc ttctttcgcc gaagcatcca | 360 |
| gaagaacatg gtgtacacgt gtcaccgcga caaaaactgt atcatcaaca aggtgaccag | 420 |
| gaatcgctgc cagtactgcc ggctacgaaa gtgcttcgaa gtgggcatgt ccaaggaagc | 480 |
| tgtgcgaaat gaccggaaca agaagaagaa agaggtgaag gaagaagggt cacctgacag | 540 |
| ctatgagctg agccctcagt tagaagagct catcaccaag gtcagcaaag cccatcagga | 600 |
| gactttcccc tcgctctgcc agctgggcaa gtataccacg aactccagtg cagaccaccg | 660 |
| cgtgcagctg gatctggggc tgtgggacaa gttcagtgag ctggctacca agtgcatcat | 720 |
| caagatcgtg gagtttgcca agcggttgcc tggctttaca gggctcagca ttgctgacca | 780 |
| gatcactctg ctcaaagctg cctgcctaga tatcctgatg ctgcgtatct gcacaaggta | 840 |
| cacccccagag caggacacca tgaccttctc gacgggctg accctgaacc ggacccagat | 900 |
| gcacaatgcc ggcttcgggc ccctcacaga ccttgtcttt gcctttgctg ggcagctcct | 960 |
| gccctggag atgatgaca ccgagacagg gctgctcagc gccatctgcc tcatctgcgg | 1020 |
| agaccgcatg gacctggagg agcccgaaaa agtggacaag ctgcaggagc cactgctgga | 1080 |
| agccctgagg ctgtacgccc ggcgccggcg gcccagccag ccctacatgt tcccaaggat | 1140 |
| gctaatgaaa atcaccgacc tccggggcat cagcactaag ggagctgaaa gggccattac | 1200 |
| tctgaagatg gagattccag gcccgatgcc tcccttaatc cgagagatgc tggagaaccc | 1260 |
| tgaaatgttt gaggatgact cctcgcagcc tggtccccac cccaatgcct ctagcgagga | 1320 |
| tgaggttcct gggggccagg gcaaaggggg cctgaagtcc ccagcctgac cagggccct | 1380 |
| gacctccccg ctgtgggggt tgggcttca ggcagcagac tgaccatctc ccagaccgcc | 1440 |
| agtgactggg ggaggacctg ctctgccctc tccccacccc ttccaatgag ctccttgttt | 1500 |
| ttgccaaagt ttctaggggt gcctctgtgt tcatccccttc cctgatctaa ccggctccct | 1560 |
| cgccagtccc gggggcctgc cctgctccca ccaggagaga gggcaaaggg atgagcctgg | 1620 |
| gtttggactc taaaatctca gcactgcccc atgggtccta | 1660 |

<210> SEQ ID NO 44
<211> LENGTH: 1660
<212> TYPE: DNA
<213> ORGANISM: Homo sapiens
<221> NAME/KEY: CDS
<222> LOCATION: (38)..(1369)

<400> SEQUENCE: 44

```
gtttccagca cccagtttcc cttcaagccg ggtcgcg atg tac gac tgt atg gaa         55
                                        Met Tyr Asp Cys Met Glu
                                         1               5 acg ttt gcc ccg ggt ccg cga cgg ctg tac ggg gcg gcc ggg ccc ggg         103
Thr Phe Ala Pro Gly Pro Arg Arg Leu Tyr Gly Ala Ala Gly Pro Gly
         10                  15                  20 gcc ggc ttg ctg cgc aga gcc acc ggc ggc tcc tgt ttc gcc gga ctt         151
Ala Gly Leu Leu Arg Arg Ala Thr Gly Gly Ser Cys Phe Ala Gly Leu
 25                  30                  35 gaa tct ttt gcc tgg ccg caa ccc gcc agc ctg caa tcg gtg gag aca         199
Glu Ser Phe Ala Trp Pro Gln Pro Ala Ser Leu Gln Ser Val Glu Thr
     40                  45                  50 cag agc acc agc tca gag gag atg gtg ccc agc tcg ccc tcg ccc cct         247
Gln Ser Thr Ser Ser Glu Glu Met Val Pro Ser Ser Pro Ser Pro Pro
 55                  60                  65                  70 ccg cct cct cgg gtc tac aag cca tgc ttc gtg tgc aat gac aag tcc         295
Pro Pro Pro Arg Val Tyr Lys Pro Cys Phe Val Cys Asn Asp Lys Ser
                 75                  80                  85 tct ggc tac cac tat ggg gtc agc tct tgt gaa ggc tgc aag ggc ttc         343
Ser Gly Tyr His Tyr Gly Val Ser Ser Cys Glu Gly Cys Lys Gly Phe
             90                  95                 100 ttt cgc cga agc atc cag aag aac atg gtg tac acg tgt cac cgc gac         391
Phe Arg Arg Ser Ile Gln Lys Asn Met Val Tyr Thr Cys His Arg Asp
        105                 110                 115 aaa aac tgt atc atc aac aag gtg acc agg aat cgc tgc cag tac tgc         439
Lys Asn Cys Ile Ile Asn Lys Val Thr Arg Asn Arg Cys Gln Tyr Cys
    120                 125                 130 cgg cta cag aag tgc ttc gaa gtg ggc atg tcc aag gaa gct gtg cga         487
Arg Leu Gln Lys Cys Phe Glu Val Gly Met Ser Lys Glu Ala Val Arg
135                 140                 145                 150 aat gac cgg aac aag aag aag aaa gag gtg aag gaa gaa ggg tca cct         535
Asn Asp Arg Asn Lys Lys Lys Lys Glu Val Lys Glu Glu Gly Ser Pro
                155                 160                 165 gac agc tat gag ctg agc cct cag tta gaa gag ctc atc acc aag gtc         583
Asp Ser Tyr Glu Leu Ser Pro Gln Leu Glu Glu Leu Ile Thr Lys Val
            170                 175                 180 agc aaa gcc cat cag gag act ttc ccc tcg ctc tgc cag ctg ggc aag         631
Ser Lys Ala His Gln Glu Thr Phe Pro Ser Leu Cys Gln Leu Gly Lys
        185                 190                 195 tat acc acg aac tcc agt gca gac cac cgc gtg cag ctg gat ctg ggg         679
Tyr Thr Thr Asn Ser Ser Ala Asp His Arg Val Gln Leu Asp Leu Gly
    200                 205                 210 ctg tgg gac aag ttc agt gag ctg gct acc aag tgc atc atc aag atc         727
Leu Trp Asp Lys Phe Ser Glu Leu Ala Thr Lys Cys Ile Ile Lys Ile
215                 220                 225                 230 gtg gag ttt gcc aag cgg ttg cct ggc ttt aca ggg ctc agc att gct         775
Val Glu Phe Ala Lys Arg Leu Pro Gly Phe Thr Gly Leu Ser Ile Ala
                235                 240                 245 gac cag atc act ctg ctc aaa gct gcc tgc cta gat atc ctg atg ctg         823
Asp Gln Ile Thr Leu Leu Lys Ala Ala Cys Leu Asp Ile Leu Met Leu
            250                 255                 260 cgt atc tgc aca agg tac acc cca gag cag gac acc atg acc ttc tcc         871
Arg Ile Cys Thr Arg Tyr Thr Pro Glu Gln Asp Thr Met Thr Phe Ser
```

```
                  265                 270                 275
gac ggg ctg acc ctg aac cgg acc cag atg cac aat gcc ggc ttc ggg    919
Asp Gly Leu Thr Leu Asn Arg Thr Gln Met His Asn Ala Gly Phe Gly
    280                 285                 290 ccc ctc aca gac ctt gtc ttt gcc ttt gct ggg cag ctc ctg ccc ctg    967
Pro Leu Thr Asp Leu Val Phe Ala Phe Ala Gly Gln Leu Leu Pro Leu
295                 300                 305                 310 gag atg gat gac acc gag aca ggg ctg ctc agc gcc atc tgc ctc atc   1015
Glu Met Asp Asp Thr Glu Thr Gly Leu Leu Ser Ala Ile Cys Leu Ile
                315                 320                 325 tgc gga gac cgc atg gac ctg gag gag ccc gaa aaa gtg gac aag ctg   1063
Cys Gly Asp Arg Met Asp Leu Glu Glu Pro Glu Lys Val Asp Lys Leu
            330                 335                 340 cag gag cca ctg ctg gaa gcc ctg agg ctg tac gcc cgg cgc cgg cgg   1111
Gln Glu Pro Leu Leu Glu Ala Leu Arg Leu Tyr Ala Arg Arg Arg Arg
        345                 350                 355 ccc agc cag ccc tac atg ttc cca agg atg cta atg aaa atc acc gac   1159
Pro Ser Gln Pro Tyr Met Phe Pro Arg Met Leu Met Lys Ile Thr Asp
    360                 365                 370 ctc cgg ggc atc agc act aag gga gct gaa agg gcc att act ctg aag   1207
Leu Arg Gly Ile Ser Thr Lys Gly Ala Glu Arg Ala Ile Thr Leu Lys
375                 380                 385                 390 atg gag att cca ggc ccg atg cct ccc tta atc cga gag atg ctg gag   1255
Met Glu Ile Pro Gly Pro Met Pro Pro Leu Ile Arg Glu Met Leu Glu
                395                 400                 405 aac cct gaa atg ttt gag gat gac tcc tcg cag cct ggt ccc cac ccc   1303
Asn Pro Glu Met Phe Glu Asp Asp Ser Ser Gln Pro Gly Pro His Pro
            410                 415                 420 aat gcc tct agc gag gat gag gtt cct ggg ggc cag ggc aaa ggg ggc   1351
Asn Ala Ser Ser Glu Asp Glu Val Pro Gly Gly Gln Gly Lys Gly Gly
        425                 430                 435 ctg aag tcc cca gcc tga ccagggcccc tgacctcccc gctgtggggg          1399
Leu Lys Ser Pro Ala
    440 ttggggcttc aggcagcaga ctgaccatct cccagaccgc cagtgactgg gggaggacct 1459 gctctgccct ctccccaccc cttccaatga gctccttgtt tttgccaaag tttctagggg 1519 tgcctctgtg ttcatcccct tcctgatcta accggctccc tcgccagtcc cgggggcctg 1579 ccctgctccc accaggagag agggcaaagg gatgagcctg ggtttggact ctaaaatctc 1639 agcactgccc catgggtcct a                                           1660

<210> SEQ ID NO 45
<211> LENGTH: 443
<212> TYPE: PRT
<213> ORGANISM: Homo sapiens

<400> SEQUENCE: 45

Met Tyr Asp Cys Met Glu Thr Phe Ala Pro Gly Pro Arg Arg Leu Tyr
1               5                   10                  15

Gly Ala Ala Gly Pro Gly Ala Gly Leu Leu Arg Arg Ala Thr Gly Gly
                20                  25                  30

Ser Cys Phe Ala Gly Leu Glu Ser Phe Ala Trp Pro Gln Pro Ala Ser
            35                  40                  45

Leu Gln Ser Val Glu Thr Gln Ser Thr Ser Glu Glu Met Val Pro
    50                  55                  60

Ser Ser Pro Ser Pro Pro Pro Arg Val Tyr Lys Pro Cys Phe
65                  70                  75                  80

Val Cys Asn Asp Lys Ser Ser Gly Tyr His Tyr Gly Val Ser Ser Cys
```

```
                    85                  90                  95
Glu Gly Cys Lys Gly Phe Phe Arg Arg Ser Ile Gln Lys Asn Met Val
                100                 105                 110
Tyr Thr Cys His Arg Asp Lys Asn Cys Ile Ile Asn Lys Val Thr Arg
            115                 120                 125
Asn Arg Cys Gln Tyr Cys Arg Leu Gln Lys Cys Phe Glu Val Gly Met
        130                 135                 140
Ser Lys Glu Ala Val Arg Asn Asp Arg Asn Lys Lys Lys Lys Glu Val
145                 150                 155                 160
Lys Glu Glu Gly Ser Pro Asp Ser Tyr Glu Leu Ser Pro Gln Leu Glu
                165                 170                 175
Glu Leu Ile Thr Lys Val Ser Lys Ala His Gln Glu Thr Phe Pro Ser
            180                 185                 190
Leu Cys Gln Leu Gly Lys Tyr Thr Thr Asn Ser Ser Ala Asp His Arg
        195                 200                 205
Val Gln Leu Asp Leu Gly Leu Trp Asp Lys Phe Ser Glu Leu Ala Thr
    210                 215                 220
Lys Cys Ile Ile Lys Ile Val Glu Phe Ala Lys Arg Leu Pro Gly Phe
225                 230                 235                 240
Thr Gly Leu Ser Ile Ala Asp Gln Ile Thr Leu Leu Lys Ala Ala Cys
                245                 250                 255
Leu Asp Ile Leu Met Leu Arg Ile Cys Thr Arg Tyr Thr Pro Glu Gln
            260                 265                 270
Asp Thr Met Thr Phe Ser Asp Gly Leu Thr Leu Asn Arg Thr Gln Met
        275                 280                 285
His Asn Ala Gly Phe Gly Pro Leu Thr Asp Leu Val Phe Ala Phe Ala
    290                 295                 300
Gly Gln Leu Leu Pro Leu Glu Met Asp Asp Thr Glu Thr Gly Leu Leu
305                 310                 315                 320
Ser Ala Ile Cys Leu Ile Cys Gly Asp Arg Met Asp Leu Glu Glu Pro
                325                 330                 335
Glu Lys Val Asp Lys Leu Gln Glu Pro Leu Leu Glu Ala Leu Arg Leu
            340                 345                 350
Tyr Ala Arg Arg Arg Pro Ser Gln Pro Tyr Met Phe Pro Arg Met
        355                 360                 365
Leu Met Lys Ile Thr Asp Leu Arg Gly Ile Ser Thr Lys Gly Ala Glu
    370                 375                 380
Arg Ala Ile Thr Leu Lys Met Glu Ile Pro Gly Pro Met Pro Pro Leu
385                 390                 395                 400
Ile Arg Glu Met Leu Glu Asn Pro Glu Met Phe Glu Asp Asp Ser Ser
                405                 410                 415
Gln Pro Gly Pro His Pro Asn Ala Ser Ser Glu Asp Glu Val Pro Gly
            420                 425                 430
Gly Gln Gly Lys Gly Gly Leu Lys Ser Pro Ala
        435                 440

<210> SEQ ID NO 46
<211> LENGTH: 187
<212> TYPE: DNA
<213> ORGANISM: Homo sapiens

<400> SEQUENCE: 46
gtttccagca cccagtttcc cttcaagccg ggtcgcgatg tacgactgta tggaaacgtt     60
tgccccgggt ccgcgacggc tgtacggggc ggccgggccc ggggccggct tgctgcgcag    120
```

```
agccaccggc ggctcctgtt tcgccggact tgaatctttt gcctggccgc aacccgccag    180
cctgcaa                                                              187
```

<210> SEQ ID NO 47
<211> LENGTH: 50
<212> TYPE: PRT
<213> ORGANISM: Homo sapiens

<400> SEQUENCE: 47

```
Met Tyr Asp Cys Met Glu Thr Phe Ala Pro Gly Pro Arg Arg Leu Tyr
1               5                   10                  15

Gly Ala Ala Gly Pro Gly Ala Gly Leu Leu Arg Arg Ala Thr Gly Gly
            20                  25                  30

Ser Cys Phe Ala Gly Leu Glu Ser Phe Ala Trp Pro Gln Pro Ala Ser
        35                  40                  45

Leu Gln
    50
```

<210> SEQ ID NO 48
<211> LENGTH: 150
<212> TYPE: DNA
<213> ORGANISM: Homo sapiens

<400> SEQUENCE: 48

```
atgtacgact gtatggaaac gtttgccccg gtccgcgac ggctgtacgg ggcggccggg     60
cccggggccg gcttgctgcg cagagccacc ggcggctcct gtttcgccgg acttgaatct   120
tttgcctggc cgcaacccgc cagcctgcaa                                    150
```

<210> SEQ ID NO 49
<211> LENGTH: 1293
<212> TYPE: DNA
<213> ORGANISM: Homo sapiens

<400> SEQUENCE: 49

```
aaaaaaaaag gtctccccag tgctagctgc cgaagcaccc agataagagc tggacggagg     60
ctaaagcggc agccccagct tcgcgccccg cccagtccct tcccctgct ggggatcccc    120 cctcttcccc gcccaccct tacccgcatg cagcccagcg ccctatgcta gccctccccc    180
tccccccctg ctggagcggg cgccgcgcgg gggaggaggg ggaatcggct gcgggtcctt    240
ggtgtttcca gcacccagtt tcccttcaag ccgggtcgcg atgtacgact gtatggaaac    300
gtttgccccg gtccgcgac ggctgtacgg ggcggccggg cccggggccg gcttgctgcg    360
cagagccacc ggcggctcct gtttcgccgg acttgaatct tttgcctggc cgcaacccgc    420
cagcctgcaa tcggtggaga cacagagcac cagctcagag gagatggtgc ccagctcgcc    480 ctcgcccct ccgcctcctc gggtctacaa gccatgcttc gtgtgcaatg acaagtcctc    540
tggctaccac tatgggtca gctcttgtga aggctgcaag aggccctctc tctttccctc    600
aactccaggg cttctttcgc cgaagcatcc agaagaacat ggtgtacacg tgtcaccgcg    660
acaaaaactg tatcatcaac aaggtgacca ggaatcgctg ccagtactgc cggctacaga    720
agtgcttcga agtgggcatg tccaaggaag ctgtgcgaaa tgaccggaac aagaagaaga    780 agaggtgaa ggaagaaggg tcacctgaca gctatgagct gagccctcag ttagaagagc    840
tcatcaccaa ggtcagcaaa gcccatcagg agactttccc ctcgctctgc cagctgggca    900
agtataccac gaactccagt gcagaccacc gcgtgcagct ggatctgggg ctgtgggaca    960
agttcagtga gctggctacc aagtgcatca tcaagatcgt ggagtttgcc aagcggttgc   1020
```

```
ctggctttac agggctcagc attgctgacc agatcactct gctcaaagct gcctgcctag    1080
atatcctgat gctgcgtatc tgcacaaggt acacccagaa gcaggacacc atgaccttct    1140
ccgacgggct gaccctgaac cggacccaga tgcacaatgc cggcttcggg cccctcacag    1200
accttgtctt tgcctttgct gggcagctcc tgccctgga gatggatgac accgagacag    1260
ggctgctcag cgccatctgc ctcatctgcg gag                                 1293

<210> SEQ ID NO 50
<211> LENGTH: 1293
<212> TYPE: DNA
<213> ORGANISM: Homo sapiens
<221> NAME/KEY: CDS
<222> LOCATION: (165)..(1292)

<400> SEQUENCE: 50
aaaaaaaaag gtctccccag tgctagctgc cgaagcaccc agataagagc tggacggagg    60
ctaaagcggc agcccagct tcgcgccccg cccagtcccc ttcccctgct ggggatcccc      120
cctcttcccc gcccacccct tacccgcatg cagcccagcg ccct atg cta gcc ctc    176
                                                 Met Leu Ala Leu
                                                  1 ccc ctc ccc ccc tgc tgg agc ggg gcg ccg ccg ggg gag gag ggg gaa    224
Pro Leu Pro Pro Cys Trp Ser Gly Ala Pro Pro Gly Glu Glu Gly Glu
 5              10                  15                  20 tcg gct gcg ggt cct tgg tgt ttc cag cac cca gtt tcc ctt caa gcc    272
Ser Ala Ala Gly Pro Trp Cys Phe Gln His Pro Val Ser Leu Gln Ala
            25                  30                  35 ggg tcg cga tgt acg act gta tgg aaa cgt ttg ccc cgg gtc cgc gac    320
Gly Ser Arg Cys Thr Thr Val Trp Lys Arg Leu Pro Arg Val Arg Asp
    40                  45                  50 ggc tgt acg ggg cgg ccg ggc ccg ggg ccg gct tgc tgc gca gag cca    368
Gly Cys Thr Gly Arg Pro Gly Pro Gly Pro Ala Cys Cys Ala Glu Pro
55                  60                  65 ccg gcg gct cct gtt tcg ccg gac ttg aat ctt ttg cct ggc cgc aac    416
Pro Ala Ala Pro Val Ser Pro Asp Leu Asn Leu Leu Pro Gly Arg Asn
 70                 75                  80 ccg cca gcc tgc aat cgg tgg aga cac aga gca cca gct cag agg aga    464
Pro Pro Ala Cys Asn Arg Trp Arg His Arg Ala Pro Ala Gln Arg Arg
85                  90                  95                 100 tgg tgc cca gct cgc cct cgc ccc ctc cgc ctc ctc ggg tct aca agc    512
Trp Cys Pro Ala Arg Pro Arg Pro Leu Arg Leu Leu Gly Ser Thr Ser
                105                 110                 115 cat gct tcg tgt gca atg aca agt cct ctg gct acc act atg ggg tca    560
His Ala Ser Cys Ala Met Thr Ser Pro Leu Ala Thr Thr Met Gly Ser
            120                 125                 130 gct ctt gtg aag gct gca aga ggc cct ctc tct ttc cct caa ctc cag    608
Ala Leu Val Lys Ala Ala Arg Gly Pro Leu Ser Phe Pro Gln Leu Gln
        135                 140                 145 ggc ttc ttt cgc cga agc atc cag aag aac atg gtg tac acg tgt cac    656
Gly Phe Phe Arg Arg Ser Ile Gln Lys Asn Met Val Tyr Thr Cys His
    150                 155                 160 cgc gac aaa aac tgt atc atc aac aag gtg acc agg aat cgc tgc cag    704
Arg Asp Lys Asn Cys Ile Ile Asn Lys Val Thr Arg Asn Arg Cys Gln
165                 170                 175                 180 tac tgc cgg cta cag aag tgc ttc gaa gtg ggc atg tcc aag gaa gct    752
Tyr Cys Arg Leu Gln Lys Cys Phe Glu Val Gly Met Ser Lys Glu Ala
                185                 190                 195 gtg cga aat gac cgg aac aag aag aag aaa gag gtg aag gaa gaa ggg    800
Val Arg Asn Asp Arg Asn Lys Lys Lys Lys Glu Val Lys Glu Glu Gly
            200                 205                 210
```

```
tca cct gac agc tat gag ctg agc cct cag tta gaa gag ctc atc acc      848
Ser Pro Asp Ser Tyr Glu Leu Ser Pro Gln Leu Glu Glu Leu Ile Thr
    215                 220                 225 aag gtc agc aaa gcc cat cag gag act ttc ccc tcg ctc tgc cag ctg      896
Lys Val Ser Lys Ala His Gln Glu Thr Phe Pro Ser Leu Cys Gln Leu
230                 235                 240 ggc aag tat acc acg aac tcc agt gca gac cac cgc gtg cag ctg gat      944
Gly Lys Tyr Thr Thr Asn Ser Ser Ala Asp His Arg Val Gln Leu Asp
245                 250                 255                 260 ctg ggg ctg tgg gac aag ttc agt gag ctg gct acc aag tgc atc atc      992
Leu Gly Leu Trp Asp Lys Phe Ser Glu Leu Ala Thr Lys Cys Ile Ile
                265                 270                 275 aag atc gtg gag ttt gcc aag cgg ttg cct ggc ttt aca ggg ctc agc     1040
Lys Ile Val Glu Phe Ala Lys Arg Leu Pro Gly Phe Thr Gly Leu Ser
            280                 285                 290 att gct gac cag atc act ctg ctc aaa gct gcc tgc cta gat atc ctg     1088
Ile Ala Asp Gln Ile Thr Leu Leu Lys Ala Ala Cys Leu Asp Ile Leu
        295                 300                 305 atg ctg cgt atc tgc aca agg tac acc cca gag cag gac acc atg acc     1136
Met Leu Arg Ile Cys Thr Arg Tyr Thr Pro Glu Gln Asp Thr Met Thr
    310                 315                 320 ttc tcc gac ggg ctg acc ctg aac cgg acc cag atg cac aat gcc ggc     1184
Phe Ser Asp Gly Leu Thr Leu Asn Arg Thr Gln Met His Asn Ala Gly
325                 330                 335                 340 ttc ggg ccc ctc aca gac ctt gtc ttt gcc ttt gct ggg cag ctc ctg     1232
Phe Gly Pro Leu Thr Asp Leu Val Phe Ala Phe Ala Gly Gln Leu Leu
                345                 350                 355 ccc ctg gag atg gat gac acc gag aca ggg ctc ctc agc gcc atc tgc     1280
Pro Leu Glu Met Asp Asp Thr Glu Thr Gly Leu Leu Ser Ala Ile Cys
            360                 365                 370 ctc atc tgc gga g                                                   1293
Leu Ile Cys Gly
        375

<210> SEQ ID NO 51
<211> LENGTH: 376
<212> TYPE: PRT
<213> ORGANISM: Homo sapiens

<400> SEQUENCE: 51

Met Leu Ala Leu Pro Leu Pro Cys Trp Ser Gly Ala Pro Pro Gly
1               5                   10                  15

Glu Glu Gly Glu Ser Ala Ala Gly Pro Trp Cys Phe Gln His Pro Val
                20                  25                  30

Ser Leu Gln Ala Gly Ser Arg Cys Thr Thr Val Trp Lys Arg Leu Pro
            35                  40                  45

Arg Val Arg Asp Gly Cys Thr Gly Arg Pro Gly Pro Gly Pro Ala Cys
        50                  55                  60

Cys Ala Glu Pro Pro Ala Ala Pro Val Ser Pro Asp Leu Asn Leu Leu
65                  70                  75                  80

Pro Gly Arg Asn Pro Pro Ala Cys Asn Arg Trp Arg His Arg Ala Pro
                85                  90                  95

Ala Gln Arg Arg Trp Cys Pro Ala Arg Pro Arg Pro Leu Arg Leu Leu
            100                 105                 110

Gly Ser Thr Ser His Ala Ser Cys Ala Met Thr Ser Pro Leu Ala Thr
        115                 120                 125

Thr Met Gly Ser Ala Leu Val Lys Ala Ala Arg Gly Pro Leu Ser Phe
    130                 135                 140

Pro Gln Leu Gln Gly Phe Phe Arg Arg Ser Ile Gln Lys Asn Met Val
```

```
                 145                 150                 155                 160
Tyr Thr Cys His Arg Asp Lys Asn Cys Ile Ile Asn Lys Val Thr Arg
                165                 170                 175

Asn Arg Cys Gln Tyr Cys Arg Leu Gln Lys Cys Phe Glu Val Gly Met
                180                 185                 190

Ser Lys Glu Ala Val Arg Asn Asp Arg Asn Lys Lys Lys Lys Glu Val
                195                 200                 205

Lys Glu Glu Gly Ser Pro Asp Ser Tyr Glu Leu Ser Pro Gln Leu Glu
                210                 215                 220

Glu Leu Ile Thr Lys Val Ser Lys Ala His Gln Glu Thr Phe Pro Ser
225                 230                 235                 240

Leu Cys Gln Leu Gly Lys Tyr Thr Thr Asn Ser Ser Ala Asp His Arg
                245                 250                 255

Val Gln Leu Asp Leu Gly Leu Trp Asp Lys Phe Ser Glu Leu Ala Thr
                260                 265                 270

Lys Cys Ile Ile Lys Ile Val Glu Phe Ala Lys Arg Leu Pro Gly Phe
                275                 280                 285

Thr Gly Leu Ser Ile Ala Asp Gln Ile Thr Leu Leu Lys Ala Ala Cys
                290                 295                 300

Leu Asp Ile Leu Met Leu Arg Ile Cys Thr Arg Tyr Thr Pro Glu Gln
305                 310                 315                 320

Asp Thr Met Thr Phe Ser Asp Gly Leu Thr Leu Asn Arg Thr Gln Met
                325                 330                 335

His Asn Ala Gly Phe Gly Pro Leu Thr Asp Leu Val Phe Ala Phe Ala
                340                 345                 350

Gly Gln Leu Leu Pro Leu Glu Met Asp Asp Thr Glu Thr Gly Leu Leu
                355                 360                 365

Ser Ala Ile Cys Leu Ile Cys Gly
                370                 375

<210> SEQ ID NO 52
<211> LENGTH: 430
<212> TYPE: DNA
<213> ORGANISM: Homo sapiens

<400> SEQUENCE: 52
aaaaaaaaag gtctcccag  tgctagctgc  cgaagcaccc  agataagagc  tggacggagg    60
ctaaagcggc agccccagct tcgcgccccg cccagtccct ttcccctgct ggggatcccc   120
cctcttcccc gcccacccct tacccgcatg cagcccagcg ccctatgcta gccctccccc   180 tcccccctg  ctggagcggg gcgccgccgg gggaggaggg ggaatcggct gcgggtcctt   240
ggtgtttcca gcaccagtt  tcccttcaag ccgggtcgcg atgtacgact gtatggaaac   300
gtttgccccg gtccgcgac  ggctgtacgg ggcggccggg cccggggccg gcttgctgcg   360
cagagccacc ggcggctcct gtttcgccgg acttgaatct tttgcctggc cgcaacccgc   420
cagcctgcaa                                                         430

<210> SEQ ID NO 53
<211> LENGTH: 28
<212> TYPE: DNA
<213> ORGANISM: Homo sapiens

<400> SEQUENCE: 53
aggccctctc tctttccctc aactccag                                      28

<210> SEQ ID NO 54
```

```
<211> LENGTH: 148
<212> TYPE: PRT
<213> ORGANISM: Homo sapiens

<400> SEQUENCE: 54

Met Leu Ala Leu Pro Leu Pro Pro Cys Trp Ser Gly Ala Pro Pro Gly
1               5                   10                  15

Glu Glu Gly Glu Ser Ala Ala Gly Pro Trp Cys Phe Gln His Pro Val
            20                  25                  30

Ser Leu Gln Ala Gly Ser Arg Cys Thr Thr Val Trp Lys Arg Leu Pro
        35                  40                  45

Arg Val Arg Asp Gly Cys Thr Gly Arg Pro Gly Pro Gly Pro Ala Cys
    50                  55                  60

Cys Ala Glu Pro Pro Ala Ala Pro Val Ser Pro Asp Leu Asn Leu Leu
65                  70                  75                  80

Pro Gly Arg Asn Pro Pro Ala Cys Asn Arg Trp Arg His Arg Ala Pro
                85                  90                  95

Ala Gln Arg Arg Trp Cys Pro Ala Arg Pro Arg Pro Leu Arg Leu Leu
            100                 105                 110

Gly Ser Thr Ser His Ala Ser Cys Ala Met Thr Ser Pro Leu Ala Thr
        115                 120                 125

Thr Met Gly Ser Ala Leu Val Lys Ala Ala Arg Gly Pro Leu Ser Phe
    130                 135                 140

Pro Gln Leu Gln
145

<210> SEQ ID NO 55
<211> LENGTH: 266
<212> TYPE: DNA
<213> ORGANISM: Homo sapiens

<400> SEQUENCE: 55
atgctagccc tcccctcc ccctgctgg agcggggcgc cgccggggga ggaggggaa       60 tcggctgcgg gtccttggtg tttccagcac ccagtttccc ttcaagccgg gtcgcgatgt    120
acgactgtat ggaaacgttt gccccgggtc cgcgacggct gtacggggcg gccgggcccg    180
gggccggctt gctgcgcaga gccaccggcg gctcctgttt cgccggactt gaatcttttg    240
cctggccgca acccgccagc ctgcaa                                         266

<210> SEQ ID NO 56
<211> LENGTH: 89
<212> TYPE: PRT
<213> ORGANISM: Homo sapiens

<400> SEQUENCE: 56

Met Leu Ala Leu Pro Leu Pro Pro Cys Trp Ser Gly Ala Pro Pro Gly
1               5                   10                  15

Glu Glu Gly Glu Ser Ala Ala Gly Pro Trp Cys Phe Gln His Pro Val
            20                  25                  30

Ser Leu Gln Ala Gly Ser Arg Cys Thr Thr Val Trp Lys Arg Leu Pro
        35                  40                  45

Arg Val Arg Asp Gly Cys Thr Gly Arg Pro Gly Pro Gly Pro Ala Cys
    50                  55                  60

Cys Ala Glu Pro Pro Ala Ala Pro Val Ser Pro Asp Leu Asn Leu Leu
65                  70                  75                  80

Pro Gly Arg Asn Pro Pro Ala Cys Asn
                85
```

<210> SEQ ID NO 57
<211> LENGTH: 10
<212> TYPE: PRT
<213> ORGANISM: Homo sapiens

<400> SEQUENCE: 57

Arg Gly Pro Leu Ser Phe Pro Gln Leu Gln
1               5                   10

<210> SEQ ID NO 58
<211> LENGTH: 1985
<212> TYPE: DNA
<213> ORGANISM: Homo sapiens

<400> SEQUENCE: 58

| | | | | |
|---|---|---|---|---|
| tggggggggg | gtggggaggg | agaaaaagaa | agaaaatatt | ttccgtgtcc | ccgcctgcag |   60 |
| agtcagtgtg | cggtttggga | gaaaatgtgt | cggatatttt | ggggcggtca | cgtgggcggg |  120 |
| cgggctccga | gaggccccgg | gacagtccca | gcctagagcc | gtgccccccc | aggagccccc |  180 |
| cagtacggcg | agccccggac | attgcgacgc | tccatccagg | agactgcccg | acgccgggac |  240 |
| ctcgggctc  | cgccgcctcc | cttccccctc | ccactccagc | agctacggcc | cagttccctc |  300 |
| aacctgaccc | agtatgtaga | agccagtctc | tgcaggcggc | cagcgggact | tttggaggcc |  360 |
| cagtgggcag | gccaggcagg | gcgggtacgg | agcctcccag | gctggggcag | tgggcatggg |  420 |
| caggggctgt | ggctgaagac | ctcgcccgcc | cactgcagac | cccaggggac | tctcacaccg |  480 |
| cagctgccat | ggccaccaat | aaggagcgac | tctttgcggc | tggtgccctg | ggcctggat |  540 |
| ctggctaccc | aggggcaggt | ttccccttcg | ccttcccagg | ggcactcagg | gggtctccgc |  600 |
| cttttcgagat | gctgagccct | agcttccggg | gcctgggcca | gcctgacctc | cccaaggaga |  660 |
| tggcctctct | gtcggtggag | acacagagca | ccagctcaga | ggagatggtg | cccagctcgc |  720 |
| cctcgccccc | tccgcctcct | cgggtctaca | agccatgctt | cgtgtgcaat | gacaagtcct |  780 |
| ctggctacca | ctatgggtc  | agctcttgtg | aaggctgcaa | gggcttcttt | cgccgaagca |  840 |
| tccagaagaa | catggtgtac | acgtgtcacc | gcgacaaaaa | ctgtatcatc | aacaaggtga |  900 |
| ccaggaatcg | ctgccagtac | tgccggctac | agaagtgctt | cgaagtgggc | atgtccaagg |  960 |
| aagctgtgcg | aaatgaccgg | aacaagaaga | agaaagaggt | gaaggaagaa | gggtcacctg | 1020 |
| acagctatga | gctgagccct | cagttagaag | agctcatcac | caaggtcagc | aaagcccatc | 1080 |
| aggagacttt | ccctcgctc  | tgccagctgg | gcaagtatac | cacgaactct | agtgcagacc | 1140 |
| accgcgtgca | gctggatctg | gggctgtggg | acaagttcag | tgagctggct | accaagtgca | 1200 |
| tcatcaagat | cgtggagttt | gccaagcggt | tgcctggctt | tacagggctc | agcattgctg | 1260 |
| accagatcac | tctgctcaaa | gctgcctgcc | tagatatcct | gatgctgcgt | atctgcacaa | 1320 |
| ggtacacccc | agagcaggac | accatgacct | tctccgacgg | gctgaccctg | aaccggacccc | 1380 |
| agatgcacaa | tgccggcttc | gggcccctca | cagaccttgt | ctttgccttt | gctgggcagc | 1440 |
| tcctgcccct | ggagatggat | gacaccgaga | cagggctgct | cagcgccatc | tgcctcatct | 1500 |
| gcggagaccg | catggacctg | gaggagcccg | aaaaagtgga | caagctgcag | gagccactgc | 1560 |
| tggaagccct | gaggctgtac | gcccggcgcc | ggcggcccag | ccagccctac | atgttcccaa | 1620 |
| ggatgctaat | gaaaatcacc | gacctccggg | gcatcagcac | taaggagct  | gaagggcca  | 1680 |
| ttactctgaa | gatggagatt | ccaggcccga | tgcctccctt | aatccgagag | atgctggaga | 1740 |
| accctgaaat | gtttgaggat | gactcctcgc | agcctggtcc | ccaccccaat | gcctctagcg | 1800 |
| aggatgaggt | tcctggggc  | cagggcaaag | ggggcctgaa | gtccccagcc | tgaccagggc | 1860 |

-continued

```
ccctgacctc ccgctgtgg gggttgggc ttcaggcagc agactgacca tctcccagac    1920
cgccagtgac tggggagga cctgccctgc cctctcccca cccttccaa tgagctcctt    1980 gtttt                                                              1985

<210> SEQ ID NO 59
<211> LENGTH: 1985
<212> TYPE: DNA
<213> ORGANISM: Homo sapiens
<221> NAME/KEY: CDS
<222> LOCATION: (489)..(1853)

<400> SEQUENCE: 59 tgggggggg gtggggaggg agaaaaagaa agaaaatatt ttccgtgtcc ccgcctgcag      60
agtcagtgtg cggtttggga gaaatgtgt cggatatttt ggggcggtca cgtgggcggg    120
cgggctccga gaggccccgg acagtccca gcctagagcc gtgcccccc aggagccccc     180 cagtacggcg agcccggac attgcgacgc tccatccagg agactgcccg acgccggac     240 ctcggggctc cgccgcctcc cttcccctc ccactccagc agctacggcc cagttccctc    300
aacctgaccc agtatgtaga agccagtctc tgcaggcggc cagcgggact tttggaggcc    360
cagtgggcag ccaggcagg gcgggtacgg agcctcccag gctggggcag tgggcatggg    420
caggggctgt ggctgaagac ctcgcccgcc cactgcagac cccaggggac tctcacaccg    480 cagctgcc atg gcc acc aat aag gag cga ctc ttt gcg gct ggt gcc ctg   530
         Met Ala Thr Asn Lys Glu Arg Leu Phe Ala Ala Gly Ala Leu
         1               5                   10 ggg cct gga tct ggc tac cca ggg gca ggt ttc ccc ttc gcc ttc cca   578
Gly Pro Gly Ser Gly Tyr Pro Gly Ala Gly Phe Pro Phe Ala Phe Pro
15                  20                  25                  30 ggg gca ctc agg ggg tct ccg cct ttc gag atg ctg agc cct agc ttc   626
Gly Ala Leu Arg Gly Ser Pro Pro Phe Glu Met Leu Ser Pro Ser Phe
                35                  40                  45 cgg ggc ctg ggc cag cct gac ctc ccc aag gag atg gcc tct ctg tcg   674
Arg Gly Leu Gly Gln Pro Asp Leu Pro Lys Glu Met Ala Ser Leu Ser
            50                  55                  60 gtg gag aca cag agc acc agc tca gag gag atg gtg ccc agc tcg ccc   722
Val Glu Thr Gln Ser Thr Ser Ser Glu Glu Met Val Pro Ser Ser Pro
        65                  70                  75 tcg ccc cct ccg cct cct cgg gtc tac aag cca tgc ttc gtg tgc aat   770
Ser Pro Pro Pro Pro Pro Arg Val Tyr Lys Pro Cys Phe Val Cys Asn
    80                  85                  90 gac aag tcc tct ggc tac cac tat ggg gtc agc tct tgt gaa ggc tgc   818
Asp Lys Ser Ser Gly Tyr His Tyr Gly Val Ser Ser Cys Glu Gly Cys
95                  100                 105                 110 aag ggc ttc ttt cgc cga agc atc cag aag aac atg gtg tac acg tgt   866
Lys Gly Phe Phe Arg Arg Ser Ile Gln Lys Asn Met Val Tyr Thr Cys
                115                 120                 125 cac cgc gac aaa aac tgt atc atc aac aag gtg acc agg aat cgc tgc   914
His Arg Asp Lys Asn Cys Ile Ile Asn Lys Val Thr Arg Asn Arg Cys
            130                 135                 140 cag tac tgc cgg cta cag aag tgc ttc gaa gtg ggc atg tcc aag gaa   962
Gln Tyr Cys Arg Leu Gln Lys Cys Phe Glu Val Gly Met Ser Lys Glu
        145                 150                 155 gct gtg cga aat gac cgg aac aag aag aaa gag gtg aag gaa gaa      1010
Ala Val Arg Asn Asp Arg Asn Lys Lys Lys Glu Val Lys Glu Glu
    160                 165                 170 ggg tca cct gac agc tat gag ctg agc cct cag tta gaa gag ctc atc  1058
Gly Ser Pro Asp Ser Tyr Glu Leu Ser Pro Gln Leu Glu Glu Leu Ile
175                 180                 185                 190
```

```
acc aag gtc agc aaa gcc cat cag gag act ttc ccc tcg ctc tgc cag    1106
Thr Lys Val Ser Lys Ala His Gln Glu Thr Phe Pro Ser Leu Cys Gln
            195                 200                 205 ctg ggc aag tat acc acg aac tct agt gca gac cac cgc gtg cag ctg    1154
Leu Gly Lys Tyr Thr Thr Asn Ser Ser Ala Asp His Arg Val Gln Leu
        210                 215                 220 gat ctg ggg ctg tgg gac aag ttc agt gag ctg gct acc aag tgc atc    1202
Asp Leu Gly Leu Trp Asp Lys Phe Ser Glu Leu Ala Thr Lys Cys Ile
    225                 230                 235 atc aag atc gtg gag ttt gcc aag cgg ttg cct ggc ttt aca ggg ctc    1250
Ile Lys Ile Val Glu Phe Ala Lys Arg Leu Pro Gly Phe Thr Gly Leu
240                 245                 250 agc att gct gac cag atc act ctg ctc aaa gct gcc tgc cta gat atc    1298
Ser Ile Ala Asp Gln Ile Thr Leu Leu Lys Ala Ala Cys Leu Asp Ile
255                 260                 265                 270 ctg atg ctg cgt atc tgc aca agg tac acc cca gag cag gac acc atg    1346
Leu Met Leu Arg Ile Cys Thr Arg Tyr Thr Pro Glu Gln Asp Thr Met
                275                 280                 285 acc ttc tcc gac ggg ctg acc ctg aac cgg acc cag atg cac aat gcc    1394
Thr Phe Ser Asp Gly Leu Thr Leu Asn Arg Thr Gln Met His Asn Ala
            290                 295                 300 ggc ttc ggg ccc ctc aca gac ctt gtc ttt gcc ttt gct ggg cag ctc    1442
Gly Phe Gly Pro Leu Thr Asp Leu Val Phe Ala Phe Ala Gly Gln Leu
        305                 310                 315 ctg ccc ctg gag atg gat gac acc gag aca ggg ctc ctc agc gcc atc    1490
Leu Pro Leu Glu Met Asp Asp Thr Glu Thr Gly Leu Leu Ser Ala Ile
    320                 325                 330 tgc ctc atc tgc gga gac cgc atg gac ctg gag gag ccc gaa aaa gtg    1538
Cys Leu Ile Cys Gly Asp Arg Met Asp Leu Glu Glu Pro Glu Lys Val
335                 340                 345                 350 gac aag ctg cag gag cca ctg ctg gaa gcc ctg agg ctg tac gcc cgg    1586
Asp Lys Leu Gln Glu Pro Leu Leu Glu Ala Leu Arg Leu Tyr Ala Arg
                355                 360                 365 cgc cgg cgg ccc agc cag ccc tac atg ttc cca agg atg cta atg aaa    1634
Arg Arg Arg Pro Ser Gln Pro Tyr Met Phe Pro Arg Met Leu Met Lys
            370                 375                 380 atc acc gac ctc cgg ggc atc agc act aag gga gct gaa agg gcc att    1682
Ile Thr Asp Leu Arg Gly Ile Ser Thr Lys Gly Ala Glu Arg Ala Ile
        385                 390                 395 act ctg aag atg gag att cca ggc ccg atg cct ccc tta atc cga gag    1730
Thr Leu Lys Met Glu Ile Pro Gly Pro Met Pro Pro Leu Ile Arg Glu
    400                 405                 410 atg ctg gag aac cct gaa atg ttt gag gat gac tcc tcg cag cct ggt    1778
Met Leu Glu Asn Pro Glu Met Phe Glu Asp Asp Ser Ser Gln Pro Gly
415                 420                 425                 430 ccc cac ccc aat gcc tct agc gag gat gag gtt cct ggg ggc cag ggc    1826
Pro His Pro Asn Ala Ser Ser Glu Asp Glu Val Pro Gly Gly Gln Gly
                435                 440                 445 aaa ggg ggc ctg aag tcc cca gcc tga ccagggcccc tgacctccc            1873
Lys Gly Gly Leu Lys Ser Pro Ala
            450 gctgtggggg ttgggggcttc aggcagcaga ctgaccatct cccagaccgc cagtgactgg  1933 gggaggacct gccctgccct ctccccaccc cttccaatga gctccttgtt tt           1985

<210> SEQ ID NO 60
<211> LENGTH: 454
<212> TYPE: PRT
<213> ORGANISM: Homo sapiens

<400> SEQUENCE: 60
```

```
Met Ala Thr Asn Lys Glu Arg Leu Phe Ala Ala Gly Ala Leu Gly Pro
1               5                   10                  15

Gly Ser Gly Tyr Pro Gly Ala Gly Phe Pro Phe Ala Phe Pro Gly Ala
                20                  25                  30

Leu Arg Gly Ser Pro Pro Phe Glu Met Leu Ser Pro Ser Phe Arg Gly
            35                  40                  45

Leu Gly Gln Pro Asp Leu Pro Lys Glu Met Ala Ser Leu Ser Val Glu
50                  55                  60

Thr Gln Ser Thr Ser Ser Glu Glu Met Val Pro Ser Ser Pro Ser Pro
65                  70                  75                  80

Pro Pro Pro Pro Arg Val Tyr Lys Pro Cys Phe Val Cys Asn Asp Lys
                85                  90                  95

Ser Ser Gly Tyr His Tyr Gly Val Ser Ser Cys Glu Gly Cys Lys Gly
                100                 105                 110

Phe Phe Arg Arg Ser Ile Gln Lys Asn Met Val Tyr Thr Cys His Arg
            115                 120                 125

Asp Lys Asn Cys Ile Ile Asn Lys Val Thr Arg Asn Arg Cys Gln Tyr
    130                 135                 140

Cys Arg Leu Gln Lys Cys Phe Glu Val Gly Met Ser Lys Glu Ala Val
145                 150                 155                 160

Arg Asn Asp Arg Asn Lys Lys Lys Lys Glu Val Lys Glu Glu Gly Ser
                165                 170                 175

Pro Asp Ser Tyr Glu Leu Ser Pro Gln Leu Glu Glu Leu Ile Thr Lys
            180                 185                 190

Val Ser Lys Ala His Gln Glu Thr Phe Pro Ser Leu Cys Gln Leu Gly
    195                 200                 205

Lys Tyr Thr Thr Asn Ser Ser Ala Asp His Arg Val Gln Leu Asp Leu
210                 215                 220

Gly Leu Trp Asp Lys Phe Ser Glu Leu Ala Thr Lys Cys Ile Ile Lys
225                 230                 235                 240

Ile Val Glu Phe Ala Lys Arg Leu Pro Gly Phe Thr Gly Leu Ser Ile
                245                 250                 255

Ala Asp Gln Ile Thr Leu Leu Lys Ala Ala Cys Leu Asp Ile Leu Met
            260                 265                 270

Leu Arg Ile Cys Thr Arg Tyr Thr Pro Glu Gln Asp Thr Met Thr Phe
        275                 280                 285

Ser Asp Gly Leu Thr Leu Asn Arg Thr Gln Met His Asn Ala Gly Phe
290                 295                 300

Gly Pro Leu Thr Asp Leu Val Phe Ala Phe Ala Gly Gln Leu Leu Pro
305                 310                 315                 320

Leu Glu Met Asp Asp Thr Glu Thr Gly Leu Leu Ser Ala Ile Cys Leu
                325                 330                 335

Ile Cys Gly Asp Arg Met Asp Leu Glu Glu Pro Glu Lys Val Asp Lys
            340                 345                 350

Leu Gln Glu Pro Leu Leu Glu Ala Leu Arg Leu Tyr Ala Arg Arg Arg
        355                 360                 365

Arg Pro Ser Gln Pro Tyr Met Phe Pro Arg Met Leu Met Lys Ile Thr
        370                 375                 380

Asp Leu Arg Gly Ile Ser Thr Lys Gly Ala Glu Arg Ala Ile Thr Leu
385                 390                 395                 400

Lys Met Glu Ile Pro Gly Pro Met Pro Pro Leu Ile Arg Glu Met Leu
                405                 410                 415

Glu Asn Pro Glu Met Phe Glu Asp Asp Ser Ser Gln Pro Gly Pro His
```

```
                420                 425                 430
Pro Asn Ala Ser Ser Glu Asp Glu Val Pro Gly Gly Gln Gly Lys Gly
        435                 440                 445

Gly Leu Lys Ser Pro Ala
    450

<210> SEQ ID NO 61
<211> LENGTH: 18
<212> TYPE: DNA
<213> ORGANISM: Artificial Sequence
<220> FEATURE:
<223> OTHER INFORMATION: forward primer used for specifically detecting
      the variants of the present invention (D-HCHON2007878.1,
      D-NTONG2006230.1, D-SPLEN2005548.1 and ENST00000338561)

<400> SEQUENCE: 61
cctgtttcgc cggacttg                                                       18

<210> SEQ ID NO 62
<211> LENGTH: 22
<212> TYPE: DNA
<213> ORGANISM: Artificial Sequence
<220> FEATURE:
<223> OTHER INFORMATION: reverse primer used for specifically detecting
      the variants of the present invention (D-HCHON2007878.1,
      D-NTONG2006230.1, D-SPLEN2005548.1 and ENST00000338561)

<400> SEQUENCE: 62
ctcctctgag ctggtgctct gt                                                  22

<210> SEQ ID NO 63
<211> LENGTH: 86
<212> TYPE: DNA
<213> ORGANISM: Artificial Sequence
<220> FEATURE:
<223> OTHER INFORMATION: partial polynucleotide specific to the variants
      of the present invention (D-HCHON2007878.1, D-NTONG2006230.1,
      D-SPLEN2005548.1 and ENST00000338561), which is obtained by PCR
      using forward primer (SEQ ID NO:61) and reverse primer (SEQ ID
      NO:62)

<400> SEQUENCE: 63
cctgtttcgc cggacttgaa tcttttgcct ggccgcaacc cgccagcctg caatcggtgg         60
agacacagag caccagctca gaggag                                              86

<210> SEQ ID NO 64
<211> LENGTH: 16
<212> TYPE: DNA
<213> ORGANISM: Artificial Sequence
<220> FEATURE:
<223> OTHER INFORMATION: forward primer used for specifically detecting
      the known variant of the gene of the present invention
      (NM_000966.3)

<400> SEQUENCE: 64
gggtctccgc ctttcg                                                         16

<210> SEQ ID NO 65
<211> LENGTH: 20
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_000966.3)

<400> SEQUENCE: 65
```

```
caccgacaga gaggccatct                                              20
```

<210> SEQ ID NO 66
<211> LENGTH: 87
<212> TYPE: DNA
<213> ORGANISM: Artificial Sequence
<220> FEATURE:
<223> OTHER INFORMATION: partial polynucleotide specific to the known
      variant of the gene of the present invention (NM_000966.3),
      which is obtained by PCR using forward primer (SEQ ID NO:64) and
      reverse primer (SEQ ID NO:65)

<400> SEQUENCE: 66

```
gggtctccgc ctttcgagat gctgagccct agcttccggg gcctgggcca gcctgacctc   60
cccaaggaga tggcctctct gtcggtg                                      87
```

<210> SEQ ID NO 67
<211> LENGTH: 16
<212> TYPE: DNA
<213> ORGANISM: Artificial Sequence
<220> FEATURE:
<223> OTHER INFORMATION: forward primer used for detecting the variants
      of the gene of the present invention (D-HCHON2007878.1,
      D-NTONG2006230.1, D-SPLEN2005548.1, ENST00000338561 and
      NM_000966.3)

<400> SEQUENCE: 67

```
tcgggcccct cacaga                                                  16
```

<210> SEQ ID NO 68
<211> LENGTH: 22
<212> TYPE: DNA
<213> ORGANISM: Artificial Sequence
<220> FEATURE:
<223> OTHER INFORMATION: reverse primer used for detecting the variants
      of the gene of the present invention (D-HCHON2007878.1,
      D-NTONG2006230.1, D-SPLEN2005548.1, ENST00000338561 and
      NM_000966.3)

<400> SEQUENCE: 68

```
ctgtctcggt gtcatccatc tc                                           22
```

<210> SEQ ID NO 69
<211> LENGTH: 75
<212> TYPE: DNA
<213> ORGANISM: Artificial Sequence
<220> FEATURE:
<223> OTHER INFORMATION: partial polynucleotide common to the variants
      of the gene of the present invention (D-HCHON2007878.1,
      D-NTONG2006230.1, D-SPLEN2005548.1, ENST00000338561 and
      NM_000966.3), which is obtained by PCR using forward primer (SEQ
      ID NO:67) and reverse primer (SEQ ID NO:68)

<400> SEQUENCE: 69

```
tcgggcccct cacagacctt gtctttgcct ttgctgggca gctcctgccc ctggagatgg   60
atgacaccga gacag                                                   75
```

<210> SEQ ID NO 70
<211> LENGTH: 342
<212> TYPE: DNA
<213> ORGANISM: Homo sapiens

<400> SEQUENCE: 70

```
ctcttccccg cccacccctt acccgcatgc agcccagcgc cctatgctag ccctcccct    60 cccccctgc tggagcgggg cgccgccggg ggaggagggg gaatcggctg cgggtccttg   120
gtgtttccag cacccagttt cccttcaagc cgggtcgcga tgtacgactg tatggaaacg  180
```

```
tttgccccgg gtccgcgacg gctgtacggg gcggccgggc ccggggccgg cttgctgcgc    240
agagccaccg gcggctcctg tttcgccgga cttgaatctt ttgcctggcc gcaacccgcc    300
agcctgcaat cggtggagac acagagcacc agctcagagg ag                      342

<210> SEQ ID NO 71
<211> LENGTH: 220
<212> TYPE: DNA
<213> ORGANISM: Homo sapiens

<400> SEQUENCE: 71
gtttccagca cccagtttcc cttcaagccg ggtcgcgatg tacgactgta tggaaacgtt     60
tgccccgggt ccgcgacggc tgtacggggc ggcgggccc ggggccggct tgctgcgcag    120
agccaccggc ggctcctgtt tcgccggact tgaatctttt gcctggccgc aacccgccag    180
cctgcaatcg gtggagacac agagcaccag ctcagaggag                         220

<210> SEQ ID NO 72
<211> LENGTH: 463
<212> TYPE: DNA
<213> ORGANISM: Homo sapiens

<400> SEQUENCE: 72
aaaaaaaaag gtctccccag tgctagctgc cgaagcaccc agataagagc tggacggagg     60
ctaaagcggc agcccagct tcgcgccccg cccagtccct ttccctgct ggggatcccc      120 cctcttcccc gcccacccct tacccgcatg cagcccagcg ccctatgcta gccctccccc    180 tccccctg ctggagcggg gcgccgccgg gggaggaggg ggaatcggct gcgggtcctt      240
ggtgtttcca gcacccagtt tcccttcaag ccgggtcgcg atgtacgact gtatggaaac    300
gtttgccccg ggtccgcgac ggctgtacgg ggcggccggg cccggggccg gcttgctgcg    360
cagagccacc ggcggctcct gtttcgccgg acttgaatct tttgcctggc cgcaacccgc    420
cagcctgcaa tcggtggaga cacagagcac cagctcagag gag                     463

<210> SEQ ID NO 73
<211> LENGTH: 2270
<212> TYPE: DNA
<213> ORGANISM: Homo sapiens

<400> SEQUENCE: 73
agttcagtcc tttggctact gtgaaagacc acgcagaagc tgtggacttg cttttttgtgc    60 ttgacaaaag tgcatagata aagacaggga ttcccggct ggggaggaggg aggagagctg    120 aagatccctg cctgggctgg ctgagctaag caaagtggga agctgagtgc ttgaaagagg    180
attatgctcg cactagaaat aagcaaaaag taaagaacaa ggatatggaa aactaagcag    240
tgatgaagac ctcgaaataa ttgttgatca aaagcagctg gtgaatgagc aacaagaaag    300
cagacccctc ctgagtccct ccatcgatga ctttctctgt gaaaccaaat cggaagcaat    360
agcaaggcca gtaacatcca atacagctgt attgaccact ggcttagatc tcctcgacct    420
gagtgaacca gtctctcaaa cccaaaccaa agccaagaag tcagagccct catcaaaaac    480
ctcatccctc aagaaaaagg ccgatggatc tgacctcatc agcacggatg ctgagcagag    540
aggccagcct ctcagagtcc ggagacttc atccttagat ctagacattc aaacacaact    600
ggaaaaatgg gacgatgtta agtttcatgg agatcgaaat accaagggac atccaatggc    660
agagagaaaa tcatcctcat ctagaactgg atcaaaagag ctcttatggt cctcagaaca    720
cagatctcaa ccagaactga gtggtggaaa aagcgccctc aactctgagt cggcttcaga    780
```

```
attggaatta gtggctccga ctcaggctcg actgaccaaa gaacatcgct ggggaagcgc    840
attactttct agaaaccact ccttagaaga agagtttgaa agggcaaaag cagcagtgga    900
gtcagataca gagttttggg ataagatgca agcagaatgg gaagaaatgg ctcggaggaa    960
ctggatatct gagaaccaag aagcccagaa ccaagtaacc atctcggcta gtgagaaggg   1020
atattacttt cacactgaaa accccttcaa ggactggcct ggagcatttg aagaaggctt   1080
aaaaaggctg aaggaagggg atctgccagt caccatcctg ttcatggaag cagcaattct   1140
tcaggaccct ggagatgcag aggcatggca gttcctcggg ataacccagg cggagaatga   1200
aaatgaacaa gcagctattg tcgccctcca gaggtgctta gaattacagc ccaacaactt   1260
aaaagctttg atggccttgg ctgtgagtta tactaacact ggctatcagc aggatgcctg   1320
tgacgctctg aagaattgga ttaagcaaaa tccaaagtac aaataccttg tgaaaagcaa   1380
gaagggatct ccaggcctca cccggcggat gtctaagtcc ccagttgata gctctgttct   1440
ggaaggggtg aaggaattat atctggaagc tgcccaccaa aatggagata tgatcgaccc   1500
agacctgcag acaggtctag gggttctgtt ccacctgagt ggagaattta atagagcaat   1560
agatgcattt aacgctgcct taactgttcg gccagaggac tattcactat ggaaccgcct   1620
cggggcgacc ttggcgaacg gagaccgcag cgaggaagcc gtggaggcct atacgcgagc   1680
actggagatt cagccaggat tcatccggtc cagatacaac ctaggaataa gctgcatcaa   1740
cctgggcgcc tacagagaag cggtcagcaa ttttctcact gccctcagtt tgcaaagaaa   1800
gagcaggaat cagcagcaag ttcctcatcc tgcaatctct gggaatatct gggctgccct   1860
cagaattgcg ctctctctga tggaccaacc agaactcttc caggcggcta atcttggtga   1920
cctggatgtc ctcttaagag ctttcaactt ggatccttga agaaagaata ataccagtac   1980
taataatccc tgatctgtgt gattgtactg aaaaatcaaa aactatttta ttatgaattt   2040
caaaaggata aatcaaatat tcaaaaggcc atggtcatat agcccaagga aattaattcc   2100
tgtggacaat gcccagtctc tgttcagatc caaaagcaca aaatgttgta tatagagtca   2160
aagtcaggct caaagaagaa attaagagac tcaagacaaa ccaagataaa gtaactgtgt   2220
gttgaatact cttccacaa gttgcaagca tattgcaaca catgttcttt              2270
```

<210> SEQ ID NO 74
<211> LENGTH: 2270
<212> TYPE: DNA
<213> ORGANISM: Homo sapiens
<221> NAME/KEY: CDS
<222> LOCATION: (656)..(1960)

<400> SEQUENCE: 74

```
agttcagtcc tttggctact gtgaaagacc acgcagaagc tgtggacttg cttttgtgc     60 ttgacaaaag tgcatagata gaagacaggg attcccggct gggaggaggg aggagagctg   120
aagatccctg cctgggctgg ctgagctaag caaagtggga agctgagtgc ttgaaagagg   180
attatgctcg cactagaaat aagcaaaaag taaagaacaa ggatatggaa aactaagcag   240
tgatgaagac ctcgaaataa ttgttgatca aaagcagctg gtgaatgagc aacaagaaag   300
cagacccctc ctgagtccct ccatcgatga cttttctctgt gaaaccaaat cggaagcaat   360
agcaaggcca gtaacatcca atacagctgt attgaccact ggcttagatc tcctcgacct   420
gagtgaacca gtctctcaaa cccaaaccaa agccaagaag tcagagccct catcaaaaac   480
ctcatccctc aagaaaaagg ccgatggatc tgacctcatc agcacggatg ctgagcagag   540
aggccagcct ctcagagtcc cggagacttc atccttagat ctagacattc aaacacaact   600
```

```
                                           -continued ggaaaaatgg gacgatgtta agtttcatgg agatcgaaat accaagggac atcca atg    658
                                                              Met
                                                                1 gca gag aga aaa tca tcc tca tct aga act gga tca aaa gag ctc tta    706
Ala Glu Arg Lys Ser Ser Ser Ser Arg Thr Gly Ser Lys Glu Leu Leu
            5                   10                  15 tgg tcc tca gaa cac aga tct caa cca gaa ctg agt ggt gga aaa agc    754
Trp Ser Ser Glu His Arg Ser Gln Pro Glu Leu Ser Gly Gly Lys Ser
        20                  25                  30 gcc ctc aac tct gag tcg gct tca gaa ttg gaa tta gtg gct ccg act    802
Ala Leu Asn Ser Glu Ser Ala Ser Glu Leu Glu Leu Val Ala Pro Thr
    35                  40                  45 cag gct cga ctg acc aaa gaa cat cgc tgg gga agc gca tta ctt tct    850
Gln Ala Arg Leu Thr Lys Glu His Arg Trp Gly Ser Ala Leu Leu Ser
50                  55                  60                  65 aga aac cac tcc tta gaa gaa gag ttt gaa agg gca aaa gca gca gtg    898
Arg Asn His Ser Leu Glu Glu Glu Phe Glu Arg Ala Lys Ala Ala Val
                70                  75                  80 gag tca gat aca gag ttt tgg gat aag atg caa gca gaa tgg gaa gaa    946
Glu Ser Asp Thr Glu Phe Trp Asp Lys Met Gln Ala Glu Trp Glu Glu
            85                  90                  95 atg gct cgg agg aac tgg ata tct gag aac caa gaa gcc cag aac caa    994
Met Ala Arg Arg Asn Trp Ile Ser Glu Asn Gln Glu Ala Gln Asn Gln
        100                 105                 110 gta acc atc tcg gct agt gag aag gga tat tac ttt cac act gaa aac    1042
Val Thr Ile Ser Ala Ser Glu Lys Gly Tyr Tyr Phe His Thr Glu Asn
    115                 120                 125 ccc ttc aag gac tgg cct gga gca ttt gaa gaa ggc tta aaa agg ctg    1090
Pro Phe Lys Asp Trp Pro Gly Ala Phe Glu Glu Gly Leu Lys Arg Leu
130                 135                 140                 145 aag gaa ggg gat ctg cca gtc acc atc ctg ttc atg gaa gca gca att    1138
Lys Glu Gly Asp Leu Pro Val Thr Ile Leu Phe Met Glu Ala Ala Ile
                150                 155                 160 ctt cag gac cct gga gat gca gag gca tgg cag ttc ctc ggg ata acc    1186
Leu Gln Asp Pro Gly Asp Ala Glu Ala Trp Gln Phe Leu Gly Ile Thr
            165                 170                 175 cag gcg gag aat gaa aat gaa caa gca gct att gtc gcc ctc cag agg    1234
Gln Ala Glu Asn Glu Asn Glu Gln Ala Ala Ile Val Ala Leu Gln Arg
        180                 185                 190 tgc tta gaa tta cag ccc aac aac tta aaa gct ttg atg gcc ttg gct    1282
Cys Leu Glu Leu Gln Pro Asn Asn Leu Lys Ala Leu Met Ala Leu Ala
    195                 200                 205 gtg agt tat act aac act ggc tat cag cag gat gcc tgt gac gct ctg    1330
Val Ser Tyr Thr Asn Thr Gly Tyr Gln Gln Asp Ala Cys Asp Ala Leu
210                 215                 220                 225 aag aat tgg att aag caa aat cca aag tac aaa tac ctt gtg aaa agc    1378
Lys Asn Trp Ile Lys Gln Asn Pro Lys Tyr Lys Tyr Leu Val Lys Ser
                230                 235                 240 aag aag gga tct cca ggc ctc acc cgg cgg atg tct aag tcc cca gtt    1426
Lys Lys Gly Ser Pro Gly Leu Thr Arg Arg Met Ser Lys Ser Pro Val
            245                 250                 255 gat agc tct gtt ctg gaa ggg gtg aag gaa tta tat ctg gaa gct gcc    1474
Asp Ser Ser Val Leu Glu Gly Val Lys Glu Leu Tyr Leu Glu Ala Ala
        260                 265                 270 cac caa aat gga gat atg atc gac cca gac ctg cag aca ggt cta ggg    1522
His Gln Asn Gly Asp Met Ile Asp Pro Asp Leu Gln Thr Gly Leu Gly
    275                 280                 285 gtt ctg ttc cac ctg agt gga gaa ttt aat aga gca ata gat gca ttt    1570
Val Leu Phe His Leu Ser Gly Glu Phe Asn Arg Ala Ile Asp Ala Phe
290                 295                 300                 305
```

```
aac gct gcc tta act gtt cgg cca gag gac tat tca cta tgg aac cgc    1618
Asn Ala Ala Leu Thr Val Arg Pro Glu Asp Tyr Ser Leu Trp Asn Arg
            310                 315                 320 ctc ggg gcg acc ttg gcg aac gga gac cgc agc gag gaa gcc gtg gag    1666
Leu Gly Ala Thr Leu Ala Asn Gly Asp Arg Ser Glu Glu Ala Val Glu
        325                 330                 335 gcc tat acg cga gca ctg gag att cag cca gga ttc atc cgg tcc aga    1714
Ala Tyr Thr Arg Ala Leu Glu Ile Gln Pro Gly Phe Ile Arg Ser Arg
    340                 345                 350 tac aac cta gga ata agc tgc atc aac ctg ggc gcc tac aga gaa gcg    1762
Tyr Asn Leu Gly Ile Ser Cys Ile Asn Leu Gly Ala Tyr Arg Glu Ala
355                 360                 365 gtc agc aat ttt ctc act gcc ctc agt ttg caa aga aag agc agg aat    1810
Val Ser Asn Phe Leu Thr Ala Leu Ser Leu Gln Arg Lys Ser Arg Asn
370                 375                 380                 385 cag cag caa gtt cct cat cct gca atc tct ggg aat atc tgg gct gcc    1858
Gln Gln Gln Val Pro His Pro Ala Ile Ser Gly Asn Ile Trp Ala Ala
                390                 395                 400 ctc aga att gcg ctc tct ctg atg gac caa cca gaa ctc ttc cag gcg    1906
Leu Arg Ile Ala Leu Ser Leu Met Asp Gln Pro Glu Leu Phe Gln Ala
            405                 410                 415 gct aat ctt ggt gac ctg gat gtc ctc tta aga gct ttc aac ttg gat    1954
Ala Asn Leu Gly Asp Leu Asp Val Leu Leu Arg Ala Phe Asn Leu Asp
        420                 425                 430 cct tga agaaagaata ataccagtac taataatccc tgatctgtgt gattgtactg    2010
Pro aaaaatcaaa aactatttta ttatgaattt caaaaggata aatcaaatat tcaaaaggcc    2070
atggtcatat agcccaagga aattaattcc tgtggacaat gcccagtctc tgttcagatc    2130
caaaagcaca aaatgttgta tatagagtca aagtcaggct caaaagaaga attaagagac    2190
tcaagacaaa ccaagataaa gtaactgtgt gttgaatact ctttccacaa gttgcaagca    2250
tattgcaaca catgttcttt                                                2270

<210> SEQ ID NO 75
<211> LENGTH: 434
<212> TYPE: PRT
<213> ORGANISM: Homo sapiens

<400> SEQUENCE: 75

Met Ala Glu Arg Lys Ser Ser Ser Arg Thr Gly Ser Lys Glu Leu
1               5                   10                  15

Leu Trp Ser Ser Glu His Arg Ser Gln Pro Leu Ser Gly Gly Lys
                20                  25                  30

Ser Ala Leu Asn Ser Glu Ser Ala Ser Glu Leu Glu Leu Val Ala Pro
            35                  40                  45

Thr Gln Ala Arg Leu Thr Lys Glu His Arg Trp Gly Ser Ala Leu Leu
        50                  55                  60

Ser Arg Asn His Ser Leu Glu Glu Glu Phe Glu Arg Ala Lys Ala Ala
65                  70                  75                  80

Val Glu Ser Asp Thr Glu Phe Trp Asp Lys Met Gln Ala Glu Trp Glu
                85                  90                  95

Glu Met Ala Arg Arg Asn Trp Ile Ser Glu Asn Gln Glu Ala Gln Asn
            100                 105                 110

Gln Val Thr Ile Ser Ala Ser Glu Lys Gly Tyr Tyr Phe His Thr Glu
        115                 120                 125

Asn Pro Phe Lys Asp Trp Pro Gly Ala Phe Glu Glu Gly Leu Lys Arg
    130                 135                 140
```

Leu Lys Glu Gly Asp Leu Pro Val Thr Ile Leu Phe Met Glu Ala Ala
145                 150                 155                 160

Ile Leu Gln Asp Pro Gly Asp Ala Glu Ala Trp Gln Phe Leu Gly Ile
            165                 170                 175

Thr Gln Ala Glu Asn Glu Asn Gln Ala Ala Ile Val Ala Leu Gln
        180                 185                 190

Arg Cys Leu Glu Leu Gln Pro Asn Asn Leu Lys Ala Leu Met Ala Leu
        195                 200                 205

Ala Val Ser Tyr Thr Asn Thr Gly Tyr Gln Gln Asp Ala Cys Asp Ala
        210                 215                 220

Leu Lys Asn Trp Ile Lys Gln Asn Pro Lys Tyr Lys Tyr Leu Val Lys
225                 230                 235                 240

Ser Lys Lys Gly Ser Pro Gly Leu Thr Arg Arg Met Ser Lys Ser Pro
            245                 250                 255

Val Asp Ser Ser Val Leu Glu Gly Val Lys Glu Leu Tyr Leu Glu Ala
            260                 265                 270

Ala His Gln Asn Gly Asp Met Ile Asp Pro Asp Leu Gln Thr Gly Leu
        275                 280                 285

Gly Val Leu Phe His Leu Ser Gly Glu Phe Asn Arg Ala Ile Asp Ala
        290                 295                 300

Phe Asn Ala Ala Leu Thr Val Arg Pro Glu Asp Tyr Ser Leu Trp Asn
305                 310                 315                 320

Arg Leu Gly Ala Thr Leu Ala Asn Gly Asp Arg Ser Glu Glu Ala Val
            325                 330                 335

Glu Ala Tyr Thr Arg Ala Leu Glu Ile Gln Pro Gly Phe Ile Arg Ser
            340                 345                 350

Arg Tyr Asn Leu Gly Ile Ser Cys Ile Asn Leu Gly Ala Tyr Arg Glu
            355                 360                 365

Ala Val Ser Asn Phe Leu Thr Ala Leu Ser Leu Gln Arg Lys Ser Arg
        370                 375                 380

Asn Gln Gln Gln Val Pro His Pro Ala Ile Ser Gly Asn Ile Trp Ala
385                 390                 395                 400

Ala Leu Arg Ile Ala Leu Ser Leu Met Asp Gln Pro Glu Leu Phe Gln
            405                 410                 415

Ala Ala Asn Leu Gly Asp Leu Asp Val Leu Leu Arg Ala Phe Asn Leu
        420                 425                 430

Asp Pro

<210> SEQ ID NO 76
<211> LENGTH: 205
<212> TYPE: DNA
<213> ORGANISM: Homo sapiens

<400> SEQUENCE: 76
agttcagtcc tttggctact gtgaaagacc acgcagaagc tgtggacttg cttttgtgc       60 ttgacaaaag tgcatagata gaagacaggg attcccggct gggaggaggg aggagagctg     120
aagatccctg cctgggctgg ctgagctaag caaagtggga agctgagtgc ttgaaagagg     180
attatgctcg cactagaaat aagca                                           205

<210> SEQ ID NO 77
<211> LENGTH: 42
<212> TYPE: DNA
<213> ORGANISM: Homo sapiens

<400> SEQUENCE: 77

```
ataattgttg atcaaaagca gctggtgaat gagcaacaag aa              42
```

<210> SEQ ID NO 78
<211> LENGTH: 655
<212> TYPE: DNA
<213> ORGANISM: Homo sapiens

<400> SEQUENCE: 78

```
agttcagtcc tttggctact gtgaaagacc acgcagaagc tgtggacttg cttttttgtgc   60
ttgacaaaag tgcatagata gaagacaggg attcccggct gggaggaggg aggagagctg  120
aagatccctg cctgggctgg ctgagctaag caaagtggga agctgagtgc ttgaaagagg  180
attatgctcg cactagaaat aagcaaaaag taaagaacaa ggatatggaa aactaagcag  240
tgatgaagac ctcgaaataa ttgttgatca aaagcagctg gtgaatgagc aacaagaaag  300
cagaccctc ctgagtccct ccatcgatga ctttctctgt gaaaccaaat cggaagcaat  360
agcaaggcca gtaacatcca atacagctgt attgaccact ggcttagatc tcctcgacct  420
gagtgaacca gtctctcaaa cccaaaccaa agccaagaag tcagagccct catcaaaaac  480
ctcatccctc aagaaaaagg ccgatggatc tgacctcatc agcacggatg ctgagcagag  540
aggccagcct ctcagagtcc cggagacttc atccttagat ctagacattc aaacacaact  600
ggaaaaatgg gacgatgtta agtttcatgg agatcgaaat accaagggac atcca       655
```

<210> SEQ ID NO 79
<211> LENGTH: 105
<212> TYPE: DNA
<213> ORGANISM: Homo sapiens

<400> SEQUENCE: 79

```
ggaaaaggct ctagggcggc agataaggct gttgccatgg tgatgaagga gataccgagg   60
gaggagtctg ctgaagaaaa gccccctcctt actatgacat cacag                 105
```

<210> SEQ ID NO 80
<211> LENGTH: 35
<212> TYPE: PRT
<213> ORGANISM: Homo sapiens

<400> SEQUENCE: 80

```
Gly Lys Gly Ser Arg Ala Ala Asp Lys Ala Val Ala Met Val Met Lys
1               5                   10                  15
Glu Ile Pro Arg Glu Glu Ser Ala Glu Glu Lys Pro Leu Leu Thr Met
            20                  25                  30
Thr Ser Gln
        35
```

<210> SEQ ID NO 81
<211> LENGTH: 2361
<212> TYPE: DNA
<213> ORGANISM: Homo sapiens

<400> SEQUENCE: 81

```
ctttggctac tgtgaaagac cacgcagaag ctgtggactt gcttttttgtg cttgacaaaa   60
gtgcatagat agaagacagg gattcccggc tgggaggagg gaggagagct gaagatccct  120
gcctgggctg gctgagctaa gcaaagtggg aagctgagtg cttggaagag gattatgctc  180
gcactagaaa taagcaaaaa gtaaagaaca aggatatgga aaactaagca gtgatgaaga  240
cctcgaaata attgttgatc aaaagcaggg aaaaggctct agggcggcag ataaggctgt  300
```

```
tgccatggtg atgaaggaga taccgaggga ggagtctgct gaagaaaagc ccctccttac     360
tatgacatca cagctggtga atgagcaaca agaaagcaga ccccctcctga gtccctccat   420
cgatgacttt ctctgtgaaa ccaaatcgga agcaatagca aggccagtaa catccaatac    480
agctgtattg accactggct tagatctcct cgacctgagt gaaccagtct ctcaaaccca    540
aaccaaagcc aagaagtcag agccctcatc aaaaacctca tccctcaaga aaaaggccga    600
tggatctgac ctcatcagca cggatgctga gcagagaggc cagcctctca gagtcccgga    660
gacttcatcc ttagatctag acattcaaac acaactggaa aaatgggacg atgttaagtt    720
tcatggagat cgaaatacca agggacatcc aatggcagag agaaaatcat cctcatctag    780
aactggatca aaagagctct tatggtcctc agaacacaga tctcaaccag aactgagtgg    840
tggaaaaagc gccctcaact ctgagtcggc ttcagaattg gaattagtgg ctccgactca    900
ggctcgactg accaaagaac atcgctgggg aagcgcatta ctttctagaa accactcctt    960
agaagaaagag tttgaaaggg caaaagcagc agtggagtca gatacagagt tttgggataa  1020
gatgcaagca gaatgggaag aaatggctcg gaggaactgg atatctgaga accaagaagc   1080
ccagaaccaa gtaaccatct cggctagtga aagggatat tactttcaca ctgaaaaccc    1140
cttcaaggac tggcctggag catttgaaga aggcttaaaa aggctgaagg aaggggatct   1200
gccagtcacc atcctgttca tggaagcagc aattcttcag gaccctggag atgcagaggc   1260
atggcagttc ctcgggataa cccaggcgga gaatgaaaat gaacaagcag ctattgtcgc   1320
cctccagagg tgcttagaat tacagcccaa caacttaaaa gctttgatgg ccttggctgt   1380
gagttatact aacactggcc atcagcagga tgcctgtgac gctctgaaga attggattaa   1440
gcaaaatcca aagtacaaat accttgtgaa aagcaagaag ggatctccag gcctcacccg   1500
gcggatgtct aagtccccag ttgatagctc tgttctggaa ggggtgaagg aattatatct   1560
ggaagctgcc caccaaaatg gagatatgat cgacccagac ctgcagacag gtctaggggt   1620
tctgttccac ctgagtggag aatttaatag agcaatagat gcatttaacg ctgccttaac   1680
tgttcggcca gaggactatt cactatggaa ccgcctcggg gcgaccttgg cgaacggaga   1740
ccgcagcgag gaagccgtgg aggcctatac gcgagcactg gagattcagc caggattcat   1800
ccggtccaga tacaacctag gaataagctg catcaacctg ggcgcctaca gagaagcggt   1860
cagcaatttt ctcactgccc tcagtttgca aagaaagagc aggaatcagc agcaagttcc   1920
tcatcccgca atctctggga atatctgggc tgccctcaga attgcgctct ctctgatgga   1980
ccaaccagaa ctcttccagg cggctaatct tggtgacctg gatgtcctct taagagcttt   2040
caacttggat ccttgaagaa agaataatac cagtactaat aatccctgat ctgtgtgatt   2100
gtactgaaaa atcaaaaact attttattat gaatttcaaa aggataaatc aaatattcaa   2160
aaggccatgg tcatatagcc caaggaaatt aattcctgtg acaatgccc agtctctgtt    2220
cagatccaaa agcacaaaat gttgtatata gagtcaaagt caggctcaaa agaagaatta   2280
agagactcaa gacaaaccaa gataaagtaa ctgtgtgttg aatactcttt ccacaagttg   2340
caagcatatt gcaacacatg t                                             2361
```

<210> SEQ ID NO 82
<211> LENGTH: 2361
<212> TYPE: DNA
<213> ORGANISM: Homo sapiens
<221> NAME/KEY: CDS
<222> LOCATION: (305)..(2056)

<400> SEQUENCE: 82

```
ctttggctac tgtgaaagac cacgcagaag ctgtggactt gcttttttgtg cttgacaaaa    60 gtgcatagat agaagacagg gattcccggc tgggaggagg gaggagagct gaagatccct    120
gcctgggctg gctgagctaa gcaaagtggg aagctgagtg cttggaagag gattatgctc    180
gcactagaaa taagcaaaaa gtaaagaaca aggatatgga aaactaagca gtgatgaaga    240
cctcgaaata attgttgatc aaaagcaggg aaaaggctct agggcggcag ataaggctgt    300
```

|     |     |     |     |     |     |     |     |     |     |     |     |     |     |     |     |     |     |
| --- | --- | --- | --- | --- | --- | --- | --- | --- | --- | --- | --- | --- | --- | --- | --- | --- | --- |
| tgcc | atg | gtg | atg | aag | gag | ata | ccg | agg | gag | gag | tct | gct | gaa | gaa | aag | | 349 |
| | Met | Val | Met | Lys | Glu | Ile | Pro | Arg | Glu | Glu | Ser | Ala | Glu | Glu | Lys | | |
| | 1 | | | | 5 | | | | | 10 | | | | | 15 | | |

| ccc | ctc | ctt | act | atg | aca | tca | cag | ctg | gtg | aat | gag | caa | caa | gaa | agc | 397 |
| --- | --- | --- | --- | --- | --- | --- | --- | --- | --- | --- | --- | --- | --- | --- | --- | --- |
| Pro | Leu | Leu | Thr | Met | Thr | Ser | Gln | Leu | Val | Asn | Glu | Gln | Gln | Glu | Ser | |
| | | | | 20 | | | | | 25 | | | | | 30 | | |

| aga | ccc | ctc | ctg | agt | ccc | tcc | atc | gat | gac | ttt | ctc | tgt | gaa | acc | aaa | 445 |
| --- | --- | --- | --- | --- | --- | --- | --- | --- | --- | --- | --- | --- | --- | --- | --- | --- |
| Arg | Pro | Leu | Leu | Ser | Pro | Ser | Ile | Asp | Asp | Phe | Leu | Cys | Glu | Thr | Lys | |
| | | | 35 | | | | | 40 | | | | | 45 | | | |

| tcg | gaa | gca | ata | gca | agg | cca | gta | aca | tcc | aat | aca | gct | gta | ttg | acc | 493 |
| --- | --- | --- | --- | --- | --- | --- | --- | --- | --- | --- | --- | --- | --- | --- | --- | --- |
| Ser | Glu | Ala | Ile | Ala | Arg | Pro | Val | Thr | Ser | Asn | Thr | Ala | Val | Leu | Thr | |
| | | 50 | | | | | 55 | | | | | 60 | | | | |

| act | ggc | tta | gat | ctc | ctc | gac | ctg | agt | gaa | cca | gtc | tct | caa | acc | caa | 541 |
| --- | --- | --- | --- | --- | --- | --- | --- | --- | --- | --- | --- | --- | --- | --- | --- | --- |
| Thr | Gly | Leu | Asp | Leu | Leu | Asp | Leu | Ser | Glu | Pro | Val | Ser | Gln | Thr | Gln | |
| | 65 | | | | | 70 | | | | | 75 | | | | | |

| acc | aaa | gcc | aag | aag | tca | gag | ccc | tca | tca | aaa | acc | tca | tcc | ctc | aag | 589 |
| --- | --- | --- | --- | --- | --- | --- | --- | --- | --- | --- | --- | --- | --- | --- | --- | --- |
| Thr | Lys | Ala | Lys | Lys | Ser | Glu | Pro | Ser | Ser | Lys | Thr | Ser | Ser | Leu | Lys | |
| 80 | | | | | 85 | | | | | 90 | | | | | 95 | |

| aaa | aag | gcc | gat | gga | tct | gac | ctc | atc | agc | acg | gat | gct | gag | cag | aga | 637 |
| --- | --- | --- | --- | --- | --- | --- | --- | --- | --- | --- | --- | --- | --- | --- | --- | --- |
| Lys | Lys | Ala | Asp | Gly | Ser | Asp | Leu | Ile | Ser | Thr | Asp | Ala | Glu | Gln | Arg | |
| | | | | 100 | | | | | 105 | | | | | 110 | | |

| ggc | cag | cct | ctc | aga | gtc | ccg | gag | act | tca | tcc | tta | gat | cta | gac | att | 685 |
| --- | --- | --- | --- | --- | --- | --- | --- | --- | --- | --- | --- | --- | --- | --- | --- | --- |
| Gly | Gln | Pro | Leu | Arg | Val | Pro | Glu | Thr | Ser | Ser | Leu | Asp | Leu | Asp | Ile | |
| | | | 115 | | | | | 120 | | | | | 125 | | | |

| caa | aca | caa | ctg | gaa | aaa | tgg | gac | gat | gtt | aag | ttt | cat | gga | gat | cga | 733 |
| --- | --- | --- | --- | --- | --- | --- | --- | --- | --- | --- | --- | --- | --- | --- | --- | --- |
| Gln | Thr | Gln | Leu | Glu | Lys | Trp | Asp | Asp | Val | Lys | Phe | His | Gly | Asp | Arg | |
| | | 130 | | | | | 135 | | | | | 140 | | | | |

| aat | acc | aag | gga | cat | cca | atg | gca | gag | aga | aaa | tca | tcc | tca | tct | aga | 781 |
| --- | --- | --- | --- | --- | --- | --- | --- | --- | --- | --- | --- | --- | --- | --- | --- | --- |
| Asn | Thr | Lys | Gly | His | Pro | Met | Ala | Glu | Arg | Lys | Ser | Ser | Ser | Ser | Arg | |
| | 145 | | | | | 150 | | | | | 155 | | | | | |

| act | gga | tca | aaa | gag | ctc | tta | tgg | tcc | tca | gaa | cac | aga | tct | caa | cca | 829 |
| --- | --- | --- | --- | --- | --- | --- | --- | --- | --- | --- | --- | --- | --- | --- | --- | --- |
| Thr | Gly | Ser | Lys | Glu | Leu | Leu | Trp | Ser | Ser | Glu | His | Arg | Ser | Gln | Pro | |
| 160 | | | | | 165 | | | | | 170 | | | | | 175 | |

| gaa | ctg | agt | ggt | gga | aaa | agc | gcc | ctc | aac | tct | gag | tcg | gct | tca | gaa | 877 |
| --- | --- | --- | --- | --- | --- | --- | --- | --- | --- | --- | --- | --- | --- | --- | --- | --- |
| Glu | Leu | Ser | Gly | Gly | Lys | Ser | Ala | Leu | Asn | Ser | Glu | Ser | Ala | Ser | Glu | |
| | | | | 180 | | | | | 185 | | | | | 190 | | |

| ttg | gaa | tta | gtg | gct | ccg | act | cag | gct | cga | ctg | acc | aaa | gaa | cat | cgc | 925 |
| --- | --- | --- | --- | --- | --- | --- | --- | --- | --- | --- | --- | --- | --- | --- | --- | --- |
| Leu | Glu | Leu | Val | Ala | Pro | Thr | Gln | Ala | Arg | Leu | Thr | Lys | Glu | His | Arg | |
| | | | 195 | | | | | 200 | | | | | 205 | | | |

| tgg | gga | agc | gca | tta | ctt | tct | aga | aac | cac | tcc | tta | gaa | gaa | gag | ttt | 973 |
| --- | --- | --- | --- | --- | --- | --- | --- | --- | --- | --- | --- | --- | --- | --- | --- | --- |
| Trp | Gly | Ser | Ala | Leu | Leu | Ser | Arg | Asn | His | Ser | Leu | Glu | Glu | Glu | Phe | |
| | | 210 | | | | | 215 | | | | | 220 | | | | |

| gaa | agg | gca | aaa | gca | gca | gtg | gag | tca | gat | aca | gag | ttt | tgg | gat | aag | 1021 |
| --- | --- | --- | --- | --- | --- | --- | --- | --- | --- | --- | --- | --- | --- | --- | --- | --- |
| Glu | Arg | Ala | Lys | Ala | Ala | Val | Glu | Ser | Asp | Thr | Glu | Phe | Trp | Asp | Lys | |
| | 225 | | | | | 230 | | | | | 235 | | | | | |

| atg | caa | gca | gaa | tgg | gaa | gaa | atg | gct | cgg | agg | aac | tgg | ata | tct | gag | 1069 |
| --- | --- | --- | --- | --- | --- | --- | --- | --- | --- | --- | --- | --- | --- | --- | --- | --- |
| Met | Gln | Ala | Glu | Trp | Glu | Glu | Met | Ala | Arg | Arg | Asn | Trp | Ile | Ser | Glu | |
| 240 | | | | | 245 | | | | | 250 | | | | | 255 | |

| aac | caa | gaa | gcc | cag | aac | caa | gta | acc | atc | tcg | gct | agt | gag | aag | gga | 1117 |
| --- | --- | --- | --- | --- | --- | --- | --- | --- | --- | --- | --- | --- | --- | --- | --- | --- |
| Asn | Gln | Glu | Ala | Gln | Asn | Gln | Val | Thr | Ile | Ser | Ala | Ser | Glu | Lys | Gly | |
| | | | | 260 | | | | | 265 | | | | | 270 | | |

| tat | tac | ttt | cac | act | gaa | aac | ccc | ttc | aag | gac | tgg | cct | gga | gca | ttt | 1165 |
| --- | --- | --- | --- | --- | --- | --- | --- | --- | --- | --- | --- | --- | --- | --- | --- | --- |
| Tyr | Tyr | Phe | His | Thr | Glu | Asn | Pro | Phe | Lys | Asp | Trp | Pro | Gly | Ala | Phe | |

```
                            275                 280                 285
gaa gaa ggc tta aaa agg ctg aag gaa ggg gat ctg cca gtc acc atc    1213
Glu Glu Gly Leu Lys Arg Leu Lys Glu Gly Asp Leu Pro Val Thr Ile
            290                 295                 300 ctg ttc atg gaa gca gca att ctt cag gac cct gga gat gca gag gca    1261
Leu Phe Met Glu Ala Ala Ile Leu Gln Asp Pro Gly Asp Ala Glu Ala
305                 310                 315 tgg cag ttc ctc ggg ata acc cag gcg gag aat gaa aat gaa caa gca    1309
Trp Gln Phe Leu Gly Ile Thr Gln Ala Glu Asn Glu Asn Glu Gln Ala
320                 325                 330                 335 gct att gtc gcc ctc cag agg tgc tta gaa tta cag ccc aac aac tta    1357
Ala Ile Val Ala Leu Gln Arg Cys Leu Glu Leu Gln Pro Asn Asn Leu
            340                 345                 350 aaa gct ttg atg gcc ttg gct gtg agt tat act aac act ggc cat cag    1405
Lys Ala Leu Met Ala Leu Ala Val Ser Tyr Thr Asn Thr Gly His Gln
            355                 360                 365 cag gat gcc tgt gac gct ctg aag aat tgg att aag caa aat cca aag    1453
Gln Asp Ala Cys Asp Ala Leu Lys Asn Trp Ile Lys Gln Asn Pro Lys
            370                 375                 380 tac aaa tac ctt gtg aaa agc aag aag gga tct cca ggc ctc acc cgg    1501
Tyr Lys Tyr Leu Val Lys Ser Lys Lys Gly Ser Pro Gly Leu Thr Arg
385                 390                 395 cgg atg tct aag tcc cca gtt gat agc tct gtt ctg gaa ggg gtg aag    1549
Arg Met Ser Lys Ser Pro Val Asp Ser Ser Val Leu Glu Gly Val Lys
400                 405                 410                 415 gaa tta tat ctg gaa gct gcc cac caa aat gga gat atg atc gac cca    1597
Glu Leu Tyr Leu Glu Ala Ala His Gln Asn Gly Asp Met Ile Asp Pro
            420                 425                 430 gac ctg cag aca ggt cta ggg gtt ctg ttc cac ctg agt gga gaa ttt    1645
Asp Leu Gln Thr Gly Leu Gly Val Leu Phe His Leu Ser Gly Glu Phe
            435                 440                 445 aat aga gca ata gat gca ttt aac gct gcc tta act gtt cgg cca gag    1693
Asn Arg Ala Ile Asp Ala Phe Asn Ala Ala Leu Thr Val Arg Pro Glu
            450                 455                 460 gac tat tca cta tgg aac cgc ctc ggg gcg acc ttg gcg aac gga gac    1741
Asp Tyr Ser Leu Trp Asn Arg Leu Gly Ala Thr Leu Ala Asn Gly Asp
465                 470                 475 cgc agc gag gaa gcc gtg gag gcc tat acg cga gca ctg gag att cag    1789
Arg Ser Glu Glu Ala Val Glu Ala Tyr Thr Arg Ala Leu Glu Ile Gln
480                 485                 490                 495 cca gga ttc atc cgg tcc aga tac aac cta gga ata agc tgc atc aac    1837
Pro Gly Phe Ile Arg Ser Arg Tyr Asn Leu Gly Ile Ser Cys Ile Asn
            500                 505                 510 ctg ggc gcc tac aga gaa gcg gtc agc aat ttt ctc act gcc ctc agt    1885
Leu Gly Ala Tyr Arg Glu Ala Val Ser Asn Phe Leu Thr Ala Leu Ser
            515                 520                 525 ttg caa aga aag agc agg aat cag cag caa gtt cct cat ccc gca atc    1933
Leu Gln Arg Lys Ser Arg Asn Gln Gln Gln Val Pro His Pro Ala Ile
            530                 535                 540 tct ggg aat atc tgg gct gcc ctc aga att gcg ctc tct ctg atg gac    1981
Ser Gly Asn Ile Trp Ala Ala Leu Arg Ile Ala Leu Ser Leu Met Asp
545                 550                 555 caa cca gaa ctc ttc cag gcg gct aat ctt ggt gac ctg gat gtc ctc    2029
Gln Pro Glu Leu Phe Gln Ala Ala Asn Leu Gly Asp Leu Asp Val Leu
560                 565                 570                 575 tta aga gct ttc aac ttg gat cct tga agaaagaata ataccagtac          2076
Leu Arg Ala Phe Asn Leu Asp Pro
                580 taataatccc tgatctgtgt gattgtactg aaaaatcaaa aactatttta ttatgaattt  2136
```

```
caaaaggata aatcaaatat tcaaaaggcc atggtcatat agcccaagga aattaattcc    2196
tgtggacaat gcccagtctc tgttcagatc caaaagcaca aatgttgta tatagagtca    2256 aagtcaggct caaaagaaga attaagagac tcaagacaaa ccaagataaa gtaactgtgt    2316
gttgaatact ctttccacaa gttgcaagca tattgcaaca catgt                    2361
```

<210> SEQ ID NO 83
<211> LENGTH: 583
<212> TYPE: PRT
<213> ORGANISM: Homo sapiens

<400> SEQUENCE: 83

```
Met Val Met Lys Glu Ile Pro Arg Glu Glu Ser Ala Glu Glu Lys Pro
1               5                   10                  15

Leu Leu Thr Met Thr Ser Gln Leu Val Asn Glu Gln Gln Glu Ser Arg
            20                  25                  30

Pro Leu Leu Ser Pro Ser Ile Asp Asp Phe Leu Cys Glu Thr Lys Ser
        35                  40                  45

Glu Ala Ile Ala Arg Pro Val Thr Ser Asn Thr Ala Val Leu Thr Thr
    50                  55                  60

Gly Leu Asp Leu Leu Asp Leu Ser Glu Pro Val Ser Gln Thr Gln Thr
65                  70                  75                  80

Lys Ala Lys Lys Ser Glu Pro Ser Ser Lys Thr Ser Ser Leu Lys Lys
                85                  90                  95

Lys Ala Asp Gly Ser Asp Leu Ile Ser Thr Asp Ala Glu Gln Arg Gly
            100                 105                 110

Gln Pro Leu Arg Val Pro Glu Thr Ser Ser Leu Asp Leu Asp Ile Gln
        115                 120                 125

Thr Gln Leu Glu Lys Trp Asp Asp Val Lys Phe His Gly Asp Arg Asn
    130                 135                 140

Thr Lys Gly His Pro Met Ala Glu Arg Lys Ser Ser Ser Ser Arg Thr
145                 150                 155                 160

Gly Ser Lys Glu Leu Leu Trp Ser Ser Glu His Arg Ser Gln Pro Glu
                165                 170                 175

Leu Ser Gly Gly Lys Ser Ala Leu Asn Ser Glu Ser Ala Ser Glu Leu
            180                 185                 190

Glu Leu Val Ala Pro Thr Gln Ala Arg Leu Thr Lys Glu His Arg Trp
        195                 200                 205

Gly Ser Ala Leu Leu Ser Arg Asn His Ser Leu Glu Glu Glu Phe Glu
    210                 215                 220

Arg Ala Lys Ala Ala Val Glu Ser Asp Thr Glu Phe Trp Asp Lys Met
225                 230                 235                 240

Gln Ala Glu Trp Glu Glu Met Ala Arg Arg Asn Trp Ile Ser Glu Asn
                245                 250                 255

Gln Glu Ala Gln Asn Gln Val Thr Ile Ser Ala Ser Glu Lys Gly Tyr
            260                 265                 270

Tyr Phe His Thr Glu Asn Pro Phe Lys Asp Trp Pro Gly Ala Phe Glu
        275                 280                 285

Glu Gly Leu Lys Arg Leu Lys Glu Gly Asp Leu Pro Val Thr Ile Leu
    290                 295                 300

Phe Met Glu Ala Ala Ile Leu Gln Asp Pro Gly Asp Ala Glu Ala Trp
305                 310                 315                 320

Gln Phe Leu Gly Ile Thr Gln Ala Glu Asn Glu Asn Glu Gln Ala Ala
                325                 330                 335

Ile Val Ala Leu Gln Arg Cys Leu Glu Leu Gln Pro Asn Asn Leu Lys
```

```
                   340                 345                 350
Ala Leu Met Ala Leu Ala Val Ser Tyr Thr Asn Thr Gly His Gln Gln
            355                 360                 365

Asp Ala Cys Asp Ala Leu Lys Asn Trp Ile Lys Gln Asn Pro Lys Tyr
        370                 375                 380

Lys Tyr Leu Val Lys Ser Lys Lys Gly Ser Pro Gly Leu Thr Arg Arg
385                 390                 395                 400

Met Ser Lys Ser Pro Val Asp Ser Val Leu Glu Gly Val Lys Glu
                405                 410                 415

Leu Tyr Leu Glu Ala Ala His Gln Asn Gly Asp Met Ile Asp Pro Asp
            420                 425                 430

Leu Gln Thr Gly Leu Gly Val Leu Phe His Leu Ser Gly Glu Phe Asn
        435                 440                 445

Arg Ala Ile Asp Ala Phe Asn Ala Ala Leu Thr Val Arg Pro Glu Asp
        450                 455                 460

Tyr Ser Leu Trp Asn Arg Leu Gly Ala Thr Leu Ala Asn Gly Asp Arg
465                 470                 475                 480

Ser Glu Glu Ala Val Glu Ala Tyr Thr Arg Ala Leu Glu Ile Gln Pro
                485                 490                 495

Gly Phe Ile Arg Ser Arg Tyr Asn Leu Gly Ile Ser Cys Ile Asn Leu
            500                 505                 510

Gly Ala Tyr Arg Glu Ala Val Ser Asn Phe Leu Thr Ala Leu Ser Leu
        515                 520                 525

Gln Arg Lys Ser Arg Asn Gln Gln Val Pro His Pro Ala Ile Ser
        530                 535                 540

Gly Asn Ile Trp Ala Ala Leu Arg Ile Ala Leu Ser Leu Met Asp Gln
545                 550                 555                 560

Pro Glu Leu Phe Gln Ala Ala Asn Leu Gly Asp Leu Asp Val Leu Leu
                565                 570                 575

Arg Ala Phe Asn Leu Asp Pro
            580

<210> SEQ ID NO 84
<211> LENGTH: 196
<212> TYPE: DNA
<213> ORGANISM: Homo sapiens

<400> SEQUENCE: 84
ctttggctac tgtgaaagac cacgcagaag ctgtggactt gcttttgtg cttgacaaaa      60 gtgcatagat agaagacagg gattcccggc tgggaggagg gaggagagct gaagatccct   120
gcctgggctg gctgagctaa gcaaagtggg aagctgagtg cttggaagag gattatgctc   180
gcactagaaa taagca                                                    196

<210> SEQ ID NO 85
<211> LENGTH: 304
<212> TYPE: DNA
<213> ORGANISM: Homo sapiens

<400> SEQUENCE: 85
ctttggctac tgtgaaagac cacgcagaag ctgtggactt gcttttgtg cttgacaaaa      60 gtgcatagat agaagacagg gattcccggc tgggaggagg gaggagagct gaagatccct   120
gcctgggctg gctgagctaa gcaaagtggg aagctgagtg cttggaagag gattatgctc   180
gcactagaaa taagcaaaaa gtaagaaca aggatatgga aaactaagca gtgatgaaga   240
cctcgaaata attgttgatc aaaagcaggg aaaaggctct agggcggcag ataaggctgt   300
``` tgcc                                                                    304

<210> SEQ ID NO 86
<211> LENGTH: 19
<212> TYPE: DNA
<213> ORGANISM: Artificial Sequence
<220> FEATURE:
<223> OTHER INFORMATION: forward primer used for detecting the variants
      of the present invention (D-BRCOC2007920.1 and D-TKIDN2010471.1)

<400> SEQUENCE: 86
cctgggctgg ctgagctaa                                                     19

<210> SEQ ID NO 87
<211> LENGTH: 28
<212> TYPE: DNA
<213> ORGANISM: Artificial Sequence
<220> FEATURE:
<223> OTHER INFORMATION: reverse primer used for detecting the variants
      of the present invention (D-BRCOC2007920.1 and D-TKIDN2010471.1)

<400> SEQUENCE: 87 acttttttgct tatttctagt gcgagcat                                          28

<210> SEQ ID NO 88
<211> LENGTH: 81
<212> TYPE: DNA
<213> ORGANISM: Artificial Sequence
<220> FEATURE:
<223> OTHER INFORMATION: partial polynucleotide specific to the variant
      of the present invention (D-BRCOC2007920.1), which is obtained by
      PCR using forward primer (SEQ ID NO:86) and reverse primer
      (SEQ ID NO:87)

<400> SEQUENCE: 88
cctgggctgg ctgagctaag caaagtggga agctgagtgc ttgaaagagg attatgctcg        60
cactagaaat aagcaaaaag t                                                  81

<210> SEQ ID NO 89
<211> LENGTH: 81
<212> TYPE: DNA
<213> ORGANISM: Artificial Sequence
<220> FEATURE:
<223> OTHER INFORMATION: partial polynucleotide specific to the variant
      of the present invention (D-TKIDN2010471.1), which is obtained by
      PCR using forward primer (SEQ ID NO:86) and reverse primer
      (SEQ ID NO:87)

<400> SEQUENCE: 89
cctgggctgg ctgagctaag caaagtggga agctgagtgc ttggaagagg attatgctcg        60
cactagaaat aagcaaaaag t                                                  81

<210> SEQ ID NO 90
<211> LENGTH: 30
<212> TYPE: DNA
<213> ORGANISM: Artificial Sequence
<220> FEATURE:
<223> OTHER INFORMATION: probe used for detecting the variants of the
      present invention (D-BRCOC2007920.1 and D-TKIDN2010471.1)

<400> SEQUENCE: 90
caaagtggga agctgagtgc ttgaaagagg                                         30

<210> SEQ ID NO 91
<211> LENGTH: 21
<212> TYPE: DNA

```
<213> ORGANISM: Artificial Sequence
<220> FEATURE:
<223> OTHER INFORMATION: forward primer used for specifically detecting
      the known variant of the gene of the present invention
      (NM_016559.1)

<400> SEQUENCE: 91
cctgaagaaa ccgaagcaga a                                             21

<210> SEQ ID NO 92
<211> LENGTH: 25
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_016559.1)

<400> SEQUENCE: 92
catcactgct tagttttcca tatcc                                         25

<210> SEQ ID NO 93
<211> LENGTH: 81
<212> TYPE: DNA
<213> ORGANISM: Artificial Sequence
<220> FEATURE:
<223> OTHER INFORMATION: partial polynucleotide specific to the known
      variant of the gene of the present invention (NM_016559.1),
      which is obtained by PCR using forward primer (SEQ ID NO:91) and
      reverse primer (SEQ ID NO:92)

<400> SEQUENCE: 93
cctgaagaaa ccgaagcaga atgtaccagg gacacatgca gaaaagtaaa gaacaaggat   60
atggaaaact aagcagtgat g                                             81

<210> SEQ ID NO 94
<211> LENGTH: 30
<212> TYPE: DNA
<213> ORGANISM: Artificial Sequence
<220> FEATURE:
<223> OTHER INFORMATION: probe used for specifically detecting the known
      variant of the gene of the present invention (NM_016559.1)

<400> SEQUENCE: 94
ccagggacac atgcagaaaa gtaaagaaca                                    30

<210> SEQ ID NO 95
<211> LENGTH: 24
<212> TYPE: DNA
<213> ORGANISM: Artificial Sequence
<220> FEATURE:
<223> OTHER INFORMATION: forward primer used for detecting the variants
      of the gene of the present invention (D-BRCOC2007920.1,
      D-TKIDN2010471.1 and NM_016559.1)

<400> SEQUENCE: 95
tcctcagaac acagatctca acca                                          24

<210> SEQ ID NO 96
<211> LENGTH: 19
<212> TYPE: DNA
<213> ORGANISM: Artificial Sequence
<220> FEATURE:
<223> OTHER INFORMATION: reverse primer used for detecting the variants
      of the gene of the present invention (D-BRCOC2007920.1,
      D-TKIDN2010471.1 and NM_016559.1)

<400> SEQUENCE: 96
```

```
tccccagcga tgttctttg                                                     19
```

<210> SEQ ID NO 97
<211> LENGTH: 126
<212> TYPE: DNA
<213> ORGANISM: Artificial Sequence
<220> FEATURE:
<223> OTHER INFORMATION: partial polynucleotide common to the variants
      of the gene of the present invention (D-BRCOC2007920.1,
      D-TKIDN2010471.1 and NM_016559.1), which is obtained by PCR using
      forward primer SEQ ID NO:95) and reverse primer (SEQ ID NO:96)

<400> SEQUENCE: 97

```
tcctcagaac acagatctca accagaactg agtggtggaa aaagcgccct caactctgag         60
tcggcttcag aattggaatt agtggctccg actcaggctc gactgaccaa agaacatcgc        120
tgggga                                                                  126
```

<210> SEQ ID NO 98
<211> LENGTH: 27
<212> TYPE: DNA
<213> ORGANISM: Artificial Sequence
<220> FEATURE:
<223> OTHER INFORMATION: probe used for detecting the variants of the
      gene of the present invention (D-BRCOC2007920.1, D-TKIDN
      2010471.1 and NM_016559.1)

<400> SEQUENCE: 98

```
aattagtggc tccgactcag gctcgac                                            27
```

<210> SEQ ID NO 99
<211> LENGTH: 211
<212> TYPE: DNA
<213> ORGANISM: Homo sapiens

<400> SEQUENCE: 99

```
agttcagtcc tttggctact gtgaaagacc acgcagaagc tgtggacttg cttttgtgc         60 ttgacaaaag tgcatagata aagacaggg attcccggct gggaggaggg aggagagctg        120
aagatccctg cctgggctgg ctgagctaag caaagtggga agctgagtgc ttgaaagagg       180
attatgctcg cactagaaat aagcaaaaag t                                      211
```

<210> SEQ ID NO 100
<211> LENGTH: 202
<212> TYPE: DNA
<213> ORGANISM: Homo sapiens

<400> SEQUENCE: 100

```
ctttggctac tgtgaaagac cacgcagaag ctgtggactt gcttttgtg cttgacaaaa         60 gtgcatagat agaagacagg gattcccggc tgggaggagg gaggagagct gaagatccct       120
gcctgggctg gctgagctaa gcaaagtggg aagctgagtg cttggaagag gattatgctc       180
gcactagaaa taagcaaaaa gt                                                202
```

<210> SEQ ID NO 101
<211> LENGTH: 1213
<212> TYPE: DNA
<213> ORGANISM: Homo sapiens

<400> SEQUENCE: 101

```
gtttatatag aatgcgccgc ggtgttgatt cgtggctctc taggaccgga gagttctttg        60
gaaggagagc gcgagcgagg gagcgggcga gctccgaggg ggtgtgggtg tagggagaga       120
gagaaagaga gcaggcagcg gcggcggcgg cagcggtggg gaaaagcgga ttccgccccg       180
```

```
aaccacaccg aggggagctc gtggtcgaga cttgccgccc taagcactct cccaagtccg    240
acccgctcgg cgaggacttc cgtcttctga gcgaaccttg tcaagcaagc tgggatctat    300
gagtggaaag gtgaccaagc ccaaagagga gaaagatgct tctaaggttc tggatgacgc    360 ccccctggc acacaggaat acattatgtt acgacaagat tccatccaat ctgcggaatt     420
aaagaaaaaa gagtcccct ttcgtgctaa gtgtcacgaa atcttctgct gcccgctgaa     480
gcaagtacac cacaaagaga acacagagcc ggaagagcct cagcttaagg gtatagttac    540
caagctatac agccgacaag ctaccactt gcagctgcag gcggatggaa ccattgatgg      600
caccaaagat gaggacagca cttacactct gtttaaccct atccctgtgg gtctgcgagt    660
ggtggctatc caaggagttc aaaccaagct gtacttggca atgaacagtg agggatactt    720
gtacacctcg gaactttca cacctgagtg caaattcaaa gaatcagtgt ttgaaaatta     780
ttatgtgaca tattcatcaa tgatataccg tcagcagcag tcaggccgag ggtggtatct    840
gggtctgaac aaagaaggag agatcatgaa aggcaaccat gtgaagaaga caagcctgc    900 agctcatttt ctgcctaaac cactgaaagt ggccatgtac aaggagccat cactgcacga    960
tctcacggag ttctcccgat ctggaagcgg acccccaacc aagagcagaa gtgtctctgg   1020
cgtgctgaac ggaggcaaat ccatgagcca caatgaatca acgtagccag tgagggcaaa   1080
agaagggctc tgtaacagaa ccttacctcc aggtgctgtt gaattcttct agcagtcctt   1140
cacccaaaag ttcaaatttg tcagtgacat ttaccaaaca aacaggcaga gttcactatt   1200
ctatctgcca tta                                                       1213

<210> SEQ ID NO 102
<211> LENGTH: 1213
<212> TYPE: DNA
<213> ORGANISM: Homo sapiens
<221> NAME/KEY: CDS
<222> LOCATION: (299)..(1066)

<400> SEQUENCE: 102
gtttatatag aatgcgccgc ggtgttgatt cgtggctctc taggaccgga gagttctttg     60
gaaggagagc gcgagcgagg gagcgggcga gctccgaggg ggtgtgggtg tagggagaga   120
gagaaagaga gcaggcagcg gcggcggcgg cagcggtggg gaaaagcgga ttccgccccg   180
aaccacaccg aggggagctc gtggtcgaga cttgccgccc taagcactct cccaagtccg   240
acccgctcgg cgaggacttc cgtcttctga gcgaaccttg tcaagcaagc tgggatct     298 atg agt gga aag gtg acc aag ccc aaa gag gag aaa gat gct tct aag     346
Met Ser Gly Lys Val Thr Lys Pro Lys Glu Glu Lys Asp Ala Ser Lys
1               5                  10                  15 gtt ctg gat gac gcc ccc cct ggc aca cag gaa tac att atg tta cga     394
Val Leu Asp Asp Ala Pro Pro Gly Thr Gln Glu Tyr Ile Met Leu Arg
            20                  25                  30 caa gat tcc atc caa tct gcg gaa tta aag aaa aaa gag tcc ccc ttt     442
Gln Asp Ser Ile Gln Ser Ala Glu Leu Lys Lys Lys Glu Ser Pro Phe
        35                  40                  45 cgt gct aag tgt cac gaa atc ttc tgc tgc ccg ctg aag caa gta cac     490
Arg Ala Lys Cys His Glu Ile Phe Cys Cys Pro Leu Lys Gln Val His
    50                  55                  60 cac aaa gag aac aca gag ccg gaa gag cct cag ctt aag ggt ata gtt     538
His Lys Glu Asn Thr Glu Pro Glu Glu Pro Gln Leu Lys Gly Ile Val
65                  70                  75                  80 acc aag cta tac agc cga caa ggc tac cac ttg cag ctg cag gcg gat     586
Thr Lys Leu Tyr Ser Arg Gln Gly Tyr His Leu Gln Leu Gln Ala Asp
                85                  90                  95
```

| | | | | | | | | | | | | | | | |
|---|---|---|---|---|---|---|---|---|---|---|---|---|---|---|---|
| gga | acc | att | gat | ggc | acc | aaa | gat | gag | gac | agc | act | tac | act | ctg | ttt | 634 |
| Gly | Thr | Ile | Asp | Gly | Thr | Lys | Asp | Glu | Asp | Ser | Thr | Tyr | Thr | Leu | Phe |
| | | | 100 | | | | | 105 | | | | | 110 | | |

```
gga acc att gat ggc acc aaa gat gag gac agc act tac act ctg ttt    634
Gly Thr Ile Asp Gly Thr Lys Asp Glu Asp Ser Thr Tyr Thr Leu Phe
            100                 105                 110 aac ctc atc cct gtg ggt ctg cga gtg gtg gct atc caa gga gtt caa    682
Asn Leu Ile Pro Val Gly Leu Arg Val Val Ala Ile Gln Gly Val Gln
            115                 120                 125 acc aag ctg tac ttg gca atg aac agt gag gga tac ttg tac acc tcg    730
Thr Lys Leu Tyr Leu Ala Met Asn Ser Glu Gly Tyr Leu Tyr Thr Ser
130                 135                 140 gaa ctt ttc aca cct gag tgc aaa ttc aaa gaa tca gtg ttt gaa aat    778
Glu Leu Phe Thr Pro Glu Cys Lys Phe Lys Glu Ser Val Phe Glu Asn
145                 150                 155                 160 tat tat gtg aca tat tca tca atg ata tac cgt cag cag cag tca ggc    826
Tyr Tyr Val Thr Tyr Ser Ser Met Ile Tyr Arg Gln Gln Gln Ser Gly
                165                 170                 175 cga ggg tgg tat ctg ggt ctg aac aaa gaa gga gag atc atg aaa ggc    874
Arg Gly Trp Tyr Leu Gly Leu Asn Lys Glu Gly Glu Ile Met Lys Gly
            180                 185                 190 aac cat gtg aag aag aac aag cct gca gct cat ttt ctg cct aaa cca    922
Asn His Val Lys Lys Asn Lys Pro Ala Ala His Phe Leu Pro Lys Pro
            195                 200                 205 ctg aaa gtg gcc atg tac aag gag cca tca ctg cac gat ctc acg gag    970
Leu Lys Val Ala Met Tyr Lys Glu Pro Ser Leu His Asp Leu Thr Glu
210                 215                 220 ttc tcc cga tct gga agc ggg acc cca acc aag agc aga agt gtc tct    1018
Phe Ser Arg Ser Gly Ser Gly Thr Pro Thr Lys Ser Arg Ser Val Ser
225                 230                 235                 240 ggc gtg ctg aac gga ggc aaa tcc atg agc cac aat gaa tca acg tag    1066
Gly Val Leu Asn Gly Gly Lys Ser Met Ser His Asn Glu Ser Thr
                245                 250                 255 ccagtgaggg caaagaagg gctctgtaac agaaccttac ctccaggtgc tgttgaattc    1126
ttctagcagt ccttcaccca aaagttcaaa tttgtcagtg acatttacca aacaaacagg    1186
cagagttcac tattctatct gccatta                                        1213
```

<210> SEQ ID NO 103
<211> LENGTH: 255
<212> TYPE: PRT
<213> ORGANISM: Homo sapiens

<400> SEQUENCE: 103

```
Met Ser Gly Lys Val Thr Lys Pro Lys Glu Glu Lys Asp Ala Ser Lys
1               5                   10                  15

Val Leu Asp Asp Ala Pro Pro Gly Thr Gln Glu Tyr Ile Met Leu Arg
            20                  25                  30

Gln Asp Ser Ile Gln Ser Ala Glu Leu Lys Lys Lys Ser Pro Phe
            35                  40                  45

Arg Ala Lys Cys His Glu Ile Phe Cys Cys Pro Leu Lys Gln Val His
50                  55                  60

His Lys Glu Asn Thr Glu Pro Glu Glu Pro Gln Leu Lys Gly Ile Val
65                  70                  75                  80

Thr Lys Leu Tyr Ser Arg Gln Gly Tyr His Leu Gln Leu Gln Ala Asp
                85                  90                  95

Gly Thr Ile Asp Gly Thr Lys Asp Glu Asp Ser Thr Tyr Thr Leu Phe
            100                 105                 110

Asn Leu Ile Pro Val Gly Leu Arg Val Val Ala Ile Gln Gly Val Gln
            115                 120                 125

Thr Lys Leu Tyr Leu Ala Met Asn Ser Glu Gly Tyr Leu Tyr Thr Ser
```

```
                130              135              140
Glu Leu Phe Thr Pro Glu Cys Lys Phe Lys Glu Ser Val Phe Glu Asn
145                 150                 155                 160

Tyr Tyr Val Thr Tyr Ser Ser Met Ile Tyr Arg Gln Gln Ser Gly
                165                 170                 175

Arg Gly Trp Tyr Leu Gly Leu Asn Lys Glu Gly Glu Ile Met Lys Gly
                180                 185                 190

Asn His Val Lys Lys Asn Lys Pro Ala Ala His Phe Leu Pro Lys Pro
                195                 200                 205

Leu Lys Val Ala Met Tyr Lys Glu Pro Ser Leu His Asp Leu Thr Glu
                210                 215                 220

Phe Ser Arg Ser Gly Ser Gly Thr Pro Thr Lys Ser Arg Ser Val Ser
225                 230                 235                 240

Gly Val Leu Asn Gly Gly Lys Ser Met Ser His Asn Glu Ser Thr
                245                 250                 255

<210> SEQ ID NO 104
<211> LENGTH: 513
<212> TYPE: DNA
<213> ORGANISM: Homo sapiens

<400> SEQUENCE: 104
gtttatatag aatgcgccgc ggtgttgatt cgtggctctc taggaccgga gagttctttg    60
gaaggagagc gcgagcgagg gagcgggcga gctccgaggg ggtgtgggtg tagggagaga   120
gagaaagaga gcaggcagcg gcggcggcgg cagcggtggg gaaaagcgga ttccgccccg   180
aaccacaccg aggggagctc gtggtcgaga cttgccgccc taagcactct cccaagtccg   240
acccgctcgg cgaggacttc cgtcttctga gcgaaccttg tcaagcaagc tgggatctat   300
gagtggaaag gtgaccaagc ccaaagagga gaaagatgct tctaaggttc tggatgacgc   360
cccccctggc acacaggaat acattatgtt acgacaagat tccatccaat ctgcggaatt   420
aaagaaaaaa gagtcccccct ttcgtgctaa gtgtcacgaa atcttctgct gcccgctgaa   480
gcaagtacac cacaaagaga acacagagcc gga                                 513

<210> SEQ ID NO 105
<211> LENGTH: 72
<212> TYPE: PRT
<213> ORGANISM: Homo sapiens

<400> SEQUENCE: 105

Met Ser Gly Lys Val Thr Lys Pro Lys Glu Glu Lys Asp Ala Ser Lys
1               5                   10                  15

Val Leu Asp Asp Ala Pro Pro Gly Thr Gln Glu Tyr Ile Met Leu Arg
                20                  25                  30

Gln Asp Ser Ile Gln Ser Ala Glu Leu Lys Lys Lys Glu Ser Pro Phe
            35                  40                  45

Arg Ala Lys Cys His Glu Ile Phe Cys Cys Pro Leu Lys Gln Val His
        50                  55                  60

His Lys Glu Asn Thr Glu Pro Glu
65                  70

<210> SEQ ID NO 106
<211> LENGTH: 215
<212> TYPE: DNA
<213> ORGANISM: Homo sapiens

<400> SEQUENCE: 106
```

```
atgagtggaa aggtgaccaa gcccaaagag gagaaagatg cttctaaggt tctggatgac    60
gccccccctg gcacacagga atacattatg ttacgacaag attccatcca atctgcggaa   120
ttaaagaaaa aagagtcccc ctttcgtgct aagtgtcacg aaatcttctg ctgcccgctg   180
aagcaagtac accacaaaga gaacacagag ccgga                              215
```

<210> SEQ ID NO 107
<211> LENGTH: 1179
<212> TYPE: DNA
<213> ORGANISM: Homo sapiens

<400> SEQUENCE: 107

```
actctctcgt aggcagcggc ggcggcggca gcggtgggga aaagcggatt ccgccccgaa    60
ccacaccgag gggagctcgt ggtcgagact tgccgcccta agcactctcc caagtccgac   120
ccgctcggcg aggacttccg tcttctgagc gaaccttgtc aagcaagctg ggatctatga   180
gtggaaaggt gaccaagccc aaagaggaga agatgcttc taaggttctg atgacgccc   240 cccctggcac acaggaatac attatgttac gacaagattc catccaatct gcggaattaa   300
agaaaaaaga gtccccctt cgtgctaagt gtcacgaaat cttctgctgc cgctgaagc   360 aagtacacca caaagagaac acagagccgg aagagcctca gcttaagggt atagttacca   420
agctatacag ccgacaaggc taccacttgc agctgcaggc ggatggaacc attgatggca   480
ccaaagatga ggacagcact tacactctgt ttaacctcat ccctgtgggt ctgcgagtgg   540
tggctatcca aggagttcaa ccaagctgt acttggcaat gaacagtgag ggatacttgt   600
acacctcgga acttttcaca cctgagtgca aattcaaaga atcagtgttt gaaaattatt   660
atgtgacata ttcatcaatg atataccgtc agcagcagtc aggccgaggg tggtatctgg   720
gtctgaacaa agaaggagag atcatgaaag gcaaccatgt gaagaagaac aagcctgcag   780
ctcattttct gcctaaacca ctgaaagtgg ccatgtacaa ggagccatca ctgcacgatc   840
tcacggagtt ctcccgatct ggaagcggga ccccaaccaa gagcagaagt gtctctggcg   900
tgctgaacgg aggcaaatcc atgagccaca atgaatcaac gtagccagtg agggcaaaag   960
aagggctctg taacagaacc ttacctccag gtgctgttga attcttctag cagtccttca  1020
cccaaaagtt caaatttgtc agtgacattt accaaacaaa caggcagagt tcactattct  1080
atctgccatt agaccttctt atcatccata ctaaagcccc attatttaga ttgagcttgt  1140
gcataagaat gccaagcatt ttagtgaact aaatctgag                          1179
```

<210> SEQ ID NO 108
<211> LENGTH: 1179
<212> TYPE: DNA
<213> ORGANISM: Homo sapiens
<221> NAME/KEY: CDS
<222> LOCATION: (177)..(944)

<400> SEQUENCE: 108

```
actctctcgt aggcagcggc ggcggcggca gcggtgggga aaagcggatt ccgccccgaa    60
ccacaccgag gggagctcgt ggtcgagact tgccgcccta agcactctcc caagtccgac   120
ccgctcggcg aggacttccg tcttctgagc gaaccttgtc aagcaagctg ggatct atg   179
                                                                Met
                                                                  1 agt gga aag gtg acc aag ccc aaa gag gag aaa gat gct tct aag gtt    227
Ser Gly Lys Val Thr Lys Pro Lys Glu Glu Lys Asp Ala Ser Lys Val
          5                  10                 15 ctg gat gac gcc ccc cct ggc aca cag gaa tac att atg tta cga caa    275
Leu Asp Asp Ala Pro Pro Gly Thr Gln Glu Tyr Ile Met Leu Arg Gln
```

```
                    20                    25                    30
gat tcc atc caa tct gcg gaa tta aag aaa aaa gag tcc ccc ttt cgt    323
Asp Ser Ile Gln Ser Ala Glu Leu Lys Lys Lys Glu Ser Pro Phe Arg
        35                    40                    45 gct aag tgt cac gaa atc ttc tgc tgc ccg ctg aag caa gta cac cac    371
Ala Lys Cys His Glu Ile Phe Cys Cys Pro Leu Lys Gln Val His His
 50                    55                    60                65 aaa gag aac aca gag ccg gaa gag cct cag ctt aag ggt ata gtt acc    419
Lys Glu Asn Thr Glu Pro Glu Glu Pro Gln Leu Lys Gly Ile Val Thr
                    70                    75                    80 aag cta tac agc cga caa ggc tac cac ttg cag ctg cag gcg gat gga    467
Lys Leu Tyr Ser Arg Gln Gly Tyr His Leu Gln Leu Gln Ala Asp Gly
                85                    90                    95 acc att gat ggc acc aaa gat gag gac agc act tac act ctg ttt aac    515
Thr Ile Asp Gly Thr Lys Asp Glu Asp Ser Thr Tyr Thr Leu Phe Asn
        100                   105                   110 ctc atc cct gtg ggt ctg cga gtg gtg gct atc caa gga gtt caa acc    563
Leu Ile Pro Val Gly Leu Arg Val Val Ala Ile Gln Gly Val Gln Thr
    115                   120                   125 aag ctg tac ttg gca atg aac agt gag gga tac ttg tac acc tcg gaa    611
Lys Leu Tyr Leu Ala Met Asn Ser Glu Gly Tyr Leu Tyr Thr Ser Glu
130                   135                   140                   145 ctt ttc aca cct gag tgc aaa ttc aaa gaa tca gtg ttt gaa aat tat    659
Leu Phe Thr Pro Glu Cys Lys Phe Lys Glu Ser Val Phe Glu Asn Tyr
                    150                   155                   160 tat gtg aca tat tca tca atg ata tac cgt cag cag cag tca ggc cga    707
Tyr Val Thr Tyr Ser Ser Met Ile Tyr Arg Gln Gln Gln Ser Gly Arg
                    165                   170                   175 ggg tgg tat ctg ggt ctg aac aaa gaa gga gag atc atg aaa ggc aac    755
Gly Trp Tyr Leu Gly Leu Asn Lys Glu Gly Glu Ile Met Lys Gly Asn
                180                   185                   190 cat gtg aag aag aac aag cct gca gct cat ttt ctg cct aaa cca ctg    803
His Val Lys Lys Asn Lys Pro Ala Ala His Phe Leu Pro Lys Pro Leu
            195                   200                   205 aaa gtg gcc atg tac aag gag cca tca ctg cac gat ctc acg gag ttc    851
Lys Val Ala Met Tyr Lys Glu Pro Ser Leu His Asp Leu Thr Glu Phe
210                   215                   220                   225 tcc cga tct gga agc ggg acc cca acc aag agc aga agt gtc tct ggc    899
Ser Arg Ser Gly Ser Gly Thr Pro Thr Lys Ser Arg Ser Val Ser Gly
                    230                   235                   240 gtg ctg aac gga ggc aaa tcc atg agc cac aat gaa tca acg tag        944
Val Leu Asn Gly Gly Lys Ser Met Ser His Asn Glu Ser Thr
                245                   250                   255 ccagtgaggg caaagaagg gctctgtaac agaaccttac ctccaggtgc tgttgaattc   1004
ttctagcagt ccttcaccca aaagttcaaa tttgtcagtg acatttacca aacaaacagg   1064
cagagttcac tattctatct gccattagac cttcttatca tccatactaa agccccatta   1124
tttagattga gcttgtgcat aagaatgcca agcattttag tgaactaaat ctgag        1179

<210> SEQ ID NO 109
<211> LENGTH: 255
<212> TYPE: PRT
<213> ORGANISM: Homo sapiens

<400> SEQUENCE: 109

Met Ser Gly Lys Val Thr Lys Pro Lys Glu Glu Lys Asp Ala Ser Lys
  1               5                  10                  15

Val Leu Asp Asp Ala Pro Pro Gly Thr Gln Glu Tyr Ile Met Leu Arg
                20                  25                  30
```

Gln Asp Ser Ile Gln Ser Ala Glu Leu Lys Lys Lys Glu Ser Pro Phe
    35                  40                  45

Arg Ala Lys Cys His Glu Ile Phe Cys Cys Pro Leu Lys Gln Val His
50                  55                  60

His Lys Glu Asn Thr Glu Pro Glu Pro Gln Leu Lys Gly Ile Val
65                  70                  75                  80

Thr Lys Leu Tyr Ser Arg Gln Gly Tyr His Leu Gln Leu Gln Ala Asp
                85                  90                  95

Gly Thr Ile Asp Gly Thr Lys Asp Glu Asp Ser Thr Tyr Thr Leu Phe
            100                 105                 110

Asn Leu Ile Pro Val Gly Leu Arg Val Val Ala Ile Gln Gly Val Gln
        115                 120                 125

Thr Lys Leu Tyr Leu Ala Met Asn Ser Glu Gly Tyr Leu Tyr Thr Ser
    130                 135                 140

Glu Leu Phe Thr Pro Glu Cys Lys Phe Lys Glu Ser Val Phe Glu Asn
145                 150                 155                 160

Tyr Tyr Val Thr Tyr Ser Ser Met Ile Tyr Arg Gln Gln Gln Ser Gly
                165                 170                 175

Arg Gly Trp Tyr Leu Gly Leu Asn Lys Glu Gly Glu Ile Met Lys Gly
            180                 185                 190

Asn His Val Lys Lys Asn Lys Pro Ala Ala His Phe Leu Pro Lys Pro
        195                 200                 205

Leu Lys Val Ala Met Tyr Lys Glu Pro Ser Leu His Asp Leu Thr Glu
    210                 215                 220

Phe Ser Arg Ser Gly Ser Gly Thr Pro Thr Lys Ser Arg Ser Val Ser
225                 230                 235                 240

Gly Val Leu Asn Gly Gly Lys Ser Met Ser His Asn Glu Ser Thr
                245                 250                 255

<210> SEQ ID NO 110
<211> LENGTH: 391
<212> TYPE: DNA
<213> ORGANISM: Homo sapiens

<400> SEQUENCE: 110
actctctcgt aggcagcggc ggcggcggca gcggtgggga aaagcggatt ccgccccgaa      60
ccacaccgag gggagctcgt ggtcgagact tgccgcccta agcactctcc caagtccgac     120
ccgctcggcg aggacttccg tcttctgagc gaaccttgtc aagcaagctg ggatctatga     180
gtggaaaggt gaccaagccc aaagaggaga aagatgcttc taaggttctg gatgacgccc     240
cccctggcac acaggaatac attatgttac gacaagattc catccaatct gcggaattaa     300
agaaaaaaga gtccccttt cgtgctaagt gtcacgaaat cttctgctgc ccgctgaagc      360
aagtacacca caaagagaac acagagccgg a                                    391

<210> SEQ ID NO 111
<211> LENGTH: 72
<212> TYPE: PRT
<213> ORGANISM: Homo sapiens

<400> SEQUENCE: 111

Met Ser Gly Lys Val Thr Lys Pro Lys Glu Glu Lys Asp Ala Ser Lys
1               5                   10                  15

Val Leu Asp Asp Ala Pro Pro Gly Thr Gln Glu Tyr Ile Met Leu Arg
            20                  25                  30

Gln Asp Ser Ile Gln Ser Ala Glu Leu Lys Lys Lys Glu Ser Pro Phe
    35                  40                  45

Arg Ala Lys Cys His Glu Ile Phe Cys Cys Pro Leu Lys Gln Val His
    50                  55                  60

His Lys Glu Asn Thr Glu Pro Glu
 65                  70

<210> SEQ ID NO 112
<211> LENGTH: 215
<212> TYPE: DNA
<213> ORGANISM: Homo sapiens

<400> SEQUENCE: 112
atgagtggaa aggtgaccaa gcccaaagag gagaaagatg cttctaaggt tctggatgac      60
gccccccctg gcacacagga atacattatg ttacgacaag attccatcca atctgcggaa     120
ttaaagaaaa aagagtcccc ctttcgtgct aagtgtcacg aaatcttctg ctgcccgctg     180
aagcaagtac accacaaaga gaacacagag ccgga                                215

<210> SEQ ID NO 113
<211> LENGTH: 1039
<212> TYPE: DNA
<213> ORGANISM: Homo sapiens

<400> SEQUENCE: 113
gtggctctct aggaccggag agttctttgg aaggagagcg cgagcgaggg agcgggcgag      60
ctccgagggg gtgtgggtgt agggagagag agaaagagag caggcagcgg cggcggcggc     120
agcggtgggg aaaagcggat tccgccccga accacaccga gggagctcg  tggtcgagac     180 ttgccgccct aagcactctc ccaagtccga cccgctcggc gaggacttcc gtcttctgag     240
cgaaccttgt caagcaagct gggatctatg agtggaaagg tgaccaagcc caaagaggag     300
aaagatgctt ctaaggagcc tcagcttaag ggtatagtta ccaagctata cagccgacaa     360
ggctaccact tgcagctgca ggcggatgga accattgatg gcaccaaaga tgaggacagc     420
acttacactc tgtttaacct catccctgtg ggtctgcgag tggtggctat ccaaggagtt     480
caaaccaagc tgtacttggc aatgaacagt gagggatact tgtacacctc ggaactttt c    540 acacctgagt gcaaattcaa agaatcagtg tttgaaaatt attatgtgac atattcatca     600
atgatatacc gtcagcagca gtcaggccga gggtggtatc tgggtctgaa caaagaagga     660
gagatcatga aaggcaacca tgtgaagaag aacaagcctg cagctcattt tctgcctaaa     720
ccactgaaag tggccatgta caaggagcca tcactgcacg atctcacgga gttctcccga     780
tctggaagcg ggaccccaac caagagcaga agtgtctctg gcgtgctgaa cggaggcaaa     840
tccatgagcc acaatgaatc aacgtagcca gtgagggcaa aagaagggct ctgtaacaga     900
accttacctc caggtgctgt tgaattcttc tagcagtcct tcacccaaaa gttcaaattt     960
gtcagtgaca tttaccaaac aaacaggcag agttcactat tctatctgcc attagacctt    1020
cttatcatcc atactaaag                                                 1039

<210> SEQ ID NO 114
<211> LENGTH: 1039
<212> TYPE: DNA
<213> ORGANISM: Homo sapiens
<221> NAME/KEY: CDS
<222> LOCATION: (268)..(867)

<400> SEQUENCE: 114
gtggctctct aggaccggag agttctttgg aaggagagcg cgagcgaggg agcgggcgag      60
ctccgagggg gtgtgggtgt agggagagag agaaagagag caggcagcgg cggcggcggc     120

```
agcggtgggg aaaagcggat tccgccccga accacaccga ggggagctcg tggtcgagac      180
ttgccgccct aagcactctc ccaagtccga cccgctcggc gaggacttcc gtcttctgag      240
cgaaccttgt caagcaagct gggatct atg agt gga aag gtg acc aag ccc aaa    294
                              Met Ser Gly Lys Val Thr Lys Pro Lys
                               1               5 gag gag aaa gat gct tct aag gag cct cag ctt aag ggt ata gtt acc      342
Glu Glu Lys Asp Ala Ser Lys Glu Pro Gln Leu Lys Gly Ile Val Thr
 10              15                  20                  25 aag cta tac agc cga caa ggc tac cac ttg cag ctg cag gcg gat gga      390
Lys Leu Tyr Ser Arg Gln Gly Tyr His Leu Gln Leu Gln Ala Asp Gly
             30                  35                  40 acc att gat ggc acc aaa gat gag gac agc act tac act ctg ttt aac      438
Thr Ile Asp Gly Thr Lys Asp Glu Asp Ser Thr Tyr Thr Leu Phe Asn
         45                  50                  55 ctc atc cct gtg ggt ctg cga gtg gtg gct atc caa gga gtt caa acc      486
Leu Ile Pro Val Gly Leu Arg Val Val Ala Ile Gln Gly Val Gln Thr
     60                  65                  70 aag ctg tac ttg gca atg aac agt gag gga tac ttg tac acc tcg gaa      534
Lys Leu Tyr Leu Ala Met Asn Ser Glu Gly Tyr Leu Tyr Thr Ser Glu
 75                  80                  85 ctt ttc aca cct gag tgc aaa ttc aaa gaa tca gtg ttt gaa aat tat      582
Leu Phe Thr Pro Glu Cys Lys Phe Lys Glu Ser Val Phe Glu Asn Tyr
 90                  95                 100                 105 tat gtg aca tat tca tca atg ata tac cgt cag cag cag tca ggc cga      630
Tyr Val Thr Tyr Ser Ser Met Ile Tyr Arg Gln Gln Gln Ser Gly Arg
             110                 115                 120 ggg tgg tat ctg ggt ctg aac aaa gaa gga gag atc atg aaa ggc aac      678
Gly Trp Tyr Leu Gly Leu Asn Lys Glu Gly Glu Ile Met Lys Gly Asn
         125                 130                 135 cat gtg aag aag aac aag cct gca gct cat ttt ctg cct aaa cca ctg      726
His Val Lys Lys Asn Lys Pro Ala Ala His Phe Leu Pro Lys Pro Leu
     140                 145                 150 aaa gtg gcc atg tac aag gag cca tca ctg cac gat ctc acg gag ttc      774
Lys Val Ala Met Tyr Lys Glu Pro Ser Leu His Asp Leu Thr Glu Phe
 155                 160                 165 tcc cga tct gga agc ggg acc cca acc aag agc aga agt gtc tct ggc      822
Ser Arg Ser Gly Ser Gly Thr Pro Thr Lys Ser Arg Ser Val Ser Gly
170                 175                 180                 185 gtg ctg aac gga ggc aaa tcc atg agc cac aat gaa tca acg tag          867
Val Leu Asn Gly Gly Lys Ser Met Ser His Asn Glu Ser Thr
             190                 195 ccagtgaggg caaaagaagg gctctgtaac agaaccttac ctccaggtgc tgttgaattc      927
ttctagcagt ccttcaccca aaagttcaaa tttgtcagtg acatttacca aacaaacagg      987
cagagttcac tattctatct gccattagac cttcttatca tccatactaa ag            1039

<210> SEQ ID NO 115
<211> LENGTH: 199
<212> TYPE: PRT
<213> ORGANISM: Homo sapiens

<400> SEQUENCE: 115

Met Ser Gly Lys Val Thr Lys Pro Lys Glu Glu Lys Asp Ala Ser Lys
 1               5                  10                  15

Glu Pro Gln Leu Lys Gly Ile Val Thr Lys Leu Tyr Ser Arg Gln Gly
             20                  25                  30

Tyr His Leu Gln Leu Gln Ala Asp Gly Thr Ile Asp Gly Thr Lys Asp
         35                  40                  45
```

```
Glu Asp Ser Thr Tyr Thr Leu Phe Asn Leu Ile Pro Val Gly Leu Arg
 50                  55                  60
Val Val Ala Ile Gln Gly Val Gln Thr Lys Leu Tyr Leu Ala Met Asn
 65                  70                  75                  80
Ser Glu Gly Tyr Leu Tyr Thr Ser Glu Leu Phe Thr Pro Glu Cys Lys
                 85                  90                  95
Phe Lys Glu Ser Val Phe Glu Asn Tyr Tyr Val Thr Tyr Ser Ser Met
            100                 105                 110
Ile Tyr Arg Gln Gln Gln Ser Gly Arg Gly Trp Tyr Leu Gly Leu Asn
        115                 120                 125
Lys Glu Gly Glu Ile Met Lys Gly Asn His Val Lys Lys Asn Lys Pro
130                 135                 140
Ala Ala His Phe Leu Pro Lys Pro Leu Lys Val Ala Met Tyr Lys Glu
145                 150                 155                 160
Pro Ser Leu His Asp Leu Thr Glu Phe Ser Arg Ser Gly Ser Gly Thr
                165                 170                 175
Pro Thr Lys Ser Arg Ser Val Ser Gly Val Leu Asn Gly Gly Lys Ser
            180                 185                 190
Met Ser His Asn Glu Ser Thr
        195
```

<210> SEQ ID NO 116
<211> LENGTH: 315
<212> TYPE: DNA
<213> ORGANISM: Homo sapiens

<400> SEQUENCE: 116

```
gtggctctct aggaccggag agttctttgg aaggagagcg cgagcgaggg agcgggcgag    60
ctccgagggg gtgtgggtgt agggagagag agaaagagag caggcagcgg cggcggcggc   120
agcggtgggg aaaagcggat tccgccccga accacaccga ggggagctcg tggtcgagac   180
ttgccgccct aagcactctc ccaagtccga cccgctcggc gaggacttcc gtcttctgag   240
cgaaccttgt caagcaagct gggatctatg agtggaaagg tgaccaagcc caaagaggag   300
aaagatgctt ctaag                                                    315
```

<210> SEQ ID NO 117
<211> LENGTH: 16
<212> TYPE: PRT
<213> ORGANISM: Homo sapiens

<400> SEQUENCE: 117

```
Met Ser Gly Lys Val Thr Lys Pro Lys Glu Glu Lys Asp Ala Ser Lys
  1               5                  10                  15
```

<210> SEQ ID NO 118
<211> LENGTH: 48
<212> TYPE: DNA
<213> ORGANISM: Homo sapiens

<400> SEQUENCE: 118

```
atgagtggaa aggtgaccaa gcccaaagag gagaaagatg cttctaag              48
```

<210> SEQ ID NO 119
<211> LENGTH: 16
<212> TYPE: DNA
<213> ORGANISM: Artificial Sequence
<220> FEATURE:
<223> OTHER INFORMATION: forward primer used for specifically detecting
      the variants of the present invention (D-FEBRA2010013.1 and
      D-FEBRA2001626.1)

<400> SEQUENCE: 119
gctgcccgct gaagca                                                          16

<210> SEQ ID NO 120
<211> LENGTH: 24
<212> TYPE: DNA
<213> ORGANISM: Artificial Sequence
<220> FEATURE:
<223> OTHER INFORMATION: reverse primer used for specifically detecting
      the variants of the present invention (D-FEBRA2010013.1 and
      D-FEBRA2001626.1)

<400> SEQUENCE: 120
ttgtcggctg tatagcttgg taac                                                 24

<210> SEQ ID NO 121
<211> LENGTH: 92
<212> TYPE: DNA
<213> ORGANISM: Artificial Sequence
<220> FEATURE:
<223> OTHER INFORMATION: partial polynucleotide specific to the variant
      of the present invention (D-FEBRA2010013.1 and D-FEBRA2001626.1),
      which is obtained by PCR using forward primer (SEQ ID NO:119) and
      reverse primer (SEQ ID NO:120)

<400> SEQUENCE: 121
gctgcccgct gaagcaagta caccacaaag agaacacaga gccggaagag cctcagctta         60
agggtatagt taccaagcta tacagccgac aa                                       92

<210> SEQ ID NO 122
<211> LENGTH: 25
<212> TYPE: DNA
<213> ORGANISM: Artificial Sequence
<220> FEATURE:
<223> OTHER INFORMATION: probe used for specifically detecting the
      variants of the present invention (D-FEBRA2010013.1 and
      D-FEBRA2001626.1)

<400> SEQUENCE: 122
aacacagagc cggaagagcc tcagc                                                25

<210> SEQ ID NO 123
<211> LENGTH: 20
<212> TYPE: DNA
<213> ORGANISM: Artificial Sequence
<220> FEATURE:
<223> OTHER INFORMATION: forward primer used for specifically detecting
      the variant of the present invention (D-TKIDN2003621.1)

<400> SEQUENCE: 123
gtgaccaagc ccaaagagga                                                      20

<210> SEQ ID NO 124
<211> LENGTH: 19
<212> TYPE: DNA
<213> ORGANISM: Artificial Sequence
<220> FEATURE:
<223> OTHER INFORMATION: reverse primer used for specifically detecting
      the variant of the present invention (D-TKIDN2003621.1)

<400> SEQUENCE: 124
tcaatggttc catccgcct                                                       19

<210> SEQ ID NO 125
<211> LENGTH: 119
<212> TYPE: DNA

-continued

```
<213> ORGANISM: Artificial Sequence
<220> FEATURE:
<223> OTHER INFORMATION: partial polynucleotide specific to the variant
      of the present invention (D-TKIDN2003621.1), which is obtained by
      PCR using forward primer (SEQ ID NO:123) and reverse primer
      (SEQ ID NO:124)

<400> SEQUENCE: 125
gtgaccaagc ccaaagagga gaaagatgct tctaaggagc ctcagcttaa gggtatagtt      60
accaagctat acagccgaca aggctaccac ttgcagctgc aggcggatgg aaccattga     119

<210> SEQ ID NO 126
<211> LENGTH: 30
<212> TYPE: DNA
<213> ORGANISM: Artificial Sequence
<220> FEATURE:
<223> OTHER INFORMATION: probe used for detecting the variant of the
      present invention (D-TKIDN2003621.1)

<400> SEQUENCE: 126
gatgcttcta aggagcctca gcttaagggt                                       30

<210> SEQ ID NO 127
<211> LENGTH: 24
<212> TYPE: DNA
<213> ORGANISM: Artificial Sequence
<220> FEATURE:
<223> OTHER INFORMATION: forward primer used for specifically detecting
      the known variant of the gene of the present invention
      (NM_033642.1)

<400> SEQUENCE: 127
aagtcgtatt cagagcctca gctt                                             24

<210> SEQ ID NO 128
<211> LENGTH: 26
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_033642.1)

<400> SEQUENCE: 128
gagtgtaagt gctgtcctca tctttg                                           26

<210> SEQ ID NO 129
<211> LENGTH: 127
<212> TYPE: DNA
<213> ORGANISM: Artificial Sequence
<220> FEATURE:
<223> OTHER INFORMATION: partial polynucleotide specific to the known
      variant of the gene of the present invention (NM_033642.1),
      which is obtained by PCR using forward primer (SEQ ID NO:127) and
      reverse primer (SEQ ID NO:128)

<400> SEQUENCE: 129
aagtcgtatt cagagcctca gcttaagggt atagttacca agctatacag ccgacaaggc      60
taccacttgc agctgcaggc ggatggaacc attgatggca ccaaagatga ggacagcact     120
tacactc                                                               127

<210> SEQ ID NO 130
<211> LENGTH: 29
<212> TYPE: DNA
<213> ORGANISM: Artificial Sequence
<220> FEATURE:
<223> OTHER INFORMATION: probe used for specifically detecting the known
```

-continued variant of the gene of the present invention (NM_033642.1)

<400> SEQUENCE: 130
gctatacagc cgacaaggct accacttgc                                    29

<210> SEQ ID NO 131
<211> LENGTH: 21
<212> TYPE: DNA
<213> ORGANISM: Artificial Sequence
<220> FEATURE:
<223> OTHER INFORMATION: forward primer used for specifically detecting
      the known variant of the gene of the present invention
      (NM_004114.2)

<400> SEQUENCE: 131
tcaaactctt cggctccaag a                                            21

<210> SEQ ID NO 132
<211> LENGTH: 21
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_004114.2)

<400> SEQUENCE: 132
tggtagcctt gtcggctgta t                                            21

<210> SEQ ID NO 133
<211> LENGTH: 94
<212> TYPE: DNA
<213> ORGANISM: Artificial Sequence
<220> FEATURE:
<223> OTHER INFORMATION: partial polynucleotide specific to the known
      variant of the gene of the present invention (NM_004114.2),
      which is obtained by PCR using forward primer (SEQ ID NO:131) and
      reverse primer (SEQ ID NO:132)

<400> SEQUENCE: 133
tcaaactctt cggctccaag aagaggcgca gaagaagacc agagcctcag cttaagggta    60
tagttaccaa gctatacagc cgacaaggct acca                               94

<210> SEQ ID NO 134
<211> LENGTH: 27
<212> TYPE: DNA
<213> ORGANISM: Artificial Sequence
<220> FEATURE:
<223> OTHER INFORMATION: probe used for specifically detecting the known
      variant of the gene of the present invention (NM_004114.2)

<400> SEQUENCE: 134
cgcagaagaa gaccagagcc tcagctt                                      27

<210> SEQ ID NO 135
<211> LENGTH: 23
<212> TYPE: DNA
<213> ORGANISM: Artificial Sequence
<220> FEATURE:
<223> OTHER INFORMATION: forward primer used for detecting the variants
      of the gene of the present invention (D-FEBRA2010013.1,
      D-FEBRA2001626.1, D-TKIDN2003621.1, NM_033642.1 and NM_004114.2)

<400> SEQUENCE: 135
cagctcattt tctgcctaaa cca                                          23

<210> SEQ ID NO 136

```
<211> LENGTH: 20
<212> TYPE: DNA
<213> ORGANISM: Artificial Sequence
<220> FEATURE:
<223> OTHER INFORMATION: reverse primer used for detecting the variants
      of the gene of the present invention (D-FEBRA2010013.1,
      D-FEBRA2001626.1, D-TKIDN2003621.1, NM_033642.1 and NM_004114.2)

<400> SEQUENCE: 136
cagcacgcca gagacacttc                                                  20

<210> SEQ ID NO 137
<211> LENGTH: 128
<212> TYPE: DNA
<213> ORGANISM: Artificial Sequence
<220> FEATURE:
<223> OTHER INFORMATION: partial polynucleotide common to the variants
      of the gene of the present invention (D-FEBRA2010013.1,
      D-FEBRA2001626.1, D-TKIDN2003621.1, NM_033642.1 and NM_004114.2),
      which is obtained by PCR using forward primer SEQ ID NO:135) and
      reverse primer (SEQ ID NO:136)

<400> SEQUENCE: 137
cagctcattt tctgcctaaa ccactgaaag tggccatgta caaggagcca tcactgcacg      60
atctcacgga gttctcccga tctggaagcg ggaccccaac caagagcaga agtgtctctg     120
gcgtgctg                                                             128

<210> SEQ ID NO 138
<211> LENGTH: 25
<212> TYPE: DNA
<213> ORGANISM: Artificial Sequence
<220> FEATURE:
<223> OTHER INFORMATION: probe used for detecting the variants of the
      gene of the present invention (D-FEBRA2010013.1, D-FEBRA2001626.1,
       D-TKIDN2003621.1, NM_033642.1 and NM_004114.2)

<400> SEQUENCE: 138
agccatcact gcacgatctc acgga                                            25

<210> SEQ ID NO 139
<211> LENGTH: 559
<212> TYPE: DNA
<213> ORGANISM: Homo sapiens

<400> SEQUENCE: 139
gtttatatag aatgcgccgc ggtgttgatt cgtggctctc taggaccgga gagttctttg      60
gaaggagagc gcgagcgagg gagcgggcga gctccgaggg ggtgtgggtg tagggagaga     120
gagaaagaga gcaggcagcg gcggcggcgg cagcggtggg gaaaagcgga ttccgccccg     180
aaccacaccg aggggagctc gtggtcgaga cttgccgccc taagcactct cccaagtccg     240
acccgctcgg cgaggacttc cgtcttctga gcgaaccttg tcaagcaagc tgggatctat     300
gagtggaaag gtgaccaagc ccaaagagga gaaagatgct tctaaggttc tggatgacgc     360
cccccctggc acacaggaat acattatgtt acgacaagat tccatccaat ctgcggaatt     420
aaagaaaaaa gagtccccct ttcgtgctaa gtgtcacgaa atcttctgct gcccgctgaa     480
gcaagtacac cacaaagaga acacagagcc ggaagagcct cagcttaagg gtatagttac     540
caagctatac agccgacaa                                                 559

<210> SEQ ID NO 140
<211> LENGTH: 437
<212> TYPE: DNA
<213> ORGANISM: Homo sapiens
```

<400> SEQUENCE: 140

```
actctctcgt aggcagcggc ggcggcggca gcggtgggga aaagcggatt ccgccccgaa      60
ccacaccgag gggagctcgt ggtcgagact tgccgcccta agcactctcc caagtccgac     120
ccgctcggcg aggacttccg tcttctgagc gaaccttgtc aagcaagctg ggatctatga     180
gtggaaaggt gaccaagccc aaagaggaga agatgcttc taaggttctg gatgacgccc      240
cccctggcac acaggaatac attatgttac gacaagattc catccaatct gcggaattaa     300
agaaaaaaga gtcccccttt cgtgctaagt gtcacgaaat cttctgctgc ccgctgaagc     360
aagtacacca caaagagaac acagagccgg aagagcctca gcttaagggt atagttacca     420
agctatacag ccgacaa                                                    437
```

<210> SEQ ID NO 141
<211> LENGTH: 398
<212> TYPE: DNA
<213> ORGANISM: Homo sapiens

<400> SEQUENCE: 141

```
gtggctctct aggaccggag agttctttgg aaggagagcg cgagcgaggg agcgggcgag      60
ctccgagggg gtgtgggtgt agggagagag agaaagagag caggcagcgg cggcggcggc     120
agcggtgggg aaaagcggat tccgccccga accacaccga gggagctcg tggtcgagac      180
ttgccgccct aagcactctc ccaagtccga cccgctcggc gaggacttcc gtcttctgag     240
cgaaccttgt caagcaagct gggatctatg agtggaaagg tgaccaagcc caaagaggag     300
aaagatgctt ctaaggagcc tcagcttaag ggtatagtta ccaagctata cagccgacaa     360
ggctaccact tgcagctgca ggcggatgga accattga                             398
```

<210> SEQ ID NO 142
<211> LENGTH: 2507
<212> TYPE: DNA
<213> ORGANISM: Homo sapiens

<400> SEQUENCE: 142

```
acactagggt acagagctcg tgcttcggga tggaaaccta tggttatctg cagagggagt      60
catgctttca aggacctcat aaatacatat cgaatgattg aacaagatga ctttgacatt     120
aacaccaggc tacacacaat tgtgagggga aagatgagg cagccatggt ggagtcagta      180
ggcctggccc tagtgaagct gccagatgtc cttaatcgcc tgaagcctga tatcatgatt     240
gttcatggag acaggtttga tgccctggct ctggccacat ctgctgcctt gatgaacatc     300
cgaatccttc acattgaagg tggggaagtc agtgggacca ttgatgactc tatcagacat     360
gccataacaa aactggctca ttatcatgtg tgctgcaccc gcagtgcaga gcagcacctg     420
atatccatgt gtgaggacca tgatcgcatc cttttggcag gctgcccttc ctatgacaaa     480
cttctctcag ccaagaacaa agactacatg agcatcattc gcatgtggct aggtgatgat     540
gtaaaatcta agattacat tgttgcacta cagcaccctg tgaccactga cattaagcat     600
tccataaaaa tgtttgaatt aacattggat gcacttatct catttaacaa gcggacccta     660
gtcctgtttc caaatattga cgcagggagc aaagagatgg ttcgagtgat gcggaagaag     720
ggcattgagc atcatcccaa cttttcgtgca gttaaacacg tcccatttga ccagtttata     780
cagttggttg cccatgctgg ctgtatgatt gggaacagca gctgtgggt tcgagaagtt     840
ggagcttttg gaacacctgt gatcaacctg ggaacacgtc agattggaag agaaacaggg     900
gagaatgttc ttcatgtccg ggatgctgac acccaagaca aatatattgca agcactgcac     960
```

```
cttcagtttg gtaaacagta cccttgttca aggatatatg gggatggaaa tgctgttcca    1020
aggattttga agtttctcaa atctatcgat cttcaagagc cactgcaaaa gaaattctgc    1080
tttcctcctg tgaaggagaa tatctctcaa gatattgacc atattcttga aactctaagt    1140
gccttggccg ttgatcttgg cgggacgaac ctccgagttg caatagtcag catgaagggt    1200
gaaatagtta agaagtatac tcagttcaat cctaaaacct atgaagagag gattaattta    1260
atcctacaga tgtgtgtgga agctgcagca gaagctgtaa aactgaactg cagaattttg    1320
ggagtaggca tttccacagg tggccgtgta atcctcgggg aaggaattgt gctgcattca    1380
accaaactga tccaagagtg gaactctgtg gaccttagga ccccccttc tgacactttg    1440 catctccctg tgtgggtaga caatgatggc aactgtgttg ccctggcgga aggaaattt    1500 ggccaaggaa agggactgga aaactttgtt acacttatca caggcacagg atcggtggt    1560 ggaattatcc atcagcatga attgatccac ggaagctcct tctgtgctgc agaactgggc    1620
caccttgttg tgtctctgga tgggcctgat tgttcctgtg aagccatgg gtgcattgaa    1680 gcatacgcct ctggaatggc cttgcagagg gaggcaaaaa agctccatga tgaggacctg    1740
ctcttggtgg aagggatgtc agtgccaaaa gatgaggctg tgggtgcgct ccatctcatc    1800
caagctgcga aacttggcaa tgcgaaggcc cagagcatcc taagaacagc tggaacagct    1860
ttgggtcttg gggttgtgaa catcctccat accatgaatc cctcccttgt gatcctctcc    1920
ggagtcctgg ccagtcacta tatccacatt gtcaaagacg tcattcgcca gcaggccttg    1980
tcctccgtgc aggacgtgga tgtggtggtt tcggatttgg ttgaccccgc cctgctgggt    2040
gctgccagca tggttctgga ctacacaaca cgcaggatct actagacctc caggaacaga    2100
catggacctt ctctccagag ctcctgagtg gaatcaagtt cttgtcttta ggatgaccgt    2160
ttcttaacaa tcaaatctgg tattgaactg caggtgactt tggcagagaa atgttttcac    2220
ttttggtctc ctcttccaga gtcacctttc cccactccta tttttgtaga tgctattctt    2280
tctgatgtct tcttactagg ggtcatttta gctcaaaccc tgtaagttac agtcacaatt    2340
ttctgtgcca aagcagctac aataatagag aggaagcctt cttagaactc tgcttactaa    2400
tgtattaata ccactgagac cttcaggcct tgcctgggat atcacttcat cctgaagttt    2460
gcattaataa tccttccagg ccgggcacag tggctcgcgc ctgtagt              2507
```

<210> SEQ ID NO 143
<211> LENGTH: 2507
<212> TYPE: DNA
<213> ORGANISM: Homo sapiens
<221> NAME/KEY: CDS
<222> LOCATION: (40)..(2085)

<400> SEQUENCE: 143

```
acactagggt acagagctcg tgcttcggga tggaaacct atg gtt atc tgc aga         54
                                          Met Val Ile Cys Arg
                                           1               5 ggg agt cat gct ttc aag gac ctc ata aat aca tat cga atg att gaa       102
Gly Ser His Ala Phe Lys Asp Leu Ile Asn Thr Tyr Arg Met Ile Glu
             10                  15                  20 caa gat gac ttt gac att aac acc agg cta cac aca att gtg agg gga      150
Gln Asp Asp Phe Asp Ile Asn Thr Arg Leu His Thr Ile Val Arg Gly
         25                  30                  35 gaa gat gag gca gcc atg gtg gag tca gta ggc ctg gcc cta gtg aag      198
Glu Asp Glu Ala Ala Met Val Glu Ser Val Gly Leu Ala Leu Val Lys
     40                  45                  50 ctg cca gat gtc ctt aat cgc ctg aag cct gat atc atg att gtt cat      246
Leu Pro Asp Val Leu Asn Arg Leu Lys Pro Asp Ile Met Ile Val His
 55                  60                  65                  70
```

```
                    55                      60                      65
gga gac agg ttt gat gcc ctg gct ctg gcc aca tct gct gcc ttg atg         294
Gly Asp Arg Phe Asp Ala Leu Ala Leu Ala Thr Ser Ala Ala Leu Met
 70                  75                      80                  85 aac atc cga atc ctt cac att gaa ggt ggg gaa gtc agt ggg acc att         342
Asn Ile Arg Ile Leu His Ile Glu Gly Gly Glu Val Ser Gly Thr Ile
                     90                      95                 100 gat gac tct atc aga cat gcc ata aca aaa ctg gct cat tat cat gtg         390
Asp Asp Ser Ile Arg His Ala Ile Thr Lys Leu Ala His Tyr His Val
                105                     110                 115 tgc tgc acc cgc agt gca gag cag cac ctg ata tcc atg tgt gag gac         438
Cys Cys Thr Arg Ser Ala Glu Gln His Leu Ile Ser Met Cys Glu Asp
            120                     125                 130 cat gat cgc atc ctt ttg gca ggc tgc cct tcc tat gac aaa ctt ctc         486
His Asp Arg Ile Leu Leu Ala Gly Cys Pro Ser Tyr Asp Lys Leu Leu
            135                     140                 145 tca gcc aag aac aaa gac tac atg agc atc att cgc atg tgg cta ggt         534
Ser Ala Lys Asn Lys Asp Tyr Met Ser Ile Ile Arg Met Trp Leu Gly
150                     155                     160                 165 gat gat gta aaa tct aaa gat tac att gtt gca cta cag cac cct gtg         582
Asp Asp Val Lys Ser Lys Asp Tyr Ile Val Ala Leu Gln His Pro Val
                170                     175                 180 acc act gac att aag cat tcc ata aaa atg ttt gaa tta aca ttg gat         630
Thr Thr Asp Ile Lys His Ser Ile Lys Met Phe Glu Leu Thr Leu Asp
                185                     190                 195 gca ctt atc tca ttt aac aag cgg acc cta gtc ctg ttt cca aat att         678
Ala Leu Ile Ser Phe Asn Lys Arg Thr Leu Val Leu Phe Pro Asn Ile
            200                     205                 210 gac gca ggg agc aaa gag atg gtt cga gtg atg cgg aag aag ggc att         726
Asp Ala Gly Ser Lys Glu Met Val Arg Val Met Arg Lys Lys Gly Ile
            215                     220                 225 gag cat cat ccc aac ttt cgt gca gtt aaa cac gtc cca ttt gac cag         774
Glu His His Pro Asn Phe Arg Ala Val Lys His Val Pro Phe Asp Gln
230                     235                     240                 245 ttt ata cag ttg gtt gcc cat gct ggc tgt atg att ggg aac agc agc         822
Phe Ile Gln Leu Val Ala His Ala Gly Cys Met Ile Gly Asn Ser Ser
                250                     255                 260 tgt ggg gtt cga gaa gtt gga gct ttt gga aca cct gtg atc aac ctg         870
Cys Gly Val Arg Glu Val Gly Ala Phe Gly Thr Pro Val Ile Asn Leu
                265                     270                 275 gga aca cgt cag att gga aga gaa aca ggg gag aat gtt ctt cat gtc         918
Gly Thr Arg Gln Ile Gly Arg Glu Thr Gly Glu Asn Val Leu His Val
            280                     285                 290 cgg gat gct gac acc caa gac aaa ata ttg caa gca ctg cac ctt cag         966
Arg Asp Ala Asp Thr Gln Asp Lys Ile Leu Gln Ala Leu His Leu Gln
            295                     300                 305 ttt ggt aaa cag tac cct tgt tca agg ata tat ggg gat gga aat gct        1014
Phe Gly Lys Gln Tyr Pro Cys Ser Arg Ile Tyr Gly Asp Gly Asn Ala
310                     315                     320                 325 gtt cca agg att ttg aag ttt ctc aaa tct atc gat ctt caa gag cca        1062
Val Pro Arg Ile Leu Lys Phe Leu Lys Ser Ile Asp Leu Gln Glu Pro
                330                     335                 340 ctg caa aag aaa ttc tgc ttt cct cct gtg aag gag aat atc tct caa        1110
Leu Gln Lys Lys Phe Cys Phe Pro Pro Val Lys Glu Asn Ile Ser Gln
            345                     350                 355 gat att gac cat att ctt gaa act cta agt gcc ttg gcc gtt gat ctt        1158
Asp Ile Asp His Ile Leu Glu Thr Leu Ser Ala Leu Ala Val Asp Leu
            360                     365                 370 ggc ggg acg aac ctc cga gtt gca ata gtc agc atg aag ggt gaa ata        1206
Gly Gly Thr Asn Leu Arg Val Ala Ile Val Ser Met Lys Gly Glu Ile
```

```
                 375                 380                 385
gtt aag aag tat act cag ttc aat cct aaa acc tat gaa gag agg att    1254
Val Lys Lys Tyr Thr Gln Phe Asn Pro Lys Thr Tyr Glu Glu Arg Ile
390                 395                 400                 405 aat tta atc cta cag atg tgt gtg gaa gct gca gca gaa gct gta aaa    1302
Asn Leu Ile Leu Gln Met Cys Val Glu Ala Ala Ala Glu Ala Val Lys
                410                 415                 420 ctg aac tgc aga att ttg gga gta ggc att tcc aca ggt ggc cgt gta    1350
Leu Asn Cys Arg Ile Leu Gly Val Gly Ile Ser Thr Gly Gly Arg Val
                425                 430                 435 aat cct cgg gaa gga att gtg ctg cat tca acc aaa ctg atc caa gag    1398
Asn Pro Arg Glu Gly Ile Val Leu His Ser Thr Lys Leu Ile Gln Glu
            440                 445                 450 tgg aac tct gtg gac ctt agg acc ccc ctt tct gac act ttg cat ctc    1446
Trp Asn Ser Val Asp Leu Arg Thr Pro Leu Ser Asp Thr Leu His Leu
            455                 460                 465 cct gtg tgg gta gac aat gat ggc aac tgt gtt gcc ctg gcg gaa agg    1494
Pro Val Trp Val Asp Asn Asp Gly Asn Cys Val Ala Leu Ala Glu Arg
470                 475                 480                 485 aaa ttt ggc caa gga aag gga ctg gaa aac ttt gtt aca ctt atc aca    1542
Lys Phe Gly Gln Gly Lys Gly Leu Glu Asn Phe Val Thr Leu Ile Thr
                490                 495                 500 ggc aca gga atc ggt ggt gga att atc cat cag cat gaa ttg atc cac    1590
Gly Thr Gly Ile Gly Gly Gly Ile Ile His Gln His Glu Leu Ile His
                505                 510                 515 gga agc tcc ttc tgt gct gca gaa ctg ggc cac ctt gtt gtg tct ctg    1638
Gly Ser Ser Phe Cys Ala Ala Glu Leu Gly His Leu Val Val Ser Leu
                520                 525                 530 gat ggg cct gat tgt tcc tgt gga agc cat ggg tgc att gaa gca tac    1686
Asp Gly Pro Asp Cys Ser Cys Gly Ser His Gly Cys Ile Glu Ala Tyr
535                 540                 545 gcc tct gga atg gcc ttg cag agg gag gca aaa aag ctc cat gat gag    1734
Ala Ser Gly Met Ala Leu Gln Arg Glu Ala Lys Lys Leu His Asp Glu
550                 555                 560                 565 gac ctg ctc ttg gtg gaa ggg atg tca gtg cca aaa gat gag gct gtg    1782
Asp Leu Leu Leu Val Glu Gly Met Ser Val Pro Lys Asp Glu Ala Val
                570                 575                 580 ggt gcg ctc cat ctc atc caa gct gcg aaa ctt ggc aat gcg aag gcc    1830
Gly Ala Leu His Leu Ile Gln Ala Ala Lys Leu Gly Asn Ala Lys Ala
                585                 590                 595 cag agc atc cta aga aca gct gga aca gct ttg ggt ctt ggg gtt gtg    1878
Gln Ser Ile Leu Arg Thr Ala Gly Thr Ala Leu Gly Leu Gly Val Val
            600                 605                 610 aac atc ctc cat acc atg aat ccc tcc ctt gtg atc ctc tcc gga gtc    1926
Asn Ile Leu His Thr Met Asn Pro Ser Leu Val Ile Leu Ser Gly Val
            615                 620                 625 ctg gcc agt cac tat atc cac att gtc aaa gac gtc att cgc cag cag    1974
Leu Ala Ser His Tyr Ile His Ile Val Lys Asp Val Ile Arg Gln Gln
630                 635                 640                 645 gcc ttg tcc tcc gtg cag gac gtg gat gtg gtg gtt tcg gat ttg gtt    2022
Ala Leu Ser Ser Val Gln Asp Val Asp Val Val Val Ser Asp Leu Val
                650                 655                 660 gac ccc gcc ctg ctg ggt gct gcc agc atg gtt ctg gac tac aca aca    2070
Asp Pro Ala Leu Leu Gly Ala Ala Ser Met Val Leu Asp Tyr Thr Thr
                665                 670                 675 cgc agg atc tac tag acctccagga acagacatgg accttctctc cagagctcct    2125
Arg Arg Ile Tyr
            680 gagtggaatc aagttcttgt ctttaggatg accgtttctt aacaatcaaa tctggtattg    2185
```

```
aactgcaggt gactttggca gagaaatgtt ttcactttg gtctcctctt ccagagtcac    2245
cttcccccac tcctattttt gtagatgcta ttctttctga tgtcttctta ctaggggtca    2305
ttttagctca aaccctgtaa gttacagtca caattttctg tgccaaagca gctacaataa    2365
tagagaggaa gccttcttag aactctgctt actaatgtat taataccact gagaccttca    2425
ggccttgcct gggatatcac ttcatcctga agtttgcatt aataatcctt ccaggccggg    2485
cacagtggct cgcgcctgta gt                                              2507
```

```
<210> SEQ ID NO 144
<211> LENGTH: 681
<212> TYPE: PRT
<213> ORGANISM: Homo sapiens

<400> SEQUENCE: 144
```

Met Val Ile Cys Arg Gly Ser His Ala Phe Lys Asp Leu Ile Asn Thr
1               5                   10                  15

Tyr Arg Met Ile Glu Gln Asp Asp Phe Asp Ile Asn Thr Arg Leu His
            20                  25                  30

Thr Ile Val Arg Gly Glu Asp Glu Ala Ala Met Val Glu Ser Val Gly
        35                  40                  45

Leu Ala Leu Val Lys Leu Pro Asp Val Leu Asn Arg Leu Lys Pro Asp
    50                  55                  60

Ile Met Ile Val His Gly Asp Arg Phe Asp Leu Ala Leu Ala Thr
65                  70                  75                  80

Ser Ala Ala Leu Met Asn Ile Arg Ile Leu His Ile Glu Gly Gly Glu
                85                  90                  95

Val Ser Gly Thr Ile Asp Asp Ser Ile Arg His Ala Ile Thr Lys Leu
            100                 105                 110

Ala His Tyr His Val Cys Cys Thr Arg Ser Ala Glu Gln His Leu Ile
        115                 120                 125

Ser Met Cys Glu Asp His Asp Arg Ile Leu Leu Ala Gly Cys Pro Ser
    130                 135                 140

Tyr Asp Lys Leu Leu Ser Ala Lys Asn Lys Asp Tyr Met Ser Ile Ile
145                 150                 155                 160

Arg Met Trp Leu Gly Asp Asp Val Lys Ser Lys Asp Tyr Ile Val Ala
                165                 170                 175

Leu Gln His Pro Val Thr Thr Asp Ile Lys His Ser Ile Lys Met Phe
            180                 185                 190

Glu Leu Thr Leu Asp Ala Leu Ile Ser Phe Asn Lys Arg Thr Leu Val
        195                 200                 205

Leu Phe Pro Asn Ile Asp Ala Gly Ser Lys Glu Met Val Arg Val Met
    210                 215                 220

Arg Lys Lys Gly Ile Glu His His Pro Asn Phe Arg Ala Val Lys His
225                 230                 235                 240

Val Pro Phe Asp Gln Phe Ile Gln Leu Val Ala His Ala Gly Cys Met
                245                 250                 255

Ile Gly Asn Ser Ser Cys Gly Val Arg Glu Val Gly Ala Phe Gly Thr
            260                 265                 270

Pro Val Ile Asn Leu Gly Thr Arg Gln Ile Gly Arg Glu Thr Gly Glu
        275                 280                 285

Asn Val Leu His Val Arg Asp Ala Asp Thr Gln Asp Lys Ile Leu Gln
    290                 295                 300

Ala Leu His Leu Gln Phe Gly Lys Gln Tyr Pro Cys Ser Arg Ile Tyr
305                 310                 315                 320

```
Gly Asp Gly Asn Ala Val Pro Arg Ile Leu Lys Phe Leu Lys Ser Ile
            325                 330                 335

Asp Leu Gln Glu Pro Leu Gln Lys Lys Phe Cys Phe Pro Pro Val Lys
        340                 345                 350

Glu Asn Ile Ser Gln Asp Ile Asp His Ile Leu Glu Thr Leu Ser Ala
            355                 360                 365

Leu Ala Val Asp Leu Gly Gly Thr Asn Leu Arg Val Ala Ile Val Ser
    370                 375                 380

Met Lys Gly Glu Ile Val Lys Lys Tyr Thr Gln Phe Asn Pro Lys Thr
385                 390                 395                 400

Tyr Glu Glu Arg Ile Asn Leu Ile Leu Gln Met Cys Val Glu Ala Ala
                405                 410                 415

Ala Glu Ala Val Lys Leu Asn Cys Arg Ile Leu Gly Val Gly Ile Ser
            420                 425                 430

Thr Gly Gly Arg Val Asn Pro Arg Glu Gly Ile Val Leu His Ser Thr
        435                 440                 445

Lys Leu Ile Gln Glu Trp Asn Ser Val Asp Leu Arg Thr Pro Leu Ser
    450                 455                 460

Asp Thr Leu His Leu Pro Val Trp Val Asp Asn Asp Gly Asn Cys Val
465                 470                 475                 480

Ala Leu Ala Glu Arg Lys Phe Gly Gln Gly Lys Gly Leu Glu Asn Phe
                485                 490                 495

Val Thr Leu Ile Thr Gly Thr Gly Ile Gly Gly Gly Ile Ile His Gln
            500                 505                 510

His Glu Leu Ile His Gly Ser Ser Phe Cys Ala Ala Glu Leu Gly His
        515                 520                 525

Leu Val Val Ser Leu Asp Gly Pro Asp Cys Ser Cys Gly Ser His Gly
    530                 535                 540

Cys Ile Glu Ala Tyr Ala Ser Gly Met Ala Leu Gln Arg Glu Ala Lys
545                 550                 555                 560

Lys Leu His Asp Glu Asp Leu Leu Val Glu Gly Met Ser Val Pro
                565                 570                 575

Lys Asp Glu Ala Val Gly Ala Leu His Leu Ile Gln Ala Ala Lys Leu
        580                 585                 590

Gly Asn Ala Lys Ala Gln Ser Ile Leu Arg Thr Ala Gly Thr Ala Leu
    595                 600                 605

Gly Leu Gly Val Val Asn Ile Leu His Thr Met Asn Pro Ser Leu Val
    610                 615                 620

Ile Leu Ser Gly Val Leu Ala Ser His Tyr Ile His Ile Val Lys Asp
625                 630                 635                 640

Val Ile Arg Gln Gln Ala Leu Ser Ser Val Gln Asp Val Asp Val Val
                645                 650                 655

Val Ser Asp Leu Val Asp Pro Ala Leu Leu Gly Ala Ala Ser Met Val
            660                 665                 670

Leu Asp Tyr Thr Thr Arg Arg Ile Tyr
        675                 680

<210> SEQ ID NO 145
<211> LENGTH: 80
<212> TYPE: DNA
<213> ORGANISM: Homo sapiens

<400> SEQUENCE: 145
acactagggt acagagctcg tgcttcggga tggaaaccta tggttatctg cagagggagt    60
catgctttca aggacctcat                                                80
```

```
<210> SEQ ID NO 146
<211> LENGTH: 14
<212> TYPE: PRT
<213> ORGANISM: Homo sapiens

<400> SEQUENCE: 146

Met Val Ile Cys Arg Gly Ser His Ala Phe Lys Asp Leu Ile
1               5                   10

<210> SEQ ID NO 147
<211> LENGTH: 41
<212> TYPE: DNA
<213> ORGANISM: Homo sapiens

<400> SEQUENCE: 147
atggttatct gcagagggag tcatgctttc aaggacctca t                          41

<210> SEQ ID NO 148
<211> LENGTH: 22
<212> TYPE: DNA
<213> ORGANISM: Artificial Sequence
<220> FEATURE:
<223> OTHER INFORMATION: forward primer used for specifically detecting
      the variant of the present invention (D-CTONG2001283.1)

<400> SEQUENCE: 148
tagggtacag agctcgtgct tc                                               22

<210> SEQ ID NO 149
<211> LENGTH: 22
<212> TYPE: DNA
<213> ORGANISM: Artificial Sequence
<220> FEATURE:
<223> OTHER INFORMATION: reverse primer used for specifically detecting
      the variant of the present invention (D-CTONG2001283.1)

<400> SEQUENCE: 149
atgaggtcct tgaaagcatg ac                                               22

<210> SEQ ID NO 150
<211> LENGTH: 76
<212> TYPE: DNA
<213> ORGANISM: Artificial Sequence
<220> FEATURE:
<223> OTHER INFORMATION: partial polynucleotide specific to the variant
      of the present invention (D-CTONG2001283.1), which is obtained by
      PCR using forward primer (SEQ ID NO:148) and reverse primer
      (SEQ ID NO:149)

<400> SEQUENCE: 150
tagggtacag agctcgtgct tcgggatgga aacctatggt tatctgcaga gggagtcatg      60
ctttcaagga cctcat                                                      76

<210> SEQ ID NO 151
<211> LENGTH: 29
<212> TYPE: DNA
<213> ORGANISM: Artificial Sequence
<220> FEATURE:
<223> OTHER INFORMATION: probe used for detecting the variants of the
      present invention (D-CTONG2001283.1)

<400> SEQUENCE: 151
atggaaacct atggttatct gcagaggga                                        29

<210> SEQ ID NO 152
```

```
<211> LENGTH: 16
<212> TYPE: DNA
<213> ORGANISM: Artificial Sequence
<220> FEATURE:
<223> OTHER INFORMATION: forward primer used for specifically detecting
      the known variant of the gene of the present invention
      (NM_005476.3)

<400> SEQUENCE: 152
ttcgtggcgc ttggtt                                                     16

<210> SEQ ID NO 153
<211> LENGTH: 20
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_005476.3)

<400> SEQUENCE: 153
gagttccaga cgccgtcaga                                                 20

<210> SEQ ID NO 154
<211> LENGTH: 79
<212> TYPE: DNA
<213> ORGANISM: Artificial Sequence
<220> FEATURE:
<223> OTHER INFORMATION: partial polynucleotide specific to the known
      variant of the gene of the present invention (NM_005476.3),
      which is obtained by PCR using forward primer (SEQ ID NO:152) and
      reverse primer (SEQ ID NO:153)

<400> SEQUENCE: 154
ttcgtggcgc ttggttcgtc cctcgcccga ggagcgcggt ggcggcgtgg gagggagcct     60
ctgacggcgt ctggaactc                                                  79

<210> SEQ ID NO 155
<211> LENGTH: 19
<212> TYPE: DNA
<213> ORGANISM: Artificial Sequence
<220> FEATURE:
<223> OTHER INFORMATION: probe used for specifically detecting the known
      variant of the gene of the present invention (NM_005476.3)

<400> SEQUENCE: 155
ctcgcccgag gagcgcggt                                                  19

<210> SEQ ID NO 156
<211> LENGTH: 22
<212> TYPE: DNA
<213> ORGANISM: Artificial Sequence
<220> FEATURE:
<223> OTHER INFORMATION: forward primer used for detecting the variants
      of the gene of the present invention (D-CTONG2001283.1 and
      NM_005476.3)

<400> SEQUENCE: 156
gggaacacgt cagattggaa ga                                              22

<210> SEQ ID NO 157
<211> LENGTH: 26
<212> TYPE: DNA
<213> ORGANISM: Artificial Sequence
<220> FEATURE:
<223> OTHER INFORMATION: reverse primer used for detecting the variants
      of the gene of the present invention (D-CTONG2001283.1 and
      NM_005476.3)
```

<400> SEQUENCE: 157 aggggtactgt ttaccaaact gaaggt                                              26

<210> SEQ ID NO 158
<211> LENGTH: 115
<212> TYPE: DNA
<213> ORGANISM: Artificial Sequence
<220> FEATURE:
<223> OTHER INFORMATION: partial polynucleotide common to the variants
      of the gene of the present invention (D-CTONG2001283.1 and
      NM_005476.3), which is obtained by PCR using forward primer
      (SEQ ID NO:156) and reverse primer (SEQ ID NO:157)

<400> SEQUENCE: 158
gggaacacgt cagattggaa gagaaacagg ggagaatgtt cttcatgtcc gggatgctga         60
cacccaagac aaaatattgc aagcactgca ccttcagttt ggtaaacagt accct             115

<210> SEQ ID NO 159
<211> LENGTH: 23
<212> TYPE: DNA
<213> ORGANISM: Artificial Sequence
<220> FEATURE:
<223> OTHER INFORMATION: probe used for detecting the variants of the
      gene of the present invention (D-CTONG2001283.1 and NM_005476.3)

<400> SEQUENCE: 159
ccgggatgct gacacccaag aca                                                  23

<210> SEQ ID NO 160
<211> LENGTH: 80
<212> TYPE: DNA
<213> ORGANISM: Homo sapiens

<400> SEQUENCE: 160
acactagggt acagagctcg tgcttcggga tggaaaccta tggttatctg cagagggagt         60
catgctttca aggacctcat                                                      80

<210> SEQ ID NO 161
<211> LENGTH: 1272
<212> TYPE: DNA
<213> ORGANISM: Homo sapiens

<400> SEQUENCE: 161
atctccgggc gccgagggtg actggacttg tggtgcgctg ccagggctcc gcagcgttgc         60
cggttgtatt cgctggatac cagagggcgg aagtgcagca gggttcagct ccgacctccg        120
cgccggtgct ttttgcggct gcgcgggctt cctggagtcc tgctaccgcg tccccgcagg        180
acagtgtgtc aggcgggcag cttgccccgc cgccccaccg gagcgcggaa tctgggcgtc        240
cccaccagtg cggggagccg gaaggaggag ccatagcttg gagtaggttt ggctttggtt        300
gaaataagaa tttagcctgt atgtactgct ttaactcctg gaagaatgac agatgacaaa        360
gatgtgcttc gagatgtgtg gtttggacga attccaactt gtttcacgct atatcaggat        420
gagataactg aaagggaagc agaaccatac tatgcattat ccaattggtt tgctatttga        480
tcttcttgca tcaagttcag ctcttccttg gaacatcaca gtacatttta agagttttcc        540
agaaaaagac cttctgcact gtccatctaa ggatgcaatt gaagctcatt ttatgtcatg        600
tatgaaagaa gctgatgctt taaaacataa aagtcaagta atcaatgaaa tgcagaaaaa        660
agatcacaag caactctgga tggaattgca aaatgacaga tttgaccagt tttgggccat        720
caatcggaaa ctcatggaat atcctgcaga agaaaatgga tttcgttata tccccttag         780

-continued

```
aatatatcag acaacgactg aaagaccttt cattcagaag ctgtttcgtc ctgtggctgc    840
agatggacag ttgcacacac taggagatct cctcaaagaa gtttgtcctt ctgctgttga    900
tcctgaagat ggggaaaaaa agaatcaagt gatgattcat ggaattgagc caatgttgga    960
aacacctctg cagtggctga gtgaacatct gagctacccg ataattttc ttcatattag    1020 tatcatccca cagccaacag attgaaggat caactatttg cctgaacaga atcatcctta   1080
aatgggattt atcagagcat gtcaccctt tgcttcaatc aggtttggtg gaggcaacct    1140
gaccagaaac acttcgctgc tgcaagccag acaggaaaaa gattccatgt cagataaggc   1200
aactgggctg gtcttacttt gcatcacctc tgctttcctc cactgccatc attaaacctc   1260
agctgtgaca tg                                                       1272

<210> SEQ ID NO 162
<211> LENGTH: 1272
<212> TYPE: DNA
<213> ORGANISM: Homo sapiens
<221> NAME/KEY: CDS
<222> LOCATION: (452)..(1045)

<400> SEQUENCE: 162
atctccgggc gccgagggtg actggacttg tggtgcgctg ccagggctcc gcagcgttgc     60
cggttgtatt cgctggatac cagagggcgg aagtgcagca gggttcagct ccgacctccg    120
cgccggtgct ttttgcggct gcgcgggctt cctggagtcc tgctaccgcg tccccgcagg    180
acagtgtgtc aggcgggcag cttgccccgc cgccccaccg gagcgcggaa tctgggcgtc    240
cccaccagtg cggggagccg gaaggaggag ccatagcttg gagtaggttt ggctttggtt    300
gaaataagaa tttagcctgt atgtactgct ttaactcctg gaagaatgac agatgacaaa    360
gatgtgcttc gagatgtgtg gtttggacga attccaactt gtttcacgct atatcaggat    420
gagataactg aaagggaagc agaaccatac t atg cat tat cca att ggt ttg       472
                                   Met His Tyr Pro Ile Gly Leu
                                    1               5 cta ttt gat ctt ctt gca tca agt tca gct ctt cct tgg aac atc aca     520
Leu Phe Asp Leu Leu Ala Ser Ser Ser Ala Leu Pro Trp Asn Ile Thr
    10              15                  20 gta cat ttt aag agt ttt cca gaa aaa gac ctt ctg cac tgt cca tct     568
Val His Phe Lys Ser Phe Pro Glu Lys Asp Leu Leu His Cys Pro Ser
 25                  30                  35 aag gat gca att gaa gct cat ttt atg tca tgt atg aaa gaa gct gat     616
Lys Asp Ala Ile Glu Ala His Phe Met Ser Cys Met Lys Glu Ala Asp
 40                  45                  50                  55 gct tta aaa cat aaa agt caa gta atc aat gaa atg cag aaa aaa gat     664
Ala Leu Lys His Lys Ser Gln Val Ile Asn Glu Met Gln Lys Lys Asp
                 60                  65                  70 cac aag caa ctc tgg atg gaa ttg caa aat gac aga ttt gac cag ttt     712
His Lys Gln Leu Trp Met Glu Leu Gln Asn Asp Arg Phe Asp Gln Phe
     75                  80                  85 tgg gcc atc aat cgg aaa ctc atg gaa tat cct gca gaa gaa aat gga     760
Trp Ala Ile Asn Arg Lys Leu Met Glu Tyr Pro Ala Glu Glu Asn Gly
         90                  95                 100 ttt cgt tat atc ccc ttt aga ata tat cag aca acg act gaa aga cct     808
Phe Arg Tyr Ile Pro Phe Arg Ile Tyr Gln Thr Thr Thr Glu Arg Pro
            105                 110                 115 ttc att cag aag ctg ttt cgt cct gtg gct gca gat gga cag ttg cac     856
Phe Ile Gln Lys Leu Phe Arg Pro Val Ala Ala Asp Gly Gln Leu His
120                 125                 130                 135 aca cta gga gat ctc ctc aaa gaa gtt tgt cct tct gct gtt gat cct     904
Thr Leu Gly Asp Leu Leu Lys Glu Val Cys Pro Ser Ala Val Asp Pro
```

|  |  |  |  |  | 140 |  |  | 145 |  |  |  | 150 |  |  |  |
|---|---|---|---|---|---|---|---|---|---|---|---|---|---|---|---|
| gaa | gat | ggg | gaa | aaa | aag | aat | caa | gtg | atg | att | cat | gga | att | gag | cca | 952 |
| Glu | Asp | Gly | Glu | Lys | Lys | Asn | Gln | Val | Met | Ile | His | Gly | Ile | Glu | Pro |  |
|  |  | 155 |  |  |  |  | 160 |  |  |  |  | 165 |  |  |  |  |
| atg | ttg | gaa | aca | cct | ctg | cag | tgg | ctg | agt | gaa | cat | ctg | agc | tac | ccg | 1000 |
| Met | Leu | Glu | Thr | Pro | Leu | Gln | Trp | Leu | Ser | Glu | His | Leu | Ser | Tyr | Pro |  |
|  |  | 170 |  |  |  |  | 175 |  |  |  |  | 180 |  |  |  |  |
| gat | aat | ttt | ctt | cat | att | agt | atc | atc | cca | cag | cca | aca | gat | tga |  | 1045 |
| Asp | Asn | Phe | Leu | His | Ile | Ser | Ile | Ile | Pro | Gln | Pro | Thr | Asp |  |  |  |
|  |  | 185 |  |  |  |  | 190 |  |  |  |  | 195 |  |  |  |  | aggatcaact atttgcctga acagaatcat ccttaaatgg gatttatcag agcatgtcac 1105 ccttttgctt caatcaggtt tggtggaggc aacctgacca gaaacacttc gctgctgcaa 1165 gccagacagg aaaaagattc catgtcagat aaggcaactg gctggtctt actttgcatc 1225 acctctgctt tcctccactg ccatcattaa acctcagctg tgacatg 1272

<210> SEQ ID NO 163
<211> LENGTH: 197
<212> TYPE: PRT
<213> ORGANISM: Homo sapiens
<400> SEQUENCE: 163

Met His Tyr Pro Ile Gly Leu Leu Phe Asp Leu Leu Ala Ser Ser Ser
1               5                   10                  15

Ala Leu Pro Trp Asn Ile Thr Val His Phe Lys Ser Phe Pro Glu Lys
            20                  25                  30

Asp Leu Leu His Cys Pro Ser Lys Asp Ala Ile Glu Ala His Phe Met
        35                  40                  45

Ser Cys Met Lys Glu Ala Asp Ala Leu Lys His Lys Ser Gln Val Ile
    50                  55                  60

Asn Glu Met Gln Lys Lys Asp His Lys Gln Leu Trp Met Glu Leu Gln
65                  70                  75                  80

Asn Asp Arg Phe Asp Gln Phe Trp Ala Ile Asn Arg Lys Leu Met Glu
                85                  90                  95

Tyr Pro Ala Glu Glu Asn Gly Phe Arg Tyr Ile Pro Arg Ile Tyr
            100                 105                 110

Gln Thr Thr Thr Glu Arg Pro Phe Ile Gln Lys Leu Phe Arg Pro Val
        115                 120                 125

Ala Ala Asp Gly Gln Leu His Thr Leu Gly Asp Leu Leu Lys Glu Val
    130                 135                 140

Cys Pro Ser Ala Val Asp Pro Glu Asp Gly Lys Lys Asn Gln Val
145                 150                 155                 160

Met Ile His Gly Ile Glu Pro Met Leu Glu Thr Pro Leu Gln Trp Leu
                165                 170                 175

Ser Glu His Leu Ser Tyr Pro Asp Asn Phe Leu His Ile Ser Ile Ile
            180                 185                 190

Pro Gln Pro Thr Asp
        195

<210> SEQ ID NO 164
<211> LENGTH: 42
<212> TYPE: DNA
<213> ORGANISM: Homo sapiens
<400> SEQUENCE: 164
agggaagcag aaccatacta tgcattatcc aattggtttg ct                            42

<210> SEQ ID NO 165
<211> LENGTH: 1
<212> TYPE: PRT
<213> ORGANISM: Homo sapiens

<400> SEQUENCE: 165

Met
1

<210> SEQ ID NO 166
<211> LENGTH: 23
<212> TYPE: DNA
<213> ORGANISM: Homo sapiens

<400> SEQUENCE: 166
atgcattatc caattggttt gct                                           23

<210> SEQ ID NO 167
<211> LENGTH: 8
<212> TYPE: PRT
<213> ORGANISM: Homo sapiens

<400> SEQUENCE: 167

Met His Tyr Pro Ile Gly Leu Leu
1               5

<210> SEQ ID NO 168
<211> LENGTH: 128
<212> TYPE: DNA
<213> ORGANISM: Homo sapiens

<400> SEQUENCE: 168
ttgcttttgc caagagtaag ttatttgacg ttggtaactg acaaagtgaa aaagcacttt      60
cagaaggtta tgagacaaga agacattagt gagatatggt ttgaatatga aggcacacca     120
ctgaaatg                                                             128

<210> SEQ ID NO 169
<211> LENGTH: 43
<212> TYPE: PRT
<213> ORGANISM: Homo sapiens

<400> SEQUENCE: 169

Leu Leu Leu Pro Arg Val Ser Tyr Leu Thr Leu Val Thr Asp Lys Val
1               5                   10                  15

Lys Lys His Phe Gln Lys Val Met Arg Gln Glu Asp Ile Ser Glu Ile
            20                  25                  30

Trp Phe Glu Tyr Glu Gly Thr Pro Leu Lys Trp
        35                  40

<210> SEQ ID NO 170
<211> LENGTH: 1767
<212> TYPE: DNA
<213> ORGANISM: Homo sapiens

<400> SEQUENCE: 170
acttgtggtg cgctgccagg gctccgcagc gttgccggtt gtattcgctg ataccagag       60 ggcggaagtg cagcagggtt cagctccgac ctccgcgccg gtgctttttg cggctgcgcg     120
ggcttcctgg agtcctgcta ccgcgtcccc gcaggacagt gtgtcaggcg ggcagcttgc     180
cccgccgccc caccggagcg cggaatctgg gcgtccccac cagtgcgggg agccggaagg     240
aggagccata gcttggagta ggtttggctt tggttgaaat aagaatttag cctgtatgta     300

```
ctgctttaac tcctggaaga atgacagatg acaaagatgt gcttcgagat gtgtggtttg      360
gacgaattcc aacttgtttc acgctatatc aggatgagat aactgaaagg gaagcagaac      420
catactattt gcttttgcca agagtaagtt atttgacgtt ggtaactgac aaagtgaaaa      480
agcactttca gaaggttatg agacaagaag acattagtga gatatggttt gaatatgaag      540
gcacaccact gaaatggcat tatccaattg gtttgctatt tgatcttctt gcatcaagtt      600
cagctcttcc ttggaacatc acagtacatt ttaagagttt tccagaaaaa gaccttctgc      660
actgtccatc taaggatgca attgaagctc attttatgtc atgtatgaaa gaagctgatg      720 cttttaaaaca taaagtcaa gtaatcaatg aaatgcagaa aaaagatcac aagcaactct      780
ggatgggatt gcaaaatgac agatttgacc agttttgggc catcaatcgg aaactcatgg      840
aatatcctgc agaagaaaat ggatttcgtt atatccccct tagaatatat cagacaacga      900
ctgaaagacc tttcattcag aagctgtttc gtcctgtggc tgcagatgga cagttgcaca      960
cactaggaga tctcctcaaa gaagtttgtc cttctgctat tgatcctgaa gatggggaaa     1020
aaaagaatca agtgatgatt catggaattg agccaatgtt ggaaacacct ctgcagtggc     1080
tgagtggaca tctgagctac ccggataatt ttcttcatat tagtatcatc ccacagccaa     1140
cagattgaag gatcaactat ttgcctgaac agaatcatcc ttaaatggga tttatcagag     1200
catgtcaccc ttttgcttca atcaggtttg gtggaggcaa cctgaccaga acacttcgc     1260 tgctgcaagc cagacaggaa aaagattcca tgtcagataa ggcaactggg ctggtcttac     1320
tttgcatcac ctctgctttc ctccactgcc atcattaaac ctcagctgtg acatgaaaga     1380
cttaccggac cactgaaggt cttctgtaaa atataatgaa gctgaaacct ttggcctaag     1440
aagaaaatgg aagtatgtgc cactcgattt gtatttctga ttaacaaata aacaggggta     1500
tttcctaagg tgaccatggt tgaactttag ctcatgaaag tggaaacatt ggtttaattt     1560
tcaagagaat taagaaagta aaagagaaat tctgttatca ataacttgca agtaattttt     1620
tgtaaaagat tgaattacag taaacccatc tttccttaac gaaaatttcc tatgtttaca     1680
gtctgtctat tggtatgcaa tcttgtaact ttgataatga acagtgagag atttttaaat     1740
aaagcctcta aatatgtttt gtcattt                                          1767

<210> SEQ ID NO 171
<211> LENGTH: 1767
<212> TYPE: DNA
<213> ORGANISM: Homo sapiens
<221> NAME/KEY: CDS
<222> LOCATION: (321)..(1148)

<400> SEQUENCE: 171
acttgtggtg cgctgccagg gctccgcagc gttgccggtt gtattcgctg gataccagag       60
ggcggaagtg cagcagggtt cagctccgac ctccgcgccg gtgcttttg cggctgcgcg      120 ggcttcctgg agtcctgcta ccgcgtcccc gcaggacagt gtgtcaggcg ggcagcttgc      180
cccgccgccc caccggagcg cggaatctgg gcgtccccac cagtgcgggg agccggaagg      240
aggagccata gcttggagta ggtttggctt tggttgaaat aagaatttag cctgtatgta      300
ctgctttaac tcctggaaga atg aca gat gac aaa gat gtg ctt cga gat gtg      353
                        Met Thr Asp Asp Lys Asp Val Leu Arg Asp Val
                         1               5                  10 tgg ttt gga cga att cca act tgt ttc acg cta tat cag gat gag ata      401
Trp Phe Gly Arg Ile Pro Thr Cys Phe Thr Leu Tyr Gln Asp Glu Ile
         15                  20                  25 act gaa agg gaa gca gaa cca tac tat ttg ctt ttg cca aga gta agt      449
Thr Glu Arg Glu Ala Glu Pro Tyr Tyr Leu Leu Leu Pro Arg Val Ser
```

-continued

```
                 30                    35                     40
tat ttg acg ttg gta act gac aaa gtg aaa aag cac ttt cag aag gtt      497
Tyr Leu Thr Leu Val Thr Asp Lys Val Lys Lys His Phe Gln Lys Val
    45                  50                  55 atg aga caa gaa gac att agt gag ata tgg ttt gaa tat gaa ggc aca      545
Met Arg Gln Glu Asp Ile Ser Glu Ile Trp Phe Glu Tyr Glu Gly Thr
60                  65                  70                  75 cca ctg aaa tgg cat tat cca att ggt ttg cta ttt gat ctt ctt gca      593
Pro Leu Lys Trp His Tyr Pro Ile Gly Leu Leu Phe Asp Leu Leu Ala
                80                  85                  90 tca agt tca gct ctt cct tgg aac atc aca gta cat ttt aag agt ttt      641
Ser Ser Ser Ala Leu Pro Trp Asn Ile Thr Val His Phe Lys Ser Phe
            95                  100                 105 cca gaa aaa gac ctt ctg cac tgt cca tct aag gat gca att gaa gct      689
Pro Glu Lys Asp Leu Leu His Cys Pro Ser Lys Asp Ala Ile Glu Ala
        110                 115                 120 cat ttt atg tca tgt atg aaa gaa gct gat gct tta aaa cat aaa agt      737
His Phe Met Ser Cys Met Lys Glu Ala Asp Ala Leu Lys His Lys Ser
    125                 130                 135 caa gta atc aat gaa atg cag aaa aaa gat cac aag caa ctc tgg atg      785
Gln Val Ile Asn Glu Met Gln Lys Lys Asp His Lys Gln Leu Trp Met
140                 145                 150                 155 gga ttg caa aat gac aga ttt gac cag ttt tgg gcc atc aat cgg aaa      833
Gly Leu Gln Asn Asp Arg Phe Asp Gln Phe Trp Ala Ile Asn Arg Lys
                160                 165                 170 ctc atg gaa tat cct gca gaa gaa aat gga ttt cgt tat atc ccc ttt      881
Leu Met Glu Tyr Pro Ala Glu Glu Asn Gly Phe Arg Tyr Ile Pro Phe
            175                 180                 185 aga ata tat cag aca acg act gaa aga cct ttc att cag aag ctg ttt      929
Arg Ile Tyr Gln Thr Thr Thr Glu Arg Pro Phe Ile Gln Lys Leu Phe
        190                 195                 200 cgt cct gtg gct gca gat gga cag ttg cac aca cta gga gat ctc ctc      977
Arg Pro Val Ala Ala Asp Gly Gln Leu His Thr Leu Gly Asp Leu Leu
    205                 210                 215 aaa gaa gtt tgt cct tct gct att gat cct gaa gat ggg gaa aaa aag     1025
Lys Glu Val Cys Pro Ser Ala Ile Asp Pro Glu Asp Gly Glu Lys Lys
220                 225                 230                 235 aat caa gtg atg att cat gga att gag cca atg ttg gaa aca cct ctg     1073
Asn Gln Val Met Ile His Gly Ile Glu Pro Met Leu Glu Thr Pro Leu
                240                 245                 250 cag tgg ctg agt gga cat ctg agc tac ccg gat aat ttt ctt cat att     1121
Gln Trp Leu Ser Gly His Leu Ser Tyr Pro Asp Asn Phe Leu His Ile
            255                 260                 265 agt atc atc cca cag cca aca gat tga aggatcaact atttgcctga           1168
Ser Ile Ile Pro Gln Pro Thr Asp
        270                 275 acagaatcat ccttaaatgg gatttatcag agcatgtcac ccttttgctt caatcaggtt   1228
tggtggaggc aacctgacca gaaacacttc gctgctgcaa gccagacagg aaaaagattc   1288
catgtcagat aaggcaactg gctggtctt actttgcatc acctctgctt tcctccactg    1348
ccatcattaa acctcagctg tgacatgaaa gacttaccgg accactgaag gtcttctgta   1408
aaatataatg aagctgaaac ctttggccta agaagaaaat ggaagtatgt gccactcgat   1468
ttgtatttct gattaacaaa taaacagggg tatttcctaa ggtgaccatg gttgaacttt   1528
agctcatgaa agtggaaaca ttggtttaat tttcaagaga attaagaaag taaagagaa    1588 attctgttat caataacttg caagtaattt tttgtaaaag attgaattac agtaaaccca   1648
tctttcctta acgaaaattt cctatgttta cagtctgtct attggtatgc aatcttgtaa   1708
```

```
ctttgataat gaacagtgag agatttttaa ataaagcctc taaatatgtt ttgtcatttt    1767

<210> SEQ ID NO 172
<211> LENGTH: 275
<212> TYPE: PRT
<213> ORGANISM: Homo sapiens

<400> SEQUENCE: 172
```

Met Thr Asp Asp Lys Asp Val Leu Arg Asp Val Trp Phe Gly Arg Ile
1               5                   10                  15

Pro Thr Cys Phe Thr Leu Tyr Gln Asp Glu Ile Thr Glu Arg Glu Ala
            20                  25                  30

Glu Pro Tyr Tyr Leu Leu Pro Arg Val Ser Tyr Leu Thr Leu Val
        35                  40                  45

Thr Asp Lys Val Lys Lys His Phe Gln Lys Val Met Arg Gln Glu Asp
    50                  55                  60

Ile Ser Glu Ile Trp Phe Glu Tyr Gly Thr Pro Leu Lys Trp His
65                  70                  75                  80

Tyr Pro Ile Gly Leu Leu Phe Asp Leu Leu Ala Ser Ser Ala Leu
            85                  90                  95

Pro Trp Asn Ile Thr Val His Phe Lys Ser Phe Pro Glu Lys Asp Leu
            100                 105                 110

Leu His Cys Pro Ser Lys Asp Ala Ile Glu Ala His Phe Met Ser Cys
        115                 120                 125

Met Lys Glu Ala Asp Ala Leu Lys His Lys Ser Gln Val Ile Asn Glu
    130                 135                 140

Met Gln Lys Lys Asp His Lys Gln Leu Trp Met Gly Leu Gln Asn Asp
145                 150                 155                 160

Arg Phe Asp Gln Phe Trp Ala Ile Asn Arg Lys Leu Met Glu Tyr Pro
                165                 170                 175

Ala Glu Glu Asn Gly Phe Arg Tyr Ile Pro Phe Arg Ile Tyr Gln Thr
            180                 185                 190

Thr Thr Glu Arg Pro Phe Ile Gln Lys Leu Phe Arg Pro Val Ala Ala
        195                 200                 205

Asp Gly Gln Leu His Thr Leu Gly Asp Leu Leu Lys Glu Val Cys Pro
    210                 215                 220

Ser Ala Ile Asp Pro Glu Asp Gly Glu Lys Lys Asn Gln Val Met Ile
225                 230                 235                 240

His Gly Ile Glu Pro Met Leu Glu Thr Pro Leu Gln Trp Leu Ser Gly
                245                 250                 255

His Leu Ser Tyr Pro Asp Asn Phe Leu His Ile Ser Ile Ile Pro Gln
            260                 265                 270

Pro Thr Asp
        275

```
<210> SEQ ID NO 173
<211> LENGTH: 24
<212> TYPE: DNA
<213> ORGANISM: Artificial Sequence
<220> FEATURE:
<223> OTHER INFORMATION: forward primer used for specifically detecting
      the variant of the present invention (D-OCBBF2013203.1)

<400> SEQUENCE: 173
ccatactatg cattatccaa ttgg                                              24

<210> SEQ ID NO 174
<211> LENGTH: 22
```

```
<212> TYPE: DNA
<213> ORGANISM: Artificial Sequence
<220> FEATURE:
<223> OTHER INFORMATION: reverse primer used for specifically detecting
      the variant of the present invention (D-OCBBF2013203.1)

<400> SEQUENCE: 174
gatggacagt gcagaaggtc tt                                              22

<210> SEQ ID NO 175
<211> LENGTH: 123
<212> TYPE: DNA
<213> ORGANISM: Artificial Sequence
<220> FEATURE:
<223> OTHER INFORMATION: partial polynucleotide specific to the variant
      of the present invention (D-OCBBF2013203.1), which is obtained by
      PCR using forward primer (SEQ ID NO:173) and reverse primer
      (SEQ ID NO:174)

<400> SEQUENCE: 175
ccatactatg cattatccaa ttggtttgct atttgatctt cttgcatcaa gttcagctct     60
tccttggaac atcacagtac attttaagag ttttccagaa aaagaccttc tgcactgtcc    120
atc                                                                 123

<210> SEQ ID NO 176
<211> LENGTH: 24
<212> TYPE: DNA
<213> ORGANISM: Artificial Sequence
<220> FEATURE:
<223> OTHER INFORMATION: forward primer used for specifically detecting
      the known variant of the gene of the present invention
      (NM_004849.1)

<400> SEQUENCE: 176
catactattt gcttttgcca agag                                            24

<210> SEQ ID NO 177
<211> LENGTH: 26
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_004849.1)

<400> SEQUENCE: 177
tcttcttgtc tcataacctt ctgaaa                                          26

<210> SEQ ID NO 178
<211> LENGTH: 91
<212> TYPE: DNA
<213> ORGANISM: Artificial Sequence
<220> FEATURE:
<223> OTHER INFORMATION: partial polynucleotide specific to the known
      variant of the gene of the present invention (NM_004849.1), which
      is obtained by PCR using forward primer (SEQ ID NO:176) and
      reverse primer (SEQ ID NO:177)

<400> SEQUENCE: 178
catactattt gcttttgcca agagtaagtt atttgacgtt ggtaactgac aaagtgaaaa     60
agcactttca gaaggttatg agacaagaag a                                    91

<210> SEQ ID NO 179
<211> LENGTH: 21
<212> TYPE: DNA
<213> ORGANISM: Artificial Sequence
<220> FEATURE:
```

```
<223> OTHER INFORMATION: forward primer used for detecting the variants
      of the gene of the present invention (D-OCBBF2013203.1 and
      NM_004849.1)

<400> SEQUENCE: 179
gctcttcctt ggaacatcac a                                              21

<210> SEQ ID NO 180
<211> LENGTH: 26
<212> TYPE: DNA
<213> ORGANISM: Artificial Sequence
<220> FEATURE:
<223> OTHER INFORMATION: reverse primer used for detecting the variants
      of the gene of the present invention (D-OCBBF2013203.1 and
      NM_004849.1)

<400> SEQUENCE: 180
catacatgac ataaaatgag cttcaa                                         26

<210> SEQ ID NO 181
<211> LENGTH: 105
<212> TYPE: DNA
<213> ORGANISM: Artificial Sequence
<220> FEATURE:
<223> OTHER INFORMATION: partial polynucleotide common to the variants
      of the gene of the present invention (D-OCBBF2013203.1 and
      NM_004849.1), which is obtained by PCR using forward primer
      (SEQ ID NO:179) and reverse primer (SEQ ID NO:180)

<400> SEQUENCE: 181
gctcttcctt ggaacatcac agtacatttt aagagttttc cagaaaaaga ccttctgcac    60
tgtccatcta aggatgcaat tgaagctcat tttatgtcat gtatg                   105

<210> SEQ ID NO 182
<211> LENGTH: 567
<212> TYPE: DNA
<213> ORGANISM: Homo sapiens

<400> SEQUENCE: 182
atctccgggc gccgagggtg actggacttg tggtgcgctg ccagggctcc gcagcgttgc    60
cggttgtatt cgctggatac cagagggcgg aagtgcagca gggttcagct ccgacctccg   120
cgccggtgct ttttgcggct gcgcgggctt cctggagtcc tgctaccgcg tcccgcagg   180 acagtgtgtc aggcgggcag cttgccccgc cgccccaccg gagcgcggaa tctgggcgtc   240
cccaccagtg cggggagccg gaaggaggag ccatagcttg gagtaggttt ggctttggtt   300
gaaataagaa tttagcctgt atgtactgct ttaactcctg gaagaatgac agatgacaaa   360
gatgtgcttc gagatgtgtg gtttggacga attccaactt gtttcacgct atatcaggat   420
gagataactg aaagggaagc agaaccatac tatgcattat ccaattggtt tgctatttga   480
tcttcttgca tcaagttcag ctcttccttg gaacatcaca gtacattta agagttttcc   540 agaaaaagac cttctgcact gtccatc                                      567

<210> SEQ ID NO 183
<211> LENGTH: 1221
<212> TYPE: DNA
<213> ORGANISM: Homo sapiens

<400> SEQUENCE: 183
ctctctccgt cgccatggaa acgaaagcgg ccaagtagag ctccgtcctg acgcgccgcc    60
tcccgtgggc tccggccggc taagccgcgg cggacaacta tgctgaaagc caagatcctc   120
ttcgtggggc cctgcgagag tggaaaaact gttttggcca actttctgac agaatcttct   180
```

-continued

```
gacatcactg aatacagccc aacccaagga gtgaggatcc tagaatttga gaacccgcat    240
gttaccagca acaacaaagg cacgggctgt gaattcgagc tatgggactg tggtggcgat    300
gctaagtttg agtcctgctg gccggccctg atgaaggatg ctcatggagt ggtgatcgtc    360
ttcaatgctg acatcccaag ccaccggaag gaaatggaga tgtggtattc ctgctttgtc    420
caacagccgt ccttacagga cacacagtgt atgctaattg cacaccacaa accaggctct    480
ggagatgata aaggaagcct gtcttttgtg aaggaaactg gaatttctct tcctcttttg    540
tcttgaatgt tttggacacc tacatattgt cccatgtcct agaaaccagc agctctgtcc    600
agttactgag cacctactgt accctaggca attgttaccc tctccatgtg agtccactac    660
gtctctacta aaaatacaaa aattagccag gcatgatggc aggcgcctgt actcccagct    720 actcagggggg ctaaggcagg agaattgctt gagcccagga ggcggagatt gcagtgagtt    780
gagatctcac cactcactc cagtttgtgt gacagggcga gacaccatct caaaaaaaa    840 aaaaaaaaag agaaagacc gggtgcggtg gctcagacct gtaatcccaa cactttggga    900
ggccaaggtg tgcggatcac ttgaggtcgg gagttctaga ccaacctggc caacacggtg    960
aaaccccatc tctactaaaa atacaaaat tggccagggg tggtggtgca tacctgtagt    1020
cccagctact caggaggctg aggcaagaga atcacttgta cctggggggt agaggttgca    1080
gtgagctgag attgtgccat tgcactccag cctggacaac aagagtgaaa ctctgtttca    1140
aaaaaaaaaa gagcagaata cagagtggga aaatccttgt agctattctt gggtacaact    1200
aggggggcac tctttctgaa a                                              1221
```

<210> SEQ ID NO 184
<211> LENGTH: 1221
<212> TYPE: DNA
<213> ORGANISM: Homo sapiens
<221> NAME/KEY: CDS
<222> LOCATION: (100)..(546)

<400> SEQUENCE: 184

```
ctctctccgt cgccatggaa acgaaagcgg ccaagtagag ctccgtcctg acgcgccgcc    60
tcccgtgggc tccggccggc taagccgcgg cggacaact atg ctg aaa gcc aag       114
                                              Met Leu Lys Ala Lys
                                              1               5 atc ctc ttc gtg ggg ccc tgc gag agt gga aaa act gtt ttg gcc aac      162
Ile Leu Phe Val Gly Pro Cys Glu Ser Gly Lys Thr Val Leu Ala Asn
            10                  15                  20 ttt ctg aca gaa tct tct gac atc act gaa tac agc cca acc caa gga      210
Phe Leu Thr Glu Ser Ser Asp Ile Thr Glu Tyr Ser Pro Thr Gln Gly
        25                  30                  35 gtg agg atc cta gaa ttt gag aac ccg cat gtt acc agc aac aac aaa      258
Val Arg Ile Leu Glu Phe Glu Asn Pro His Val Thr Ser Asn Asn Lys
    40                  45                  50 ggc acg ggc tgt gaa ttc gag cta tgg gac tgt ggt ggc gat gct aag      306
Gly Thr Gly Cys Glu Phe Glu Leu Trp Asp Cys Gly Gly Asp Ala Lys
55                  60                  65 ttt gag tcc tgc tgg ccg gcc ctg atg aag gat gct cat gga gtg gtg      354
Phe Glu Ser Cys Trp Pro Ala Leu Met Lys Asp Ala His Gly Val Val
70                  75                  80                  85 atc gtc ttc aat gct gac atc cca agc cac cgg aag gaa atg gag atg      402
Ile Val Phe Asn Ala Asp Ile Pro Ser His Arg Lys Glu Met Glu Met
            90                  95                 100 tgg tat tcc tgc ttt gtc caa cag ccg tcc tta cag gac aca cag tgt      450
Trp Tyr Ser Cys Phe Val Gln Gln Pro Ser Leu Gln Asp Thr Gln Cys
        105                 110                 115
```

```
atg cta att gca cac cac aaa cca ggc tct gga gat gat aaa gga agc       498
Met Leu Ile Ala His His Lys Pro Gly Ser Gly Asp Asp Lys Gly Ser
    120                 125                 130 ctg tct ttg tgt aag gaa act gga att tct ctt cct ctt ttg tct tga       546
Leu Ser Leu Cys Lys Glu Thr Gly Ile Ser Leu Pro Leu Leu Ser
    135                 140                 145 atgttttgga cacctacata ttgtcccatg tcctagaaac cagcagctct gtccagttac     606
tgagcaccta ctgtacccta ggcaattgtt accctctcca tgtgagtcca ctacgtctct    666
actaaaaata caaaaattag ccaggcatga tggcaggcgc ctgtactccc agctactcag    726
ggggctaagg caggagaatt gcttgagccc aggaggcgga gattgcagtg agttgagatc    786
tcaccactac actccagttt gtgtgacagg gcgagacacc atctcaaaaa aaaaaaaaaa    846
aaagagaaaa gaccgggtgc ggtggctcag acctgtaatc ccaacactttt gggaggccaa   906
ggtgtgcgga tcacttgagg tcgggagttc tagaccaacc tggccaacac ggtgaaaccc    966
catctctact aaaaatacaa aaattggcca ggggtggtgg tgcatacctg tagtcccagc    1026
tactcaggag gctgaggcaa gagaatcact tgtacctggg gggtagaggt tgcagtgagc    1086
tgagattgtg ccattgcact ccagcctgga caacaagagt gaaactctgt ttcaaaaaaa   1146
aaaagagcag aatacagagt gggaaaatcc ttgtagctat tcttgggtac aactaggggg    1206
gcactctttc tgaaa                                                    1221
```

<210> SEQ ID NO 185
<211> LENGTH: 148
<212> TYPE: PRT
<213> ORGANISM: Homo sapiens

<400> SEQUENCE: 185

```
Met Leu Lys Ala Lys Ile Leu Phe Val Gly Pro Cys Glu Ser Gly Lys
1               5                   10                  15

Thr Val Leu Ala Asn Phe Leu Thr Glu Ser Ser Asp Ile Thr Glu Tyr
            20                  25                  30

Ser Pro Thr Gln Gly Val Arg Ile Leu Glu Phe Glu Asn Pro His Val
        35                  40                  45

Thr Ser Asn Asn Lys Gly Thr Gly Cys Glu Phe Glu Leu Trp Asp Cys
    50                  55                  60

Gly Gly Asp Ala Lys Phe Glu Ser Cys Trp Pro Ala Leu Met Lys Asp
65                  70                  75                  80

Ala His Gly Val Val Ile Val Phe Asn Ala Asp Ile Pro Ser His Arg
                85                  90                  95

Lys Glu Met Glu Met Trp Tyr Ser Cys Phe Val Gln Gln Pro Ser Leu
            100                 105                 110

Gln Asp Thr Gln Cys Met Leu Ile Ala His His Lys Pro Gly Ser Gly
        115                 120                 125

Asp Asp Lys Gly Ser Leu Ser Leu Cys Lys Glu Thr Gly Ile Ser Leu
    130                 135                 140

Pro Leu Leu Ser
145
```

<210> SEQ ID NO 186
<211> LENGTH: 713
<212> TYPE: DNA
<213> ORGANISM: Homo sapiens

<400> SEQUENCE: 186

```
gtaaggaaac tggaatttct cttcctcttt tgtcttgaat gttttggaca cctacatatt     60
```

```
gtcccatgtc ctagaaacca gcagctctgt ccagttactg agcacctact gtaccctagg    120
caattgttac cctctccatg tgagtccact acgtctctac taaaaataca aaaattagcc    180
aggcatgatg gcaggcgcct gtactcccag ctactcaggg ggctaaggca ggagaattgc    240
ttgagcccag gaggcggaga ttgcagtgag ttgagatctc accactacac tccagtttgt    300
gtgacagggc gagacaccat ctcaaaaaaa aaaaaaaaaa agagaaaaga ccgggtgcgg    360
tggctcagac ctgtaatccc aacactttgg gaggccaagg tgtgcggatc acttgaggtc    420
gggagttcta gaccaacctg gccaacacgt gaaacccca tctctactaa aaatacaaaa     480
attggccagg ggtggtggtg catacctgta gtcccagcta ctcaggaggc tgaggcaaga    540
gaatcacttg tacctggggg gtagaggttg cagtgagctg agattgtgcc attgcactcc    600
agcctggaca acaagagtga aactctgttt caaaaaaaaa aagagcagaa tacagagtgg    660
gaaaatcctt gtagctattc ttgggtacaa ctagggggggc actctttctg aaa          713

<210> SEQ ID NO 187
<211> LENGTH: 12
<212> TYPE: PRT
<213> ORGANISM: Homo sapiens

<400> SEQUENCE: 187

Cys Lys Glu Thr Gly Ile Ser Leu Pro Leu Leu Ser
1               5                   10

<210> SEQ ID NO 188
<211> LENGTH: 38
<212> TYPE: DNA
<213> ORGANISM: Homo sapiens

<400> SEQUENCE: 188
gtaaggaaac tggaatttct cttcctcttt tgtcttga                              38

<210> SEQ ID NO 189
<211> LENGTH: 1177
<212> TYPE: DNA
<213> ORGANISM: Homo sapiens

<400> SEQUENCE: 189
aaaaaaaaaa cgaaagcggc caagtagagc tccgtcctga cgcgccgcct cccgtgggct     60
ccggccggct aagccgcggc ggacaactat gctgaaagcc aagatcctct tcgtggggcc    120
ttgcgaggtt tgagtcctgc tggccggccc tgatgaagga tgctcatgga gtggtgatcg    180
tcttcaatgc tgacatccca agccaccgga ggaaatgga gatgtggtat tcctgctttg     240
tccaacagcc gtccttacag gacacacagt gtatgctaat tgcacaccac aaaccaggct    300
ctggagatga taaaggaagc ctgtctttgt gtaaggaaac tggaatttct cttcctcttt    360
tgtcttgaat gttttggaca cctacatatt gtcccatgtc ctagaaacca gcagctctgt    420
ccagttactg agcacctact gtaccctagg caattgttac cctctccatg tgagtccact    480
acgtctctac taaaaataca aaaattagcc aggcatgatg gcaggcgcct gtactcccag    540
ctactcaggg ggctaaggca ggagaattgc ttgagcccag gaggcggaga ttgcagtgag    600
ttgagatctc accactacac tccagtttgt gtgacagggc gagacaccat ctcaaaaaaa    660
aaaaaaaaaa aagagaaaag accgggtgcg gtggctcaga cctgtaatcc caacactttg    720
ggaggccaag gtgtgcggat cacttgaggt cgggagttct agaccaacct ggccaacacg    780
gtgaaacccc atctctacta aaatacaaaa attagccag gggtggtggt gcatacctgt     840
```

```
aatcccagct actcaggagg ctgaggcaag agaatcactt gtacctggga ggtagaggtt    900
gcagtgagct gagattgtgc cattgcactc cagcctggac aacaagagtg aaactctgtt    960
tcaaaaaaaa aaagagcaga atacagagtg ggaaaatcct tgtagctatt cttgggtaca   1020 actaggggg cactctttct gaaagaactt ttctggagaa aaacctccaa ttcacataac    1080
acacatccca gaggtgacac agtcatcctg aaaagaact cacaaaatat tcagaaacaa    1140
aatgagaata atagagaatc tattcctttc tggttta                             1177
```

<210> SEQ ID NO 190
<211> LENGTH: 1177
<212> TYPE: DNA
<213> ORGANISM: Homo sapiens
<221> NAME/KEY: CDS
<222> LOCATION: (307)..(747)

<400> SEQUENCE: 190

```
aaaaaaaaaa cgaaagcggc caagtagagc tccgtcctga cgcgccgcct cccgtgggct     60
ccggccggct aagccgcggc ggacaactat gctgaaagcc aagatcctct tcgtggggcc    120
ttgcgaggtt tgagtcctgc tggccggccc tgatgaagga tgctcatgga gtggtgatcg    180
tcttcaatgc tgacatccca agccaccgga aggaaatgga gatgtggtat tcctgctttg    240
tccaacagcc gtccttacag gacacacagt gtatgctaat tgcacaccac aaaccaggct    300 ctggag atg ata aag gaa gcc tgt ctt tgt gta agg aaa ctg gaa ttt     348
       Met Ile Lys Glu Ala Cys Leu Cys Val Arg Lys Leu Glu Phe
         1               5                  10 ctc ttc ctc ttt tgt ctt gaa tgt ttt gga cac cta cat att gtc cca     396
Leu Phe Leu Phe Cys Leu Glu Cys Phe Gly His Leu His Ile Val Pro
 15              20                  25                  30 tgt cct aga aac cag cag ctc tgt cca gtt act gag cac cta ctg tac     444
Cys Pro Arg Asn Gln Gln Leu Cys Pro Val Thr Glu His Leu Leu Tyr
                 35                  40                  45 cct agg caa ttg tta ccc tct cca tgt gag tcc act acg tct cta cta     492
Pro Arg Gln Leu Leu Pro Ser Pro Cys Glu Ser Thr Thr Ser Leu Leu
             50                  55                  60 aaa ata caa aaa tta gcc agg cat gat ggc agg cgc ctg tac tcc cag     540
Lys Ile Gln Lys Leu Ala Arg His Asp Gly Arg Arg Leu Tyr Ser Gln
 65                  70                  75 cta ctc agg ggg cta agg cag gag aat tgc ttg agc cca gga ggc gga     588
Leu Leu Arg Gly Leu Arg Gln Glu Asn Cys Leu Ser Pro Gly Gly Gly
         80                  85                  90 gat tgc agt gag ttg aga tct cac cac tac act cca gtt tgt gtg aca     636
Asp Cys Ser Glu Leu Arg Ser His His Tyr Thr Pro Val Cys Val Thr
 95                 100                 105                 110 ggg cga gac acc atc tca aaa aaa aaa aaa aaa gag aaa aga ccg          684
Gly Arg Asp Thr Ile Ser Lys Lys Lys Lys Lys Glu Lys Arg Pro
                115                 120                 125 ggt gcg gtg gct cag acc tgt aat ccc aac act ttg gga ggc caa ggt     732
Gly Ala Val Ala Gln Thr Cys Asn Pro Asn Thr Leu Gly Gly Gln Gly
            130                 135                 140 gtg cgg atc act tga ggtcgggagt ctagaccaa cctggccaac acggtgaaac      787
Val Arg Ile Thr
            145 cccatctcta ctaaaaatac aaaaattagc caggggtggt ggtgcatacc tgtaatccca    847 gctactcagg aggctgaggc aagagaatca cttgtacctg ggaggtagag gttgcagtga    907 gctgagattg tgccattgca ctccagcctg acaacaaga gtgaaactct gtttcaaaaa    967 aaaaagagc agaatacaga gtgggaaaat ccttgtagct attcttgggt acaactaggg   1027
```

```
gggcactctt tctgaaagaa ctttctgga gaaaaacctc caattcacat aacacacatc    1087
ccagaggtga cacagtcatc ctgaaaaaga actcacaaaa tattcagaaa caaaatgaga    1147
ataatagaga atctattcct ttctggttta                                    1177
```

<210> SEQ ID NO 191
<211> LENGTH: 146
<212> TYPE: PRT
<213> ORGANISM: Homo sapiens

<400> SEQUENCE: 191

```
Met Ile Lys Glu Ala Cys Leu Cys Val Arg Lys Leu Glu Phe Leu Phe
1               5                   10                  15

Leu Phe Cys Leu Glu Cys Phe Gly His Leu His Ile Val Pro Cys Pro
            20                  25                  30

Arg Asn Gln Gln Leu Cys Pro Val Thr Glu His Leu Leu Tyr Pro Arg
        35                  40                  45

Gln Leu Leu Pro Ser Pro Cys Glu Ser Thr Thr Ser Leu Leu Lys Ile
    50                  55                  60

Gln Lys Leu Ala Arg His Asp Gly Arg Arg Leu Tyr Ser Gln Leu Leu
65                  70                  75                  80

Arg Gly Leu Arg Gln Glu Asn Cys Leu Ser Pro Gly Gly Gly Asp Cys
                85                  90                  95

Ser Glu Leu Arg Ser His His Tyr Thr Pro Val Cys Val Thr Gly Arg
            100                 105                 110

Asp Thr Ile Ser Lys Lys Lys Lys Lys Glu Lys Arg Pro Gly Ala
        115                 120                 125

Val Ala Gln Thr Cys Asn Pro Asn Thr Leu Gly Gly Gln Gly Val Arg
    130                 135                 140

Ile Thr
145
```

<210> SEQ ID NO 192
<211> LENGTH: 42
<212> TYPE: DNA
<213> ORGANISM: Homo sapiens

<400> SEQUENCE: 192

```
ctcttcgtgg ggccttgcga ggtttgagtc ctgctggccg gc                       42
```

<210> SEQ ID NO 193
<211> LENGTH: 847
<212> TYPE: DNA
<213> ORGANISM: Homo sapiens

<400> SEQUENCE: 193

```
gtaaggaaac tggaatttct cttcctcttt tgtcttgaat gttttggaca cctacatatt     60
gtcccatgtc ctagaaacca gcagctctgt ccagttactg agcacctact gtaccctagg    120
caattgttac cctctccatg tgagtccact acgtctctac taaaaataca aaaattagcc    180
aggcatgatg gcaggcgcct gtactcccag ctactcaggg ggctaaggca ggagaattgc    240
ttgagcccag gaggcggaga ttgcagtgag ttgagatctc accactacac tccagtttgt    300
gtgacagggc gagacaccat ctcaaaaaaa aaaaaaaaa aagagaaaag accgggtgcg    360
gtggctcaga cctgtaatcc caacactttg ggaggccaag gtgtgcggat cacttgaggt    420
cgggagttct agaccaacct ggccaacacg gtgaaacccc atctctacta aaaatacaaa    480
aattagccag gggtggtggt gcatacctgt aatcccagct actcaggagg ctgaggcaag    540
```

-continued

```
agaatcactt gtacctggga ggtagaggtt gcagtgagct gagattgtgc cattgcactc    600
cagcctggac aacaagagtg aaactctgtt tcaaaaaaaa aaagagcaga atacagagtg    660
ggaaaatcct tgtagctatt cttgggtaca actaggggggg cactctttct gaaagaactt   720
ttctggagaa aaacctccaa ttcacataac acacatccca gaggtgacac agtcatcctg    780
aaaaagaact cacaaaatat tcagaaacaa aatgagaata atagagaatc tattcctttc    840
tggttta                                                              847

<210> SEQ ID NO 194
<211> LENGTH: 417
<212> TYPE: DNA
<213> ORGANISM: Homo sapiens

<400> SEQUENCE: 194
gtaaggaaac tggaatttct cttcctcttt tgtcttgaat gttttggaca cctacatatt     60
gtcccatgtc ctagaaacca gcagctctgt ccagttactg agcacctact gtaccctagg    120
caattgttac cctctccatg tgagtccact acgtctctac taaaaataca aaaattagcc    180
aggcatgatg gcaggcgcct gtactcccag ctactcaggg ggctaaggca ggagaattgc    240
ttgagcccag gaggcggaga ttgcagtgag ttgagatctc accactacac tccagtttgt    300
gtgacagggc gagacaccat ctcaaaaaaa aaaaaaaaa aagagaaaag accgggtgcg     360
gtggctcaga cctgtaatcc caacactttg ggaggccaag gtgtgcggat cacttga       417

<210> SEQ ID NO 195
<211> LENGTH: 138
<212> TYPE: PRT
<213> ORGANISM: Homo sapiens

<400> SEQUENCE: 195

Val Arg Lys Leu Glu Phe Leu Phe Leu Phe Cys Leu Glu Cys Phe Gly
 1               5                  10                  15

His Leu His Ile Val Pro Cys Pro Arg Asn Gln Gln Leu Cys Pro Val
                20                  25                  30

Thr Glu His Leu Leu Tyr Pro Arg Gln Leu Leu Pro Ser Pro Cys Glu
            35                  40                  45

Ser Thr Thr Ser Leu Leu Lys Ile Gln Lys Leu Ala Arg His Asp Gly
        50                  55                  60

Arg Arg Leu Tyr Ser Gln Leu Leu Arg Gly Leu Arg Gln Glu Asn Cys
    65                  70                  75                  80

Leu Ser Pro Gly Gly Asp Cys Ser Glu Leu Arg Ser His His Tyr
                85                  90                  95

Thr Pro Val Cys Val Thr Gly Arg Asp Thr Ile Ser Lys Lys Lys
               100                 105                 110

Lys Lys Glu Lys Arg Pro Gly Ala Val Ala Gln Thr Cys Asn Pro Asn
           115                 120                 125

Thr Leu Gly Gly Gln Gly Val Arg Ile Thr
       130                 135

<210> SEQ ID NO 196
<211> LENGTH: 167
<212> TYPE: DNA
<213> ORGANISM: Homo sapiens

<400> SEQUENCE: 196
agtggaaaaa ctgttttggc caactttctg acagaatctt ctgacatcac tgaatacagc     60
ccaacccaag gagtgaggat cctagaattt gagaacccgc atgttaccag caacaacaaa    120
```

```
ggcacgggct gtgaattcga gctatgggac tgtggtggcg atgctaa          167
```

<210> SEQ ID NO 197
<211> LENGTH: 56
<212> TYPE: PRT
<213> ORGANISM: Homo sapiens

<400> SEQUENCE: 197

```
Ser Gly Lys Thr Val Leu Ala Asn Phe Leu Thr Glu Ser Ser Asp Ile
1               5                   10                  15

Thr Glu Tyr Ser Pro Thr Gln Gly Val Arg Ile Leu Glu Phe Glu Asn
            20                  25                  30

Pro His Val Thr Ser Asn Asn Lys Gly Thr Gly Cys Glu Phe Glu Leu
        35                  40                  45

Trp Asp Cys Gly Gly Asp Ala Lys
    50                  55
```

<210> SEQ ID NO 198
<211> LENGTH: 27
<212> TYPE: DNA
<213> ORGANISM: Artificial Sequence
<220> FEATURE:
<223> OTHER INFORMATION: forward primer used for specifically detecting
      the variant of the present invention (D-BRAWH2011787.1)

<400> SEQUENCE: 198

```
gtctttgtgt aaggaaactg gaatttc                                27
```

<210> SEQ ID NO 199
<211> LENGTH: 23
<212> TYPE: DNA
<213> ORGANISM: Artificial Sequence
<220> FEATURE:
<223> OTHER INFORMATION: reverse primer used for specifically detecting
      the variant of the present invention (D-BRAWH2011787.1)

<400> SEQUENCE: 199

```
cacatggaga gggtaacaat tgc                                    23
```

<210> SEQ ID NO 200
<211> LENGTH: 150
<212> TYPE: DNA
<213> ORGANISM: Artificial Sequence
<220> FEATURE:
<223> OTHER INFORMATION: partial polynucleotide specific to the variant
      of the present invention (D-BRAWH2011787.1), which is obtained by
      PCR using forward primer (SEQ ID NO:198) and reverse primer
      (SEQ ID NO:199)

<400> SEQUENCE: 200

```
gtctttgtgt aaggaaactg gaatttctct tcctcttttg tcttgaatgt tttggacacc  60
tacatattgt cccatgtcct agaaaccagc agctctgtcc agttactgag cacctactgt 120
accctaggca attgttaccc tctccatgtg                                 150
```

<210> SEQ ID NO 201
<211> LENGTH: 20
<212> TYPE: DNA
<213> ORGANISM: Artificial Sequence
<220> FEATURE:
<223> OTHER INFORMATION: forward primer used for specifically detecting
      the known variant of the gene of the present invention
      (NM_022777.1)

<400> SEQUENCE: 201

-continued ctttgtcgcc acccttgaac                                              20

<210> SEQ ID NO 202
<211> LENGTH: 24
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_022777.1)

<400> SEQUENCE: 202
ctttatgaat tccatccgga tctc                                         24

<210> SEQ ID NO 203
<211> LENGTH: 86
<212> TYPE: DNA
<213> ORGANISM: Artificial Sequence
<220> FEATURE:
<223> OTHER INFORMATION: partial polynucleotide specific to the known
      variant of the gene of the present invention (NM_022777.1), which
      is obtained by PCR using forward primer (SEQ ID NO:201) and
      reverse primer (SEQ ID NO:202)

<400> SEQUENCE: 203
ctttgtcgcc acccttgaac aagctgaagc tggtgcactc aaacctggaa gatgaccctg    60
aggagatccg gatggaattc ataaag                                       86

<210> SEQ ID NO 204
<211> LENGTH: 22
<212> TYPE: DNA
<213> ORGANISM: Artificial Sequence
<220> FEATURE:
<223> OTHER INFORMATION: forward primer used for detecting the variants
      of the gene of the present invention (D-BRAWH2011787.1 and
      NM_022777.1)

<400> SEQUENCE: 204
tcatggagtg gtgatcgtct tc                                           22

<210> SEQ ID NO 205
<211> LENGTH: 23
<212> TYPE: DNA
<213> ORGANISM: Artificial Sequence
<220> FEATURE:
<223> OTHER INFORMATION: reverse primer used for detecting the variants
      of the gene of the present invention (D-BRAWH2011787.1 and
      NM_022777.1)

<400> SEQUENCE: 205
gcaggaatac cacatctcca ttt                                          23

<210> SEQ ID NO 206
<211> LENGTH: 73
<212> TYPE: DNA
<213> ORGANISM: Artificial Sequence
<220> FEATURE:
<223> OTHER INFORMATION: partial polynucleotide common to the variants
      of the gene of the present invention (D-BRAWH2011787.1 and
      NM_022777.1), which is obtained by PCR using forward primer
      (SEQ ID NO:204) and reverse primer (SEQ ID NO:205)

<400> SEQUENCE: 206
tcatggagtg gtgatcgtct tcaatgctga catcccaagc caccggaagg aaatggagat    60
gtggtattcc tgc                                                     73

<210> SEQ ID NO 207

```
<211> LENGTH: 650
<212> TYPE: DNA
<213> ORGANISM: Homo sapiens

<400> SEQUENCE: 207
ctctctccgt cgccatggaa acgaaagcgg ccaagtagag ctccgtcctg acgcgccgcc      60
tcccgtgggc tccggccggc taagccgcgg cggacaacta tgctgaaagc caagatcctc     120
ttcgtggggc cctgcgagag tggaaaaact gttttggcca actttctgac agaatcttct     180
gacatcactg aatacagccc aacccaagga gtgaggatcc tagaatttga gaacccgcat     240
gttaccagca acaacaaagg cacgggctgt gaattcgagc tatgggactg tggtggcgat     300
gctaagtttg agtcctgctg gccggccctg atgaaggatg ctcatggagt ggtgatcgtc     360
ttcaatgctg acatcccaag ccaccggaag gaaatggaga tgtggtattc ctgctttgtc     420
caacagccgt ccttacagga cacacagtgt atgctaattg cacaccacaa accaggctct     480
ggagatgata aggaagcct gtctttgtgt aaggaaactg gaatttctct tcctcttttg      540
tcttgaatgt tttggacacc tacatattgt cccatgtcct agaaaccagc agctctgtcc     600
agttactgag cacctactgt accctaggca attgttaccc tctccatgtg                650

<210> SEQ ID NO 208
<211> LENGTH: 1441
<212> TYPE: DNA
<213> ORGANISM: Homo sapiens

<400> SEQUENCE: 208
agacatctct tgttttccag atactacggg tcataatccc taactccaat cactggcaac      60
tcctgagatc agaggaaaac cagcaacagc gtgggagttt ggggagaggc attccatacc     120
agattctgtg gcctgcaggt gacatgctgc ctaagagaag caggagaaca gtcagcaaaa     180
gcattggtcc cacctgcccc tttgctggaa gctgtgaagt cagcaagact cagaggcgcc     240
actgcccagc ctgcaggttg cagaagtgct tagatgctgg catgaggaaa gacatgatac     300
tgtcggcaga agccctggca ttgcggcgag caaggcaggc ccagcggcgg gcacagcaaa     360
cacctgtgca actgagtaag gagcaagaag agctgatccg gacactcctg ggggcccaca     420
cccgccacat gggcaccatg tttgaacagt ttgtgcagtt taggcctcca gctcatctgt     480
tcatccatca ccagcccttg cccacccctgg ccctgtgct gcctctggtc acacacttcg     540
cagacatcaa cactttcatg gtactgcaag tcatcaagtt tactaaggac ctgcctgtct     600
tccgttccct gccattgaa gaccagatct ccttctcaa gggagcagct gtggaaatct      660
gtcacatcgt actcaatacc actttctgtc tccaaacaca aaacttcctc tgcgggcctc     720
ttcgctacac aattgaagat ggagcccgtg tggggttcca ggtagagttt ttggagttgc     780 tcttttcactt ccatggaaca ctacgaaaac tgcagctcca agagcctgag tatgtgctct     840
tggctgccat ggccctcttc tctcctgacc gacctggagt tacccagaga gatgagattg     900
atcagctgca agaggagatg gcactgactc tgcaaagcta catcaagggc cagcagcgaa     960
ggccccggga tcggtacggt gggacactga aggcttggag ccacaccag ggcaggaagg     1020 ggttggtgaa acattgagct tgggaggaat gttttttac tgtcctttcc ttagggaatt     1080
caggtatctt ggggtctagt ccttccccct ggccatccct gtctcacatc gtttcagcat     1140
ccaaattgct gtatttggat actgctgttt catctcactt ttttccagatt ttttttttat     1200 tcagtacaga tgcaaagtag tagctcgag gctctgggta atagcattcc tgagattgat     1260
gacatccatt acctcactag tccaacttct ccagactaat gcagacttt tctcttccctt     1320
```

-continued

```
ggcctttcct ctcctcgcca ttgggccaat tccttcgatt tctcatttcc cttgaagtta    1380
gggccattca cagtttcatg gtcaaagcca gttccaggtt caatagtctg tgatttatcc    1440
a                                                                     1441
```

<210> SEQ ID NO 209
<211> LENGTH: 1441
<212> TYPE: DNA
<213> ORGANISM: Homo sapiens
<221> NAME/KEY: CDS
<222> LOCATION: (144)..(1037)

<400> SEQUENCE: 209

```
agacatctct tgttttccag atactacggg tcataatccc taactccaat cactggcaac    60
tcctgagatc agaggaaaac cagcaacagc gtgggagttt ggggagaggc attccatacc    120
agattctgtg gcctgcaggt gac atg ctg cct aag aga agc agg aga aca gtc   173
                          Met Leu Pro Lys Arg Ser Arg Arg Thr Val
                            1               5                  10 agc aaa agc att ggt ccc acc tgc ccc ttt gct gga agc tgt gaa gtc      221
Ser Lys Ser Ile Gly Pro Thr Cys Pro Phe Ala Gly Ser Cys Glu Val
                15                  20                  25 agc aag act cag agg cgc cac tgc cca gcc tgc agg ttg cag aag tgc      269
Ser Lys Thr Gln Arg Arg His Cys Pro Ala Cys Arg Leu Gln Lys Cys
         30                  35                  40 tta gat gct ggc atg agg aaa gac atg ata ctg tcg gca gaa gcc ctg      317
Leu Asp Ala Gly Met Arg Lys Asp Met Ile Leu Ser Ala Glu Ala Leu
     45                  50                  55 gca ttg cgg cga gca agg cag gcc cag cgg cgg gca cag caa aca cct      365
Ala Leu Arg Arg Ala Arg Gln Ala Gln Arg Arg Ala Gln Gln Thr Pro
 60                  65                  70 gtg caa ctg agt aag gag caa gaa gag ctg atc cgg aca ctc ctg ggg      413
Val Gln Leu Ser Lys Glu Gln Glu Glu Leu Ile Arg Thr Leu Leu Gly
 75                  80                  85                  90 gcc cac acc cgc cac atg ggc acc atg ttt gaa cag ttt gtg cag ttt      461
Ala His Thr Arg His Met Gly Thr Met Phe Glu Gln Phe Val Gln Phe
                 95                 100                 105 agg cct cca gct cat ctg ttc atc cat cac cag ccc ttg ccc acc ctg      509
Arg Pro Pro Ala His Leu Phe Ile His His Gln Pro Leu Pro Thr Leu
            110                 115                 120 gcc cct gtg ctg cct ctg gtc aca cac ttc gca gac atc aac act ttc      557
Ala Pro Val Leu Pro Leu Val Thr His Phe Ala Asp Ile Asn Thr Phe
        125                 130                 135 atg gta ctg caa gtc atc aag ttt act aag gac ctg cct gtc ttc cgt      605
Met Val Leu Gln Val Ile Lys Phe Thr Lys Asp Leu Pro Val Phe Arg
    140                 145                 150 tcc ctg ccc att gaa gac cag atc tcc ctt ctc aag gga gca gct gtg      653
Ser Leu Pro Ile Glu Asp Gln Ile Ser Leu Leu Lys Gly Ala Ala Val
155                 160                 165                 170 gaa atc tgt cac atc gta ctc aat acc act ttc tgt ctc caa aca caa      701
Glu Ile Cys His Ile Val Leu Asn Thr Thr Phe Cys Leu Gln Thr Gln
                175                 180                 185 aac ttc ctc tgc ggg cct ctt cgc tac aca att gaa gat gga gcc cgt      749
Asn Phe Leu Cys Gly Pro Leu Arg Tyr Thr Ile Glu Asp Gly Ala Arg
            190                 195                 200 gtg ggg ttc cag gta gag ttt ttg gag ttg ctc ttt cac ttc cat gga      797
Val Gly Phe Gln Val Glu Phe Leu Glu Leu Leu Phe His Phe His Gly
        205                 210                 215 aca cta cga aaa ctg cag ctc caa gag cct gag tat gtg ctc ttg gct      845
Thr Leu Arg Lys Leu Gln Leu Gln Glu Pro Glu Tyr Val Leu Leu Ala
    220                 225                 230
```

```
gcc atg gcc ctc ttc tct cct gac cga cct gga gtt acc cag aga gat    893
Ala Met Ala Leu Phe Ser Pro Asp Arg Pro Gly Val Thr Gln Arg Asp
235                 240                 245                 250 gag att gat cag ctg caa gag gag atg gca ctg act ctg caa agc tac    941
Glu Ile Asp Gln Leu Gln Glu Glu Met Ala Leu Thr Leu Gln Ser Tyr
                255                 260                 265 atc aag ggc cag cag cga agg ccc cgg gat cgg tac ggt ggg aca ctg    989
Ile Lys Gly Gln Gln Arg Arg Pro Arg Asp Arg Tyr Gly Gly Thr Leu
            270                 275                 280 aag gct tgg agg cca cac cag ggc agg aag ggg ttg gtg aaa cat tga   1037
Lys Ala Trp Arg Pro His Gln Gly Arg Lys Gly Leu Val Lys His
        285                 290                 295 gcttgggagg aatgtttttt tactgtcctt tccttaggga attcaggtat cttggggtct  1097
agtccttccc cctggccatc cctgtctcac atcgtttcag catccaaatt gctgtatttg  1157
gatactgctg tttcatctca ctttttccag atttttttt tattcagtac agatgcaaag  1217
tagtagctca gaggctctgg gtaatagcat tcctgagatt gatgacatcc attacctcac  1277
tagtccaact tctccagact aatgcagact tttctcttcc cttggccttt cctctcctcg  1337
ccattgggcc aattccttcg atttctcatt tcccttgaag ttagggccat tcacagtttc  1397
atggtcaaag ccagttccag gttcaatagt ctgtgattta tcca                   1441

<210> SEQ ID NO 210
<211> LENGTH: 297
<212> TYPE: PRT
<213> ORGANISM: Homo sapiens

<400> SEQUENCE: 210

Met Leu Pro Lys Arg Ser Arg Arg Thr Val Ser Lys Ser Ile Gly Pro
1               5                   10                  15

Thr Cys Pro Phe Ala Gly Ser Cys Glu Val Ser Lys Thr Gln Arg Arg
                20                  25                  30

His Cys Pro Ala Cys Arg Leu Gln Lys Cys Leu Asp Ala Gly Met Arg
            35                  40                  45

Lys Asp Met Ile Leu Ser Ala Glu Ala Leu Ala Leu Arg Arg Ala Arg
50                  55                  60

Gln Ala Gln Arg Arg Ala Gln Gln Thr Pro Val Gln Leu Ser Lys Glu
65                  70                  75                  80

Gln Glu Glu Leu Ile Arg Thr Leu Leu Gly Ala His Thr Arg His Met
                85                  90                  95

Gly Thr Met Phe Glu Gln Phe Val Gln Phe Arg Pro Pro Ala His Leu
            100                 105                 110

Phe Ile His His Gln Pro Leu Pro Thr Leu Ala Pro Val Leu Pro Leu
        115                 120                 125

Val Thr His Phe Ala Asp Ile Asn Thr Phe Met Val Leu Gln Val Ile
    130                 135                 140

Lys Phe Thr Lys Asp Leu Pro Val Phe Arg Ser Leu Pro Ile Glu Asp
145                 150                 155                 160

Gln Ile Ser Leu Leu Lys Gly Ala Ala Val Glu Ile Cys His Ile Val
                165                 170                 175

Leu Asn Thr Thr Phe Cys Leu Gln Thr Gln Asn Phe Leu Cys Gly Pro
            180                 185                 190

Leu Arg Tyr Thr Ile Glu Asp Gly Ala Arg Val Gly Phe Gln Val Glu
        195                 200                 205

Phe Leu Glu Leu Leu Phe His Phe His Gly Thr Leu Arg Lys Leu Gln
    210                 215                 220
```

```
Leu Gln Glu Pro Glu Tyr Val Leu Leu Ala Ala Met Ala Leu Phe Ser
225                 230                 235                 240

Pro Asp Arg Pro Gly Val Thr Gln Arg Asp Glu Ile Asp Gln Leu Gln
            245                 250                 255

Glu Glu Met Ala Leu Thr Leu Ser Tyr Ile Lys Gly Gln Gln Arg
        260                 265                 270

Arg Pro Arg Asp Arg Tyr Gly Gly Thr Leu Lys Ala Trp Arg Pro His
    275                 280                 285

Gln Gly Arg Lys Gly Leu Val Lys His
    290                 295

<210> SEQ ID NO 211
<211> LENGTH: 42
<212> TYPE: DNA
<213> ORGANISM: Homo sapiens

<400> SEQUENCE: 211
catgctgcct aagagaagca ggagaacagt cagcaaaagc at             42

<210> SEQ ID NO 212
<211> LENGTH: 7
<212> TYPE: PRT
<213> ORGANISM: Homo sapiens

<400> SEQUENCE: 212

Met Leu Pro Lys Arg Ser Arg
1               5

<210> SEQ ID NO 213
<211> LENGTH: 41
<212> TYPE: DNA
<213> ORGANISM: Homo sapiens

<400> SEQUENCE: 213
atgctgccta agagaagcag gagaacagtc agcaaaagca t             41

<210> SEQ ID NO 214
<211> LENGTH: 140
<212> TYPE: DNA
<213> ORGANISM: Homo sapiens

<400> SEQUENCE: 214
gagtctgtga cagccacccc aacacgtgac gtcatggcca gtagggaaga tgagctgagg       60
aactgtgtgg tatgtgggga ccaagccaca ggctaccact taatgcgct gacttgtgag       120 ggctgcaagg gtttcttcag                                                   140

<210> SEQ ID NO 215
<211> LENGTH: 36
<212> TYPE: PRT
<213> ORGANISM: Homo sapiens

<400> SEQUENCE: 215

Met Ala Ser Arg Glu Asp Glu Leu Arg Asn Cys Val Val Cys Gly Asp
1               5                   10                  15

Gln Ala Thr Gly Tyr His Phe Asn Ala Leu Thr Cys Glu Gly Cys Lys
            20                  25                  30

Gly Phe Phe Arg
        35

<210> SEQ ID NO 216
<211> LENGTH: 466
```

```
<212> TYPE: DNA
<213> ORGANISM: Homo sapiens

<400> SEQUENCE: 216
acggtgggac actgaaggct tggaggccac accagggcag aaggggttg gtgaaacatt     60
gagcttggga ggaatgtttt tttactgtcc tttccttagg gaattcaggt atcttggggt    120
ctagtccttc ccctggcca tccctgtctc acatcgtttc agcatccaaa ttgctgtatt    180
tggatactgc tgtttcatct cactttttcc agatttttt tttattcagt acagatgcaa    240
agtagtagct cagaggctct gggtaatagc attcctgaga ttgatgacat ccattacctc    300
actagtccaa cttctccaga ctaatgcaga cttttctctt cccttggcct ttcctctcct    360
cgccattggg ccaattcctt cgatttctca tttcccttga gttagggcc attcacagtt     420
tcatggtcaa agccagttcc aggttcaata gtctgtgatt tatcca                  466

<210> SEQ ID NO 217
<211> LENGTH: 20
<212> TYPE: PRT
<213> ORGANISM: Homo sapiens

<400> SEQUENCE: 217

Tyr Gly Gly Thr Leu Lys Ala Trp Arg Pro His Gln Gly Arg Lys Gly
1               5                   10                  15
Leu Val Lys His
            20

<210> SEQ ID NO 218
<211> LENGTH: 62
<212> TYPE: DNA
<213> ORGANISM: Homo sapiens

<400> SEQUENCE: 218
acggtgggac actgaaggct tggaggccac accagggcag aaggggttg gtgaaacatt     60
ga                                                                   62

<210> SEQ ID NO 219
<211> LENGTH: 971
<212> TYPE: DNA
<213> ORGANISM: Homo sapiens

<400> SEQUENCE: 219
aaccccacag tcactgagag caactggagg ccacataaaa cagacatctc ttgttttcca     60
gatactacgg gtcataatcc ctaactccaa tcactggcaa ctcctgagat cagaggaaaa    120
ccagcaacag cgtgggagtt tggggagagg cattccatac cagattctgt ggcctgcagg    180
tgacatgctg cctaagagaa gcaggagtct gtgacagcca ccccaacacg tgacgtcatg    240
gccagtaggg aagatgagct gaggaactgt gtggtatgtg gggaccaagc cacaggctac    300
cactttaatg cgctgacttg tgagggctgc aagggtttct tcaggagaac agtcagcaaa    360
agcattggtc ccacctgccc ctttgctgga agctgtgaag tcagcaagac tcagaggcgc    420
cactgcccag cctgcaggtt gcagaagtgc ttagatgctg gcatgaggaa agacatgata    480
ctgtcggcag aagccctggc attgcggcga gcaaagcagg cccagcggcg ggcacagcaa    540
acacctgtgc aactgagtaa ggagcaagaa gagctgatcc ggacactcct ggggggccac    600
acccgccaca tggcaccat gtttgaacag tttgtgcagt ttaggcctcc agctcatctg    660
ttcatccatc accagccctt gcccaccctg gcccctgtgc tgcctctggt cacacacttc    720
gcagacatca acactttcat ggtactgcaa gtcatcaagt ttactaagga cctgcctgtc    780
```

| | | |
|---|---|---|
| ttccgttccc tgcccattga agaccagatc tcccttctca agggagcagc tgtggaaatc | 840 | |
| tgtcacatcg tactcaatac cactttctgt ctccaaacac aaaacttcct ctgcgggcct | 900 | |
| cttcgctaca caattgaaga tggagcccgt ggtgagatgg tgctagagca atagggggca | 960 | |
| tgtgtcctca t | 971 | |

<210> SEQ ID NO 220
<211> LENGTH: 971
<212> TYPE: DNA
<213> ORGANISM: Homo sapiens
<221> NAME/KEY: CDS
<222> LOCATION: (238)..(954)

<400> SEQUENCE: 220

| | | |
|---|---|---|
| aaccccacag tcactgagag caactggagg ccacataaaa cagacatctc ttgttttcca | 60 | |
| gatactacgg gtcataatcc ctaactccaa tcactggcaa ctcctgagat cagaggaaaa | 120 | |
| ccagcaacag cgtgggagtt tggggagagg cattccatac cagattctgt ggcctgcagg | 180 | |
| tgacatgctg cctaagagaa gcaggagtct gtgacagcca ccccaacacg tgacgtc | 237 | |

| | | |
|---|---|---|
| atg gcc agt agg gaa gat gag ctg agg aac tgt gtg gta tgt ggg gac<br>Met Ala Ser Arg Glu Asp Glu Leu Arg Asn Cys Val Val Cys Gly Asp<br>1                  5                  10                15 | 285 | |
| caa gcc aca ggc tac cac ttt aat gcg ctg act tgt gag ggc tgc aag<br>Gln Ala Thr Gly Tyr His Phe Asn Ala Leu Thr Cys Glu Gly Cys Lys<br>                  20                  25                  30 | 333 | |
| ggt ttc ttc agg aga aca gtc agc aaa agc att ggt ccc acc tgc ccc<br>Gly Phe Phe Arg Arg Thr Val Ser Lys Ser Ile Gly Pro Thr Cys Pro<br>35                  40                  45 | 381 | |
| ttt gct gga agc tgt gaa gtc agc aag act cag agg cgc cac tgc cca<br>Phe Ala Gly Ser Cys Glu Val Ser Lys Thr Gln Arg Arg His Cys Pro<br>50                  55                  60 | 429 | |
| gcc tgc agg ttg cag aag tgc tta gat gct ggc atg agg aaa gac atg<br>Ala Cys Arg Leu Gln Lys Cys Leu Asp Ala Gly Met Arg Lys Asp Met<br>65                  70                  75                  80 | 477 | |
| ata ctg tcg gca gaa gcc ctg gca ttg cgg cga gca aag cag gcc cag<br>Ile Leu Ser Ala Glu Ala Leu Ala Leu Arg Arg Ala Lys Gln Ala Gln<br>                  85                  90                  95 | 525 | |
| cgg cgg gca cag caa aca cct gtg caa ctg agt aag gag caa gaa gag<br>Arg Arg Ala Gln Gln Thr Pro Val Gln Leu Ser Lys Glu Gln Glu Glu<br>100                 105                 110 | 573 | |
| ctg atc cgg aca ctc ctg ggg gcc cac acc cgc cac atg ggc acc atg<br>Leu Ile Arg Thr Leu Leu Gly Ala His Thr Arg His Met Gly Thr Met<br>115                 120                 125 | 621 | |
| ttt gaa cag ttt gtg cag ttt agg cct cca gct cat ctg ttc atc cat<br>Phe Glu Gln Phe Val Gln Phe Arg Pro Pro Ala His Leu Phe Ile His<br>130                 135                 140 | 669 | |
| cac cag ccc ttg ccc acc ctg gcc cct gtg ctg cct ctg gtc aca cac<br>His Gln Pro Leu Pro Thr Leu Ala Pro Val Leu Pro Leu Val Thr His<br>145                 150                 155                 160 | 717 | |
| ttc gca gac atc aac act ttc atg gta ctg caa gtc atc aag ttt act<br>Phe Ala Asp Ile Asn Thr Phe Met Val Leu Gln Val Ile Lys Phe Thr<br>                  165                 170                 175 | 765 | |
| aag gac ctg cct gtc ttc cgt tcc ctg ccc att gaa gac cag atc tcc<br>Lys Asp Leu Pro Val Phe Arg Ser Leu Pro Ile Glu Asp Gln Ile Ser<br>180                 185                 190 | 813 | |
| ctt ctc aag gga gca gct gtg gaa atc tgt cac atc gta ctc aat acc<br>Leu Leu Lys Gly Ala Ala Val Glu Ile Cys His Ile Val Leu Asn Thr<br>195                 200                 205 | 861 | |
| act ttc tgt ctc caa aca caa aac ttc ctc tgc ggg cct ctt cgc tac<br>Thr Phe Cys Leu Gln Thr Gln Asn Phe Leu Cys Gly Pro Leu Arg Tyr | 909 | |

```
Thr Phe Cys Leu Gln Thr Gln Asn Phe Leu Cys Gly Pro Leu Arg Tyr
            210                 215                 220 aca att gaa gat gga gcc cgt ggt gag atg gtg cta gag caa tag         954
Thr Ile Glu Asp Gly Ala Arg Gly Glu Met Val Leu Glu Gln
225                 230                 235 ggggcatgtg tcctcat                                                  971

<210> SEQ ID NO 221
<211> LENGTH: 238
<212> TYPE: PRT
<213> ORGANISM: Homo sapiens

<400> SEQUENCE: 221

Met Ala Ser Arg Glu Asp Glu Leu Arg Asn Cys Val Val Cys Gly Asp
1               5                   10                  15

Gln Ala Thr Gly Tyr His Phe Asn Ala Leu Thr Cys Glu Gly Cys Lys
            20                  25                  30

Gly Phe Phe Arg Arg Thr Val Ser Lys Ser Ile Gly Pro Thr Cys Pro
        35                  40                  45

Phe Ala Gly Ser Cys Glu Val Ser Lys Thr Gln Arg Arg His Cys Pro
    50                  55                  60

Ala Cys Arg Leu Gln Lys Cys Leu Asp Ala Gly Met Arg Lys Asp Met
65                  70                  75                  80

Ile Leu Ser Ala Glu Ala Leu Ala Leu Arg Arg Ala Lys Gln Ala Gln
                85                  90                  95

Arg Arg Ala Gln Gln Thr Pro Val Gln Leu Ser Lys Glu Gln Glu Glu
            100                 105                 110

Leu Ile Arg Thr Leu Leu Gly Ala His Thr Arg His Met Gly Thr Met
        115                 120                 125

Phe Glu Gln Phe Val Gln Phe Arg Pro Pro Ala His Leu Phe Ile His
    130                 135                 140

His Gln Pro Leu Pro Thr Leu Ala Pro Val Leu Pro Leu Val Thr His
145                 150                 155                 160

Phe Ala Asp Ile Asn Thr Phe Met Val Leu Gln Val Ile Lys Phe Thr
                165                 170                 175

Lys Asp Leu Pro Val Phe Arg Ser Leu Pro Ile Glu Asp Gln Ile Ser
            180                 185                 190

Leu Leu Lys Gly Ala Ala Val Glu Ile Cys His Ile Val Leu Asn Thr
        195                 200                 205

Thr Phe Cys Leu Gln Thr Gln Asn Phe Leu Cys Gly Pro Leu Arg Tyr
    210                 215                 220

Thr Ile Glu Asp Gly Ala Arg Gly Glu Met Val Leu Glu Gln
225                 230                 235

<210> SEQ ID NO 222
<211> LENGTH: 40
<212> TYPE: DNA
<213> ORGANISM: Homo sapiens

<400> SEQUENCE: 222
gtgagatggt gctagagcaa taggggggcat gtgtcctcat                         40

<210> SEQ ID NO 223
<211> LENGTH: 7
<212> TYPE: PRT
<213> ORGANISM: Homo sapiens

<400> SEQUENCE: 223
```

Gly Glu Met Val Leu Glu Gln
1               5

<210> SEQ ID NO 224
<211> LENGTH: 23
<212> TYPE: DNA
<213> ORGANISM: Homo sapiens

<400> SEQUENCE: 224
gtgagatggt gctagagcaa tag                                           23

<210> SEQ ID NO 225
<211> LENGTH: 1051
<212> TYPE: DNA
<213> ORGANISM: Homo sapiens

<400> SEQUENCE: 225
gacatctctt gttttccaga tactacgggt cataatccct aactccaatc actggcaact    60
cctgagatca gaggaaaaacc agcaacagcg tgggagtttg gggagaggca ttccatacca  120
gattctgtgg cctgcaggtg acatgctgcc taagagaagc aggagtctgt gacagccacc  180
ccaacacgtg acgtcatggc cagtaggaa gatgagctga ggaactgtgt ggtatgtggg   240
gaccaagcca caggctacca ctttaatgcg ctgacttgtg agggctgcaa gggtttcttc  300
aggagaacag tcagcaaaag cattggtccc acctgcccct tgctggaag ctgtgaagtc   360 agcaagactc agaggcgcca ctgcccagcc tgcaggttgc agaagtgctt agatgctggc  420
atgaggaaag acatgatact gtcggcagaa gccctggcat gcggcgagc aaagcaggcc   480 cagcggcggg cacagcaaac acctgtgcaa ctgagtaagg agcaagaaga gctgatccgg  540
acactcctgg gggcccacac ccgccacatg gcaccatgtt tgaacagtt tgtgcagttt   600 aggcctccag ctcatctgtt catccatcac cagcccttgc ccaccctggc ccctgtgctg  660
cctctggtca cacacttcgc agacatcaac actttcatgg tactgcaagt catcaagttt  720
actaaggacc tgcccgtctt ccgttccctg cccattgaag accagatctc ccttctcaag  780
ggagcagctg tggaaatctg tcacatcgta ctcaatacca ctttctgtct ccaaacacaa  840
aacttcctct gcgggcctct tcgctacaca attgaagatg gagcccgtgg tgagatggtg  900
ctagagcaat aggggggcatg tgtcctcatg gtacaggatg tggtcaggtg acctagaggc  960
tcctaatcct agtatctccc acagtggggt tccaggtaga gttttggag ttgctctttc   1020 acttccatgg aacactacga aaactgcagc t                                  1051

<210> SEQ ID NO 226
<211> LENGTH: 1051
<212> TYPE: DNA
<213> ORGANISM: Homo sapiens
<221> NAME/KEY: CDS
<222> LOCATION: (196)..(912)

<400> SEQUENCE: 226
gacatctctt gttttccaga tactacgggt cataatccct aactccaatc actggcaact    60
cctgagatca gaggaaaaacc agcaacagcg tgggagtttg gggagaggca ttccatacca  120
gattctgtgg cctgcaggtg acatgctgcc taagagaagc aggagtctgt gacagccacc  180
ccaacacgtg acgtc atg gcc agt agg gaa gat gag ctg agg aac tgt gtg    231
                 Met Ala Ser Arg Glu Asp Glu Leu Arg Asn Cys Val
                 1               5                   10 gta tgt ggg gac caa gcc aca ggc tac cac ttt aat gcg ctg act tgt     279
Val Cys Gly Asp Gln Ala Thr Gly Tyr His Phe Asn Ala Leu Thr Cys
        15                  20                  25

```
gag ggc tgc aag ggt ttc ttc agg aga aca gtc agc aaa agc att ggt    327
Glu Gly Cys Lys Gly Phe Phe Arg Arg Thr Val Ser Lys Ser Ile Gly
         30                  35                  40 ccc acc tgc ccc ttt gct gga agc tgt gaa gtc agc aag act cag agg    375
Pro Thr Cys Pro Phe Ala Gly Ser Cys Glu Val Ser Lys Thr Gln Arg
 45                  50                  55                  60 cgc cac tgc cca gcc tgc agg ttg cag aag tgc tta gat gct ggc atg    423
Arg His Cys Pro Ala Cys Arg Leu Gln Lys Cys Leu Asp Ala Gly Met
                 65                  70                  75 agg aaa gac atg ata ctg tcg gca gaa gcc ctg gca ttg cgg cga gca    471
Arg Lys Asp Met Ile Leu Ser Ala Glu Ala Leu Ala Leu Arg Arg Ala
             80                  85                  90 aag cag gcc cag cgg cgg gca cag caa aca cct gtg caa ctg agt aag    519
Lys Gln Ala Gln Arg Arg Ala Gln Gln Thr Pro Val Gln Leu Ser Lys
         95                 100                 105 gag caa gaa gag ctg atc cgg aca ctc ctg ggg gcc cac acc cgc cac    567
Glu Gln Glu Glu Leu Ile Arg Thr Leu Leu Gly Ala His Thr Arg His
    110                 115                 120 atg ggc acc atg ttt gaa cag ttt gtg cag ttt agg cct cca gct cat    615
Met Gly Thr Met Phe Glu Gln Phe Val Gln Phe Arg Pro Pro Ala His
125                 130                 135                 140 ctg ttc atc cat cac cag ccc ttg ccc acc ctg gcc cct gtg ctg cct    663
Leu Phe Ile His His Gln Pro Leu Pro Thr Leu Ala Pro Val Leu Pro
                145                 150                 155 ctg gtc aca cac ttc gca gac atc aac act ttc atg gta ctg caa gtc    711
Leu Val Thr His Phe Ala Asp Ile Asn Thr Phe Met Val Leu Gln Val
            160                 165                 170 atc aag ttt act aag gac ctg ccc gtc ttc cgt tcc ctg ccc att gaa    759
Ile Lys Phe Thr Lys Asp Leu Pro Val Phe Arg Ser Leu Pro Ile Glu
        175                 180                 185 gac cag atc tcc ctt ctc aag gga gca gct gtg gaa atc tgt cac atc    807
Asp Gln Ile Ser Leu Leu Lys Gly Ala Ala Val Glu Ile Cys His Ile
    190                 195                 200 gta ctc aat acc act ttc tgt ctc caa aca caa aac ttc ctc tgc ggg    855
Val Leu Asn Thr Thr Phe Cys Leu Gln Thr Gln Asn Phe Leu Cys Gly
205                 210                 215                 220 cct ctt cgc tac aca att gaa gat gga gcc cgt ggt gag atg gtg cta    903
Pro Leu Arg Tyr Thr Ile Glu Asp Gly Ala Arg Gly Glu Met Val Leu
                225                 230                 235 gag caa tag ggggcatgtg tcctcatggt acaggatgtg gtcaggtgac             952
Glu Gln ctagaggctc ctaatcctag tatctcccac agtggggttc caggtagagt ttttggagtt  1012
gctctttcac ttccatggaa cactacgaaa actgcagct                         1051
```

<210> SEQ ID NO 227
<211> LENGTH: 238
<212> TYPE: PRT
<213> ORGANISM: Homo sapiens

<400> SEQUENCE: 227

```
Met Ala Ser Arg Glu Asp Glu Leu Arg Asn Cys Val Val Cys Gly Asp
1               5                   10                  15

Gln Ala Thr Gly Tyr His Phe Asn Ala Leu Thr Cys Glu Gly Cys Lys
            20                  25                  30

Gly Phe Phe Arg Arg Thr Val Ser Lys Ser Ile Gly Pro Thr Cys Pro
        35                  40                  45

Phe Ala Gly Ser Cys Glu Val Ser Lys Thr Gln Arg Arg His Cys Pro
    50                  55                  60
```

```
Ala Cys Arg Leu Gln Lys Cys Leu Asp Ala Gly Met Arg Lys Asp Met
 65                  70                  75                  80

Ile Leu Ser Ala Glu Ala Leu Ala Leu Arg Ala Lys Gln Ala Gln
                 85                  90                  95

Arg Arg Ala Gln Gln Thr Pro Val Gln Leu Ser Lys Glu Gln Glu Glu
            100                 105                 110

Leu Ile Arg Thr Leu Leu Gly Ala His Thr Arg His Met Gly Thr Met
            115                 120                 125

Phe Glu Gln Phe Val Gln Phe Arg Pro Ala His Leu Phe Ile His
130                 135                 140

His Gln Pro Leu Pro Thr Leu Ala Pro Val Leu Pro Leu Val Thr His
145                 150                 155                 160

Phe Ala Asp Ile Asn Thr Phe Met Val Leu Gln Val Ile Lys Phe Thr
                165                 170                 175

Lys Asp Leu Pro Val Phe Arg Ser Leu Pro Ile Glu Asp Gln Ile Ser
                180                 185                 190

Leu Leu Lys Gly Ala Ala Val Glu Ile Cys His Ile Val Leu Asn Thr
            195                 200                 205

Thr Phe Cys Leu Gln Thr Gln Asn Phe Leu Cys Gly Pro Leu Arg Tyr
210                 215                 220

Thr Ile Glu Asp Gly Ala Arg Gly Glu Met Val Leu Glu Gln
225                 230                 235

<210> SEQ ID NO 228
<211> LENGTH: 95
<212> TYPE: DNA
<213> ORGANISM: Homo sapiens

<400> SEQUENCE: 228
gtgagatggt gctagagcaa taggggcat gtgtcctcat ggtacaggat gtggtcaggt    60
gacctagagg ctcctaatcc tagtatctcc cacag                              95

<210> SEQ ID NO 229
<211> LENGTH: 7
<212> TYPE: PRT
<213> ORGANISM: Homo sapiens

<400> SEQUENCE: 229

Gly Glu Met Val Leu Glu Gln
1               5

<210> SEQ ID NO 230
<211> LENGTH: 23
<212> TYPE: DNA
<213> ORGANISM: Homo sapiens

<400> SEQUENCE: 230
gtgagatggt gctagagcaa tag                                           23

<210> SEQ ID NO 231
<211> LENGTH: 22
<212> TYPE: DNA
<213> ORGANISM: Artificial Sequence
<220> FEATURE:
<223> OTHER INFORMATION: forward primer used for specifically detecting
      the variant of the present invention (D-TLIVE2001566.1)

<400> SEQUENCE: 231
gagatcagag gaaaaccagc aa                                            22
```

<210> SEQ ID NO 232
<211> LENGTH: 25
<212> TYPE: DNA
<213> ORGANISM: Artificial Sequence
<220> FEATURE:
<223> OTHER INFORMATION: reverse primer used for specifically detecting
      the variant of the present invention (D-TLIVE2001566.1)

<400> SEQUENCE: 232
ctgactgttc tcctgcttct cttag                                          25

<210> SEQ ID NO 233
<211> LENGTH: 111
<212> TYPE: DNA
<213> ORGANISM: Artificial Sequence
<220> FEATURE:
<223> OTHER INFORMATION: partial polynucleotide specific to the variant
      of the present invention (D-TLIVE2001566.1), which is obtained by
      PCR using forward primer (SEQ ID NO:231) and reverse primer
      (SEQ ID NO:232)

<400> SEQUENCE: 233
gagatcagag gaaaaccagc aacagcgtgg gagtttgggg agaggcattc cataccagat    60
tctgtggcct gcaggtgaca tgctgcctaa gagaagcagg agaacagtca g            111

<210> SEQ ID NO 234
<211> LENGTH: 25
<212> TYPE: DNA
<213> ORGANISM: Artificial Sequence
<220> FEATURE:
<223> OTHER INFORMATION: forward primer used for specifically detecting
      the known variant of the gene of the present invention
      (NM_005122.2)

<400> SEQUENCE: 234
ctaagagaag caggagtctg tgaca                                          25

<210> SEQ ID NO 235
<211> LENGTH: 20
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_005122.2)

<400> SEQUENCE: 235
ccctcacaag tcagcgcatt                                                20

<210> SEQ ID NO 236
<211> LENGTH: 135
<212> TYPE: DNA
<213> ORGANISM: Artificial Sequence
<220> FEATURE:
<223> OTHER INFORMATION: partial polynucleotide specific to the known
      variant of the gene of the present invention (NM_005122.2), which
      is obtained by PCR using forward primer (SEQ ID NO:234) and
      reverse primer (SEQ ID NO:235)

<400> SEQUENCE: 236
ctaagagaag caggagtctg tgacagccac cccaacacgt gacgtcatgg ccagtaggga    60
agatgagctg aggaactgtg tggtatgtgg ggaccaagcc acaggctacc actttaatgc   120
gctgacttgt gaggg                                                    135

<210> SEQ ID NO 237
<211> LENGTH: 16
<212> TYPE: DNA

```
<213> ORGANISM: Artificial Sequence
<220> FEATURE:
<223> OTHER INFORMATION: forward primer used for specifically detecting
      the variant of the present invention (D-TLIVE2001566.1)

<400> SEQUENCE: 237
aagggccagc agcgaa                                                         16

<210> SEQ ID NO 238
<211> LENGTH: 17
<212> TYPE: DNA
<213> ORGANISM: Artificial Sequence
<220> FEATURE:
<223> OTHER INFORMATION: reverse primer used for specifically detecting
      the variant of the present invention (D-TLIVE2001566.1)

<400> SEQUENCE: 238
tggcctccaa gccttca                                                        17

<210> SEQ ID NO 239
<211> LENGTH: 60
<212> TYPE: DNA
<213> ORGANISM: Artificial Sequence
<220> FEATURE:
<223> OTHER INFORMATION: partial polynucleotide specific to the variant
      of the present invention (D-TLIVE2001566.1), which is obtained by
      PCR using forward primer (SEQ ID NO:237) and reverse primer
      (SEQ ID NO:238)

<400> SEQUENCE: 239
aagggccagc agcgaaggcc ccgggatcgg tacggtggga cactgaaggc ttggaggcca        60

<210> SEQ ID NO 240
<211> LENGTH: 20
<212> TYPE: DNA
<213> ORGANISM: Artificial Sequence
<220> FEATURE:
<223> OTHER INFORMATION: forward primer used for specifically detecting
      the known variant of the gene of the present invention
      (NM_005122.2)

<400> SEQUENCE: 240
ccgggatcgg tttctgtatg                                                     20

<210> SEQ ID NO 241
<211> LENGTH: 17
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_005122.2)

<400> SEQUENCE: 241
ggagcagcgg catcatg                                                        17

<210> SEQ ID NO 242
<211> LENGTH: 122
<212> TYPE: DNA
<213> ORGANISM: Artificial Sequence
<220> FEATURE:
<223> OTHER INFORMATION: partial polynucleotide specific to the known
      variant of the gene of the present invention (NM_005122.2), which
      is obtained by PCR using forward primer (SEQ ID NO:240) and
      reverse primer (SEQ ID NO:241)

<400> SEQUENCE: 242
ccgggatcgg tttctgtatg cgaagttgct aggcctgctg gctgagctcc ggagcattaa        60
```

```
tgaggcctac gggtaccaaa tccagcacat ccagggcctg tctgccatga tgccgctgct    120
cc                                                                    122

<210> SEQ ID NO 243
<211> LENGTH: 23
<212> TYPE: DNA
<213> ORGANISM: Artificial Sequence
<220> FEATURE:
<223> OTHER INFORMATION: forward primer used for detecting the variants
      of the gene of the present invention (D-TLIVE2001566.1,
      D-TLIVE2006761.1, D-LIVER2001320.1 and NM_005122.2)

<400> SEQUENCE: 243
cagctcatct gttcatccat cac                                             23

<210> SEQ ID NO 244
<211> LENGTH: 24
<212> TYPE: DNA
<213> ORGANISM: Artificial Sequence
<220> FEATURE:
<223> OTHER INFORMATION: reverse primer used for detecting the variants
      of the gene of the present invention (D-TLIVE2001566.1,
      D-TLIVE2006761.1, D-LIVER2001320.1 and NM_005122.2)

<400> SEQUENCE: 244
ttgatgactt gcagtaccat gaaa                                            24

<210> SEQ ID NO 245
<211> LENGTH: 109
<212> TYPE: DNA
<213> ORGANISM: Artificial Sequence
<220> FEATURE:
<223> OTHER INFORMATION: partial polynucleotide common to the variants
      of the gene of the present invention (D-TLIVE2001566.1,
      D-TLIVE2006761.1, D-LIVER2001320.1 and NM_005122.2), which is
      obtained by PCR using forward primer (SEQ ID NO:243) and reverse
      primer (SEQ ID NO:244)

<400> SEQUENCE: 245
cagctcatct gttcatccat caccagccct tgcccaccct ggcccctgtg ctgcctctgg    60
tcacacactt cgcagacatc aacactttca tggtactgca agtcatcaa               109

<210> SEQ ID NO 246
<211> LENGTH: 157
<212> TYPE: DNA
<213> ORGANISM: Homo sapiens

<400> SEQUENCE: 246
agacatctct tgttttccag atactacggg tcataatccc taactccaat cactggcaac    60
tcctgagatc agaggaaaac cagcaacagc gtgggagttt ggggagaggc attccatacc   120
agattctgtg gcctgcaggt gacatgctgc ctaagag                            157

<210> SEQ ID NO 247
<211> LENGTH: 497
<212> TYPE: DNA
<213> ORGANISM: Homo sapiens

<400> SEQUENCE: 247
aagggccagc agcgaaggcc ccgggatcgg tacggtggga cactgaaggc ttggaggcca    60
caccagggca ggaagggggtt ggtgaaacat tgagcttggg aggaatgttt ttttactgtc   120
ctttccttag ggaattcagg tatcttgggg tctagtcctt cccccctgcc atccctgtct   180
cacatcgttt cagcatccaa attgctgtat ttggatactg ctgtttcatc tcactttttc   240
```

```
cagattttt  ttttattcag  tacagatgca  aagtagtagc  tcagaggctc  tgggtaatag      300
cattcctgag  attgatgaca  tccattacct  cactagtcca  acttctccag  actaatgcag      360
acttttctct  tcccttggcc  tttcctctcc  tcgccattgg  gccaattcct  tcgatttctc      420
atttcccttg  aagttagggc  cattcacagt  ttcatggtca  aagccagttc  caggttcaat      480
agtctgtgat  ttatcca                                                          497
```

<210> SEQ ID NO 248
<211> LENGTH: 14
<212> TYPE: PRT
<213> ORGANISM: Homo sapiens

<400> SEQUENCE: 248

```
Met Leu Pro Lys Arg Ser Arg Arg Thr Val Ser Lys Ser Ile
1               5                   10
```

The invention claimed is:

1. An isolated polypeptide comprising at least 8 consecutive amino acids of the amino acid sequence of SEQ ID NO: 54.

2. The polypeptide of claim 1 comprising at least 10 consecutive amino acids of the amino acid sequence of SEQ ID NO: 54.

3. The polypeptide of claim 2 comprising the amino acid sequence of SEQ ID NO: 54.

4. The polypeptide of claim 1 consisting of 8 to 148 consecutive amino acids of the amino acid sequence of SEQ ID NO: 54.

5. The polypeptide of claim 4 consisting of 10 to 148 consecutive amino acids of the amino acid sequence of SEQ ID NO: 54.

6. The polypeptide of claim 5 consisting of the amino acid sequence of SEQ ID NO: 54.

7. An isolated polypeptide comprising at least 8 consecutive amino acids of the amino acid sequence of SEQ ID NO: 56.

8. The polypeptide of claim 7 comprising at least 10 consecutive amino acids of the amino acid sequence of SEQ ID NO: 56.

9. The polypeptide of claim 8 comprising the amino acid sequence of SEQ ID NO: 56.

10. The polypeptide of claim 7 consisting of 8 to 89 consecutive amino acids of the amino acid sequence of SEQ ID NO: 56.

11. The polypeptide of claim 10 consisting of 10 to 89 consecutive amino acids of the amino acid sequence of SEQ ID NO: 56.

12. The polypeptide of claim 11 consisting of the amino acid sequence of SEQ ID NO: 56.

13. An isolated polypeptide comprising at least 8 consecutive amino acids of the amino acid sequence of SEQ ID NO: 57.

14. The polypeptide of claim 13 comprising the amino acid sequence of SEQ ID NO: 57.

15. The polypeptide of claim 13 consisting of 8 to 10 consecutive amino acids of the amino acid sequence of SEQ ID NO: 57.

16. The polypeptide of claim 15 consisting of the amino acid sequence of SEQ ID NO: 57.

* * * * *